US012291524B2

(12) United States Patent
Pettersen et al.

(10) Patent No.: US 12,291,524 B2
(45) Date of Patent: *May 6, 2025

(54) AMIDO HETEROAROMATIC COMPOUNDS

(71) Applicant: AstraZeneca AB, Södertälje (SE)

(72) Inventors: Daniel Tor Pettersen, Södertälje (SE);
Stéphanie Marcelle Gueret, Södertälje (SE); Nidhal Selmi, Södertälje (SE);
Erik Lars Malmerberg, Södertälje (SE); Tord Bertil Inghardt, Södertälje (SE); Jan Åke Lindberg, Södertälje (SE); Jens Peter Brandt, Södertälje (SE); Jon Paul Janet, Södertälje (SE);
Björn Erik Anton Holm, Södertälje (SE)

(73) Assignee: ASTRAZENECA AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/884,381

(22) Filed: Sep. 13, 2024

(65) Prior Publication Data

US 2025/0011311 A1     Jan. 9, 2025

Related U.S. Application Data

(63) Continuation of application No. 18/319,560, filed on May 18, 2023.

(60) Provisional application No. 63/383,982, filed on Nov. 16, 2022, provisional application No. 63/367,843, filed on Jul. 7, 2022, provisional application No. 63/364,976, filed on May 19, 2022.

(51) Int. Cl.
| | | |
|---|---|---|
| *C07D 413/06* | (2006.01) | |
| *C07D 271/06* | (2006.01) | |
| *C07D 409/06* | (2006.01) | |
| *C07D 413/04* | (2006.01) | |
| *C07D 413/12* | (2006.01) | |
| *C07D 413/14* | (2006.01) | |
| *C07D 471/04* | (2006.01) | |
| *C07D 487/04* | (2006.01) | |
| *C07D 498/10* | (2006.01) | |

(52) U.S. Cl.
CPC ......... *C07D 413/06* (2013.01); *C07D 271/06* (2013.01); *C07D 409/06* (2013.01); *C07D 413/04* (2013.01); *C07D 413/12* (2013.01); *C07D 413/14* (2013.01); *C07D 471/04* (2013.01); *C07D 487/04* (2013.01); *C07D 498/10* (2013.01)

(58) Field of Classification Search
CPC .................. C07D 413/06; C07D 271/06
USPC .................................... 514/210.18
See application file for complete search history.

(56) References Cited

U.S. PATENT DOCUMENTS

| | | |
|---|---|---|
| 4,987,132 A | 1/1991 | Mase et al. |
| 9,212,151 B2 | 12/2015 | Arnold et al. |
| 2009/0318429 A1 | 12/2009 | Doyle et al. |
| 2010/0144733 A1 | 6/2010 | Doyle et al. |
| 2022/0127258 A1 | 4/2022 | Yin et al. |

FOREIGN PATENT DOCUMENTS

| | | |
|---|---|---|
| EP | 0279681 A2 | 8/1988 |
| JP | H0249726 A | 2/1990 |
| KR | 20150049698 A | 5/2015 |
| WO | 2004014370 A2 | 2/2004 |
| WO | 2004014881 A2 | 2/2004 |
| WO | 2004014902 A2 | 2/2004 |
| WO | 2005077345 A1 | 8/2005 |
| WO | 2005077368 A2 | 8/2005 |
| WO | 2005077373 A2 | 8/2005 |
| WO | 2005097750 A1 | 10/2005 |
| WO | 2006014185 A1 | 2/2006 |
| WO | 2008147557 A2 | 12/2008 |
| WO | 2008152099 A2 | 12/2008 |
| WO | 2009126782 A1 | 10/2009 |
| WO | 2010045303 A2 | 4/2010 |
| WO | 2015090579 A1 | 6/2015 |
| WO | 2016046078 A1 | 3/2016 |
| WO | 2016073633 A1 | 5/2016 |
| WO | 2016172631 A2 | 10/2016 |
| WO | 2017161028 A1 | 9/2017 |
| WO | 2018112077 A1 | 6/2018 |
| WO | 2018237084 A1 | 12/2018 |
| WO | 2019036562 A1 | 2/2019 |

(Continued)

OTHER PUBLICATIONS

Abdelsamieet A.S., al., "Design, Synthesis, and Biological Characterization of Orally Active 17β-Hydroxysteroid Dehydrogenase Type 2 Inhibitors Targeting the Prevention of Osteoporosis", Journal of medicinal chemistry, Aug. 2019, vol. 62, No. 15, pp. 7289-7301, https://doi.org/10.1021/acs.jmedchem.9b00932.

(Continued)

*Primary Examiner* — Kahsay Habte

(57) ABSTRACT

The specification relates to compounds of Formula (I):

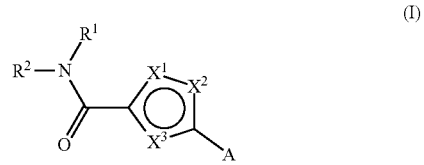

and to pharmaceutically acceptable salts thereof, to processes and intermediates used for their preparation, to pharmaceutical compositions containing them and to their use in the treatment of diseases such as liver disease.

26 Claims, 1 Drawing Sheet

(56) References Cited

FOREIGN PATENT DOCUMENTS

| | | | |
|---|---|---|---|
| WO | 2019145729 A1 | 8/2019 |
| WO | 2019209962 A1 | 10/2019 |
| WO | 2020051207 A2 | 3/2020 |
| WO | 2021003295 A1 | 1/2021 |
| WO | 2021050555 A1 | 3/2021 |
| WO | 2021138450 A1 | 7/2021 |
| WO | 2021211974 A1 | 10/2021 |
| WO | 2021252555 A1 | 12/2021 |
| WO | 2022020714 A1 | 1/2022 |
| WO | 2022040324 A1 | 2/2022 |
| WO | 2022072491 A1 | 4/2022 |
| WO | 2022072512 A1 | 4/2022 |
| WO | 2022072517 A1 | 4/2022 |
| WO | 2022103960 A1 | 5/2022 |
| WO | 2022149617 A1 | 7/2022 |
| WO | 2022149618 A1 | 7/2022 |
| WO | 2022216626 A1 | 10/2022 |
| WO | 2022216627 A1 | 10/2022 |
| WO | 2022226349 A1 | 10/2022 |
| WO | 2022253645 A1 | 12/2022 |
| WO | 2023146897 A1 | 8/2023 |

OTHER PUBLICATIONS

Ambinter: "PubChem Substance Record for SID 365202679", May 25, 2018, National Center for Biotechnology Information, PubChem, https://pubchem.ncbi.nlm.nih.gov/substance/365202679.

Anan K., et al, "Discovery of NR2B-selective Antagonists via Scaffold Hopping and Pharmacokinetic Profile Optimization", Bioorganic Medicinal Chemistry Letters, May 2019, vol. 29, No. 9, pp. 1143-1147.

Aurora Fine Chemicals: "PubChem Substance Record for SID 282670940", Jan. 13, 2016, National Center for Biotechnology Information, PubChem, https://pubchem.ncbi.nlm.nih.gov/substance/282670940.

Bertoletti N., et al., "New Insights into Human 17B-Hydroxysteroid Dehydrogenase Type 14: First Crystal Structures in Complex with a Steroidal Ligand and with a Potent Nonsteroidal Inhibitor", Journal of medicinal chemistry, 2016, vol. 59, No. 14, pp. 6961-6967, DOI: 10.1021/acs.jmedchem.6b00293.

Bertron J.L., et al., "Discovery and Optimization of a Novel Series of Competitive and Central Nervous System—Penetrant Protease-Activated Receptor 4 (PAR4) Inhibitors", ACS Chemical Neuroscience, vol. 12, No. 24, Dec. 2, 2021, pp. 4524-4534, XP093062119, US, ISSN: 1948-7193, DOI: 10.1021/acschemneuro.1c00557, example 15.

Braun F., et al., "Structure-based Design and Profiling of Novel 17β-HSD14 Inhibitors", European Journal of Medicinal Chemistry, Jul. 15, 2018, vol. 155, pp. 61-76, DOI: 10.1016/j.ejmech.2018.05.029.

CAS Registry No. 2401065-72-1, CAS Registry, 2023, 1 page, https://scifindern.cas.org/searchDetail/substance/64f83ba4aa3b5f324l715f07/substanceDetails.

CAS Registry No. 2403522-30-3, CAS Registry, 2023, 1 page, https://scifindern.cas.org/searchDetail/substance/64f83aebaa3b5f324171455c/substanceDetails.

Chembridge: "PubChem Substance Record for SID 251931991", Jun. 3, 2015, National Center for Biotechnology Information, PubChem, https://pubchem.ncbi.nlm.nih.gov/substance/251931991.

Cheung P.K., "A Parallel Synthesis Approach to the Identification of Novel Diheteroarylamide-Based Compounds Blocking HIV Replication: Potential Inhibitors of HIV-1 Pre-mRNA Alternative Splicing", Journal of Medicinal Chemistry, Feb. 15, 2016, vol. 59, No. 5, pp. 1869-1879.

Gargano E.M., et al., "Metabolic Stability Optimization and Metabolite Identification of 2,5-thiophene amide 17[beta]-hydroxysteroid dehydrogenase Type 2 Inhibitors", European Journal of Medicinal Chemistry, Elsevier, Amsterdam, NL, vol. 87, Sep. 20, 2014, pp. 203-219, XP029019072, ISSN: 0223-5234, DOI: 10.1016/J.EJMECH.2014.09.061 p. 206, example 8.

International Search Report and Written Opinion for International Application No. PCT/EP2023/063423, mailed Jul. 14, 2023, 14 Pages.

International Search Report and Written Opinion for International Application No. PCT/EP2023/063424, mailed Jul. 18, 2023, 13 Pages.

Liu S., et al., "Structural Basis of Lipid-droplet Localization of 17-Beta-hydroxysteroid Dehydrogenase 13", Nature Communications, Aug. 2023, vol. 14, No. 1, Article No. 5158, 14 Pages, https://doi.org/10.1038/s41467-023-40766-0.

Poirier D., "17β-Hydroxysteroid Dehydrogenase Inhibitors: a Patent Review", Expert opinion on therapeutic patents, Sep. 2010, vol. 20, No. 9, pp. 1123-1145, DOI: 10.1517/13543776.2010.505604.

Roy S., et al., "Discovery, Synthesis, and Optimization of Diarylisoxazole-3-carboxamides as Potent Inhibitors of the Mitochondrial Permeability Transition Pore", Chemmedchem Communications, vol. 10, No. 10, Aug. 18, 2015, pp. 1655-1671, XP093062116, DE ISSN: 1860-7179, DOI: 10.1002/cmdc.201500284, examples 54, 69, 74-76, 81, 83.

Siebenbuerger L., et al., "Highly Potent 17β-HSD2 Inhibitors with a Promising Pharmacokinetic Profile for Targeted Osteoporosis Therapy", Journal of medicinal chemistry, Dec. 2018, vol. 61, No. 23, pp. 10724-10738, DOI: 10.1021/acs.jmedchem.8b01373.

Sigalapalli D.K., et al., "Microwave-Assisted TBHP-Mediated Synthesis of 2-Amino-1,3,4-oxadiazoles in Water", Chemistryselect, vol. 5, No. 42, Nov. 13, 2020, pp. 13248-13258, XP093061563, DE ISSN: 2365-6549, DOI: 10.1002/slct.202003516, p. 13249.

Thamm S., et al., "Discovery of a Novel Potent and Selective HSD17B13 Inhibitor, BI-3231, a Well-Characterized Chemical Probe Available for Open Science", Journal of medicinal chemistry, Feb. 2023, vol. 66, No. 4, pp. 2832-2850, https://doi.org/10.1021/acs.jmedchem.2c01884.

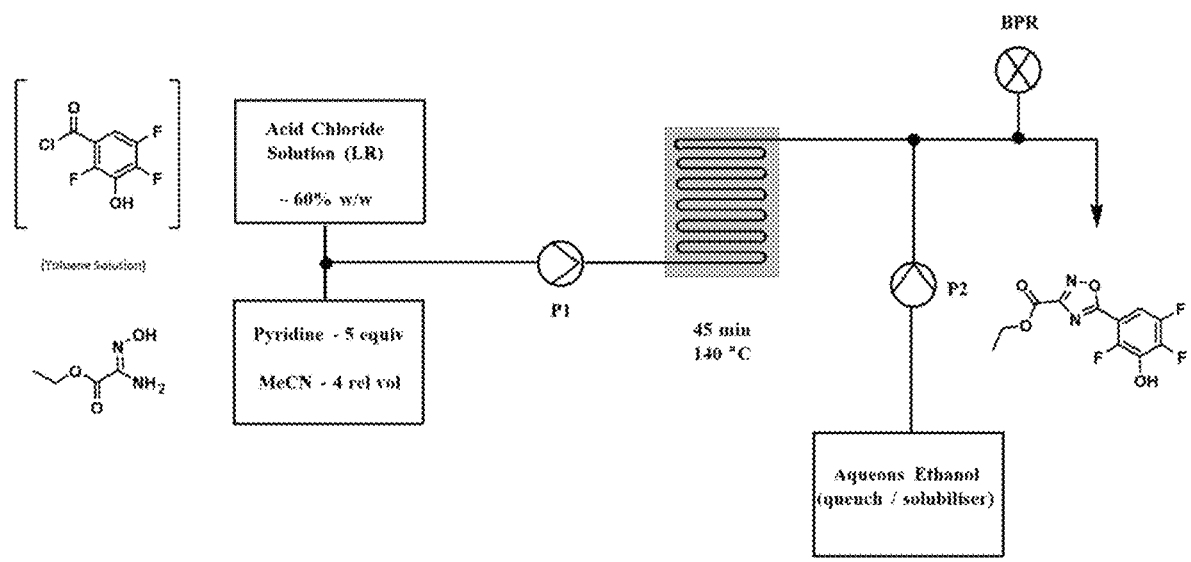

AMIDO HETEROAROMATIC COMPOUNDS

CROSS-REFERENCE TO RELATED PATENT APPLICATIONS

This specification is a Continuation of U.S. application Ser. No. 18/319,560 (filed 18 May 2023), which claims the benefit of priority to U.S. Provisional Patent Application No. 63/364,976 (filed 19 May 2022), 63/367,843 (filed 7 Jul. 2022) and 63/383,982 (filed 16 Nov. 2022). The entire text of the above-referenced patent applications is incorporated by reference into this specification.

This specification relates to certain amido heteroaromatic compounds and pharmaceutically acceptable salts thereof that inhibit 17β hydroxy steroid dehydrogenase 13 (17βHSD13 or HSD17B13), and their use in treating diseases such as liver disease. This specification also relates to processes and intermediate compounds involved in the preparation of the amido heteroaromatic compounds and to pharmaceutical compositions containing them.

INTRODUCTION

Non-alcoholic fatty liver disease (NAFLD) represents a spectrum of liver disease ranging from simple steatosis (non-alcoholic fatty liver), to non-alcoholic steatohepatitis (NASH) with or without fibrosis, to cirrhosis. Hepatic steatosis is defined as excess fat accumulation in the liver with greater than 5% induced by causes other than alcohol intake. NASH is defined by hepatic steatosis with inflammation and hepatocyte injury, with or without fibrosis. It is estimated that approximately 25% of the global population has NAFLD, and mortality due to NAFLD-related disease is expected to increase significantly through 2030.

To date, there are no approved treatments for NAFLD (such as NASH) and therapeutic interventions focus on addressing co-morbidities that contribute to the pathogenesis of NAFLD, including treating insulin resistance, obesity, type II diabetes mellitus, and dyslipidemia.

Recently, a variant in the 17βHSD13 gene, was associated in an allele dose-dependent manner with decreased serum aminotransferases levels, as well as a lower risk of liver disease, including alcoholic and non-alcoholic liver disease, cirrhosis and hepatocellular carcinoma (HCC) (Abul-Husn et al, N Engl J Med. 2018, 378(12), 1096-106, Wang et al, Eur Rev Med Pharmacol Sci, 2020, 24(17), 8997-9007). The 17βHSD13 splice variant (rs72613567:TA) results in a truncated, unstable and enzymatically inactive protein and has thus been characterized as an 17βHSD13 Loss of Function (LoF) variant (Ma et al, Hepatology 2019, 69(4), 1504-19). The association between the LoF 17βHSD13 (rs72613567:TA) and decreased disease severity has been replicated in additional cohorts with histologically proven NAFLD and was also associated with lower plasma transaminases, reduced risk of cirrhosis, HCC and liver related mortality in a study of 111612 individuals from the Danish general population (Gellert-Kristensen et al, Hepatology, 2020, 71(1), 56-66). Interestingly, the protective effect of the LoF 17βHSD13 (rs72613567:TA) variant on plasma transaminases levels appears to be amplified by several key risk factors of liver disease such as obesity, alcohol consumption, as well as established genetic risk factors such as, but not limited to, the (rs738409 C>G) variant in patatin-like phospholipase domain-containing protein 3 (PNPLA3). Further, two additional 17βHSD13LoF variants (rs62305723) and (rs143404524) were also reported to confer protection from chronic liver disease progression (Kozlitina et al, N Engl J Med, 2018, 379(19), 1876-7). In general, the LoF 17βHSD13 protective variants has a stronger association with fibrosis and progression to advance liver disease but is not associated with steatosis.

Based on the genetic validation of 17βHSD13LoF variants conferring protection against liver disease risk and progression, inhibition of 17βHSD13 activity with small molecules inhibitors could be an effective therapeutic approach for treating liver diseases such as NAFLD (for example NASH, liver fibrosis, cirrhosis and isolated steatosis), liver inflammation, alcoholic steatohepatitis (ASH), hepatitis C virus (HCV) and hepatocellular carcinoma (HCC), such as in individuals harbouring several key risk factors of liver disease such as obesity, alcohol consumption, as well as established genetic risk factors such as the (rs738409 C>G) variant in PNPLA3.

The compounds of the disclosure provide an anti-liver disease effect by, as a minimum, acting as 17βHSD13 inhibitors. Further, compounds of the disclosure may selectively inhibit 17βHSD13 over 17βHSD4 and/or 17βHSD9.

Fifteen 17βHSD (HSD17B) members have been identified in human. The sequence homology among the different members is rather low, but the overall structure seems conserved. 17β-Hydroxysteroid dehydrogenases are mainly involved in sex hormone metabolism. Some 17βHSD enzymes also play key roles in cholesterol and fatty acid metabolism (Labrie et al. Journal of Molecular Endocrinology, 2000, 25, 1-16, Wen Su et al. Molecular and Cellular Endocrinology, 2019, 489, 119-125). A clean off-target profile is an advantage for a 17βHSD13 inhibitor to avoid potential toxicity caused by off-target activity. This includes selectivity to other 17βHSD members.

17βHSD4/D-bifunctional protein (DBP) is involved in fatty acid β-oxidation and steroid metabolism. 17βHSD4 is ubiquitously expressed and play an important role in the inactivation of estrogens in a large series of peripheral tissues. Mutations in 17βHSD4 are known to cause DBP deficiency, an autosomal-recessive disorder of peroxisomal fatty acid β-oxidation that is generally fatal within the first two years of life. A homozygous missense variant in 17βHSD4 has been identified in Perrault syndrome, a recessive disorder characterized by ovarian dysgenesis in females, sensorineural deafness in both males and females, and in some patients, neurological manifestations (Pierce et al. Am. J. Hum. Genet., 2010, 87, 282-8; and Chen et al. BMC Med Genet., 2017, 18, 91).

17βHSD9/RDH5 (retinol dehydrogenase 5) is involved in retinoid metabolism. The enzyme is mainly expressed in the retinal pigment epithelium. The RDH5 gene encodes the enzyme that is a part of the visual cycle, the 11-cis retinol dehydrogenase, catalysing the reduction of 11-cis-retinol to 11-cis-retinal. RDH5 gene mutations cause a progressive cone dystrophy or macular dystrophy as well as night blindness. Fundus albipunctatus is a rare, congenital form of night blindness with rod system impairment, characterised by the presence of numerous small, white-yellow retinal lesions. This disorder is caused mostly by mutations in the RDH5 gene (Hotta et al. Am. J. Ophthalmol., 2003, 135, 917-9; and Skorczyk-Werner et al. J. Appl. Genet., 2015, 56, 317-27).

The compounds of the specification may also exhibit advantageous physical properties (for example, lower lipophilicity, higher aqueous solubility, higher permeability, lower plasma protein binding, and/or greater chemical stability), and/or favourable toxicity profiles (for example a decreased activity at hERG), and/or favourable metabolic or pharmacokinetic profiles, in comparison with other known 17βHSD13 inhibitors. Such compounds may therefore be especially suitable as therapeutic agents, such as for the treatment of liver disease.

GENERAL DESCRIPTION

According to one aspect of the specification there is provided a compound of Formula (I);

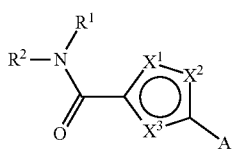
(I)

wherein,
A is selected from

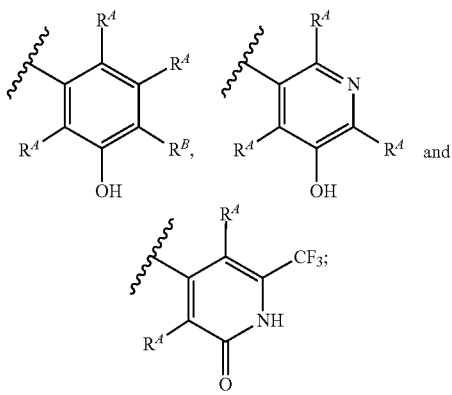
and each $R^A$ is independently selected from H, halo, $R^X$, —$OR^x$, and —CN, wherein each $R^X$ is independently $C_{1-3}$alkyl optionally substituted with one to three F;
$R^B$ is halo, —$CHF_2$, —$CF_3$, —$OCHF_2$ or —$OCF_3$;
one of $X^1$, $X^2$ and $X^3$ is selected from NH, O and S and the other two of $X^1$, $X^2$ and $X^3$ are independently selected from N and $CR^Y$, wherein each $R^Y$ is independently H, —CN, —C(=O)N($R^7$)$_2$ or $R^{XA}$, wherein $R^{XA}$ is independently $C_{1-3}$ alkyl optionally substituted with one to three F;
$R^1$ and $R^2$ are such that;
(i) $R^1$ and $R^2$, taken together with the N atom to which they are attached, form a ring system, wherein the ring system is optionally substituted with one or more $R^C$, wherein each $R^C$ is independently selected from F, $R^3$, $R^4$, —O($R^4$), —O($R^5$), $R^5$, $R^6$, —OH, —CN, oxo and —C(=O)N($R^{7A}$)$_2$;
(ii) $R^1$ is selected from $R^8$ and $R^{4A}$, and $R^2$ is selected from $R^{8A}$ and H; or
(iii) $R^1$ is RSA and $R^2$ is $R^{8B}$;
each $R^3$ is independently $C_{1-4}$ alkyl or $C_{3-6}$ cycloalkyl, each of which are optionally substituted with one or more groups independently selected from $R^{4X}$, $R^{5x}$, —O($R^{4X}$), —O($R^{5X}$) and F;
each $R^{3X}$ is independently $C_{1-4}$ alkyl or $C_{3-6}$ cycloalkyl, each of which are optionally substituted with one or more F;
each $R^4$ and $R^{4B}$ are independently monocyclic or bicyclic 5 to 9 membered heteroaryl, each of which are optionally substituted with one or more groups independently selected from $R^{4X}$, —O($R^{4X}$), $R^{5X}$, —O($R^{5X}$), —OH, —CN, $C_{1-4}$ alkoxy, —C(=O)OH, —C(=O)O($C_{1-4}$ alkyl), —C(=O)N($R^{7B}$)$_2$, $R^3$ and halo;
$R^{4A}$ is a 5 membered monocyclic heteroaryl, optionally substituted with one or more groups independently selected from $R^{4X}$, —O($R^{4X}$), $R^{5X}$, —O($R^{5X}$), —OH, —CN, $C_{1-4}$ alkoxy, —C(=O)OH, —C(=O)O($C_{1-4}$ alkyl), —C(=O)N($R^{7B}$)$_2$, $R^3$ and halo;
each $R^5$, $R^{5A}$ and $R^{5B}$ are independently phenyl, each of which are optionally substituted with one or more groups independently selected from $R^{4X}$, —O($R^{4X}$), $R^{5X}$, —O($R^{5X}$), —OH, —CN, $C_{1-4}$ alkoxy, —C(=O)OH, —C(=O)O($C_{1-4}$ alkyl), —C(=O)N($R^{7B}$)$_2$, $R^3$ and halo;
each $R^{4X}$ is independently monocyclic or bicyclic 5 to 9 membered heteroaryl, each of which are optionally substituted with one or more groups independently selected from —OH, —CN, $C_{1-4}$ alkoxy, —C(=O)OH, —C(=O)N($R^{7B}$)$_2$, $R^{3X}$ and halo;
each $R^{5X}$ is independently phenyl, each of which are optionally substituted with one or more groups independently selected from —OH, —CN, $C_{1-4}$ alkoxy, —C(=O)OH, —C(=O)N($R^{7B}$)$_2$, $R^{3x}$ and halo;
$R^6$ is $C_{1-4}$ alkoxy optionally substituted with one or more groups independently selected from $R^{4X}$, $R^{5x}$ and F;
each $R^7$, $R^{7A}$, $R^{7B}$ and $R^{7C}$ are independently H, $C_{1-4}$ alkyl or $C_{3-6}$ cycloalkyl;
$R^8$, $R^{8A}$, $R^{8B}$ are independently $C_{1-4}$ alkyl or $C_{3-6}$ cycloalkyl, each of which are optionally substituted with one or more groups independently selected from $R^{4B}$, $R^{5B}$, F, —OH, —CN, $C_{1-4}$ alkoxy, —C(=O)O($C_{1-4}$ alkyl) and —C(=O)N($R^{7C}$)$_2$;
wherein the ring system is a saturated or partly saturated, monocyclic, bicyclic or tricyclic, 4-13 membered ring comprising one N atom, and optionally one or two further heteroatoms independently selected from N, O and S; and
wherein each heteroaryl is independently an aromatic ring containing one or more heteroatoms independently selected from N, O and S,
or a pharmaceutically acceptable salt thereof.

In a further aspect there is provided a pharmaceutical composition comprising a compound of Formula (I) or a pharmaceutically acceptable salt thereof, and a pharmaceutically acceptable excipient.

In a further aspect there is provided a compound of Formula (I) or a pharmaceutically acceptable salt thereof, for use in therapy.

In a further aspect there is provided a compound of Formula (I) or a pharmaceutically acceptable salt thereof, for use in the treatment of liver disease.

In a further aspect there is provided the use of a compound of Formula (I) or a pharmaceutically acceptable salt thereof, in the manufacture of a medicament.

In a further aspect there is provided the use of a compound of Formula (I) or a pharmaceutically acceptable salt thereof, in the manufacture of a medicament for the treatment of liver disease.

In a further aspect there is provided a method of treating liver disease in a patient comprising administering to the patient an effective amount of a compound of Formula (I) or a pharmaceutically acceptable salt thereof.

In a further aspect there is provided intermediates useful for the synthesis of a compound of Formula (I) or a pharmaceutically acceptable salt thereof.

Definitions

So that the present specification may be more readily understood, certain terms are explicitly defined below. In addition, definitions are set forth as appropriate throughout the detailed description.

As used herein the term "alkyl" refers to both straight and branched chain saturated hydrocarbon radicals having the specified number of carbon atoms.

In this specification the prefix $C_{x-y}$, as used in terms such as "$C_{x-y}$ alkyl" and the like where x and y are integers, indicates the numerical range of carbon atoms that are present in the group. Examples of suitable $C_{1-3}$ alkyl groups include methyl, ethyl, n-propyl, and i-propyl. Examples of suitable $C_{1-4}$alkyl groups include methyl, ethyl, n-propyl, i-propyl, n-butyl, i-butyl, s-butyl and t-butyl.

In this specification the prefix X-Y membered, as used in terms such as "X-Y membered ring" and the like where X and Y are integers, indicates the numerical range of atoms (i.e. carbon atoms and heteroatoms) that are present in the group.

As used herein the term "alkoxy" refers to a saturated group comprising the specified number of carbon atoms and one oxygen atom. For the avoidance of doubt, the alkoxy group may be a straight chain or a branched chain. Examples of suitable $C_{1-3}$ alkoxy groups include methoxy (OMe), ethoxy (OEt), n-propoxy (O$^n$Pr) and i-propoxy (O$^i$Pr). Examples of suitable $C_{1-4}$alkoxy groups include methoxy (OMe), ethoxy (OEt), n-propoxy (O$^n$Pr), i-propoxy (O$^i$Pr), n-butoxy (O$^n$Bu), i-butoxy (O$^i$Bu), s-butoxy (O$^s$Bu) and t-butoxy (O$^t$Bu).

As used herein the term "cycloalkane" refers to a saturated carbocyclic ring. Examples of $C_{3-6}$ cycloalkane groups are cyclopropane, cyclobutane, cyclopentane and cyclohexane.

As used herein the term "cycloalkylidyne" refers to a 1,1-diradical of a cycloalkane. Examples of $C_{3-6}$ cycloalkylidyne are cyclopropylidene

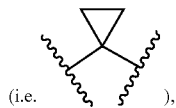

(i.e. ), cyclobutylidene

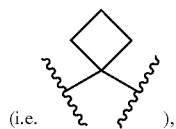

(i.e. ), cyclopentylidene

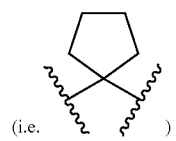 [SMILES: *C1(*)CCCC1]

(i.e. )

and cyclohexylidene

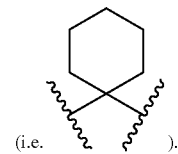 [SMILES: *C1(*)CCCCC1]

(i.e. ).

Unless otherwise stated, "halo" is selected from Cl, F, Br and I. In embodiments, halo is selected from Cl and F.

The term "heteroatom" refers to N, O or S.

Unless otherwise stated, the term "heteroaryl" is an aromatic, monocyclic or bicyclic, 5 to 9 membered ring containing one or more heteroatoms independently selected from N, O and S. Where a compound of the disclosure comprises more than one heteroaryl groups, the heteroaryl groups may be the same or different. A heteroaryl may be a 5 or 6 membered monocyclic heteroaryl. Examples of suitable 5 membered heteroaryl groups include pyrrolyl, furanyl, thiophenyl, pyrazolyl, imidazolyl, oxazolyl, isoxazolyl, thiazolyl, isothiazolyl, 1,2,3-triazolyl, 1,2,4-triazolyl, 1,2,3-oxadiazolyl, furazanyl, 1,3,4-thiadiazolyl and tetrazolyl. Examples of suitable 6 membered heteroaryl groups include pyridyl (such as 2-pyridyl, 3-pyridyl or 4-pyridyl), pyridazinyl, pyrimidinyl, pyrazinyl and 1,3,4-triazinyl. A heteroaryl may be a 9-membered bicyclic heteroaryl. Where a heteroaryl is bicyclic, one or both rings may be aromatic. Examples of a suitable 9 membered heteroaryl groups include indolyl, isoindolyl, benzofuranyl, isobenzofuranyl, indolinyl, isoindolinyl, benzothiophenyl, isobenzothiophenyl, indazolyl, benzimidazolyl, benzthiazolyl, purinyl, [1,2,4]triazolo[4,3-b]pyridazinyl (such as 6-[1,2,4]triazolo[4,3-b]pyridazinyl) and benzo[d]oxazolyl (such as 2-benzo[d]oxazolyl).

Unless otherwise stated, the term "heterocycloalkyl" refers to a saturated monocyclic, bicyclic or tricyclic ring comprising one N atom, and one further heteroatom selected from N, O and S. For the avoidance of doubt, the other atoms of the ring are carbon. Examples of suitable heterocycloalkyl groups include 4-8 membered monocyclic heterocycloalkyl, 8-11 membered spirocyclic bicyclic heterocycloalkyl, 7-10 membered fused bicyclic heterocycloalkyl and 8-10 membered bridged bicyclic heterocycloalkyl.

The term "4-8 membered monocyclic heterocycloalkyl" refers to a saturated, 4-8 membered monocyclic ring comprising one nitrogen atom and optionally one further heteroatom selected from nitrogen, oxygen and sulfur, For the avoidance of doubt, the other atoms of the ring are carbon. A suitable 4 membered heterocycloalkyl group is azetidin-1-yl. A suitable 5 membered heterocycloalkyl group is pyrrolidin-1-yl. Examples of suitable 6 membered heterocycloalkyl groups include piperidin-1-yl, piperazin-1-yl, morpholin-4-yl and thiomorpholin-4-yl. Examples of suitable 7 membered heterocycloalkyl groups include azepan-1-yl, 1,4-diazepan-1-yl, 1,4-oxazepan-4-yl and 1,4-thiazepan-4-yl. Examples of suitable 8 membered heterocycloalkyl groups include azocan-1-yl, 1,4-diazocan-1-yl, 1,5-diazocan-1-yl, 1,4-oxazocan-4-yl, 1,5-oxazocan-5-yl, 1,4-thiazocanyl and 1,5-thiazocanyl.

The term "8-11 membered spirocyclic bicyclic heterocycloalkyl" refers to a saturated, 8-11 membered bicyclic, spirocyclic ring comprising one nitrogen atom and optionally one further heteroatom selected from N, O and S. For the avoidance of doubt, the other atoms of the ring are carbon. Examples of suitable 8 membered spirocyclic heterocycloalkyl groups include 5-azaspiro[2.5]octan-5-yl, 4,7- diazaspiro[2.5]octan-7-yl, 4-oxa-7-azaspiro[2.5]octan-7-yl and 4-thia-7-azaspiro[2.5]octan-7-yl. Examples of suitable 9 membered spirocyclic heterocycloalkyl groups include 6-azaspiro[3.5]nonan-6-yl, 5,8-diazaspiro[3.5]nonan-8-yl, 5-oxa-8-azaspiro[3.5]nonan-8-yl and 5-thia-8-azaspiro[3.5] nonan-8-yl. Examples of suitable 10 membered spirocyclic heterocycloalkyl groups include 7-azaspiro[4.5]decan-7-yl, 6,9-diazaspiro[4.5]decan-9-yl, 6-oxa-9-azaspiro[4.5]decan-9-yl and 6-thia-9-azaspiro[4.5]decan-9-yl. Examples of suitable 11 membered spirocyclic heterocycloalkyl groups include 2-azaspiro[5.5]undecane-2-yl, 1,4-diazaspiro[5.5] undecan-4-yl, 1-oxa-4-azaspiro[5.5]undecan-4-yl and 1-thia-4-azaspiro[5.5]undecan4-yl.

The term "7-10 membered fused bicyclic heterocycloalkyl" refers to a saturated, 7-10 membered bicyclic, fused ring comprising one nitrogen atom and optionally one further heteroatom selected from N, O and S. For the avoidance of doubt, the other atoms of the ring are carbon. Examples of suitable 7 membered fused bicyclic heterocycloalkyl groups include 2-azabicyclo[4.1.0]heptan-2-yl, 2,5-diazabicyclo[4.1.0]heptan-2-yl, 2-oxa-5-azabicyclo[4.1.0]heptan-5-yl and 2-thia-5-azabicyclo[4.1.0]heptan-5-yl. Examples of suitable 8 membered fused bicyclic heterocycloalkyl groups include 2-azabicyclo[4.2.0]octan-2-yl, 2,5-diazabicyclo[4.2.0]octan-2-yl, 2-oxa-5-azabicyclo[4.2.0]octan-5-yl and 2-thia-5-azabicyclo[4.2.0]octan-5-yl. Examples of suitable 9 membered fused bicyclic heterocycloalkyl groups include octahydro-1H-cyclopenta[b]pyridin-1-yl, octahydro-1H-cyclopenta[b]pyrazin-1-yl, octahydrocyclopenta[b][1,4]oxazin-4-yl and octahydrocyclopenta[b][1,4]thiazin-4-yl. Examples of suitable 10 membered fused bicyclic heterocycloalkyl groups include decahydroquinolin-1-yl, decahydroquinoxalin-1-yl, octahydro-2H-benzo[b][1,4]oxazin-4-yl and octahydro-2H-benzo[b][1,4]thiazin-4-yl.

The term "8-10 membered bridged bicyclic heterocycloalkyl" refers to a saturated, 8-10 membered bicyclic, bridged ring comprising one nitrogen atom and optionally one further heteroatom selected from nitrogen, oxygen and sulfur, wherein the remaining atoms of the 8-10 membered fused bicyclic heterocycloalkyl group are carbon. Examples of a suitable 8-10 membered bridged bicyclic heterocycloalkyl groups include 3-azabicyclo[3.2.1]octan-3-yl, 3-azabicyclo[3.2.2]nonane and 3-azabicyclo[3.3.2]decan-3-yl.

The term "oxo" refers to a oxygen atom forming a double bond (i.e. =O) to a suitable atom, such as carbon.

Unless otherwise stated, the term "ring system" refers to a saturated or partly saturated, monocyclic, bicyclic or tricyclic, 4-13 membered ring comprising one N atom, and optionally one or two further heteroatoms independently selected from N, O and S. For the avoidance of doubt, the other atoms of the ring are carbon. Where the ring system is bicyclic, it may be spirocyclic, fused or bridged. Examples of suitable monocyclic ring systems include 4-6 membered heterocycloalkyl. Examples of suitable bicyclic ring systems include 8-11 membered spirocyclic bicyclic heterocycloalkyl, 7-10 membered fused bicyclic heterocycloalkyl and 8-10 membered bridged bicyclic heterocycloalkyl.

The term "saturated or partially saturated" ring system refers to a ring system that is aliphatic, or which contains at least one aliphatic ring and one or two aromatic rings.

Unless specifically stated, the bonding of an atom or group may be any suitable atom of that group; for example, propyl includes prop-1-yl and prop-2-yl.

For the avoidance of doubt, where multiple substituents are independently selected from a given group, the selected substituents may comprise the same substituents or different substituents from within the given group.

For the avoidance of doubt, the use of a circle within a 5 membered ring indicates that the 5 membered ring is an aromatic ring. By way of illustration only,

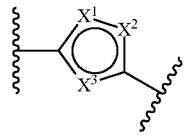

indicates an aromatic ring selected from

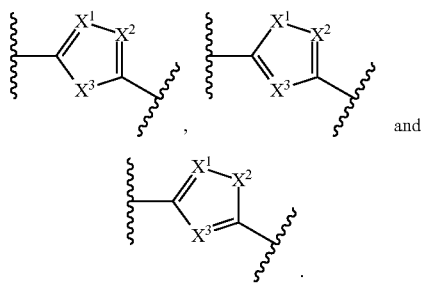

For the avoidance of doubt, the use of

in formulas of this specification denotes the point of attachment between different groups. By way of illustration only,

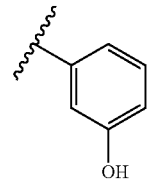 [SMILES: *c1cccc(O)c1]

denotes a 3-hydroxyphenyl radical which is attached to a different group through the carbon atom meta- to the OH substituent.

For the avoidance of doubt, the use of a bond between a substituent and the centre of a ring denotes that the substituent may replace any hydrogen atom directly attached to the ring, whether that hydrogen atom be attached to a C or N atom. By way of illustration only,

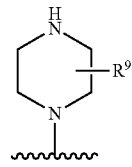

indicates a group selected from

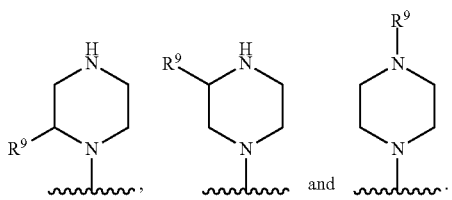

Where any embodiment within this specification includes a group which is said to be "optionally substituted", then a further embodiment will include that embodiment wherein the said group is unsubstituted.

For the avoidance of doubt, where multiple substituents are independently selected from a given group, the selected substituents may comprise the same substituents or different substituents from within the given group.

Units, prefixes, and symbols are denoted in their International System of Units (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary of Biochemistry and Molecular Biology, Revised, 2000, Oxford University Press, provide one of skill with a general dictionary of many of the terms used in this disclosure.

DESCRIPTION OF FIGURE

Embodiments and experiments illustrating the principles of the disclosure will now be discussed with reference to the accompanying FIGURE in which:

FIG. 1 illustrates the synthesis of Intermediate 1 in flow.

DETAILED DESCRIPTION

In one aspect there is provided a compound of Formula (I), or a pharmaceutically acceptable salt thereof, as defined above.

In embodiments, there is provided a compound of Formula (I), or a pharmaceutically acceptable salt thereof, wherein the ring system is an aliphatic, monocyclic, bicyclic or tricyclic, 4-13 membered ring comprising one N atom, and optionally one or two further heteroatoms independently selected from N, O and S.

In embodiments, there is provided a compound of Formula (I), or a pharmaceutically acceptable salt thereof, wherein the ring system is an aliphatic, monocyclic or bicyclic, 4-11 membered ring comprising one N atom, and optionally one or two further heteroatoms independently selected from N, O and S (wherein the ring system is optionally substituted with one or more $R^C$).

In embodiments, there is provided a compound of Formula (I), or a pharmaceutically acceptable salt thereof, wherein the ring system is an aliphatic, monocyclic or bicyclic, 5-11 membered ring comprising one N atom, and optionally one further heteroatom selected from N, O and S (wherein the ring system is optionally substituted with one or more $R^C$).

In embodiments, there is provided a compound of Formula (I), or a pharmaceutically acceptable salt thereof, wherein the ring system is an aliphatic, monocyclic or bicyclic, 5-8 membered ring comprising one N atom, and optionally one further heteroatom selected from N, O and S (wherein the ring system is optionally substituted with one or more $R^C$).

In embodiments, there is provided a compound of Formula (I), or a pharmaceutically acceptable salt thereof, wherein the ring system is an aliphatic, monocyclic or bicyclic, 5-11 membered ring comprising one N atom, and one further heteroatom selected from N, O and S (wherein the ring system is optionally substituted with one or more $R^C$).

In embodiments, there is provided a compound of Formula (I), or a pharmaceutically acceptable salt thereof, wherein the ring system is an aliphatic, monocyclic or bicyclic, 5-8 membered ring comprising one N atom, and one further heteroatom selected from N, O and S (wherein the ring system is optionally substituted with one or more $R^C$).

In embodiments, there is provided a compound of Formula (I), or a pharmaceutically acceptable salt thereof, wherein the ring system is an aliphatic, monocyclic or bicyclic, 5-8 membered ring comprising one N atom and one O atom (wherein the ring system is optionally substituted with one or more $R^C$).

In embodiments, there is provided a compound of Formula (I), or a pharmaceutically acceptable salt thereof, wherein the ring system is an aliphatic monocyclic 5-8 membered ring comprising one N atom and one O atom (wherein the ring system is optionally substituted with one or more $R^C$).

In embodiments, there is provided a compound of Formula (I), or a pharmaceutically acceptable salt thereof, wherein the ring system is a 4-8 membered monocyclic heterocycloalkyl, optionally substituted with one or more $R^C$.

In embodiments, there is provided a compound of Formula (I), or a pharmaceutically acceptable salt thereof, wherein the ring system is a 5-7 membered monocyclic heterocycloalkyl, optionally substituted with one or more $R^C$.

In embodiments, there is provided a compound of Formula (I), or a pharmaceutically acceptable salt thereof, wherein the ring system is an 8-11 membered spirocyclic bicyclic heterocycloalkyl, optionally substituted with one or more $R^C$.

In embodiments, there is provided a compound of Formula (I), or a pharmaceutically acceptable salt thereof, wherein the ring system is an 7-10 membered fused bicyclic heterocycloalkyl, optionally substituted with one or more $R^C$.

In embodiments, there is provided a compound of Formula (I), or a pharmaceutically acceptable salt thereof, wherein the ring system is an 8-10 membered bridged bicyclic heterocycloalkyl, optionally substituted with one or more $R^C$.

In embodiments, there is provided a compound of Formula (I), or a pharmaceutically acceptable salt thereof, wherein the ring system is optionally substituted with one or more $R^C$. In further embodiments, the ring system is optionally substituted with one to three $R^C$. In further embodiments, the ring system is optionally substituted with one or two $R^C$. In further embodiments, the ring system is not substituted.

In embodiments, there is provided a compound of Formula (I), or a pharmaceutically acceptable salt thereof, wherein each $R^C$ is independently selected from F, $R^3$, $R^4$, —O($R^4$), —O($R^5$), $R^5$, $R^6$, —OH, —CN and —C(=O)N($R^{7A}$)$_2$. In further embodiments, each $R^C$ is independently selected from $R^3$, $R^4$, —O($R^4$), —O($R^5$), $R^5$ and $R^6$. In further embodiments, each $R^C$ is independently selected from $R^3$, $R^4$ and $R^5$. In further embodiments, each $R^C$ is independently $R^3$. In further embodiments, each $R^C$ is independently $C_{1-4}$ alkyl, optionally substituted with one or more (such as one to three) F. In further embodiments, each $R^C$ is independently selected from $C_{1-4}$alkyl, phenyl and —O(phenyl). In further embodiments, each $R^C$ is independently $C_{1-4}$ alkyl. In further embodiments, each $R^C$ is $CH_3$.

In embodiments, there is provided a compound of Formula (I), or a pharmaceutically acceptable salt thereof, wherein $NR^1R^2$ is a group selected from

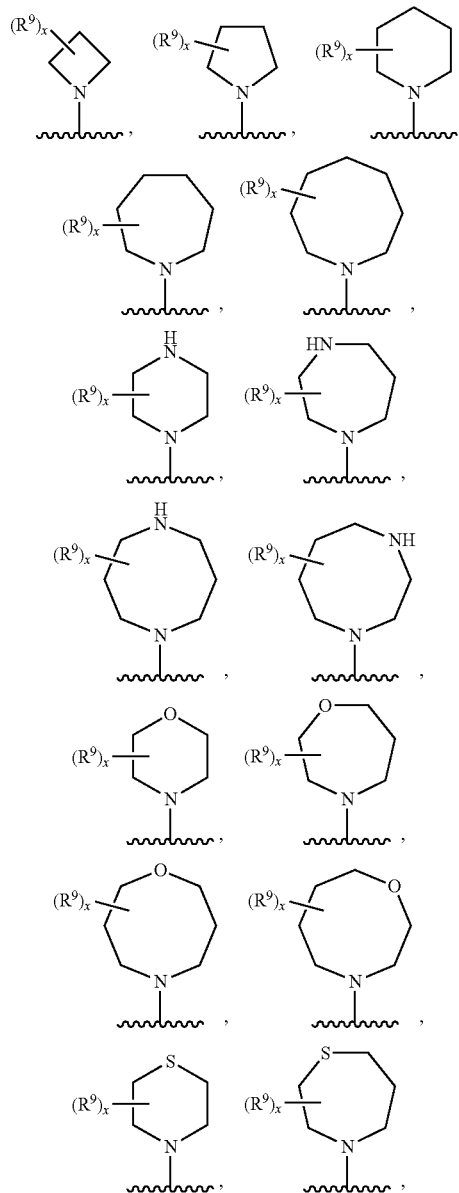

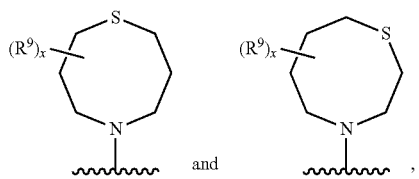

wherein x is selected from 0 to 3, and each $R^9$ is independently selected from $R^3$, $R^4$ and $R^5$.

In embodiments, there is provided a compound of Formula (I), or a pharmaceutically acceptable salt thereof, wherein $NR^1R^2$ is a group selected from

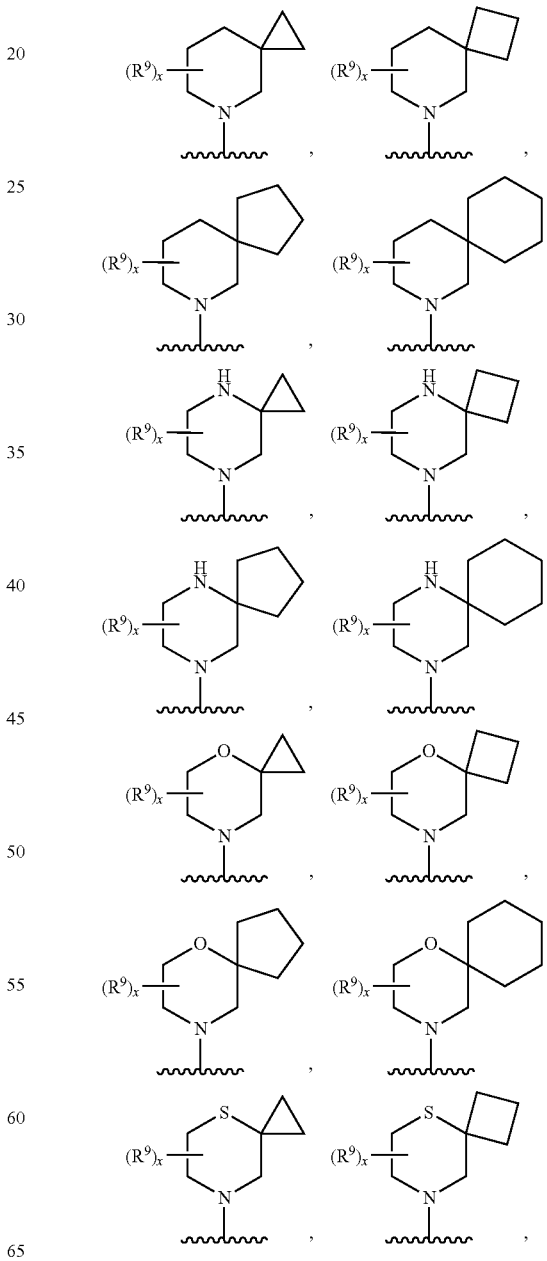

13

-continued

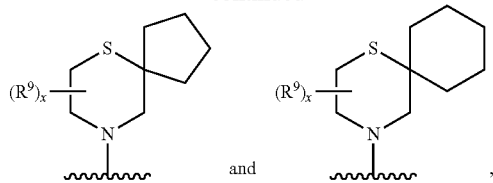

and wherein x is selected from 0 to 3, and each $R^9$ is independently selected from $R^3$, $R^4$ and $R^5$.

In embodiments, there is provided a compound of Formula (I), or a pharmaceutically acceptable salt thereof, wherein $NR^1R^2$ is a group selected from,

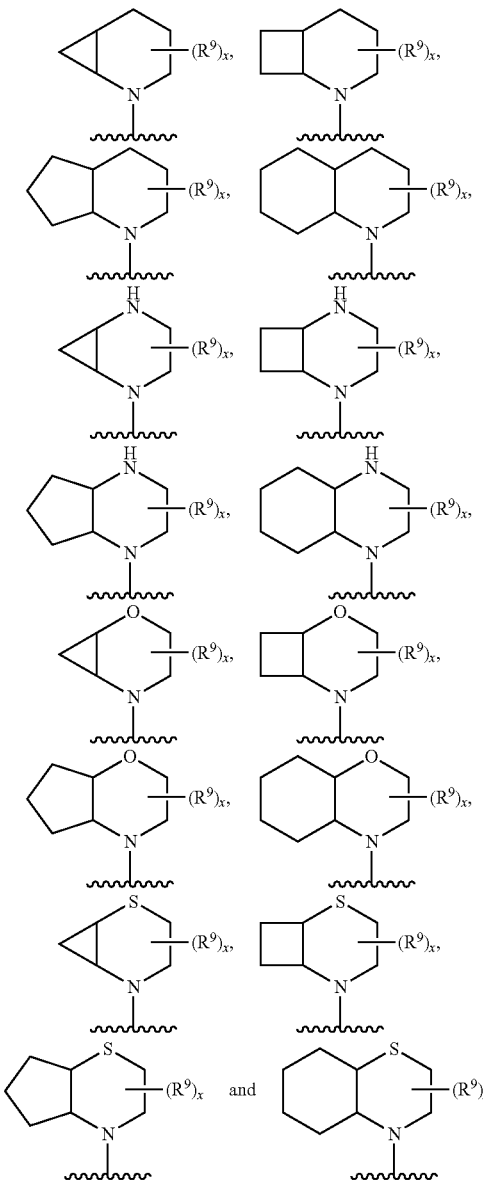

wherein x is selected from 0 to 3, and each $R^9$ is independently selected from $R^3$, $R^4$ and $R^5$.

In embodiments, there is provided a compound of Formula (I), or a pharmaceutically acceptable salt thereof, wherein $NR^1R^2$ is

14

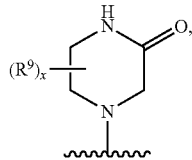

wherein x is selected from 0 to 3, and each $R^9$ is independently selected from $R^3$, $R^4$ and $R^5$.

In embodiments, the compound of Formula (I) is a compound of Formula (II):

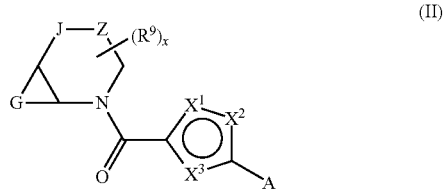

(II)

wherein

J is selected from O, S, $CH_2$, NH and a covalent bond,

G is either absent or, together with the carbon atoms to which it is attached, forms a $C_{3-6}$ cycloalkane ring;

Z is such that (i) where G is absent and J is selected from O, S, $CH_2$ and a covalent bond, Z is selected from $CH_2$, $CH_2CH_2$ and $C_{3-6}$ cycloalkylidyne, (ii) where G is absent and J is NH, Z is selected from $CH_2$, $CH_2CH_2$, $C_{3-6}$ cycloalkylidyne and C(=O), and (iii) where G, together with the carbon atoms to which it is attached, forms a $C_{3-6}$ cycloalkane ring, Z is $CH_2$;

x is selected from 0 to 3; and each $R^9$ is independently selected from $R^3$, $R^4$ and $R^5$, or a pharmaceutically acceptable salt thereof.

In embodiments, the compound of Formula (II) is a compound of Formula (IIA) or Formula (IIB)

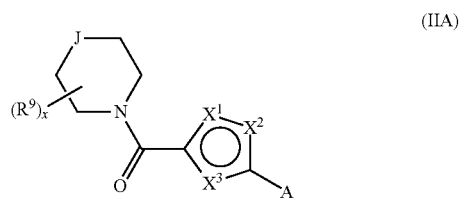

(IIA)

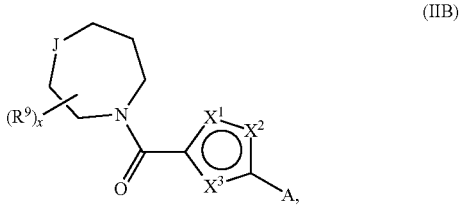

(IIB)

wherein $X^1$, $X^2$, $X^3$, A, J, $R^9$ and x are as defined for a compound of Formula (II).

In embodiments, the compound of Formula (II) is a compound of Formula (IIC)

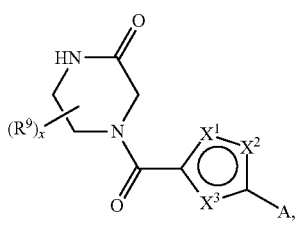
(IIC)

wherein $X^1$, $X^2$, $X^3$, A, J, $R^9$ and x are as defined for a compound of Formula (II).

In embodiments, the compound of Formula (II) is a compound of Formula (IID)

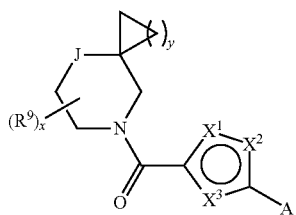
(IID)

wherein $X^1$, $X^2$, $X^3$, A, J, $R^9$ and x are as are as defined for a compound of Formula (II), and y is an integer from 1 to 4.

In embodiments, the compound of Formula (II) is a compound of Formula (IIE)

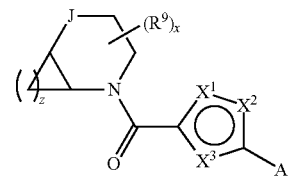
(IIE)

wherein $X^1$, $X^2$, $X^3$, A, J, $R^9$ and x are as are as defined for a compound of Formula (II), and z is an integer from 1 to 4.

In embodiments, there is provided a compound of Formula (I), or a pharmaceutically acceptable salt thereof, wherein $NR^1R^2$ is a group selected from

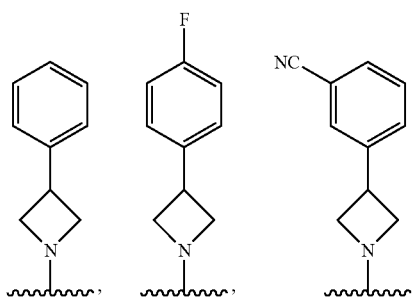

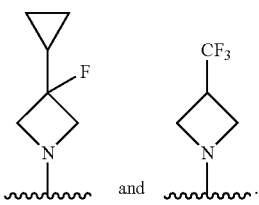

In embodiments, there is provided a compound of Formula (I), or a pharmaceutically acceptable salt thereof, wherein $NR^1R^2$ is a group selected from

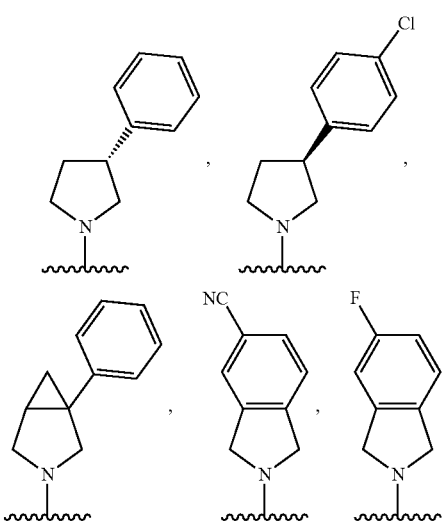

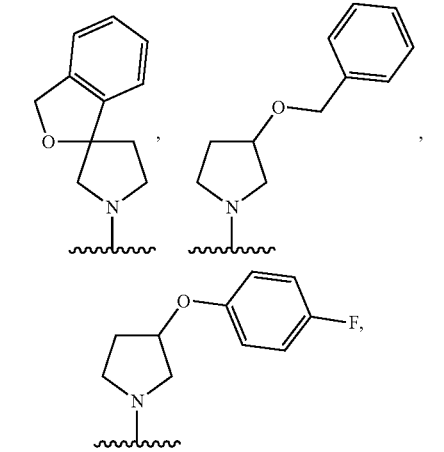

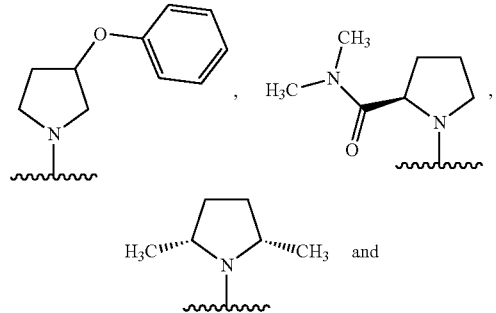

-continued

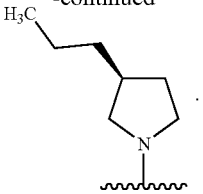

In embodiments, there is provided a compound of Formula (I), or a pharmaceutically acceptable salt thereof, wherein NR$^1$R$^2$ is a group selected from

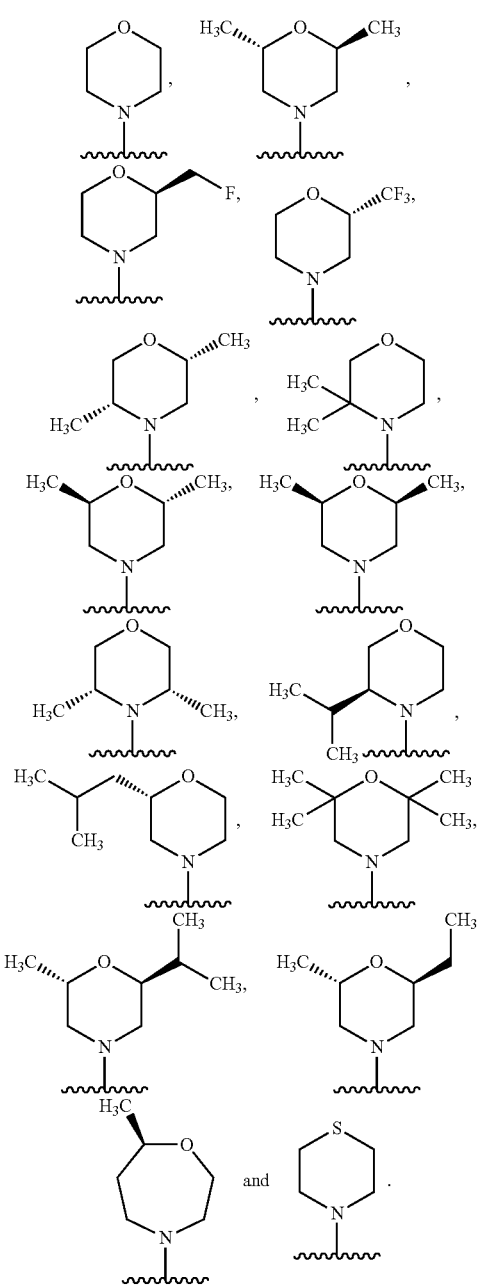

In embodiments, there is provided a compound of Formula (I), or a pharmaceutically acceptable salt thereof, wherein NR$^1$R$^2$ is a group selected from

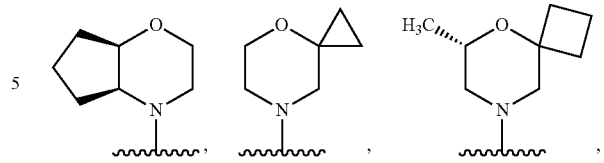

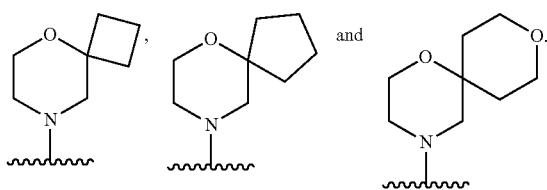

In embodiments, there is provided a compound of Formula (I), or a pharmaceutically acceptable salt thereof, wherein NR$^1$R$^2$ is a group selected from

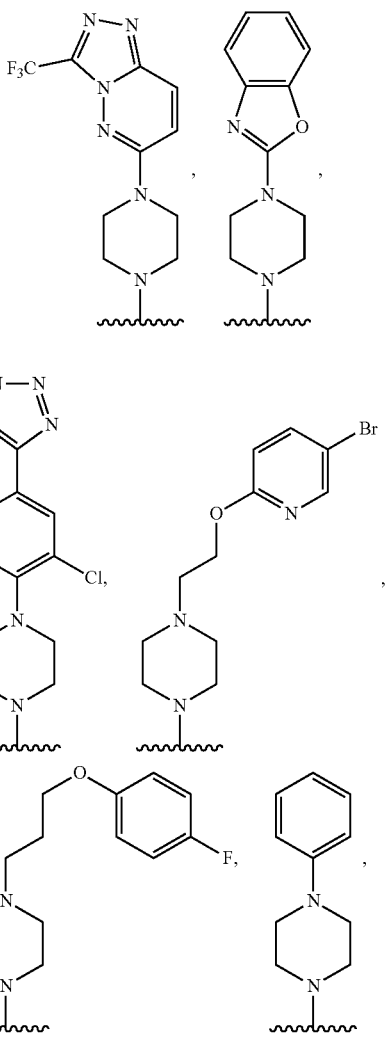

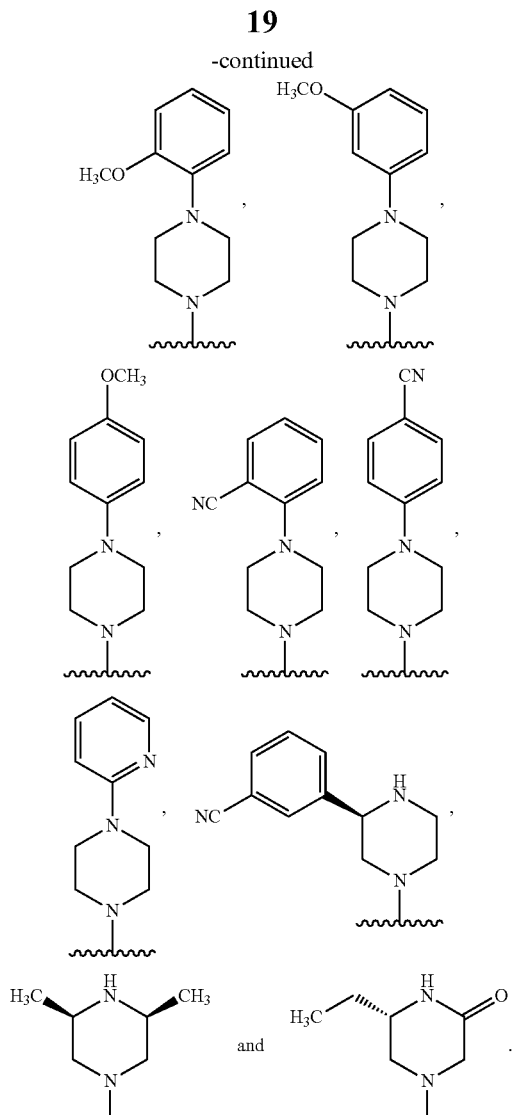

In embodiments, there is provided a compound of Formula (I), or a pharmaceutically acceptable salt thereof, wherein the ring system is selected from

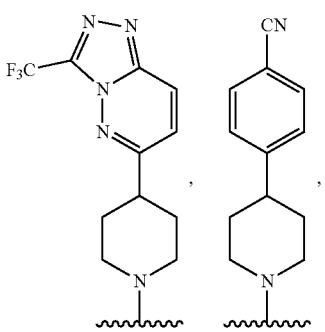

In embodiments, there is provided a compound of Formula (I), or a pharmaceutically acceptable salt thereof, wherein the ring system is selected from

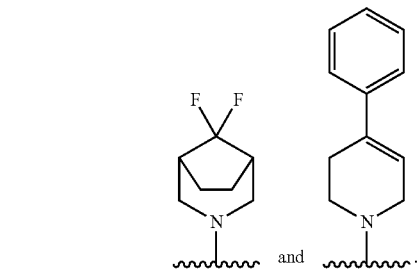 [SMILES: *N1CC2CCC(C1)C2(F)F ; *N1CC=C(c2ccccc2)CC1]

In embodiments, there is provided a compound of Formula (I), or a pharmaceutically acceptable salt thereof, wherein the ring system is selected from

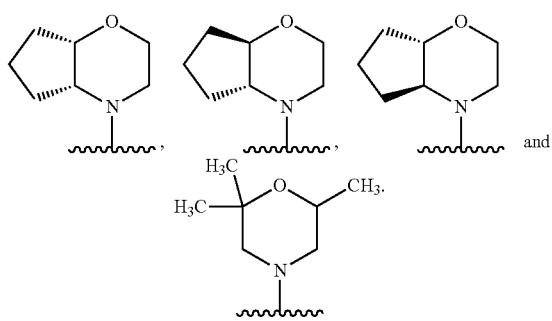

In embodiments, there is provided a compound of Formula (I), or a pharmaceutically acceptable salt thereof, wherein $R^1$ is selected from $R^8$ and $R^{4A}$, and $R^2$ is selected from $R^{8A}$ and H.

In embodiments, there is provided a compound of Formula (I), or a pharmaceutically acceptable salt thereof, wherein $R^1$ is $R^8$, and $R^2$ is selected from $R^{8A}$ and H.

In embodiments, there is provided a compound of Formula (I), or a pharmaceutically acceptable salt thereof, wherein $R^8$ is $C_{1-4}$ alkyl or $C_{3-6}$ cycloalkyl (such as $C_{1-4}$ alkyl), each of which are optionally substituted with one or more groups (such as one to three groups) independently selected from $R^{4B}$ (such as $R^{4x}$), $R^{5B}$ (such as $R^{5x}$), F, —OH, —CN, $C_{1-4}$ alkoxy, —C(=O)O($C_{1-4}$ alkyl) and —C(=O)N($R^{7C}$)$_2$. In further embodiments, $R^8$ is $C_{1-4}$ alkyl (such as $CH_3$) optionally substituted with one or two groups (such as one group) independently selected from $R^{4B}$ (such as $R^{4x}$), $R^{5B}$ (such as $R^{5x}$), F, —OH, —CN, $C_{1-4}$ alkoxy, —C(=O)O($C_{1-4}$ alkyl) and —C(=O)N($R^{7C}$)$_2$. In further embodiments, $R^8$ is $C_{1-4}$ alkyl (such as $CH_3$) optionally substituted with one or two groups (such as one group) independently selected from $R^{4B}$ (such as $R^{4x}$) and $R^{5B}$ (such as $R^{5x}$). In further embodiments, $R^8$ is $C_{1-4}$ alkyl (such as $CH_3$) optionally substituted with one or two groups (such as one group) independently selected from monocyclic or bicyclic 5 to 9 membered heteroaryl (such as a monocyclic 5- or 6-membered heteroaryl) and phenyl, wherein the heteroaryl and phenyl are optionally substituted with one or more groups (such as one or two groups) selected from $C_{1-4}$ alkyl (such as $CH_3$), $C_{3-6}$ cycloalkyl (such as cyclohexyl) and phenyl.

In embodiments, there is provided a compound of Formula (I), or a pharmaceutically acceptable salt thereof, wherein $R^8$ is $C_{1-4}$ alkyl or $C_{3-6}$ cycloalkyl (such as $C_{1-4}$ alkyl), each of which are substituted with one or more groups (such as one to three groups) independently selected from $R^{4B}$ (such as $R^{4x}$) $R^{5B}$ (such as $R^{5x}$), F, —OH, —CN, $C_{1-4}$ alkoxy, —C(=O)O($C_{1-4}$ alkyl) and —C(=O)N($R^{7C}$)$_2$. In further embodiments, $R^8$ is $C_{1-4}$ alkyl (such as $CH_3$) substituted with one or two groups (such as one group) independently selected from $R^{4B}$ (such as $R^{4x}$), $R^{5B}$ (such as $R^{5x}$), F, —OH, —CN, $C_{1-4}$ alkoxy, —C(=O)O($C_{1-4}$ alkyl) and —C(=O)N($R^{7C}$)$_2$. In further embodiments, $R^8$ is $C_{1-4}$ alkyl (such as $CH_3$) substituted with one or two groups (such as one group) independently selected from $R^{4B}$ (such as $R^{4x}$) and $R^{5B}$ (such as $R^{5x}$). In further embodiments, $R^8$ is $C_{1-4}$ alkyl (such as $CH_3$) substituted with a either a phenyl or a monocyclic or bicyclic 5 to 9 membered heteroaryl, wherein the phenyl or monocyclic or bicyclic 5 to 9 membered heteroaryl is optionally substituted with one or two groups independently selected from $C_{1-4}$ alkyl, $C_{3-6}$ cycloalkyl and $C_{1-4}$ alkoxy.

In embodiments, there is provided a compound of Formula (I), or a pharmaceutically acceptable salt thereof, wherein $R^{4A}$ is 5 membered monocyclic heteroaryl optionally substituted with one or more groups (such as one to three groups) independently selected from $R^{4X}$, —O($R^{4X}$), $R^{5X}$, —O($R^{5X}$), —OH, —CN, $C_{1-4}$ alkoxy, —C(=O)OH, —C(=O)O($C_{1-4}$ alkyl), —C(=O)N($R^{7B}$)$_2$, $R^3$ and halo. In further embodiments, $R^{4A}$ is 5 membered monocyclic heteroaryl optionally substituted with one or two groups independently selected from $R^{4X}$, $R^{5X}$ and $R^{3X}$. In further embodiments, $R^{4A}$ is 5 membered monocyclic heteroaryl optionally substituted with one or two groups selected from $C_{1-4}$ alkyl, $C_{3-6}$ cycloalkyl and phenyl. In further embodiments, $R^{4A}$ is 1H-pyrazolyl (such as 3-1H-pyrazolyl) tetrazolyl (such as 5-tetrazolyl), pyridyl (such as 2-pyridyl, 3-pyridyl or 4-pyridyl) or 1H-benzo[d]imidazolyl (such as 2-1H-benzo[d]imidazole), each of which is optionally substituted with one or more groups (such as one or two groups) selected from $C_{1-4}$ alkyl (such as $CH_3$), $C_{3-6}$ cycloalkyl (such as cyclohexyl) and phenyl.

In embodiments, there is provided a compound of Formula (I), or a pharmaceutically acceptable salt thereof, wherein $R^{4A}$ is

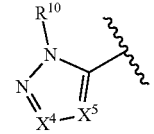

wherein $R^{10}$ is $R^3$ or $R^{5x}$, and $X^4$ and $X^5$ are independently N or CH. In further embodiments, $X^4$ is CH. In further embodiments, $X^5$ in CH.

In embodiments, there is provided a compound of Formula (I), or a pharmaceutically acceptable salt thereof, wherein each $R^{4B}$ is independently monocyclic or bicyclic 5 to 9 membered heteroaryl, optionally substituted with one or more (such as one to three) groups independently selected from $R^{4X}$, —O($R^{4X}$), $R^{5X}$, —O($R^{5X}$), —OH, —CN, $C_{1-4}$ alkoxy, —C(=O)OH, —C(=O)O($C_{1-4}$ alkyl), —C(=O)N($R^{7B}$)$_2$, $R^3$ and halo. In further embodiments, each $R^{4B}$ is independently monocyclic or bicyclic 5 to 9 membered heteroaryl (such as a monocyclic 5- or 6-membered heteroaryl) optionally substituted with one or more (such as one to three) groups independently selected from halo, $C_{1-4}$ alkyl, $C_{3-6}$ cycloalkyl, $C_{1-4}$ alkoxy and CN. In further embodiments, $R^{4B}$ is 1H-pyrazolyl (such as 3-1H-pyrazolyl), tetrazolyl (such as 5-tetrazolyl), pyridyl (such as 2-pyridyl, 3-pyridyl or 4-pyridyl) or 1H-benzo[d]imidazolyl (such as 2-1H-benzo[d]imidazole), each of which is optionally substituted with one or two groups selected from $C_{1-4}$ alkyl, $C_{3-6}$ cycloalkyl and phenyl.

In embodiments, there is provided a compound of Formula (I), or a pharmaceutically acceptable salt thereof, wherein $R^{8A}$ is $C_{1-4}$ alkyl. In further embodiments, $R^{8A}$ is $CH_3$, $CH(CH_3)_2$ or $C(CH_3)_3$.

In embodiments, there is provided a compound of Formula (I), or a pharmaceutically acceptable salt thereof, wherein $R^1$ is $R^{5A}$ and $R^2$ is $R^{8B}$.

In embodiments, there is provided a compound of Formula (I), or a pharmaceutically acceptable salt thereof, wherein $R^{5A}$ is phenyl, optionally substituted with one or more groups (such as one to three groups) independently selected from —OH, —CN, $C_{1-4}$ alkoxy, —C(=O)OH, —C(=O)N($R^{7B}$)$_2$, $R^{3x}$ and halo. In further embodiments, $R^{5A}$ is phenyl, optionally substituted with one or two groups independently selected from —OH, —CN, $C_{1-4}$ alkoxy, —C(=O)OH, —C(=O)N($R^{7B}$)$_2$, $R^{3x}$ and halo. In further embodiments, $R^{5A}$ is phenyl, optionally substituted with one or two groups independently selected from —CN, $C_{1-4}$ alkoxy, $R^{3x}$ and halo. In further embodiments, $R^{5A}$ is phenyl, optionally substituted with —CN.

In embodiments, there is provided a compound of Formula (I), or a pharmaceutically acceptable salt thereof, wherein $R^{5B}$ is phenyl, optionally substituted with one or more groups (such as one to three groups) independently selected from —OH, —CN, $C_{1-4}$ alkoxy, —C(=O)OH, —C(=O)N($R^{7B}$)$_2$, $R^{3x}$ and halo. In further embodiments, $R^{5B}$ is phenyl, optionally substituted with one or two groups independently selected from —CN, $C_{1-4}$ alkoxy, $R^{3x}$ and halo. In further embodiments, $R^{5B}$ is phenyl, optionally substituted with $C_{1-4}$ alkoxy.

In embodiments, there is provided a compound of Formula (I), or a pharmaceutically acceptable salt thereof, wherein $R^{8B}$ is $C_{1-4}$ alkyl. In further embodiments, $R^{8B}$ is $CH_3$, $CH(CH_3)_2$ or $C(CH_3)_3$.

In embodiments, there is provided a compound of Formula (I), or a pharmaceutically acceptable salt thereof, wherein $NR^1R^2$ is selected from

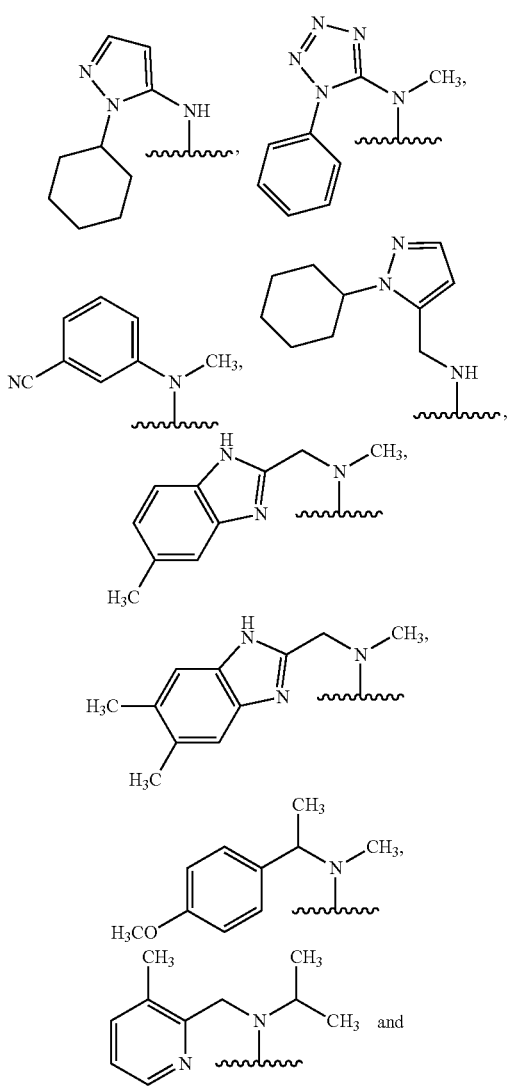

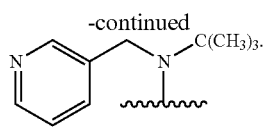

In embodiments, there is provided a compound of Formula (I), (II), (IIA), (IIB), (IIC), (IID) or (IIE), or a pharmaceutically acceptable salt thereof, wherein each $R^A$ is independently selected from H, halo, $R^X$, —$OR^x$, and —CN, wherein each $R^X$ is independently $C_{1-3}$ alkyl optionally substituted with one to three F. In further embodiments, each $R^A$ is independently selected from H, halo, $C_{1-3}$ alkyl, $C_{1-3}$ alkoxy, $CF_3$, $OCF_3$, $CHF_2$, $OCHF_2$ and —CN. In further embodiments, each $R^A$ is independently selected from H, F and Cl. In further embodiments, each $R^A$ is independently selected from H and F.

In embodiments, there is provided a compound of Formula (I), (II), (IIA), (IIB), (IIC), (IID) or (IIE), or a pharmaceutically acceptable salt thereof, wherein A is selected from

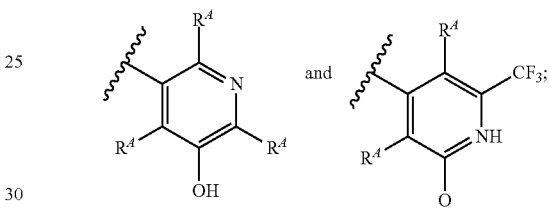

wherein $R^A$ is as defined above.

In embodiments, there is provided a compound of Formula (I), (II), (IIA), (IIB), (IIC), (IID) or (IIE), or a pharmaceutically acceptable salt thereof, wherein A is

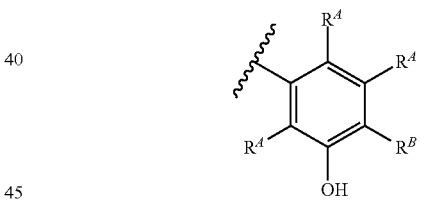

wherein $R^A$ and $R^B$ are as defined above. In further embodiments, $R^B$ is F, Cl or $CF_3$. In further embodiments, one or more $R^A$ is F. In further embodiments, two or more $R^A$ is F. In further embodiments, each $R^A$ is F.

In embodiments, there is provided a compound of Formula (I), (II), (IIA), (IIB), (IIC), (IID) or (IIE), or a pharmaceutically acceptable salt thereof, wherein A is

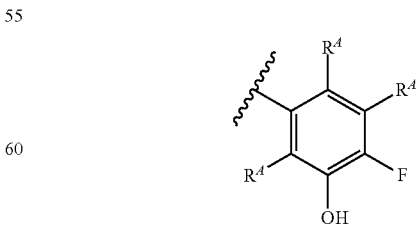

wherein $R^A$ is as defined above. In further embodiments, each $R^A$ is independently H, F or Cl. In further embodiments, each $R^A$ is H or F.

In embodiments, there is provided a compound of Formula (I), (II), (IIA), (IIB), (IIC), (IID) or (IIE), or a pharmaceutically acceptable salt thereof, wherein A is

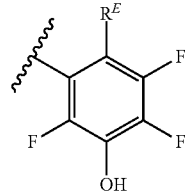

wherein $R^E$ is H or halo.

In embodiments, there is provided a compound of Formula (I) which is a compound of Formula (III):

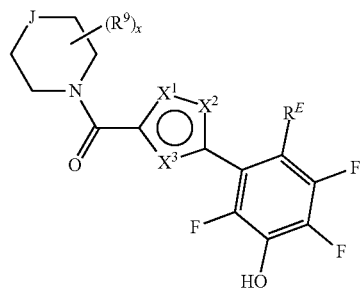

(III)

wherein
J is selected from O, S, CH$_2$, NH and a covalent bond,
x is selected from 0 to 3;
each $R^9$ is independently selected from $R^3$, $R^4$ and $R^5$; and
$R^E$ is H or halo,
or a pharmaceutically acceptable salt thereof.

In embodiments, the compound of Formula (III) is a compound of Formula (IIIA), (IIIB) or (IIIC)

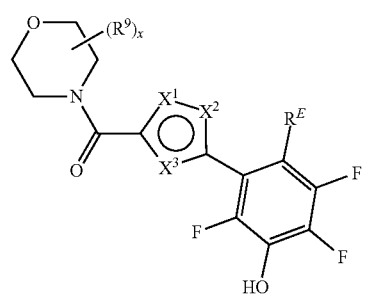

(IIIA)

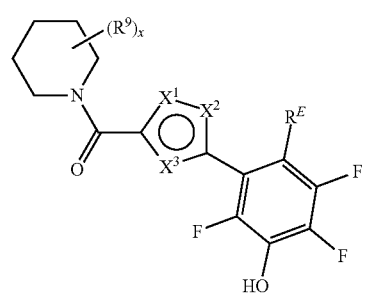

(IIIB)

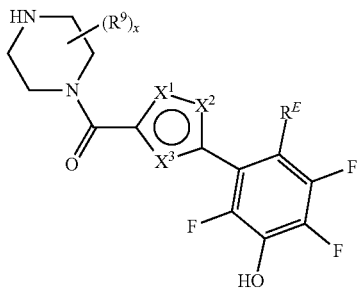

(IIIC)

or a pharmaceutically acceptable salt thereof, wherein $X^1$, $X^2$, $X^3$, $R^E$, $R^9$ and x are as are as defined for a compound of Formula (III). In further embodiments, each $R^9$ is independently selected from C$_{1-4}$ alkyl. In further embodiments, x is selected from 1, 2 and 3.

In embodiments, the compound of Formula (III) is a compound of Formula (IIID)

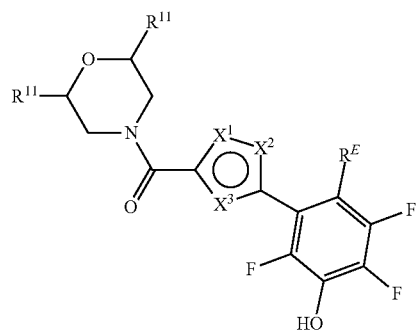

(IIID)

or a pharmaceutically acceptable salt thereof, wherein $X^1$, $X^2$, $X^3$ and $R^E$ are as are as defined for a compound of Formula (III), and each $R^{11}$ is independently selected from H, $R^3$, $R^4$ and $R^5$. In further embodiments, each $R^{11}$ is independently H, $R^3$, $R^{4x}$ or $R^{5x}$. In further embodiments, each $R^{11}$ is independently H, $R^{3x}$, $R^{4x}$ or $R^{5x}$. In further embodiments, each $R^{11}$ is independently H or $R^{3x}$. In further embodiments, each $R^{11}$ is independently H or C$_{1-4}$ alkyl. In further embodiments, each $R^{11}$ is independently H or CH$_3$.

In embodiments, there is provided a compound of Formula (III), (IIIA), (IIIB), (IIIC) or (IIID), or a pharmaceutically acceptable salt thereof, wherein $R^E$ is H, F or Cl. In further embodiments, $R^E$ is H or F.

In embodiments, there is provided a compound of Formula (I), (II), (IIA), (IIB), (IIC), (IID), (IIE), (III), (IIIA), (IIIB), (IIIC) or (IIID), or a pharmaceutically acceptable salt thereof, wherein one of $X^1$, $X^2$ and $X^3$ is O and the other two of $X^1$, $X^2$ and $X^3$ are selected from N and CR$^Y$. In further embodiments, $R^Y$ is H.

In embodiments, there is provided a compound of Formula (I), (II), (IIA), (IIB), (IIC), (IID), (IIE), (III), (IIIA), (IIIB), (IIIC) or (IIID), or a pharmaceutically acceptable salt thereof, wherein one of $X^1$, $X^2$ and $X^3$ is S and the other two of $X^1$, $X^2$ and $X^3$ are selected from N and CR$^Y$. In further embodiments, $R^Y$ is H.

In embodiments, there is provided a compound of Formula (I), (II), (IIA), (IIB), (IIC), (IID), (IIE), (III), (IIIA), (IIIB), (IIIC) or (IIID), or a pharmaceutically acceptable salt thereof, wherein one of $X^1$, $X^2$ and $X^3$ is O and the other two of $X^1$, $X^2$ and $X^3$ are both N.

In embodiments, there is provided a compound of Formula (I), (II), (IIA), (IIB), (IIC), (IID), (IIE), (III), (IIIA), (IIIB), (IIIC) or (IIID), or a pharmaceutically acceptable salt thereof, wherein one of $X^1$, $X^2$ and $X^3$ is O, one of $X^1$, $X^2$ and $X^3$ is N, and one of $X^1$, $X^2$ and $X^3$ is $CR^Y$. In further embodiments, $R^Y$ is H or —CN.

In embodiments, there is provided a compound of Formula (I), (II), (IIA), (IIB), (IIC), (IID), (IIE), (III), (IIIA), (IIIB), (IIIC) or (IIID), or a pharmaceutically acceptable salt thereof, wherein one of $X^1$, $X^2$ and $X^3$ is S and the other two of $X^1$, $X^2$ and $X^3$ are both N.

In embodiments, there is provided a compound of Formula (I), (II), (IIA), (IIB), (IIC), (IID), (IIE), (III), (IIIA), (IIIB), (IIIC) or (IIID), or a pharmaceutically acceptable salt thereof, wherein one of $X^1$, $X^2$ and $X^3$ is S, one of $X^1$, $X^2$ and $X^3$ is N, and one of $X^1$, $X^2$ and $X^3$ is $CR^Y$. In further embodiments, $R^Y$ is H.

In embodiments, there is provided a compound of Formula (I), (II), (IIA), (IIB), (IIC), (IID), (IIE), (III), (IIIA), (IIIB), (IIIC) or (IIID), or a pharmaceutically acceptable salt thereof, wherein one of $X^1$, $X^2$ and $X^3$ is S and the other two of $X^1$, $X^2$ and $X^3$ are both $CR^Y$. In further embodiments, each $R^Y$ is H.

In embodiments, there is provided a compound of Formula (I), (II), (IIA), (IIB), (IIC), (IID), (IIE), (III), (IIIA), (IIIB), (IIIC) or (IIID), or a pharmaceutically acceptable salt thereof, wherein
(i) $X^1$ is N, $X^2$ is O and $X^3$ is N,
(ii) $X^1$ is N, $X^2$ is N and $X^3$ is O;
(iii) $X^1$ is $CR^Y$, $X^2$ is $CR^Y$ and $X^3$ is S;
(iv) $X^1$ is O, $X^2$ is N and $X^3$ is $CR^Y$;
(v) $X^1$ is N, $X^2$ is O and $X^3$ is $CR^Y$;
(vi) $X^1$ is $CR^Y$, $X^2$ is N and $X^3$ is O;
(vii) $X^1$ is O, $X^2$ is N and $X^3$ is N;
(viii) $X^1$ is N, $X^2$ is N and $X^3$ is S; or
(ix) $X^1$ is $CR^Y$, $X^2$ is S and $X^3$ is $CR^Y$.

In embodiments, there is provided a compound of Formula (I), (II), (IIA), (IIB), (IIC), (IID), (IIE), (III), (IIIA), (IIIB), (IIIC) or (IIID), or a pharmaceutically acceptable salt thereof, wherein
(i) $X^1$ is N, $X^2$ is O and $X^3$ is N,
(ii) $X^1$ is N, $X^2$ is N and $X^3$ is O;
(iii) $X^1$ is $CR^Y$, $X^2$ is $CR^Y$ and $X^3$ is S;
(iv) $X^1$ is O, $X^2$ is N and $X^3$ is $CR^Y$;
(v) $X^1$ is N, $X^2$ is O and $X^3$ is CR;
(vi) $X^1$ is $CR^Y$, $X^2$ is N and $X^3$ is O;
(vii) $X^1$ is O, $X^2$ is N and $X^3$ is N;
(viii) $X^1$ is N, $X^2$ is N and $X^3$ is S;
(ix) $X^1$ is $CR^Y$, $X^2$ is S and $X^3$ is $CR^Y$ or
(x) $X^1$ is $CR^Y$, $X^2$ is N and $X^3$ is S.

In embodiments, there is provided a compound of Formula (I), (II), (IIA), (IIB), (IIC), (IID), (IIE), (III), (IIIA), (IIIB), (IIIC) or (IIID), or a pharmaceutically acceptable salt thereof, wherein
(i) $X^1$ is N, $X^2$ is O and $X^3$ is N,
(ii) $X^1$ is N, $X^2$ is N and $X^3$ is O;
(iii) $X^1$ is CH, $X^2$ is CH and $X^3$ is S;
(iv) $X^1$ is O, $X^2$ is N and $X^3$ is CH;
(v) $X^1$ is N, $X^2$ is O and $X^3$ is CH;
(vi) $X^1$ is CH, $X^2$ is N and $X^3$ is O;
(vii) $X^1$ is O, $X^2$ is N and $X^3$ is N;
(viii) $X^1$ is N, $X^2$ is N and $X^3$ is S; or
(ix) $X^1$ is CH, $X^2$ is S and $X^3$ is CH.

In embodiments, there is provided a compound of Formula (I), (II), (IIA), (IIB), (IIC), (IID), (IIE), (III), (IIIA), (IIIB), (IIIC) or (IIID), or a pharmaceutically acceptable salt thereof, wherein
(i) $X^1$ is N, $X^2$ is O and $X^3$ is N,
(ii) $X^1$ is N, $X^2$ is N and $X^3$ is O;
(iii) $X^1$ is CH, $X^2$ is CH and $X^3$ is S;
(iv) $X^1$ is O, $X^2$ is N and $X^3$ is CH;
(v) $X^1$ is N, $X^2$ is O and $X^3$ is CH;
(vi) $X^1$ is CH, $X^2$ is N and $X^3$ is O;
(vii) $X^1$ is O, $X^2$ is N and $X^3$ is N;
(viii) $X^1$ is N, $X^2$ is N and $X^3$ is S;
(ix) $X^1$ is CH, $X^2$ is S and $X^3$ is CH; or
(x) $X^1$ is CH, $X^2$ is N and $X^3$ is S.

In embodiments, there is provided a compound of Formula (I), (II), (IIA), (IIB), (IIC), (IID), (IIE), (III), (IIIA), (IIIB), (IIIC) or (IIID), or a pharmaceutically acceptable salt thereof, wherein $X^1$ is N, $X^2$ is O and $X^3$ is N.

In embodiments, there is provided a compound of Formula (I), (II), (IIA), (IIB), (IIC), (IID), (IIE), (III), (IIIA), (IIIB), (IIIC) or (IIID), or a pharmaceutically acceptable salt thereof, wherein $X^1$ is N, $X^2$ is N and $X^3$ is O.

In embodiments, there is provided a compound of Formula (I), (II), (IIA), (IIB), (IIC), (IID), (IIE), (III), (IIIA), (IIIB), (IIIC) or (IIID), or a pharmaceutically acceptable salt thereof, wherein $X^1$ is N, $X^2$ is N and $X^3$ is S.

In embodiments, there is provided a compound of Formula (I), (II), (IIA), (IIB), (IIC), (IID), (IIE), (III), (IIIA), (IIIB), (IIIC) or (IIID), or a pharmaceutically acceptable salt thereof, wherein $X^1$ is N, $X^2$ is O and $X^3$ is $CR^Y$. In further embodiments, $R^1$ is H or —CN.

In embodiments, there is provided a compound of Formula (I), (II), (IIA), (IIB), (IIC), (IID), (IIE), (III), (IIIA), (IIIB), (IIIC) or (IIID), or a pharmaceutically acceptable salt thereof, wherein $X^1$ is $CR^Y$, $X^2$ is N and $X^3$ is O. In further embodiments, each $R^1$ is H.

In embodiments, there is provided a compound of Formula (I), (II), (IIA), (IIB), (IIC), (IID), (IIE), (III), (IIIA), (IIIB), (IIIC) or (IIID), or a pharmaceutically acceptable salt thereof, wherein $X^1$ is $CR^Y$, $X^2$ is S and $X^3$ is $CR^Y$. In further embodiments, each $R^1$ is H.

In embodiments, there is provided a compound of Formula (I) which is a compound of Formula (IV):

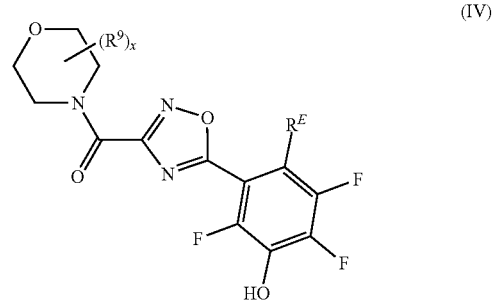

x is selected from 0 to 3;
each $R^9$ is independently selected from $R^3$, $R^4$ and $R^5$; and
$R^E$ is H or halo,
or a pharmaceutically acceptable salt thereof.

In embodiments, there is provided a compound of Formula (I) which is a compound of Formula (V):

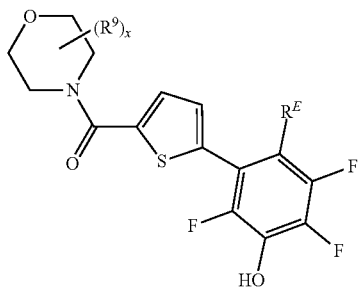

(V)

x is selected from 0 to 3;
each $R^9$ is independently selected from $R^3$, $R^4$ and $R^5$; and
$R^E$ is H or halo,
or a pharmaceutically acceptable salt thereof.

In embodiments, there is provided a compound of Formula (I) which is a compound of Formula (VI):

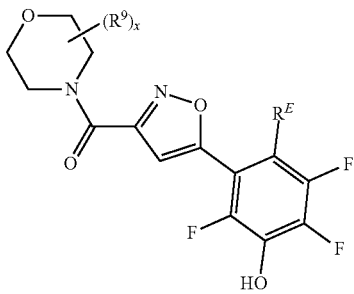

(VI)

x is selected from 0 to 3;
each $R^9$ is independently selected from $R^3$, $R^4$ and $R^5$; and
$R^E$ is H or halo,
or a pharmaceutically acceptable salt thereof.

In embodiments, there is provided a compound of Formula (I) which is a compound of Formula (VII):

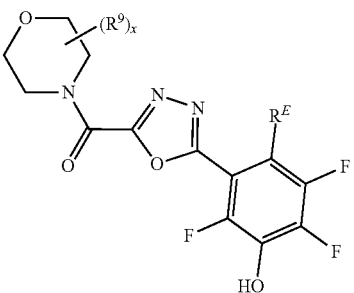

(VII)

x is selected from 0 to 3;
each $R^9$ is independently selected from $R^3$, $R^4$ and $R^5$; and
$R^E$ is H or halo,
or a pharmaceutically acceptable salt thereof.

In embodiments, there is provided a compound of Formula (II), (IIA), (IIB), (IIC), (IID), (IIE), (III), (IIIA), (IIIB), (IIIC), (IIID), (IV), (V), (VI) or (VII), wherein each $R^9$ is independently selected from $C_{1-4}$ alkyl, $C_{3-6}$ cycloalkyl and phenyl. In further embodiments, each $R^9$ is independently $C_{1-4}$ alkyl. In further embodiments, each $R^9$ is $CH_3$.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, wherein each $R^3$ is independently $C_{1-4}$ alkyl or $C_{3-6}$ cycloalkyl, each of which are optionally substituted with one or more (such as one to three) groups independently selected from $R^{4X}$, $R^{5x}$, —O($R^{4X}$), —O($R^{5X}$) and F. In further embodiments, each $R^3$ is independently $C_{1-4}$ alkyl optionally substituted with one to three (such as one or two) groups independently selected from $R^{4X}$, $R^{5x}$ and F. In embodiments, In further embodiments, each $R^3$ is independently $C_{1-4}$ alkyl, $CF_3$, $CHF_2$ or $CH_2F$.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, wherein each $R^3$ is $R^{3X}$.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, wherein each $R^{3X}$ is independently $C_{1-4}$ alkyl or $C_{3-6}$ cycloalkyl, each of which are optionally substituted with one or more (such as one to three) F. In further embodiments, each $R^{3X}$ is independently $C_{1-4}$ alkyl optionally substituted with one to three F. In further embodiments, each $R^{3X}$ is independently $C_{1-4}$ alkyl, $CF_3$, $CHF_2$ or $CH_2F$. In further embodiments, each $R^{3X}$ is $C_{1-4}$ alkyl.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, wherein each $R^4$ is independently monocyclic or bicyclic 5 to 9 membered heteroaryl (such as a monocyclic 5- or 6-membered heteroaryl), each of which are optionally substituted with one or more (such as one to three) groups independently selected from $R^{4X}$, —O($R^{4X}$), $R^{5X}$, —O($R^{5X}$), —OH, —CN, $C_{1-4}$ alkoxy, —C(=O)OH, —C(=O)O($C_{1-4}$ alkyl), —C(=O)N($R^{7B}$)$_2$, $R^3$ and halo. In further embodiments, each $R^4$ is independently monocyclic or bicyclic 5 to 9 membered (such as a monocyclic 5 or 6 membered heteroaryl) optionally substituted with one or more (such as one to three) groups independently selected from halo (such as F or Cl), $C_{1-4}$ alkyl, $C_{3-6}$ cycloalkyl, $C_{1-4}$alkoxy and CN. In further embodiments, each $R^4$ is independently selected from [1,2,4]triazolo[4,3-b]pyridazinyl (such as 6-[1,2,4]triazolo[4,3-b]pyridazinyl), pyridyl (such as 2-pyridyl, 3-pyridyl or 4-pyridyl), benzo[d]oxazolyl (such as 2-benzo[d]oxazolyl), each of which is optionally substituted with one or more (such as one to three) groups independently selected from halo (such as F or Cl), $C_{1-4}$ alkyl, $C_{3-6}$ cycloalkyl, $C_{1-4}$ alkoxy and CN.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, wherein each $R^{4X}$ is independently monocyclic or bicyclic 5 to 9 membered heteroaryl (such as a monocyclic 5 or 6 membered heteroaryl), each of which are optionally substituted with one or more (such as one to three) groups independently selected from —OH, —CN, $C_{1-4}$ alkoxy, —C(=O)OH, —C(=O)N($R^{7B}$)$_2$, $R^{3X}$ and halo. In further embodiments, each $R^{4x}$ is independently monocyclic or bicyclic 5 to 9 membered heteroaryl (such as a monocyclic 5- or 6-membered heteroaryl) optionally substituted with one or more (such as one to three) groups independently selected from halo (such as F or Cl), $C_{1-4}$ alkyl, $C_{3-6}$ cycloalkyl, $C_{1-4}$alkoxy and CN. In further embodiments, each $R^{4x}$ is independently a tetrazolyl (such as 5-tetrazolyl) optionally substituted with $C_{1-4}$ alkyl (such as $CH_3$).

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, wherein each $R^5$ is independently phenyl, optionally substituted with one or more (such as one to three) groups independently selected from $R^{4X}$, —O($R^{4X}$), $R^{5X}$, —O($R^{5X}$), —OH, —CN, $C_{1-4}$ alkoxy, —C(=O)OH, —C(=O)O($C_{1-4}$ alkyl), —C(=O)N($R^{7B}$)$_2$, $R^3$ and halo. In further embodiments, each $R^5$ is independently phenyl optionally substituted with one or more (such as one to three) groups independently selected from halo (such as F or Cl), $C_{1-4}$ alkyl, $C_{3-6}$ cycloalkyl, $C_{1-4}$alkoxy and CN. In further embodiments, each $R^5$ is phenyl.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, wherein each $R^{5X}$ is independently phenyl, optionally substituted with one or more (such as one to three) groups independently selected from —OH, —CN, $C_{1-4}$ alkoxy, —C(=O)OH, —C(=O)N($R^{7B}$)$_2$, $R^{3x}$ and halo. In further embodiments, each $R^{5X}$ is independently phenyl optionally substituted with one or more (such as one to three) groups independently selected from halo (such as F or Cl), $C_{1-4}$ alkyl, $C_{3-6}$ cycloalkyl, $C_{1-4}$alkoxy and CN. In further embodiments, each $R^{5X}$ is phenyl.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, wherein $R^6$ is $C_{1-4}$ alkoxy optionally substituted with one or more groups (such as one to three groups) independently selected from $R^{4X}$, $R^{5x}$ and F. In further embodiments, $R^6$ is $C_{1-4}$ alkoxy optionally substituted with one or more (such as one to three) F. In further embodiments, $R^6$ is $C_{1-4}$ alkoxy.

In embodiments, there is provided a compound of Formula (II), (IIA), (IIB), (IIC), (IID), (IIE), (III), (IIIA), (IIIB), (IIIC), (IV), (V), (VI) or (VII), wherein x is 0, 1, 2 or 3. In further embodiments, x is 1, 2 or 3.

In embodiments, there is provided a compound of Formula (I), (II), (IIA), (IIB), (IIC), (IID), (IIE), or a pharmaceutically acceptable salt thereof, with the proviso that when A is

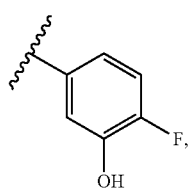 [SMILES: *c1ccc(F)c(O)c1]

and $X^3$ is N, that $X^1$ is N.

In embodiments, there is provided a compound of Formula (I), (II) or (IIA), or a pharmaceutically acceptable salt thereof, with the proviso that when A is

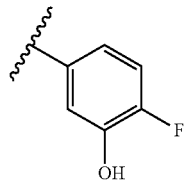 [SMILES: *c1ccc(F)c(O)c1]

and $X^3$ is N, that $X^2$ is O.

In embodiments, there is provided a compound of Formula (I), (II) or (IIA), or a pharmaceutically acceptable salt thereof, with the proviso that the compound is other than (3-(4-fluoro-3-hydroxyphenyl)-1,2,4-oxadiazol-5-yl)(3-methylpiperidin-1-yl)methanone and (3-(4-fluoro-3-hydroxyphenyl)-1,2,4-oxadiazol-5-yl)(4-methylpiperidin-1-yl)methanone.

In embodiments, there is provided a compound of Formula (I), or a pharmaceutically acceptable salt thereof, wherein the compound is selected from:
(R)-(5-(4-Fluoro-3-hydroxyphenyl)-1,3,4-oxadiazol-2-yl)(3-phenylpyrrolidin-1-yl)methanone;
(3-Phenoxyazetidin-1-yl)(5-(2,4,5-trifluoro-3-hydroxyphenyl)-1,2,4-oxadiazol-3-yl)methanone;
((2R,6S)-2,6-Dimethylmorpholino)(5-(2,4,5-trifluoro-3-hydroxyphenyl)thiophen-2-yl)methanone;
(3-(2-Methoxyphenyl)pyrrolidin-1-yl)(5-(2,4,5-trifluoro-3-hydroxyphenyl)-1,2,4-oxadiazol-3-yl)methanone;
N-(1-Cyclohexyl-1H-pyrazol-5-yl)-3-(4-fluoro-3-hydroxyphenyl)-N-methylisoxazole-5-carboxamide;
(3-(4-Fluoro-3-hydroxyphenyl)isoxazol-5-yl)(3-phenylpyrrolidin-1-yl)methanone
N-(1-Cyclohexyl-1H-pyrazol-5-yl)-5-(4-fluoro-3-hydroxyphenyl)-N-methylisoxazole-3-carboxamide;
(R)-(3-(4-Chlorophenyl)pyrrolidin-1-yl)(5-(2,4,5-trifluoro-3-hydroxyphenyl)isoxazol-3-yl)methanone;
4-(3-(3-Phenylpyrrolidine-1-carbonyl)-1,2,4-oxadiazol-5-yl)-6-(trifluoromethyl)pyridin-2(1H)-one;
4-(3-(4-(3-Methoxyphenyl)piperazine-1-carbonyl)-1,2,4-oxadiazol-5-yl)-6-(trifluoromethyl)pyridin-2(1H)-one;
(R)-(5-(4-Fluoro-3-hydroxyphenyl)-1,2,4-oxadiazol-3-yl)(3-phenylpyrrolidin-1-yl)methanone;
N-(1-Cyclohexyl-1H-pyrazol-5-yl)-2-(4-fluoro-3-hydroxyphenyl)oxazole-5-carboxamide;
5-(4-Fluoro-3-hydroxyphenyl)-3-(3-phenylpyrrolidine-1-carbonyl)isoxazole-4-carbonitrile;
3-(4-(3-(4-Fluorophenoxy)propyl)piperazine-1-carbonyl)-5-(2,4,5-trifluoro-3-hydroxyphenyl)isoxazole-4-carbonitrile;
3-(4-(Pyridin-2-yl)piperazine-1-carbonyl)-5-(2,4,5-trifluoro-3-hydroxyphenyl)isoxazole-4-carbonitrile;
3-(4-(3-Methoxyphenyl)piperazine-1-carbonyl)-5-(2,4,5-trifluoro-3-hydroxyphenyl)isoxazole-4-carbonitrile;
5-(2,4,5-Trifluoro-3-hydroxyphenyl)-3-(4-(3-(trifluoromethyl)-[1,2,4]triazolo[4,3-b]pyridazin-6-yl)piperazine-1-carbonyl)isoxazole-4-carbonitrile;
3-(5-Fluoroisoindoline-2-carbonyl)-5-(2,4,5-trifluoro-3-hydroxyphenyl)isoxazole-4-carbonitrile; N-(tert-Butyl)-4-cyano-N-(pyridin-2-ylmethyl)-5-(2,4,5-trifluoro-3-hydroxyphenyl)isoxazole-3-carboxamide;
3-(3-Cyclopropyl-1-methyl-4,5,6,7-tetrahydro-1H-pyrazolo[4,3-c]pyridine-5-carbonyl)-5-(2,4,5-trifluoro-3-hydroxyphenyl)isoxazole-4-carbonitrile;
(S)-3-(3-(4-Chlorophenyl)pyrrolidine-1-carbonyl)-5-(2,4,5-trifluoro-3-hydroxyphenyl)isoxazole-4-carbonitrile;

3-((2R,6S)-2,6-Dimethylmorpholine-4-carbonyl)-5-(2,4,5-trifluoro-3-hydroxyphenyl)isoxazole-4-carbonitrile;

3-(4-(Benzo[d]oxazol-2-yl)piperazine-1-carbonyl)-5-(2,4,5-trifluoro-3-hydroxyphenyl)isoxazole-4-carbonitrile;

3-(4-(4-(4-Fluorophenyl)-2-oxo-2,3-dihydro-1H-imidazol-1-yl)piperidine-1-carbonyl)-5-(2,4,5-trifluoro-3-hydroxyphenyl)isoxazole-4-carbonitrile;

3-(4-((5-Methoxypyridin-2-yl)oxy)piperidine-1-carbonyl)-5-(2,4,5-trifluoro-3-hydroxyphenyl)isoxazole-4-carbonitrile;

3-(4-Hydroxy-4-(trifluoromethyl)piperidine-1-carbonyl)-5-(2,4,5-trifluoro-3-hydroxyphenyl)isoxazole-4-carbonitrile;

3-(3-Cyclopropyl-3-fluoroazetidine-1-carbonyl)-5-(2,4,5-trifluoro-3-hydroxyphenyl)isoxazole-4-carbonitrile;

5-(2,4,5-Trifluoro-3-hydroxyphenyl)-3-(3-(trifluoromethyl)azetidine-1-carbonyl)isoxazole-4-carbonitrile;

3-(7-Cyano-1,2,3,4-tetrahydroisoquinoline-2-carbonyl)-5-(2,4,5-trifluoro-3-hydroxyphenyl)isoxazole-4-carbonitrile;

2-(5-(2-Bromo-3,4,6-trifluoro-5-hydroxyphenyl)-1,2,4-oxadiazole-3-carbonyl)-1,2,3,4-tetrahydroisoquinoline-5-carbonitrile;

2-(5-(2,4,5-Trifluoro-3-hydroxyphenyl)-1,2,4-oxadiazole-3-carbonyl)-1,2,3,4-tetrahydroisoquinoline-6-carbonitrile;

(2,2,6,6-Tetramethylmorpholino)(5-(2,4,5-trifluoro-3-hydroxyphenyl)-1,2,4-oxadiazol-3-yl)methanone;

(R)-(3-Phenylpyrrolidin-1-yl)(5-(2,4,5-trifluoro-3-hydroxyphenyl)thiophen-2-yl)methanone;

(S)-6-Ethyl-4-(5-(2,4,5-trifluoro-3-hydroxyphenyl)-1,2,4-oxadiazole-3-carbonyl)piperazin-2-one;

(3-Isopropylmorpholino)(5-(2,4,5-trifluoro-3-hydroxyphenyl)-1,2,4-oxadiazol-3-yl)methanone;

((3R,5S)-3,5-Dimethylmorpholino)(5-(2,4,5-trifluoro-3-hydroxyphenyl)-1,2,4-oxadiazol-3-yl)methanone;

((3R,5S)-3,5-Dimethylpiperidin-1-yl)(5-(2,4,5-trifluoro-3-hydroxyphenyl)-1,2,4-oxadiazol-3-yl)methanone;

((2R,5S)-2,5-Dimethylpyrrolidin-1-yl)(5-(2,4,5-trifluoro-3-hydroxyphenyl)-1,2,4-oxadiazol-3-yl)methanone;

Morpholino(5-(2,4,5-trifluoro-3-hydroxyphenyl)-1,2,4-oxadiazol-3-yl)methanone;

Thiomorpholino(5-(2,4,5-trifluoro-3-hydroxyphenyl)-1,2,4-oxadiazol-3-yl)methanone;

(Hexahydrocyclopenta[b][1,4]oxazin-4(4aH)-yl)(5-(2,4,5-trifluoro-3-hydroxyphenyl)-1,2,4-oxadiazol-3-yl)methanone;

3-(4-(5-(2,4,5-Trifluoro-3-hydroxyphenyl)-1,2,4-oxadiazole-3-carbonyl)piperazin-2-yl)benzonitrile;

(8,8-Difluoro-3-azabicyclo[3.2.1]octan-3-yl)(5-(2,4,5-trifluoro-3-hydroxyphenyl)-1,2,4-oxadiazol-3-yl)methanone;

Piperidin-1-yl(5-(2,4,5-trifluoro-3-hydroxyphenyl)-1,2,4-oxadiazol-3-yl)methanone;

(6-Oxa-9-azaspiro[4.5]decan-9-yl)(5-(2,4,5-trifluoro-3-hydroxyphenyl)-1,2,4-oxadiazol-3-yl)methanone;

(S)-(5-(2,4,5-Trifluoro-3-hydroxyphenyl)-1,2,4-oxadiazol-3-yl)(2-(trifluoromethyl)morpholino)methanone;

(2-Isobutylmorpholino)(5-(2,4,5-trifluoro-3-hydroxyphenyl)-1,2,4-oxadiazol-3-yl)methanone;

(3,3-Dimethylmorpholino)(5-(2,4,5-trifluoro-3-hydroxyphenyl)-1,2,4-oxadiazol-3-yl)methanone;

(R)-(2-(Fluoromethyl)morpholino)(5-(2,4,5-trifluoro-3-hydroxyphenyl)-1,2,4-oxadiazol-3-yl)methanone;

((2R,5R)-2,5-Dimethylmorpholino)(5-(2,4,5-trifluoro-3-hydroxyphenyl)-1,2,4-oxadiazol-3-yl)methanone;

(R)-(7-Methyl-1,4-oxazepan-4-yl)(5-(2,4,5-trifluoro-3-hydroxyphenyl)-1,2,4-oxadiazol-3-yl)methanone;

(5-Oxa-8-azaspiro[3.5]nonan-8-yl)(5-(2,4,5-trifluoro-3-hydroxyphenyl)-1,2,4-oxadiazol-3-yl)methanone;

(1,9-Dioxa-4-azaspiro[5.5]undecan-4-yl)(5-(2,4,5-trifluoro-3-hydroxyphenyl)-1,2,4-oxadiazol-3-yl)methanone;

((2S,6S)-2,6-Dimethylmorpholino)(5-(2,4,5-trifluoro-3-hydroxyphenyl)-1,2,4-oxadiazol-3-yl)methanone;

(4-(4-Methoxyphenyl)piperazin-1-yl)(5-(2,4,5-trifluoro-3-hydroxyphenyl)-1,2,4-oxadiazol-3-yl)methanone;

4-(1-(5-(2,4,5-Trifluoro-3-hydroxyphenyl)-1,2,4-oxadiazole-3-carbonyl)piperidin-4-yl)benzonitrile;

(4-(3-(4-Fluorophenoxy)propyl)piperazin-1-yl)(5-(2,4,5-trifluoro-3-hydroxyphenyl)-1,2,4-oxadiazol-3-yl)methanone;

(4-(Pyridin-2-yl)piperazin-1-yl)(5-(2,4,5-trifluoro-3-hydroxyphenyl)-1,2,4-oxadiazol-3-yl)methanone;

4-(1-(5-(2,4,5-Trifluoro-3-hydroxyphenyl)-1,2,4-oxadiazole-3-carbonyl)azetidin-3-yl)benzonitrile;

(3-Phenylazetidin-1-yl)(5-(2,4,5-trifluoro-3-hydroxyphenyl)-1,2,4-oxadiazol-3-yl)methanone;

(4-(3-Methoxyphenyl)piperazin-1-yl)(5-(2,4,5-trifluoro-3-hydroxyphenyl)-1,2,4-oxadiazol-3-yl)methanone;

(4-Phenyl-3,6-dihydropyridin-1(2H)-yl)(5-(2,4,5-trifluoro-3-hydroxyphenyl)-1,2,4-oxadiazol-3-yl)methanone;

N-(3-Cyanophenyl)-N-methyl-5-(2,4,5-trifluoro-3-hydroxyphenyl)-1,2,4-oxadiazole-3-carboxamide;

(3,4-Dihydroisoquinolin-2(1H)-yl)(5-(2,4,5-trifluoro-3-hydroxyphenyl)-1,2,4-oxadiazol-3-yl)methanone;

(5-Fluoroisoindolin-2-yl)(5-(2,4,5-trifluoro-3-hydroxyphenyl)-1,2,4-oxadiazol-3-yl)methanone;

2-(5-(2,4,5-Trifluoro-3-hydroxyphenyl)-1,2,4-oxadiazole-3-carbonyl)-1,2,3,4-tetrahydroisoquinoline-5-carbonitrile;

(4-(3-Chloro-5-(2-methyl-2H-tetrazol-5-yl)pyridin-2-yl)piperazin-1-yl)(5-(2,4,5-trifluoro-3-hydroxyphenyl)-1,2,4-oxadiazol-3-yl)methanone;

(4-((5-Methoxypyridin-2-yl)oxy)piperidin-1-yl)(5-(2,4,5-trifluoro-3-hydroxyphenyl)-1,2,4-oxadiazol-3-yl)methanone;

(4-(2-((5-Bromopyridin-2-yl)oxy)ethyl)piperazin-1-yl)(5-(2,4,5-trifluoro-3-hydroxyphenyl)-1,2,4-oxadiazol-3-yl)methanone;

(4-(Pyridin-3-yloxy)piperidin-1-yl)(5-(2,4,5-trifluoro-3-hydroxyphenyl)-1,2,4-oxadiazol-3-yl)methanone;

N-((5,6-Dimethyl-1H-benzo[d]imidazol-2-yl)methyl)-N-methyl-5-(2,4,5-trifluoro-3-hydroxyphenyl)-1,2,4-oxadiazole-3-carboxamide;

(4-(Benzo[d]oxazol-2-yl)piperazin-1-yl)(5-(2,4,5-trifluoro-3-hydroxyphenyl)-1,2,4-oxadiazol-3-yl)methanone;

N-Methyl-N-((5-methyl-1H-benzo[d]imidazol-2-yl)methyl)-5-(2,4,5-trifluoro-3-hydroxyphenyl)-1,2,4-oxadiazole-3-carboxamide;

(3-(4-Fluorophenyl)azetidin-1-yl)(5-(2,4,5-trifluoro-3-hydroxyphenyl)-1,2,4-oxadiazol-3-yl)methanone;

N-Isopropyl-N-((3-methylpyridin-2-yl)methyl)-5-(2,4,5-trifluoro-3-hydroxyphenyl)-1,2,4-oxadiazole-3-carboxamide;

(3-Propylpyrrolidin-1-yl)(5-(2,4,5-trifluoro-3-hydroxyphenyl)-1,2,4-oxadiazol-3-yl)methanone;

(1-Phenyl-3-azabicyclo[3.1.0]hexan-3-yl)(5-(2,4,5-trifluoro-3-hydroxyphenyl)-1,2,4-oxadiazol-3-yl)methanone;

N-(1-(4-Methoxyphenyl)ethyl)-N-methyl-5-(2,4,5-trifluoro-3-hydroxyphenyl)-1,2,4-oxadiazole-3-carboxamide;

(3-(4-Fluorophenoxy)pyrrolidin-1-yl)(5-(2,4,5-trifluoro-3-hydroxyphenyl)-1,2,4-oxadiazol-3-yl)methanone;

4-Phenyl-1-(5-(2,4,5-trifluoro-3-hydroxyphenyl)-1,2,4-oxadiazole-3-carbonyl)piperidine-4-carbonitrile;

(4-Phenylpiperazin-1-yl)(5-(2,4,5-trifluoro-3-hydroxyphenyl)-1,2,4-oxadiazol-3-yl)methanone;

2-(4-(5-(2,4,5-Trifluoro-3-hydroxyphenyl)-1,2,4-oxadiazole-3-carbonyl)piperazin-1-yl)benzonitrile;

4-(4-(5-(2,4,5-Trifluoro-3-hydroxyphenyl)-1,2,4-oxadiazole-3-carbonyl)piperazin-1-yl)benzonitrile;

(4-(2-Methoxyphenyl)piperazin-1-yl)(5-(2,4,5-trifluoro-3-hydroxyphenyl)-1,2,4-oxadiazol-3-yl)methanone;

3-(1-(5-(2,4,5-Trifluoro-3-hydroxyphenyl)-1,2,4-oxadiazole-3-carbonyl)azetidin-3-yl)benzonitrile;

2-(5-(2,4,5-Trifluoro-3-hydroxyphenyl)-1,2,4-oxadiazole-3-carbonyl)-1,2,3,4-tetrahydroisoquinoline-7-carbonitrile;

((2R,6S)-2,6-Dimethylmorpholino)(5-(2,4,5-trifluoro-3-hydroxyphenyl)-1,2,4-oxadiazol-3-yl)methanone;

((2R,6R)-2,6-Dimethylmorpholino)(5-(2,4,5-trifluoro-3-hydroxyphenyl)-1,2,4-oxadiazol-3-yl)methanone;

((2R,6S)-2,6-Dimethylmorpholino)(5-(2,4,5-trifluoro-3-hydroxyphenyl)isoxazol-3-yl)methanone;

(5-(4-Fluoro-3-hydroxyphenyl)-1,3,4-oxadiazol-2-yl)(5-oxa-8-azaspiro[3.5]nonan-8-yl)methanone;

5-(4-Fluoro-3-hydroxyphenyl)-N-methyl-N-(1-phenyl-1H-tetrazol-5-yl)-1,3,4-oxadiazole-2-carboxamide;

5-(4-Fluoro-3-hydroxyphenyl)-N-methyl-N-(1-phenyl-1H-tetrazol-5-yl)-1,2,4-oxadiazole-3-carboxamide;

(S)-(3-Phenoxypyrrolidin-1-yl)(5-(2,4,5-trifluoro-3-hydroxyphenyl)-1,2,4-oxadiazol-3-yl)methanone;

(3-(Benzyloxy)piperidin-1-yl)(5-(2,4,5-trifluoro-3-hydroxyphenyl)-1,2,4-oxadiazol-3-yl)methanone;

(R)-(3-(4-Chlorophenyl)pyrrolidin-1-yl)(5-(2,4,5-trifluoro-3-hydroxyphenyl)-1,2,4-oxadiazol-3-yl)methanone;

(3-Phenylpyrrolidin-1-yl)(5-(2,4,5-trifluoro-3-hydroxyphenyl)-1,2,4-oxadiazol-3-yl)methanone;

(3-(Benzyloxy)pyrrolidin-1-yl)(5-(2,4,5-trifluoro-3-hydroxyphenyl)-1,2,4-oxadiazol-3-yl)methanone;

(R)-(3-Phenoxypyrrolidin-1-yl)(5-(2,4,5-trifluoro-3-hydroxyphenyl)-1,2,4-oxadiazol-3-yl)methanone;

N-(1-Cyclohexyl-1H-pyrazol-5-yl)-5-(4-fluoro-3-hydroxyphenyl)isoxazole-3-carboxamide;

N-((1-Cyclohexyl-1H-pyrazol-5-yl)methyl)-2-(4-fluoro-3-hydroxyphenyl)oxazole-5-carboxamide;

(R)-(5-(4-Fluoro-3-hydroxyphenyl)isoxazol-3-yl)(3-phenylpyrrolidin-1-yl)methanone;

(3H-Spiro[isobenzofuran-1,3'-pyrrolidin]-1'-yl)(5-(2,4,5-trifluoro-3-hydroxyphenyl)-1,2,4-oxadiazol-3-yl)methanone;

(S)-(3-(4-Chlorophenyl)pyrrolidin-1-yl)(5-(2,4,5-trifluoro-3-hydroxyphenyl)-1,2,4-oxadiazol-3-yl)methanone;

(R)-(3-Phenylpyrrolidin-1-yl)(5-(2,4,5-trifluoro-3-hydroxyphenyl)isoxazol-3-yl)methanone;

N,N-Dimethyl-1-(5-(2,4,5-trifluoro-3-hydroxyphenyl)thiophene-2-carbonyl)pyrrolidine-2-carboxamide;

2-(5-(2,4,5-Trifluoro-3-hydroxyphenyl)-1,2,4-oxadiazole-3-carbonyl)isoindoline-5-carbonitrile;

(4-(3-Isopropyl-1,2,4-oxadiazol-5-yl)-3,6-dihydropyridin-1(2H)-yl)(5-(2,4,5-trifluoro-3-hydroxyphenyl)-1,2,4-oxadiazol-3-yl)methanone;

((2S,6R)-2,6-Dimethylmorpholino)(5-(2,4,5-trifluoro-3-hydroxy-6-iodophenyl)-1,2,4-oxadiazol-3-yl)methanone;

2-(5-(2,4,5-Trifluoro-3-hydroxy-6-iodophenyl)-1,2,4-oxadiazole-3-carbonyl)-1,2,3,4-tetrahydroisoquinoline-5-carbonitrile;

((2R,6S)-2,6-Dimethylmorpholino)(3-(2,4,5-trifluoro-3-hydroxyphenyl)-1,2,4-oxadiazol-5-yl)methanone; and ((3R,5S)-3,5-Dimethylpiperidin-1-yl)(3-(2,4,5-trifluoro-3-hydroxyphenyl)-1,2,4-oxadiazol-5-yl)methanone.

In embodiments, there is provided a compound of Formula (I), or a pharmaceutically acceptable salt thereof, wherein the compound is selected from:

((4aR,7aS)-Hexahydrocyclopenta[b][1,4]oxazin-4(4aH)-yl)(5-(2,4,5-trifluoro-3-hydroxyphenyl)-1,2,4-oxadiazol-3-yl)methanone;

((4aS,7aR)-Hexahydrocyclopenta[b][1,4]oxazin-4(4aH)-yl)(5-(2,4,5-trifluoro-3-hydroxyphenyl)-1,2,4-oxadiazol-3-yl)methanone;

((4aR,7aR)-Hexahydrocyclopenta[b][1,4]oxazin-4(4aH)-yl)(5-(2,4,5-trifluoro-3-hydroxyphenyl)-1,2,4-oxadiazol-3-yl)methanone;

((4aS,7aS)-Hexahydrocyclopenta[b][1,4]oxazin-4(4aH)-yl)(5-(2,4,5-trifluoro-3-hydroxyphenyl)-1,2,4-oxadiazol-3-yl)methanone;

(5-(3,4-Difluoro-5-hydroxyphenyl)-1,2,4-oxadiazol-3-yl)((2R,6S)-2,6-dimethylmorpholino)methanone;

(5-(2,4,5-Trifluoro-3-hydroxyphenyl)-1,2,4-oxadiazol-3-yl)(2,2,6-trimethylmorpholino)methanone;

(4-Oxa-7-azaspiro[2.5]octan-7-yl)(5-(2,4,5-trifluoro-3-hydroxyphenyl)-1,2,4-oxadiazol-3-yl)methanone;

((3R,5S)-3,5-Dimethylpiperazin-1-yl)(5-(2,4,5-trifluoro-3-hydroxyphenyl)-1,2,4-oxadiazol-3-yl)methanone; and ((2R,6S)-2,6-Dimethylmorpholino)(2-(2,4,5-trifluoro-3-hydroxyphenyl)thiazol-5-yl)methanone.

In embodiments, there is provided a compound of Formula (I), or a pharmaceutically acceptable salt thereof, wherein the compound is selected from:

rac-((2R,6S)-2-Ethyl-6-methylmorpholino)(5-(2,4,5-trifluoro-3-hydroxyphenyl)-1,2,4-oxadiazol-3-yl)methanone;

rac-((2R,6S)-2-isopropyl-6-methylmorpholino)(5-(2,4,5-trifluoro-3-hydroxyphenyl)-1,2,4-oxadiazol-3-yl)methanone;

(6-Methyl-5-oxa-8-azaspiro[3.5]nonan-8-yl)(5-(2,4,5-trifluoro-3-hydroxyphenyl)-1,2,4-oxadiazol-3-yl)methanone; and (5-(2-Bromo-3,4,6-trifluoro-5-hydroxyphenyl)-1,2,4-oxadiazol-3-yl)((2R,6S)-2,6-dimethylmorpholino)methanone.

A further feature is any of the embodiments described in the specification with the proviso that any of the specific Examples are individually disclaimed. A further feature is any of the embodiments described in the specification with the proviso that any one or more of the compounds selected from the above list of Examples of compounds of the specification are individually disclaimed.

The compounds disclosed herein may contain one or more chiral centers. Accordingly, if desired, such compounds can be prepared or isolated as pure stereoisomers, i.e. as individual enantiomers, diastereoisomers, or as a stereoisomerically enriched mixture. All such stereoisomer (and enriched) mixtures are included within the scope of the embodiments, unless otherwise stated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Unless stereochemistry is explicitly indicated in a chemical structure or chemical name, the chemical structure or chemical name is intended to embrace all possible stereoisomers, diastereoisomers, conformers, rotamers and tautomers of the compound depicted. For example, a compound containing a chiral carbon atom is intended to embrace both the (R) enantiomer and the (S) enantiomer, as well as mixtures of the enantiomers, including racemic mixtures; and a compound containing two chiral carbons is intended to embrace all enantiomers and diastereoisomers including (R,R), (S,S), (R,S) and (S,R).

In embodiments, there is provided a pharmaceutical composition which comprises a compound of the Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, in association with a pharmaceutically acceptable excipient, optionally further comprising one or more of the other stereoisomeric forms of the compound of Formula (I), (II), (IIA), (IIB), (IIC), (IID), (IIE), (III), (IIIA), (IIIB), (IIIC), (IIID), (IV), (V), (VI), or (VII) or pharmaceutically acceptable salt thereof, wherein the compound of Formula (I), (II), (IIA), (IIB), (IIC), (IID), (IIE), (III), (IIIA), (IIIB), (IIIC), (IIID), (IV), (V), (VI) or (VII), or pharmaceutically acceptable salt thereof is present within the composition with an enantiomeric excess (% ee) of >90% and a diastereomeric excess (% de) of 90%.

The compound of Formula (I), (II), (IIA), (IIB), (IIC), (IID), (IIE), (III), (IIIA), (IIIB), (IIIC), (IIID), (IV), (V), (VI) or (VII), and pharmaceutically acceptable salts thereof, may be prepared, used or supplied in amorphous form, crystalline form, or semicrystalline form and any given compound of Formula (I), (II), (IIA), (IIB), (IIC), (IID), (IIE), (III), (IIIA), (IIIB), (IIIC), (IIID), (IV), (V), (VI) or (VII), or pharmaceutically acceptable salt thereof, may be capable of being formed into more than one crystalline/polymorphic form, including hydrated (e.g. hemi hydrate, a mono hydrate, a di hydrate, a tri hydrate or other stoichiometry of hydrate) and/or solvated forms. It is to be understood that the present specification encompasses any and all such solid forms of the compound of Formula (I), (II), (IIA), (IIB), (IIC), (IID), (IIE), (III), (IIIA), (IIIB), (IIIC), (IIID), (IV), (V), (VI) or (VII), and pharmaceutically acceptable salts thereof.

In further embodiments there is provided a compound of Formula (I), (II), (IIA), (IIB), (IIC), (IID), (IIE), (III), (IIIA), (IIIB), (IIIC), (IIID), (IV), (V), (VI) or (VII), or pharmaceutically acceptable salts thereof, which is obtainable by the methods described in the "Examples" section hereinafter.

The present specification is intended to include all isotopes of atoms occurring in the present compounds. Isotopes will be understood to include those atoms having the same atomic number but different mass numbers. For example, isotopes of hydrogen include tritium and deuterium. Isotopes of carbon include $^{13}C$ and $^{14}C$. Isotopes of nitrogen include $^{15}N$. Isotopes of fluorine include $^{18}F$.

A suitable pharmaceutically acceptable salt of a compound of Formula (I), (II), (IIA), (IIB), (IIC), (IID), (IIE), (III), (IIIA), (IIIB), (IIIC), (IIID), (IV), (V), (VI) or (VII) is, for example, a base addition salt. A base addition salt of a compound of Formula (I), (II), (IIA), (IIB), (IIC), (IID), (IIE), (III), (IIIA), (IIIB), (IIIC), (IIID), (IV), (V), (VI) or (VII) may be formed by bringing the compound into contact with a suitable inorganic or organic base under conditions known to the skilled person. A base addition salt may for example be an alkali metal salt (such as a sodium, potassium, or lithium salt) or an alkaline earth metal salt (such as a calcium salt), which may be formed using an alkali metal or alkaline earth metal hydroxide or alkoxide (e.g., an ethoxide or methoxide). A base addition salt may also be formed using a suitably basic organic amine (e.g., a choline or meglumine salt).

A suitable pharmaceutically acceptable salt of a compound of Formula (I), (II), (IIA), (IIB), (IIC), (IID), (IIE), (III), (IIIA), (IIIB), (IIIC), (IIID), (IV), (V), (VI) or (VII) is, for example, an acid addition salt. An acid addition salt of a compound of Formula (I), (II), (IIA), (IIB), (IIC), (IID), (IIE), (III), (IIIA), (IIIB), (IIIC), (IIID), (IV), (V), (VI) or (VII) may be formed by bringing the compound into contact with a suitable inorganic or organic acid under conditions known to the skilled person. An acid addition salt may for example be formed using an inorganic acid selected from hydrochloric acid, hydrobromic acid, sulphuric acid and phosphoric acid. An acid addition salt may also be formed using an organic acid selected from trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and para-toluenesulfonic acid.

A further suitable pharmaceutically acceptable salt of a compound of Formula (I), (II), (IIA), (IIB), (IIC), (IID), (IIE), (III), (IIIA), (IIIB), (IIIC), (IIID), (IV), (V), (VI) or (VII) is, for example, a salt formed within a patient's body after administration of a compound of Formula (I), (II), (IIA), (IIB), (IIC), (IID), (IIE), (III), (IIIA), (IIIB), (IIIC), (IIID), (IV), (V), (VI) or (VII) to the patient.

The compound of Formula (I), (II), (IIA), (IIB), (IIC), (IID), (IIE), (III), (IIIA), (IIIB), (IIIC), (IIID), (IV), (V), (VI) or (VII), or pharmaceutically acceptable salt thereof, may be prepared as a co-crystal solid form. It is to be understood that a pharmaceutically acceptable co-crystal of an compound of Formula (I), (II), (IIA), (IIB), (IIC), (IID), (IIE), (III), (IIIA), (IIIB), (IIIC), (IIID), (IV), (V), (VI) or (VII), or pharmaceutically acceptable salts thereof, form an aspect of the present specification.

In a further aspect there is provided a pharmaceutical composition comprising a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof and a pharmaceutically acceptable excipient.

The term "pharmaceutical composition" refers to a preparation which is in such form as to permit the biological activity of the active ingredient, and which contains no additional components which are unacceptably toxic to a patient to which the composition would be administered. Such compositions can be sterile. A pharmaceutical composition according to the present specification will comprise a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, and a pharmaceutically acceptable excipient. For example, the composition may be in a form suitable for oral use (for example as tablets, lozenges, hard or soft capsules, aqueous or oily suspensions, emulsions, dispersible powders or granules, syrups or elixirs) or for parenteral administration (for example as a sterile aqueous or oily solution for intravenous, subcutaneous, intramuscular or intramuscular dosing or as a suppository for rectal dosing). Such compositions may be obtained by conventional procedures using conventional pharmaceutical excipients, well known in the art. Thus, compositions intended for oral use may contain, for example, one or more colouring, sweetening, flavouring and/or preservative agents. An effective amount of the compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, will normally be present in the composition.

The compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, will normally be administered via the oral route though parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable salt or solvate thereof, or a solvate of such a salt, in a pharmaceutically acceptable dosage form may be possible. Depending upon the disorder and patient to be treated and the route of administration, the compositions may be administered at varying doses.

The pharmaceutical formulations of the compound of Formula (I), (II), (IIA), (IIB), (IIC), (IID), (IIE), (III), (IIIA), (IIIB), (IIIC), (IIID), (IV), (V), (VI) or (VII) described above may be prepared e.g. for parenteral, subcutaneous, intramuscular or intravenous administration.

The pharmaceutical formulations of the compound of Formula (I), (II), (IIA), (IIB), (IIC), (IID), (IIE), (III), (IIIA), (IIIB), (IIIC), (IIID), (IV), (V), (VI) or (VII) described above may conveniently be administered in unit dosage form and may be prepared by any of the methods well-known in the pharmaceutical art, for example as described in Remington's Pharmaceutical Sciences, 17th ed., Mack Publishing Company, Easton, PA., (1985).

Pharmaceutical formulations suitable for oral administration may comprise one or more physiologically compatible carriers and/or excipients and may be in solid or liquid form. Tablets and capsules may be prepared with binding agents; fillers; lubricants; and surfactants. Liquid compositions may contain conventional additives such as suspending agents; emulsifying agents; and preservatives Liquid compositions may be encapsulated in, for example, gelatin to provide a unit dosage form. Solid oral dosage forms include tablets, two-piece hard shell capsules and soft elastic gelatin (SEG) capsules. An exemplary oral composition would comprise a compound of Formula (I), (II), (IIA), (IIB), (IIC), (IID), (IIE), (III), (IIIA), (IIIB), (IIIC), (IIID), (IV), (V), (VI) or (VII) and at least one pharmaceutically acceptable excipient filled into a two-piece hard shell capsule or a soft elastic gelatin (SEG) capsule.

As a result of their 17BHSD13 inhibitory activity, the compounds of Formula (I), (II), (IIA), (IIB), (IIC), (IID), (IIE), (III), (IIIA), (IIIB), (IIIC), (IIID), (IV), (V), (VI) or (VII), and pharmaceutically acceptable salts thereof are expected to be useful in therapy, for example in the treatment of diseases or medical conditions mediated at least in part by 17BHSD13, including liver disease, such as NASH.

In one aspect of the present specification there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in therapy.

In one aspect of the present specification there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of liver disease. In embodiments, the liver disease is selected from alcoholic liver disease, non-alcoholic liver disease, NAFLD (such as NASH, liver fibrosis, cirrhosis, and isolated steatosis), liver inflammation, alcoholic steatoheptatis (ASH), hepatitis C virus (HCV) and hepatocellular carcinoma (HCC).

The term "therapy" is intended to have its normal meaning of dealing with a disease in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment" is used synonymously with "therapy". Similarly the term "treat" can be regarded as "applying therapy" where "therapy" is as defined herein.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in providing an inhibitory effect on 17βHSD13.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of a disease mediated by 17βHSD13, such as liver disease (e.g. NASH).

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of fatty liver disease.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of nonalcoholic Fatty Liver Disease (NAFLD), such as isolated steatosis, Nonalcoholic Steatohepatitis (NASH), liver fibrosis or cirrhosis. In further embodiments, the liver disease is end stage liver disease.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of liver disease, such as NASH, wherein the patient is also suffering from or susceptible to one or more conditions selected from the group consisting of obesity, dyslipidemia, insulin resistance, Type 2 diabetes, and renal insufficiency.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of liver disease, such as NASH, wherein the patient has a body mass index (BMI) of 27 kg/m$^2$ to 40 kg/m$^2$. In further embodiments, the subject has a BMI of 30 kg/m$^2$ to 39.9 kg/m$^2$. In further embodiments, the patient has a BMI of at least 40 kg/m$^2$. In further embodiments, the patient is overweight. In further embodiments, the patient is obese.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of liver disease, such as NASH, wherein the patient is also suffering from or susceptible to dyslipidemia.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of liver disease, such as NASH, wherein the patient is also suffering from or susceptible to insulin resistance.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of liver disease, such as NASH, wherein the patient is also suffering from or susceptible to Type 2 diabetes.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of liver disease, such as NASH, wherein the patient is also suffering from or susceptible to renal insufficiency.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of liver disease, such as NASH, wherein the patient is also suffering from or susceptible to liver fibrosis. In further embodiments, the patient is (i) suffering from or susceptible to liver fibrosis, and (ii) suffering from or susceptible to one or more conditions selected from the group consisting of obesity, dyslipidemia, insulin resistance, Type 2 diabetes, and renal insufficiency.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of liver disease, such as NASH, wherein the patient is also suffering from or susceptible to cirrhosis. In further embodiments, the patient is (i) suffering from or susceptible to cirrhosis, and (ii) suffering from or susceptible to one or more conditions selected from the group consisting of obesity, dyslipidemia, insulin resistance, Type 2 diabetes, and renal insufficiency.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of NAFLD. In further embodiments, the NAFLD is Stage 1 NAFLD. In further embodiments, the NAFLD is Stage 2 NAFLD. In further embodiments, the NAFLD is Stage 3 NAFLD. In further embodiments, the NAFLD is Stage 4 NAFLD. See, e.g., "The Diagnosis and Management of Nonalcoholic Fatty Liver Disease: Practice Guidance From the American Association for the Study of Liver Diseases," Hepatology, Vol. 67, No. 1, 2018.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of NAFLD, such as NASH. In further embodiments, the patient is obese. In further embodiments, the patient has alcoholic liver disease. In further embodiments, the patient has a genetic risk factor for liver disease, such as the (rs738409 C>G) variant in PNPLA3.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of NASH. In further embodiments, the NASH is Stage 1 NASH. In further embodiments, the NASH is Stage 2 NASH. In further embodiments, the NASH is Stage 3 NASH. In further embodiments, the NASH is Stage 4 NASH. In further embodiments, the patient is also suffering from or susceptible to one or more conditions selected from obesity, dyslipidemia, insulin resistance, Type 2 diabetes, and renal insufficiency.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of liver fibrosis. In further embodiments, the liver fibrosis is Stage 3 liver fibrosis. In further embodiments, the patient is also suffering from or susceptible to one or more conditions selected from obesity, dyslipidemia, insulin resistance, Type 2 diabetes, and renal insufficiency.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of cirrhosis. In further embodiments, the cirrhosis is stage F4 cirrhosis. In further embodiments, the patient is also suffering from or susceptible to one or more conditions selected from obesity, dyslipidemia, insulin resistance, Type 2 diabetes, and renal insufficiency.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of liver inflammation. In further embodiments, the inflammation is chronic inflammation. In further embodiments, the chronic inflammation is selected from the group consisting of rheumatoid arthritis, osteoarthritis, and Crohn's disease. In further embodiments, the chronic inflammation is rheumatoid arthritis.

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of hepatocellular carcinoma (HCC).

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of alcoholic steatoheptatis (ASH).

In embodiments, there is provided a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, for use in the treatment of hepatitis C virus (HCV).

In one aspect of the present specification there is provided the use of a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, as described herein, in the manufacture of a medicament, such as a medicament for the treatment of disease (e.g. NASH).

In one aspect of the present specification there is provided a method of treating disease, such as NASH, in a patient comprising administering to the patient an effective amount of a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof.

Terms such as "treating" or "treatment" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented.

The term "effective amount" means an amount of an active ingredient which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

The term "patient" refers to any animal (e.g., a mammal), including, but not limited to humans, non-human primates, rodents, and the like, which is to be the recipient of a particular treatment. Typically, the term "patient" refers to a human subject.

In embodiments, there is provided a method of treating disease in a patient comprising administering to the patient an effective amount of a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, wherein the disease is selected from isolated steatosis, NASH, liver fibrosis and cirrhosis.

In embodiments, there is provided a method of treating a 17βHSD13 mediated disease in a patient comprising administering to the patient an effective amount of a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, such as NASH.

The compounds of the present disclosure may be used in the methods described above as either as single pharmacological agents or in combination with other pharmacological agents or techniques.

Such combination therapies may be achieved by way of the simultaneous, sequential or separate dosing of the individual components of the treatment. These combination therapies (and corresponding combination products) employ the compounds of the present disclosure and the other pharmacological agent(s).

In embodiments, there is provided a combination for use in the treatment of liver disease, such as NASH, comprising a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, and a sodium-glucose transport protein 2 (SGLT2) inhibitor. In further embodiments, the SGLT2 inhibitor is selected from canagliflozin, dapagliflozin, empagliflozin, ertugliflozin, ipragliflozin, luseogliflozin, and remogliflozin.

In embodiments, there is provided a combination for use in the treatment of liver disease, such as NASH, comprising a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, and metformin, or a pharmaceutically acceptable salt thereof.

In embodiments, there is provided a combination for use in the treatment of liver disease, such as NASH, comprising a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, and a glucagon-like peptide-1 receptor (GLP1) agonist. In further embodiments, the GLP1 agonist is selected from exenatide, liraglutide, lixisenatide, albiglutide, dulaglutide, and semaglutide.

In embodiments, there is provided a combination for use in the treatment of liver disease, such as NASH, comprising a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, and a dipeptidyl peptidase 4 (DPP4) inhibitor. In further embodiments, the DPP4 inhibitor is selected sitagliptin, vildagliptin, saxagliptin, linagliptin, gemigliptin, anagliptin, teneligliptin, alogliptin, trelagliptin, omarigliptin, evogliptin, gosogliptin, and dutogliptin.

In embodiments, there is provided a combination for use in the treatment of liver disease, such as NASH, comprising a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, and a PPAR agonist. In further embodiments, the PPAR agonist is a PPARα agonist. In further embodiments, the PPAR agonist is a PPARγ agonist. In further embodiments, the PPAR agonist is a PPARα/γ agonist. In further embodiments, the PPAR agonist is selected from clofibrate, gemfibrozil, ciprofibrate, bezafibrate, and fenofibrate. In further embodiments, the PPAR agonist is a thiazolidinedione. In further embodiments, the thiazolidinedione is selected from pioglitazone, rosiglitazone, lobeglitazone, and rivoglitazone. In further embodiments, the PPAR agonist stimulates liver expression of FGF21.

In embodiments, there is provided a combination for use in the treatment of liver disease, such as NASH, comprising a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, and a Pan-PPAR agonist. In further embodiments, the Pan-PPAR agonist is lanifibranor.

In embodiments, there is provided a combination for use in the treatment of liver disease, such as NASH, comprising a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, and a ThrB agonist. In further embodiments, the ThrB agonist is resmetirom.

In embodiments, there is provided a combination for use in the treatment of liver disease, such as NASH, comprising a compound of Formula (I), (II), (IIA), (IIB), (IIC), (IID), (IIE), (III), (IIIA), (IIIB), (IIIC), (IIID), (IV), (V), (VI) or (VII), or a pharmaceutically acceptable salt thereof, and a FXR agonist. In further embodiments, the FXR agonist is obeticholic acid.

Although the compounds of the Formula (I), (II), (IIA), (IIB), (IIC), (IID), (IIE), (III), (IIIA), (IIIB), (IIIC), (IIID), (IV), (V), (VI) or (VII) are primarily of value as therapeutic agents for use in patients, they are also useful whenever it is required to inhibit 17βHSD13. Thus, they are useful as pharmacological standards for use in the development of new biological tests and in the search for new pharmacological agents.

In one aspect of the present specification there is provided intermediates and methods useful for the synthesis of compounds of Formula (I), and pharmaceutically acceptable salts thereof. Schemes P1-P10 disclose intermediates and methods useful for the synthesis of compounds of Formula (I), wherein $X^1$, $X^2$, $X^3$, $R^1$, $R^2$ and A are defined as for a compound of Formula (I) herein, LG is a leaving group (e.g. Cl, Br or I), $B^1$ is a boronic acid, or a derivative thereof (e.g. a boronic acid, boronate ester or trifluoroborate) and, unless other stated, $R^P$ is a $C_{1-4}$ alkyl group.

Scheme P1

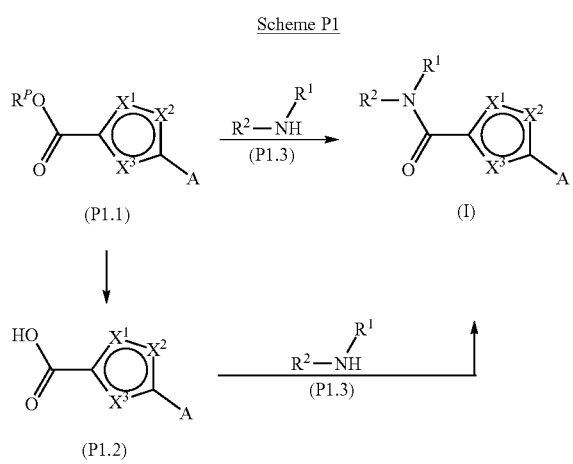

A compound of Formula (I) may be formed by reaction of a carboxylic acid of formula (P1.2) with an amine of Formula (P1.3), or a salt thereof (e.g. a HCl salt), in presence of a coupling reagent (such as DIC, EDC, COMU, TBTU or HATU) in the presence of a base (such as DIPEA or 2,6-lutidine) in a solvent (such as DMF, MeCN, EtOAc or mixtures thereof), optionally at a temperature range 18 to 60° C.

Optionally, the reaction may be performed in presence of HOBt. A compound of Formula (P1.2) may be formed by hydrolysis of an ester of Formula (P1.1) by standard methods. For esters such as Me or Et, the hydrolysis may be performed using a base (such as LiOH or NaOH) in a solvent (such as $H_2O$, MeOH, THF or mixtures thereof), optionally at a temperature in the range 18 to 60° C. For acid labile esters (e.g. $^t$Bu) the hydrolysis may be performed using an acid (e.g. TFA), either neat or in a solvent (such as DCM or $H_2O$), optionally at 18° C.

A compound of Formula (I) may also be formed by reaction of an ester of Formula (P1.1), in which $R^P$ is Me or Et, with an amine of Formula (P1.3) optionally in the presence of $AlMe_3$ or $DABAL-Me_3$ in a solvent (such as toluene or DMF), optionally at a temperature in the range 18 to 70° C. (such as 50 to 70° C.).

Scheme P2

A compound of Formula (P2.4) may be formed by reaction of a compound of Formula (P2.2) with a compound of Formula (P2.3) (where $R^P$ is Me or Et), optionally in pyridine, optionally at a temperature of 18 to 50° C. A compound of Formula (P2.2) may be formed from nitriles of Formula (P2.1) by reaction with hydroxylamine (or a salt thereof, e.g. HCl) in a solvent (such as $H_2O$, MeOH or EtOH or mixtures thereof), optionally at a temperature in the range 50 to 80° C. If a hydroxylammonium salt (e.g. HCl) is used, an additional base (e.g. $NaHCO_3$) may be added.

Scheme P3

A compound of Formula (P3.3) may be formed by reaction of a compound of Formula (P3.1) and a compound of Formula (P3.2), with EDC and a base (e.g. $NaHCO_3$), optionally in DMF, optionally at a temperature of 100° C. Optionally, $R^P$ is Me or Et.

Scheme P4

A compound of Formula (P4.4), in which $R^P$ is Me or Et, may be formed by reaction of a compound of Formula (P4.3) by reaction with a dehydrating reagent (e.g. $POCl_3$, $SOCl_2$ or EDC), either neat or in a solvent (such as toluene or DCM), optionally at a temperature in the range 18 to 90° C., optionally in presence of a base (such as pyridine). A compound of Formula (P4.3) may be formed by reaction of a hydrazide of Formula (P4.1) with a compound of Formula (P4.2) in a solvent (such as dioxane, THF, DCM or mixtures thereof), optionally at a temperature of 0 to 18° C., optionally in presence of a base (such as TEA or DIPEA).

Scheme P5

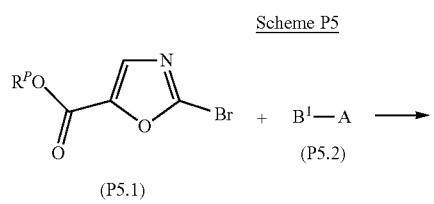

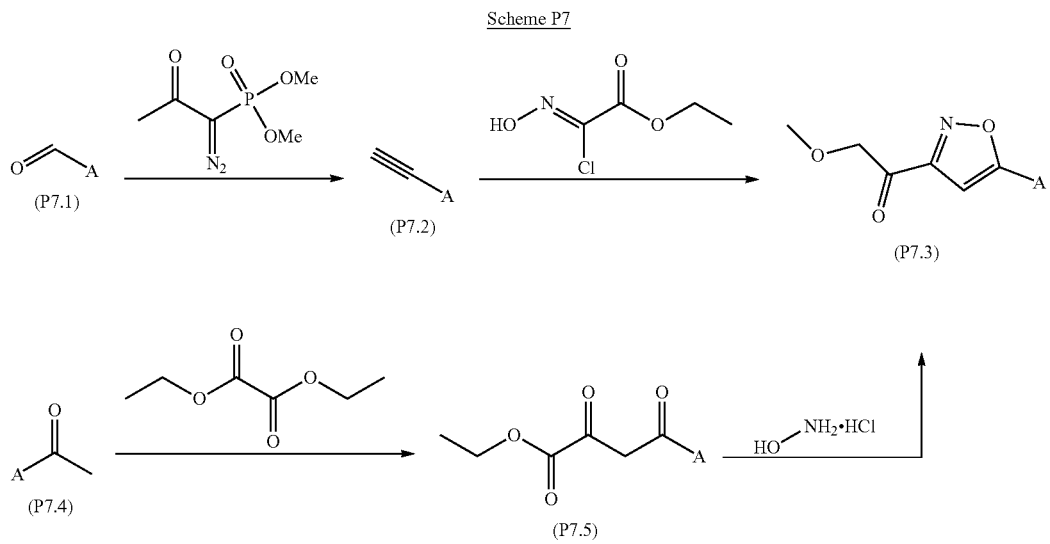

-continued

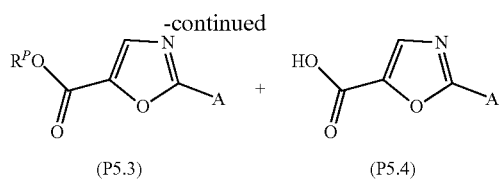

A compound of Formula (5.1) may be reacted with a compound of Formula (P5.2). The reaction may be performed with a Pd-reagent (e.g. XPhos Pd G3) in presence of H₂O and a base (e.g. K₃PO₄) in a solvent (such as dioxane, THF or mixtures thereof), optionally at 60° C.

Scheme P6

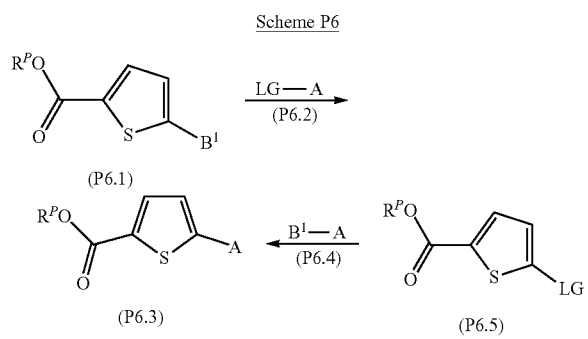

A compound of Formula (P6.3) may be formed by reacting a compound of Formula (P6.2) with a compound of Formula (P6.1). The reaction may be catalyzed by a Pd-reagent (e.g. Pd-118) in presence of a base (e.g. Cs₂CO₃, K₂CO₃ or Na₂CO₃) and H₂O in a solvent (such as dioxane, THF, EtOH, DMF or mixtures thereof), optionally at a temperature of 60° C. Alternatively, a compound of Formula (P6.3) may be formed by reaction of a compound of Formula (P6.4) with a compound of Formula (P6.5), wherein LG is optionally Br. The reaction may be catalyzed by a Pd-reagent (e.g. Pd-118) in presence of a base (e.g. K₂CO₃) and H₂O in a solvent (such as 1,4-dioxane), optionally at temperature in the range 50 to 80° C.

A compound of Formula (P7.3) may be formed by reaction of an alkyne of Formula (P7.2) with ethyl (Z)-2-chloro-2-(hydroxyimino)acetate in presence of a base (e.g. TEA) in a solvent (such as DCM), optionally at a temperature in the range 18 to 45° C. A compound of Formula (P7.2) may be formed by reaction of an aldehyde of Formula (P7.1) with dimethyl (1-diazo-2-oxopropyl)phosphonate in presence of a base (e.g. K₂CO₃) in a solvent (such as MeOH), optionally at rt.

Alternatively, a compound of Formula (P7.3) may be formed by reaction of a di-ketone of Formula (P7.5) with hydroxylammonium chloride in a solvent (e.g. EtOH, acetic acid or formic acid), optionally at a temperature in the range 50 to 100° C. A di-ketone of Formula (P7.5) may be formed by reaction of a methyl ketone of Formula (P7.4) with a base (e.g. LiHMDS or NaOEt) and diethyl oxalate in a solvent (such as THF), optionally at a temperature in the range −78° C. to 18° C.

Scheme P8

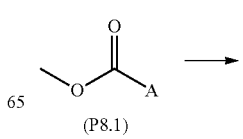

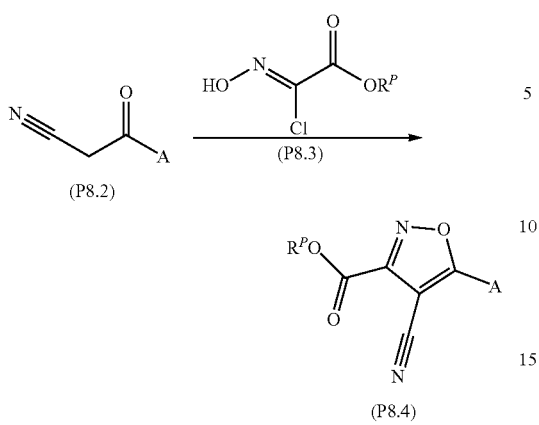

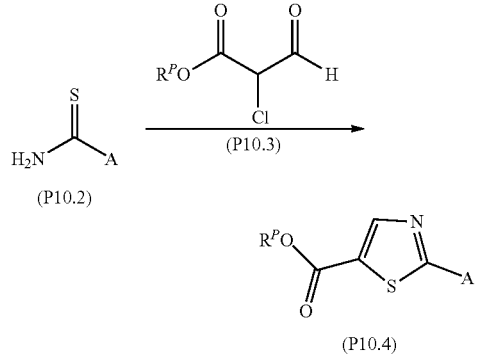

A compound of Formula (P8.4), where $R^P$=Et, may be formed from a compound of Formula (P8.2) by reaction with a compound of Formula (P8.3) in the presence of a base (e.g. TEA) in a solvent (such as EtOH), optionally at room temperature. A compound of Formula (P8.2) may be formed from an ester of Formula (P8.1) by reaction with MeCN and a strong base (e.g. NaH) in a solvent (e.g. THF), optionally at a temperature in the range 18 to 50° C.

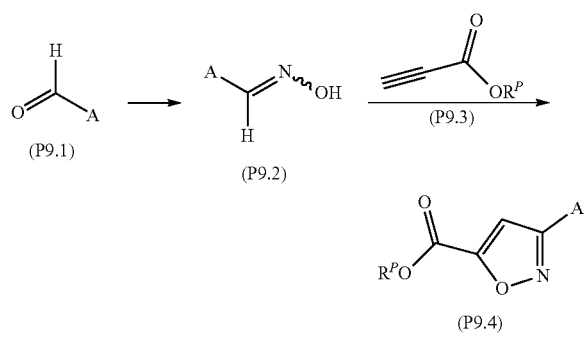

A compound of Formula (P9.4) in which $R^P$ is Me or $^t$Bu, may be formed from a compound of Formula (P9.2) by reaction with a compound of Formula (P9.3) and OXONE (potassium peroxymonosulfate) in the presence of KCl in a solvent (such as H$_2$O or aqueous MeCN), optionally at a temperature in the range 0 to 18° C. A compound of Formula (P9.2) may be formed from an aldehyde of Formula (P9.1) by reaction with hydroxylamine or a salt thereof (e.g. HCl) in a solvent (e.g. H$_2$O, MeOH or EtOH or mixtures thereof), optionally at a temperature in the range 0 to 18° C. If a hydroxylammonium salt (e.g. HCl) is used an additional base (e.g. NaOH, NaOAc or Na$_2$CO$_3$) may be added.

Scheme P10

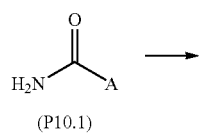

A compound of Formula (P10.4), where $R^P$ is Me or Et, may be formed from a compound of Formula (P10.2) by reacting with a compound of Formula (P10.3) in a solvent (such as toluene), optionally at a temperature in the range 105 to 110° C. A compound of Formula (P10.2) may be formed by reacting a primary amide of Formula (P10.1) with Lawesson's reagent in a solvent (e.g. THF), optionally at a temperature in the range 18 to 65° C.

It is understood that organic reactions described herein are performed according to laboratory practice known to person skilled in the art. It is understood that some of the reactions described herein may optionally be performed in different orders than laid out herein. It is understood that chiral isomers of compounds herein can be resolved at any stage in the synthetic process using chiral resolving agents described in the literature and known to person skilled in the art, or using chiral chromatography methods described in the literature and known to person skilled in the art, or as described further in the Examples.

It is understood that additional and/or other protective groups may optionally be needed in some of the steps described above, and it is further understood that a deprotection step therefore optionally may be performed, using method described in the literature and known to person skilled in the art. The protection and deprotection of functional groups is described in "Protective Groups in Organic Synthesis" 3rd Ed, T. W. Greene and P. G. M. Wutz, Wiley-Interscience (1999), which is incorporated herein by reference.

EXAMPLES

The specification will now be illustrated by the following non-limiting Examples in which, generally:
(i) operations were carried out at room temperature (rt), i.e. in the range 17 to 28° C. and where needed under an atmosphere of an inert gas such as N$_2$;
(ii) where reactions refer to being degassed or purged, this can be performed for example by purging the reaction solvent with a constant flow of nitrogen for a suitable period of time (for example 5 to 10 min) or by repeatedly evacuating the vessel and backfill with appropriate inert atmosphere (for example nitrogen (g) or argon (g));
(iii) where reactions refer to the use of a microwave reactor, one of the following microwave reactors were used: BIOTAGE INITIATOR, PERSONAL CHEMISTRY EMRYS OPTIMIZER, PERSONAL CHEMISTRY SMITH CREATOR or CEM EXPLORER;
(iv) in general, the course of reactions was followed by thin layer chromatography (TLC) and/or analytical high performance liquid chromatography (HPLC or UPLC) which was usually coupled to a mass spectrometer (LCMS).

(v) when necessary, organic solutions were dried over anhydrous $MgSO_4$ or $Na_2SO_4$, or passed through a phase-separator using ISOLUTE Phase Separator, and workup procedures were carried out using traditional phase separating techniques. When a drying agent such as e.g. $MgSO_4$ or $Na_2SO_4$ is used for drying an organic layer, it is understood that said organic layer is filtered before concentration of said layer.

(vi), evaporations were carried out either by rotary evaporation in vacuo or in a GENEVAC HT-4/EZ-2 or BIOTAGE V10;

(vii) unless otherwise stated, flash column chromatography was performed on straight phase silica, using either MERCK Silica Gel (Art. 9385) or prep-packed cartridges such as BIOTAGE SNAP cartridges (40-63 μm silica, 4-330 g), BIOTAGE Sfar Silica HC D cartridges (20 μm, 10-100 g), INTERCHIM PURIFLASH cartridges (25 μm, 4-120 g), INTERCHIM PURIFLASH cartridges (50 μm, 25-330 g), GRACE GRACERESOLV Silica Flash Cartridges (4-120 g) or AGELA Flash Colum Silica-CS cartridges (80-330 g), or on reversed phase silica using AGELA TECHNOLOGIES C-18, spherical cartridges (20-35 μm, 100 A, 80-330 g), manually or automated using a GRACE REVELERIS X2 Flash system or similar system;

(viii) preparative reverse phase HPLC and preparative reverse phase SFC were performed using standard HPLC and SFC instruments, respectively, equipped with either a MS and/or UV triggered fraction collecting instrument, using either isocratic or a gradient of the mobile phase as described in the experimental section and using one of the following methods: PrepMethod A: The compound was purified by preparative HPLC on a WATERS SUNFIRE C18 ODB column (5 μm, 150×19 mm ID) using a gradient of MeCN in $H_2O$/FA (0.1 M) as mobile phase; PrepMethod B: The compound was purified by preparative HPLC on a XBRIDGE C18 ODB column (5 μm, 150×30 mm ID) using a gradient of MeCN in $H_2O/NH_4HCO_3$ (10 mM) as mobile phase; PrepMethod C: The compound was purified by preparative HPLC on a KROMASIL C8 column (10 μm, 250×20 mm ID) using a gradient of MeCN in $H_2O$/MeCN/FA (95/5/0.2) as mobile phase; PrepMethod D: The compound was purified by preparative HPLC on a KROMASIL C8 column (10 μm, 250×50 mm ID) using a gradient of MeCN in $H_2O$/MeCN/FA (95/5/0.2) as mobile phase; PrepMethod E: The compound was purified by preparative HPLC on a WATERS SUNFIRE C18 ODB column (5 μm, 150×30 mm ID) using a gradient of MeCN in $H_2O$/FA (0.1 M) as mobile phase; PrepMethod F: The compound was purified by preparative HPLC on a Waters HSS C18 column (5 μm, 100×10 mm ID) using a gradient of MeCN in $H_2O$/FA (0.1 M) as mobile phase; PrepMethod G: The compound was purified by preparative HPLC on a WATERS SUNFIRE C18 column (5 μm, 100×10 mm ID) using a gradient of MeCN in $H_2O$/FA (0.1 M, pH3) as mobile phase; PrepMethod H: The compound was purified by preparative HPLC on a WATERS XBRIDGE C18 column (5 μm, 100×10 mm ID) using a gradient of MeCN in a $H_2O/NH_3$ (0.2%, pH 10) as mobile phase; PrepMethod I: The compound was purified by preparative HPLC on a WATERS XSELECT CSH Fluoro Phenyl column, (5 μm, 100×10 mm ID) using a gradient of MeCN in $H_2O$/FA (0.1 M) as mobile phase; PrepMethod J: The compound was purified by preparative HPLC on a XBRIDGE C18 column (10 μm, 250×50 mm ID) using a gradient of MeCN in $H_2O$/MeCN/$NH_3$ (95/5/0.2) as mobile phase; PrepMethod K: The compound was purified by preparative HPLC on a XBRIDGE Prep OBD C18 column, (5 μm, 30×150 mm) using a gradient of MeCN in $H_2O$/FA (0.1%) as mobile phase; PrepMethod L: The compound was purified by preparative HPLC on a YMC-ACTUS TRIART C18 column, (5 μm, 30×250 mm) using a gradient of MeCN in $H_2O/NH_3$ (0.05%) as mobile phase; PrepMethod M: The compound was purified by preparative HPLC on a WATERS XSELECT CSH Fluoro Phenyl column, (5 μm, 100×10 mm ID) using a gradient of MeCN in $H_2O$/TFA (0.05%) as mobile phase; PrepMethod N: The compound was purified by preparative HPLC on a WATERS XSELECT CSH OBD column, (5 μm, 150×30 mm ID) using a gradient of MeCN in $H_2O$/FA (0.1%) as mobile phase; PrepMethod O: The compound was purified by preparative HPLC on a YMC-Actus Triart C18 ExRS column, (5 μm, 30×150 mm) using a gradient of MeCN in $H_2O/NH_4HCO_3$ (10 mM)+0.1% $NH_4OH$ as mobile phase; PrepMethod P: The compound was purified by preparative HPLC on a XBRIDGE C18 ODB column (5 μm, 250×19 mm ID) using a gradient of MeCN in $H_2O/NH_4HCO_3$ (10 mM)+0.1% $NH_4OH$ as mobile phase; PrepMethod Q: The compound was purified by preparative HPLC on a WATERS SUNFIRE C18 column (5 μm, 150×30 mm ID) using a gradient of MeCN in $H_2O$/FA (0.1 M) as mobile phase; PrepMethod R: The compound was purified by preparative HPLC on a XBRIDGE SHIELD RP18 OBD column (5 μm, 150×30 mm ID) using a gradient of MeCN in $H_2O/NH_4HCO_3$ (10 mM) as mobile phase; PrepMethod S: The compound was purified by preparative SFC on a Phenomenex Luna Hilic column (5 μm, 250×30 mm ID) using a gradient of MeOH/$NH_3$ (20 mM) in $CO_2$ as mobile phase; PrepMethod T: The compound was purified by preparative HPLC on a WATERS XSELECT CSH OBD column, (5 μm, 150×30 mm ID) using a gradient of MeCN in $H_2O$/FA (0.1 M) as mobile phase; PrepMethod U: The compound was purified by preparative SFC on a PHENOMENEX Luna Hilic column (5 μm, 250×30 mm ID) using a gradient of EtOH/FA (20 mM) in $CO_2$ as mobile phase; PrepMethod V: The compound was purified by preparative HPLC on a Waters Xselect CSH OBD column, (5 μm, 250×19 mm ID) using a gradient of MeCN in $H_2O$/FA (0.1 M) as mobile phase; PrepMethod X: The compound was purified by preparative HPLC on a XBridge™ C18 ODB column (5 μm, 250×30 mm ID) using a gradient of MeCN in $H_2O/NH_4HCO_3$ (10 mM)+0.1% $NH_4OH$ as mobile phase; PrepMethod Y: The compound was purified by preparative HPLC on a XBridge™ C18 ODB column (5 μm, 150×30 mm ID) using a gradient of MeCN in $H_2O/NH_4HCO_3$ (10 mM)+0.1% $NH_4OH$ as mobile phase; PrepMethod Z: The compound was purified by preparative HPLC on a XBridge™ C18 ODB column (5 μm, 150×30 mm ID) using a gradient of MeCN in $H_2O$/AcOH (0.1%) as mobile phase. SFC Prep Methods: PrepMethod SFC-A: The compound was purified by preparative SFC on a Waters™ BEH, (5 μm, 250×30 mm ID) using MeOH/$H_2O(NH_3$ 50 mM) (97/3) in $CO_2$ as mobile phase;

In some instances the compound may be dissolved in a solvent e.g. DMSO and filtered through a syringe filter prior to purification on preparative HPLC.

Relevant fractions were collected, combined and freeze-dried or evaporated to give the purified compound or relevant fractions were collected, combined and concentrated at reduced pressure, extracted with DCM or EtOAc, and the organic phase was dried either over $Na_2SO_4$ or by using a phase-separator, and then concentrated at reduced pressure to give the purified compound.

(ix) chiral preparative chromatography was carried out using HPLC or SFC on a standard HPLC or SFC instruments, respectively, and using either isocratic or gradient run with mobile phase as described below;

(x) yields, where present, are not necessarily the maximum attainable, and when necessary, reactions were repeated if a larger amount of the reaction product was required;

(xi) where certain compounds were obtained as an acid-addition salt, for example a mono-hydrochloride salt or a di-hydrochloride salt, the stoichiometry of the salt was based on the number and nature of the basic groups in the compound, the exact stoichiometry of the salt was generally not determined, for example by means of elemental analysis data;

(xii) in general, the structures of the end-products of the Formula (I) were confirmed by nuclear magnetic resonance (NMR) and/or mass spectral techniques; proton NMR chemical shift values were measured on the delta scale using BRUKER AVANCE III 300, 400, 500 and 600 spectrometers, operating at $^1H$ frequencies of 300, 400, 500 and 600 MHz, respectively. The experiments were typically recorded at 25° C. Chemical shifts are given in parts per million with the solvent as internal standard. Protons on heteroatoms such as NH and OH protons are only reported when detected in NMR and can therefore be missing. In certain instances, protons can be masked or partially masked by solvent peaks and will therefore either be missing and not reported or reported as multiplets overlapping with solvent. The following abbreviations have been used (and derivatives thereof, e.g. dd, doublet of doublets, etc.): s, singlet; d, doublet; t, triplet; q, quartet; m, multiplet; br, broad; qn, quintet; p, pentet. In some cases, the structures of the end-products of the Formula (I) might appear as rotamers in the NMR-spectrum, in which instances only peaks of the major rotamer are reported. In certain instances, the structures of the intermediates and/or the end-products of the Formula (I) might appear as rotamers in the NMR-spectrum, in which instances peaks of all rotamers are reported, and only the total number of protons are reported. The ratio of major vs minor rotamer is reported if known. Electrospray mass spectral data were obtained using a WATERS ACQUITY UPLC coupled to a WATERS single quadrupole mass spectrometer or similar equipment, acquiring both positive and negative ion data, and generally, only ions relating to the parent structure are reported; high resolution electrospray mass spectral data were obtained using a WATERS XEVO qToF mass spectrometer or similar equipment, coupled to a WATERS ACQUITY UPLC, acquiring either positive and negative ion data, and generally, only ions relating to the parent structure are reported;

(xiii) intermediates were not necessarily fully purified but their structures and purity were assessed by TLC, analytical HPLC/UPLC, analytical GCMS and/or NMR analysis and/or mass spectrometry;

(xiv) unless stated otherwise compounds containing an asymmetric carbon and/or sulfur atom were not resolved;

(xv) in general Examples and Intermediate compounds are named using CHEMDRAW PROFESSIONAL version 20.1.1.125 from PerkinElmer. CHEMDRAW PROFESSIONAL version 20.1.1.125 generates the names of chemical structures using the Cahn-Ingold-Prelog (CIP) rules for stereochemistry and follows IUPAC rules as closely as possible when generating chemical names. Stereoisomers are differentiated from each other by stereodescriptors cited in names and assigned in accordance with the CIP rules. A "rac-" prefix indicates that a compound is racemic.

(xvi) in addition to the ones mentioned above, the following abbreviations and units have been used:

AcOH Acetic acid
Aq Aqueous
Boc tert-butyloxycarbonyl
t-BuOH tert-Butanol
Brine Saturated aqueous sodium chloride solution
Calcd Calculated
CBz Benzyloxycarbonyl
COMU (1-Cyano-2-ethoxy-2-oxoethylidenaminooxy)dimethylamino-morpholino-carbenium hexafluorophosphate (CAS Registry Number 1075198-30-9)
18-Crown-6 1,4,7,10,13,16-hexaoxacyclooctadecane
DABAL-Me$_3$ CAS Registry Number 137203-34-0
DCM Dichloromethane
DEAD Diethyl azodicarboxylate
DIC Diisopropylmethanediimine
DIPEA N-ethyl-N-isopropyl-propan-2-amine
DMAP N,N-dimethylpyridin-4-amine
DMF N,N-dimethylformamide
DMSO Dimethyl sulfoxide
DPPA Diphenyl phosphorazidate
EDC 3-(((ethylimino)methylene)amino)-N,N-dimethyl-propan-1-amine
ESI Electrospray ionization
Et$_2$O Diethyl ether
EtOAc Ethyl acetate
EtOH Ethanol
eq equivalents
FA Formic acid
(g) gas
GC gas chromatography
HPLC High performance liquid chromatography
HATU (1-(Bis(dimethylamino)methylene]-1H-1,2,3-triazolo[4,5-b]pyridinium-3-oxo hexafluorophosphate
HOBt 1-hydroxybenzotriazole; hydrate
HRMS High resolution mass spectrometry
ID inner diameter
Lawesson's reagent 2,4-bis(4-Methoxyphenyl)-1,3,2,4-dithiadiphosphetane 2,4-disulfide
LiHMDS Lithium bis(trimethylsilyl)amide
LC Liquid chromatography
Me$_3$Al Trimethyl aluminum
MeCN Acetonitrile
MeI iodomethane
MeMgBr Methylmagnesium bromide
MeOH Methanol
MS Mass spectrometry
MTBE Methyl tert-butyl ether
m/z mass spectrometry peak(s)

NBS N-bromosuccinimide
NIS 1-Iodopyrrolidine-2,5-dione
NMR Nuclear magnetic resonance
PE petroleum ether
Pd-118 [1,1'-Bis(di-tert-butylphosphino)ferrocene]dichloropalladium(II)
Pd—C Palladium on charcoal
PPh$_3$ Triphenylphosphane
sat Saturated
SFC Supercritical fluid chromatography
TBTU 2-(1H-benzo[d][1,2,3]triazol-1-yl)-1,1,3,3-tetramethyluronium tetrafluoroborate
TEA Triethylamine
TFA Trifluoroacetic acid
THF Tetrahydrofuran
TLC Thin layer chromatography
UPLC ultra performance liquid chromatography
UV ultraviolet
Xphos Pd G3 (2-Dicyclohexylphosphino-2',4',6'-triisopropyl-1,1'-biphenyl)[2-(2'-amino-1,1'-biphenyl)]palladium(II) methanesulfonate Intermediate 1: Ethyl 5-(2,4,5-trifluoro-3-hydroxyphenyl)-1,2,4-oxadiazole-3-carboxylate

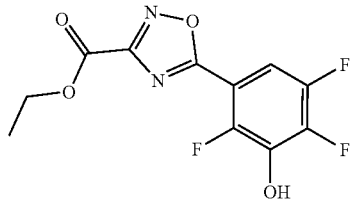 [SMILES: CCOC(=O)c1noc(-c2cc(F)c(F)c(O)c2F)n1]

EDC (43.5 g, 227.07 mmol) and HOBt (15.34 g, 113.53 mmol) were added to ethyl (Z)-2-amino-2-(hydroxyimino)acetate (15 g, 113.53 mmol), 2,4,5-trifluoro-3-hydroxybenzoic acid (21.81 g, 113.53 mmol) and NaHCO$_3$ (28.6 g, 340.60 mmol) in DMF (150 mL) under a N$_2$(g) atmosphere. The resulting solution was stirred at 100° C. for 1 h. The reaction mixture was filtered through CELITE, and the filtrate was concentrated, diluted with DCM (300 mL) and washed with water (300 mL). The organic layer was dried over Na$_2$SO$_4$, filtered and evaporated. The crude product was purified by flash chromatography on a C18 column (gradient 50-60% MeCN in water (FA)) to give the title compound (7.0 g, 21%) as a white solid; MS (ESI) m/z [M+H]$^+$ 289; $^1$H NMR (300 MHz, DMSO-d$_6$) δ 1.36 (t, 3H), 4.45 (m, 2H), 7.28-7.81 (m, 1H), 11.70 (s, 1H).

Alternative Synthesis of Intermediate 1: SOCl$_2$ (1.7 mol eq, 0.96 L) was added to a mixture of 2,4,5-trifluoro-3-hydroxybenzoic acid (1.45 kg, 7.55 mol) and toluene (14.5 L) at 75-85° C. over 4 hours. The temperature was adjusted to 85-95° C., and the mixture stirred for 20 h. The mixture was concentrated to about 4 L at below 50° C. and then charged with toluene (14.5 L). This process of concentration and charging with toluene was repeated twice, before the resulting mixture was charged with toluene (14.5 L) and concentrated to about 3 L at below 50° C. to give a solution of 2,4,5-trifluoro-3-hydroxybenzoyl chloride. This was added to a mixture of ethyl 2-amino-2-(hydroxyimino)acetate (966.4 g, 7.31 mol, 1.05 eq), pyridine (2629.9 g, 33.25 mol, 5 eq) and MeCN (5.6 L) at 20-30° C. The resulting mixture was stirred at 20-30° C. for 0.5-1.5 h before being heated to 55-65° C. The mixture was then heated with a residence time of 45 minutes in flow at a temperature of 140° C. (see FIG. 1). After heating, the reaction mixture was quenched in flow with a mixture of EtOH (1.4 L) and water (1.4 L) pre-heated to a temperature of 20-30° C. At the end of the flow reaction, the resulting mixture was adjusted to pH 2-3 with 2 M HCl (13.72 L) over 6 h at 5-15° C. EtOAc (14 L) was added and the mixture stirred for 2 h at 20-30° C. The organic was then separated and the aqueous extracted with EtOAc (14 L). The combined organics were then concentrated under vacuum at 35-45° C. before being charged with EtOH (14 L). The process of concentration and charging with EtOH was repeated and then the mixture was concentrated under vacuum at 35-45° C. The mixture was then treated with water (12.6 L) over 2 hours at 20-30° C. and then stirred at 20-30° C. for 16 h. The resulting mixture was filtered and rinsed with water (2.8 L) and n-heptane (4.2 L) and the resulting filter cake dried at 30-40° C. for 16 h to give the title compound as a solid (1.52 kg @95.28% w/w, 1.45 Kg @ 100% w/w, 5.03 mol, 66.6% yield across the 2 stages).

Intermediate 2: 5-(2,4,5-Trifluoro-3-hydroxyphenyl)-1,2,4-oxadiazole-3-carboxylic acid

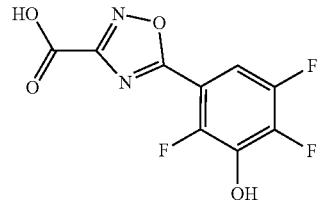 [SMILES: O=C(O)c1noc(-c2cc(F)c(F)c(O)c2F)n1]

LiOH (0.482 g, 20.13 mmol) dissolved in water (10 mL) was added to ethyl 5-(2,4,5-trifluoro-3-hydroxyphenyl)-1,2,4-oxadiazole-3-carboxylate Intermediate 1 (1.45 g, 5.03 mmol) in THF (10 mL) at 20° C. The solution was stirred for 2 h at rt and then at 60° C. for 1 h. The THF was evaporated off and the water phase was cooled to 0° C., acidified with 1 M HCl, and then freeze dried overnight. The white solid was dissolved in EtOAc and washed with a small amount of 1 M HCl. The organic layer was passed through a phase separator and concentrated to give the title compound (1.08 g, 83%) as a white beige solid; MS m/z (ESI) [M−H]$^−$ 259.0; $^1$H NMR (500 MHz, DMSO-d$_6$) δ 6.93-7.21 (1H, m), 10.60 (1H, s).

Intermediate 3: (R)-(3-Phenylpyrrolidin-1-yl)(5-(2,4,5-trifluoro-3-methoxyphenyl)thiophen-2-yl)methanone

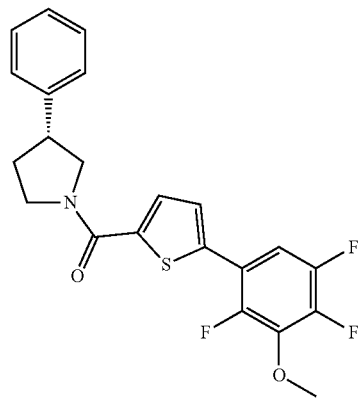 [SMILES: COc1c(F)c(F)cc(-c2ccc(C(=O)N3CC[C@H](c4ccccc4)C3)s2)c1F]

In a vial 5-(2,4,5-trifluoro-3-methoxyphenyl)thiophene-2-carboxylic acid Intermediate 23 (22 mg, 0.08 mmol), NaHCO$_3$ (20 mg, 0.24 mmol), HOBt (17 mg, 0.09 mmol) and EDC (25 mg, 0.13 mmol) were dissolved in DMF (0.4 mL) and stirred for 5 min. Then a solution of (R)-3-phenylpyrrolidine HCl (14 mg, 0.08 mmol) in DMF (0.4 mL) was added and the reaction mixture was stirred at rt over night. The reaction was quenched with sat NH$_4$Cl (aq, 2 mL) and the mixture was extracted with DCM (×3). The combined organic layers were washed with 1 M KHSO$_4$ and brine, passed through a phase separator and concentrated. The crude was purified by flash chromatography on silica (gradient: 10-50% EtOAc in heptane) to give the title compound (17 mg, 53%) as a white solid; MS (ESI) m/z [M+H]$^+$ 418.1.

Intermediate 4: Ethyl (S)—N-benzyl-N-(2-((tert-butoxycarbonyl)amino)butanoyl)glycinate

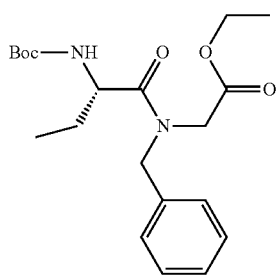

To a stirred solution of (S)-2-((tert-butoxycarbonyl)amino)butanoic acid (600 g, 3.0 mol) and ethyl benzylglycinate (600 g, 3.0 mol) in 5 L of DCM was added TEA (597 g, 6.0 mol) and TBTU (1043 g, 3.3 mol). The solution was stirred at rt overnight, and then diluted with 10% HCl (1 L). The organic layer was separated and washed with sat NaHCO$_3$ (1 L) and brine (1 L), dried over MgSO$_4$. The DCM was removed under vacuum, and the crude product was purified by column chromatography on silica (gradient: 0-10% EtOAc in PE) to give the title compound (1005 g, 90%) as a yellow liquid; MS (ESI) m/z [M+Na]$^+$ 401.1.

Intermediate 5: Ethyl (S)—N-benzyl-N-(2-((tert-butoxycarbonyl)amino)butyl)glycinate

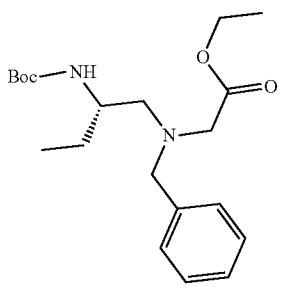 [SMILES: CCOC(=O)CN(Cc1ccccc1)C[C@H](CC)NC(=O)OC(C)(C)C]

The reaction was carried out in three parallel reactions. To a solution of ethyl (S)—N-benzyl-N-(2-((tert-butoxycarbonyl)amino)butanoyl)glycinate Intermediate 4 (357 g, 0.94 mol) in 2 L of anhydrous THF was added dropwise a solution of BH$_3$ (10 M, 240 mL) at 0° C. within 2 h and under a N$_2$(g) atmosphere. The reaction mixture was stirred at 35° C. overnight. The reaction was quenched with MeOH (100 mL) and water (500 mL), and the mixture was extracted with DCM (3×500 mL). The organic layer was combined, dried over MgSO$_4$, and evaporated under vacuum. The crude product was purified by column chromatography on silica (gradient: 0-5% EtOAc in PE) to give the title compound (110 g, 32%) as a yellow liquid; MS (ESI) m/z [M+H]$^+$ 365.1.

Intermediate 6: (S)-4-Benzyl-6-ethylpiperazin-2-one

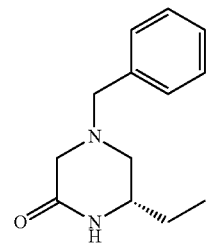 [SMILES: CC[C@H]1CN(Cc2ccccc2)CC(=O)N1]

To a solution of ethyl (S)—N-benzyl-N-(2-((tert-butoxycarbonyl)amino)butyl)glycinate Intermediate 5 (300 g, 0.82 mol) dissolved in dry DCM (500 mL) was added dropwise TFA (500 mL) at 0° C. The solution was stirred at 20° C. for 10 h. The solvent was removed and sat Na$_2$CO$_3$ (500 mL) was added, and the solution was stirred for another 10 h. The mixture was extracted with DCM (3×200 mL). The combined organic layers were dried over MgSO$_4$, and evaporated under vacuum to give the title compound (144 g, 80%) as a pale yellow solid; MS (ESI) m/z [M+H]$^+$ 218.9.

Intermediate 7: (S)-6-Ethylpiperazin-2-one

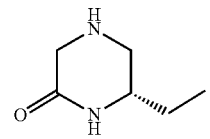

To a solution of (S)-4-benzyl-6-ethylpiperazin-2-one Intermediate 6 (87 g, 0.4 mol) in MeOH was added Pd/C (17 g, 16 mmol). The mixture was stirred at 50° C. under H$_2$(g) (50 psi) for 2 days. The mixture was filtered, and the filtrate was concentrated in vacuum to give the title compound (42 g, 82%) as a white solid; MS (ESI) m/z [M+H]$^+$ 129.1.

Intermediate 8: 4-(((2-Hydroxyethyl)amino)methyl)tetrahydro-2H-pyran-4-ol

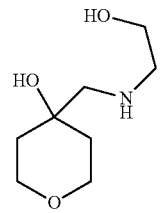

A solution of 1,6-dioxaspiro[2.5]octane (100 g, 0.877 mol) and 2-aminoethan-1-ol (64 g 1.05 mol) in dry EtOH (1 L) was stirred at 50° C. for 14 h. The mixture was concentrated in vacuum to give the title compound (110 g, 92%); MS (ESI) m/z [M+H]$^+$ 176.

Intermediate 9: Benzyl (2-hydroxyethyl)((4-hydroxytetrahydro-2H-pyran-4-yl)methyl)carbamate

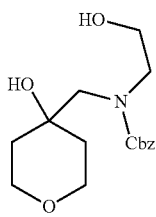

To crude 4-(((2-hydroxyethyl)amino)methyl)tetrahydro-2H-pyran-4-ol Intermediate 8 (180 g, 1.02 mol) and TEA (203 g, 2.01 mol) in dry DCM (2 L) was added benzyl carbonochloridate (183 g, 1.07 mol) dropwise at 0° C. After the addition, the reaction was stirred at 25° C. for 3 h. The reaction mixture was concentrated and purified by flash chromatography (PE:EtOAc, 2:1) to give the title compound (280 g, 88%); MS (ESI) m/z [M+Na]$^+$ 332.

Intermediate 10: Benzyl 1,9-dioxa-4-azaspiro[5.5]undecane-4-carboxylate

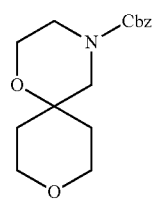 [SMILES: O=C(OCc1ccccc1)N1CCOC2(CCOCC2)C1]

Crude benzyl (2-hydroxyethyl)((4-hydroxytetrahydro-2H-pyran-4-yl)methyl)carbamate Intermediate 9 (140 g, 0.45 mol) and PPh$_3$ (140 g, 0.53 mol) were dissolved under a N$_2$(g) atmosphere in dry THF (1800 mL) and the mixture was stirred at 25° C. A solution of DEAD (94 g, 0.53 mol) in dry THF (200 mL) was added dropwise and the reaction mixture was stirred at 25° C. for 12 h. The reaction mixture was concentrated and purified by flash column chromatography (PE:EtOAc, 3:1) to give the title compound (100 g, 76%); $^1$H NMR (CDCl$_3$, 400 MHz) 7.29-7.33 (m, 5H); 5.11-5.12 (m, 2H); 4.08-4.16 (m, 6H); 3.47 (br s, 2H); 3.33 (br s, 2H); 2.01-2.02 (d, 2H); 1.71-1.74 (m, 2H).

Intermediate 11: 1,9-Dioxa-4-azaspiro[5.5]undecane

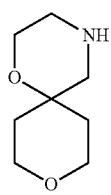

The benzyl 1,9-dioxa-4-azaspiro[5.5]undecane-4-carboxylate Intermediate 10 (60 g, 210 mmol) and Pd/C (10 g) in THF (1 L) was stirred at 25° C. under H$_2$(g) (40 psi) for 12 h. The suspension was filtered and the filtrates were concentrated to dryness to give crude product. EtOAc/HCl (100 mL) was added and the mixture was stirred at rt for 2 h. The solids were filtered off and dried under vacuum to give the title compound (22.5 g, 58%) as a HCl salt; MS (ESI) m/z [M+H]$^+$ 158.

Intermediate 12: tert-Butyl 4-(2-((5-bromopyridin-2-yl)oxy)ethyl)piperazine-1-carboxylate

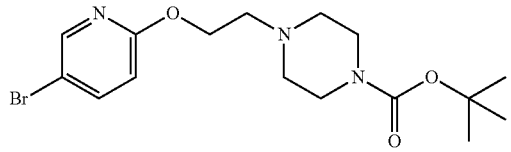 [SMILES: CC(C)(C)OC(=O)N1CCN(CCOc2ccc(Br)cn2)CC1]

5-Bromo-2-chloropyridine (8.36 g, 43.42 mmol), tert-butyl 4-(2-hydroxyethyl)piperazine-1-carboxylate (10 g, 43.42 mmol), KOH (4.87 g, 86.84 mmol) and 18-crown-6 (0.459 g, 1.74 mmol) were dissolved in toluene (150 mL) and heated at reflux for 4 h. The reaction mixture was cooled and 80% of the solvent was evaporated. The reaction was quenched with water (100 mL) and extracted with Et$_2$O (3×100 mL). The organic layer was dried over MgSO$_4$, filtered and evaporated to afford a yellow liquid. The crude gum was triturated with Et$_2$O and then evaporated to give the title compound (16.45 g, 98%) as an off white solid; MS (ESI) m/z [M+H]$^+$ 388.0.

Intermediate 13: 1-(2-((5-Bromopyridin-2-yl)oxy)ethyl)piperazine

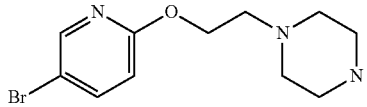 [SMILES: Brc1ccc(OCCN2CCNCC2)nc1]

tert-Butyl 4-(2-((5-bromopyridin-2-yl)oxy)ethyl)piperazine-1-carboxylate Intermediate 12 (16.6 g, 42.97 mmol) and 6.0 M HCl in propan-2-ol (91 mL, 3.00 mol) were stirred over night at 25° C. to afford a white solid. Et$_2$O (50 mL) was added to the reaction mixture and the precipitate was collected by filtration, washed with Et$_2$O and dried under vacuum to give the title compound (15 g, 97%) as a white solid; MS (ESI) m/z [M+H]$^+$ 287.9.

Intermediate 14: 2,4,5-Trifluoro-N,3-dimethoxy-N-methylbenzamide

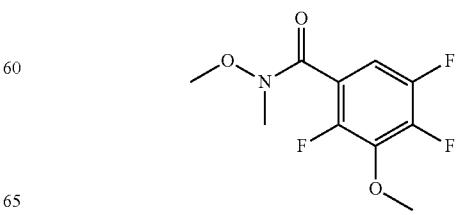

To 2,4,5-trifluoro-3-methoxybenzoic acid (1 g, 4.85 mmol) and HATU (2.214 g, 5.82 mmol) in DMF (14 mL) was added DIPEA (2.54 mL, 14.55 mmol) and N,O-dimethylhydroxylamine HCl (0.6 g, 6.15 mmol). The resulting solution was stirred at rt overnight. The reaction mixture was diluted with EtOAc and washed with 1 M HCl (aq), 1 M NaHCO$_3$ (aq), water and brine. The organic phase was separated using a phase separator then concentrated. The crude oil was purified by flash chromatography on silica (gradient: 30-70% EtOAc in heptane) to give the title compound (1.03 g, 85%) as a light yellow oil; MS (ESI) m/z [M+H]$^+$ 250.1.

Intermediate 15:
1-(2,4,5-Trifluoro-3-methoxyphenyl)ethan-1-one

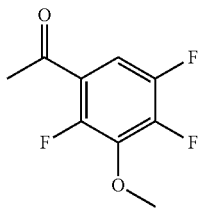

MeMgBr in THF (3.4 M, 5.31 mL, 18.06 mmol) was added dropwise to 2,4,5-trifluoro-N,3-dimethoxy-N-methylbenzamide Intermediate 14 (0.9 g, 3.61 mmol) in THF (12 mL) at 0° C. and under a N$_2$(g) atmosphere. The solution was stirred at rt for 1 h. The reaction was quenched when poured into an ice cooled mixture of 1 M HCl (aq, 15 mL) and THF (10 mL). The mixture was diluted with EtOAc. The layers were separated and the water layer was extracted with EtOAc. The combined organic layer was washed with brine, and evaporated to give the crude title compound (0.736 g, 100%) as a light yellow oil; $^1$H NMR (500 MHz, CDCl$_3$) δ 2.63 (3H, d), 4.07 (3H, t), 7.38-7.47 (1H, m).

Intermediate 16: Ethyl 2,4-dioxo-4-(2,4,5-trifluoro-3-methoxyphenyl)butanoate

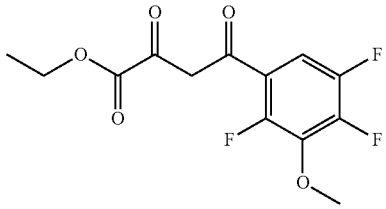 [SMILES: CCOC(=O)C(=O)CC(=O)c1cc(F)c(F)c(OC)c1F]

LiHMDS in toluene (1 M, 4 mL, 4.00 mmol) was added to 1-(2,4,5-trifluoro-3-methoxyphenyl)ethan-1-one Intermediate 15 (0.736 g, 3.61 mmol) in THF (10 mL) and cooled to −20° C. under a N$_2$(g) atmosphere. The mixture was stirred at −20° C. for 40 min. Diethyl oxalate (0.5 mL, 3.68 mmol) was added and the solution was stirred at rt for 40 min. The reaction was quenched by adding 1 M HCl (aq, 15 mL) and then EtOAc. The phases were separated and the organic layer was washed with water and then concentrated to give a yellow solid. The crude residue was purified by flash chromatography on silica (gradient: 30-50% EtOAc (containing 1% AcOH) in heptane) to give the title compound (0.924 g, 84%) as a beige solid; MS (ESI) m/z [M+H]$^+$ 305.0.

Intermediate 17: Ethyl 5-(2,4,5-trifluoro-3-methoxyphenyl)isoxazole-3-carboxylate

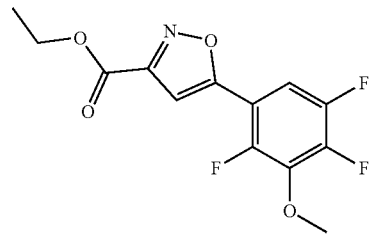 [SMILES: CCOC(=O)c1cc(-c2cc(F)c(F)c(OC)c2F)on1]

Ethyl 2,4-dioxo-4-(2,4,5-trifluoro-3-methoxyphenyl)butanoate Intermediate 16 (0.924 g, 3.04 mmol) was dissolved in EtOH (99%, 10 mL) and hydroxylamine HCl (0.488 g, 7.02 mmol) was added. The yellow solution was stirred at 80° C. for 3 h. The reaction mixture was cooled to rt and diluted with EtOAc, and washed once with 1 M HCl (aq) and once with water. The phases were separated using a phase separator and the organic phase was concentrated. The crude product was purified by flash chromatography on silica (gradient: 20-40% EtOAc in heptane) to give the title compound (0.585 g, 64%) as a white solid; MS (ESI) m/z [M+H]$^+$ 302.0.

Intermediate 18: ((2R,6S)-2,6-Dimethylmorpholino) (5-(2,4,5-trifluoro-3-methoxyphenyl)isoxazol-3-yl) methanone

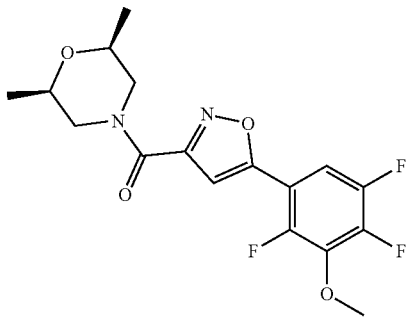 [SMILES: COc1c(F)c(F)cc(-c2cc(C(=O)N3C[C@@H](C)O[C@@H](C)C3)no2)c1F]

(2R,6S)-2,6-Dimethylmorpholine (0.102 g, 0.89 mmol) was dissolved in dry toluene (1 mL) and Me$_3$Al in toluene (2 M, 0.830 mL, 1.66 mmol) was added dropwise at rt under N$_2$(g) atmosphere. The resulting clear solution was stirred at rt for 45 min. The above solution was added dropwise at rt to a stirred solution of ethyl 5-(2,4,5-trifluoro-3-methoxyphenyl)isoxazole-3-carboxylate Intermediate 17 (0.2 g, 0.66 mmol) in toluene (1.3 mL) under N$_2$(g) atmosphere. The solution was heated to 60° C. for 20 h. Tartaric acid (30%, aq, 5 mL) was added dropwise until 2 clear phases appeared. The mixture was extracted with EtOAc. The phases were separated. The water phase was extracted again with EtOAc. The organic phases were combined and concentrated. The residue was purified by preparative HPLC, PrepMethod D (gradient: 15-65%) to give the title compound (143 mg, 58%) as an yellow oil that became a solid when standing; MS (ESI) m/z [M+H]+ 371.2.

Intermediate 19: Methyl 2-(2-(4-fluoro-3-hydroxybenzoyl)hydrazineyl)-2-oxoacetate

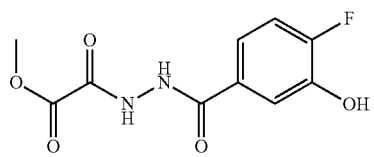 [SMILES: COC(=O)C(=O)NNC(=O)c1ccc(F)c(O)c1]

Methyl 2-chloro-2-oxoacetate (5.60 mL, 60.8 mmol) was added dropwise to 4-fluoro-3-hydroxybenzohydrazide, WO2009105214, (6.9 g, 40.55 mmol) in 1,4-dioxane (200 mL) and THF (200 mL) at 5° C. and under a $N_2$(g) atmosphere. The resulting mixture was stirred at 25° C. for 0.5 h. The solvent was removed under reduced pressure to afford the title compound (10.20 g, 98%) as a white solid; MS (ESI) m/z [M+H]+ 257.

Intermediate 20: Methyl 5-(4-fluoro-3-hydroxyphenyl)-1,3,4-oxadiazole-2-carboxylate

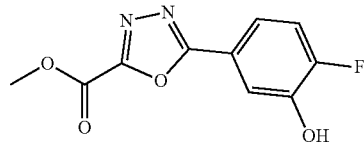 [SMILES: COC(=O)c1nnc(-c2ccc(F)c(O)c2)o1]

A mixture of methyl 2-(2-(4-fluoro-3-hydroxybenzoyl)hydrazineyl)-2-oxoacetate Intermediate 19 (10 g, 39.03 mmol) in $POCl_3$ (150 mL) was stirred at 90° C. for 1 h. The solvent was removed under reduced pressure and water was added to the residue. The precipitate was collected by filtration, washed with water (20 mL) and dried under vacuum to afford the title compound (6.40 g, 69%) as a light brown solid; MS (ESI) m/z [M+H]+ 239.

Intermediate 21: 1,2,4-Trifluoro-5-iodo-3-methoxybenzene

An oven-dried 20 mL microwave vial was charged with 2,4,5-trifluoro-3-methoxybenzoic acid (0.5 g, 2.43 mmol), $K_3PO_4$ (0.515 g, 2.43 mmol) and iodine (2.463 g, 9.70 mmol) and a stirring bar. The vial was capped, evacuated and backfilled with $N_2$(g). Anhydrous MeCN (8 mL) was added and the reaction mixture was heated at 120° C. for 23 h. The reaction mixture was allowed to reach rt and 15% $Na_2SO_3$ (aq) was added until the dark colour disappeared. A second batch was prepared as described above and the reaction mixtures were combined and extracted with DCM (×3). The combined organic layer was washed with 8% $Na_2CO_3$ (aq), passed through a phase separator and concentrated. The residue was purified by straight phase flash chromatography on silica (gradient: 5-17% MTBE in pentane) to give the title compound (0.841 g, 60%) as a nearly colourless oil; MS (EI) m/z [M]+ 288.0.

Intermediate 22 tert-Butyl 5-(2,4,5-trifluoro-3-methoxyphenyl)thiophene-2-carboxylate

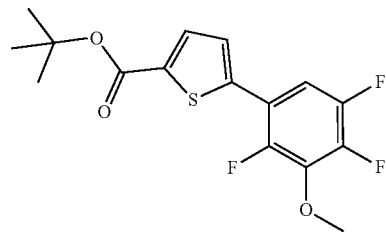 [SMILES: COc1c(F)c(F)cc(-c2ccc(C(=O)OC(C)(C)C)s2)c1F]

A 20 mL microwave vial was charged with 1,2,4-trifluoro-5-iodo-3-methoxybenzene Intermediate 21 (407 mg, 1.41 mmol), EtOH (12 ml), (5-(tert-butoxycarbonyl)thiophen-2-yl)boronic acid (322 mg, 1.41 mmol), Pd-118 (138 mg, 0.21 mmol), 2 M $K_2CO_3$ (aq) (2.12 ml, 4.24 mmol) and a stirring bar. The vial was capped, evacuated and backfilled with $N_2$(g) (×3) and then heated at 80° C. for 1.5 h. EtOAc and water was added and the mixture was washed with 8% $NaHCO_3$ (aq). The aqueous layer was extracted with EtOAc and the combined organic layers were passed through a phase separator and concentrated. The residue was purified by straight phase flash chromatography on silica (gradient: 0-30% EtOAc in heptane). Fractions containing the title compound were pooled and concentrated, and the residue was dissolved in MTBE (ca 10 mL) and treated with SILIAMET S THIOL (1 g, loading: 1.4 mmol/g) at 40° C. for 30 min. The mixture was filtered and the solid was washed with MTBE. The combined filtrates were concentrated and the residue was purified by preparative HPLC, PrepMethod J, (gradient: 50-100%) to give the title compound (176 mg, 36%); $^1$H NMR (500 MHz, $CDCl_3$) δ 1.59 (9H, s), 4.08 (3H, d), 7.13 (1H, ddd), 7.34 (1H, dd), 7.69 (1H, dd).

Intermediate 23: 5-(2,4,5-Trifluoro-3-methoxyphenyl)thiophene-2-carboxylic acid

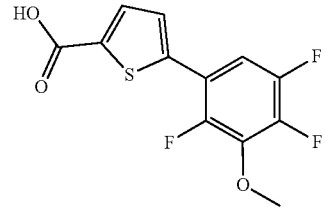 [SMILES: COc1c(F)c(F)cc(-c2ccc(C(=O)O)s2)c1F]

TFA (0.5 mL) was added to a solution of tert-butyl 5-(2,4,5-trifluoro-3-methoxyphenyl)thiophene-2-carboxylate Intermediate 22 (167 mg, 0.48 mmol) in DCM (1 mL) and the solution was stirred at rt for 1.5 h during which a precipitate formed. Volatiles were removed in vacuo and the crude was further azeotroped with MeCN (×3) to give the title compound (137 mg, 98%) as an off-white solid; MS m/z (ESI) [M−H]⁻ 287.1.

Intermediate 24: ((2R,6S)-2,6-Dimethylmorpholino) (5-(2,4,5-trifluoro-3-methoxyphenyl)thiophen-2-yl) methanone

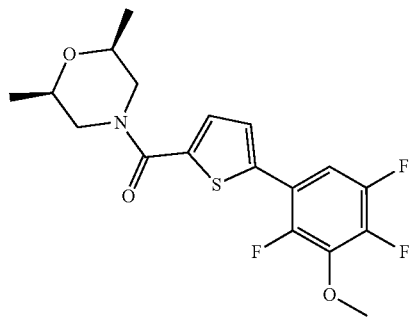 [SMILES: COc1c(F)c(F)cc(-c2ccc(C(=O)N3C[C@@H](C)O[C@@H](C)C3)s2)c1F]

HATU (206 mg, 0.54 mmol) was added to a stirred solution of 5-(2,4,5-trifluoro-3-methoxyphenyl)thiophene-2-carboxylic acid Intermediate 23 (130 mg, 0.45 mmol) and DIPEA (0.236 mL, 1.35 mmol) in a mixture of MeCN (3 mL) and EtOAc (3 mL) and the resulting solution was stirred at rt for 2-3 min. (2R,6S)-2,6-Dimethylmorpholine (0.074 mL, 0.59 mmol) was added and the reaction mixture was stirred at rt for 30 min. The reaction solution was diluted with EtOAc and washed sequentially with sat Na₂CO₃ (aq) and water. The organic layer was passed through a phase separator and concentrated. The residue was purified by preparative HPLC, PrepMethod J, (gradient: 40-85%). The fractions containing the title compound were pooled and concentrated to near dryness and then partitioned between DCM and water using a phase separator. The organic layer was concentrated to give the title compound (145 mg, 83%) as a solid; MS m/z (ESI) [M+H]⁺ 386.2.

Intermediate 25: tert-Butyl (1-cyclohexyl-1H-pyrazol-5-yl)carbamate

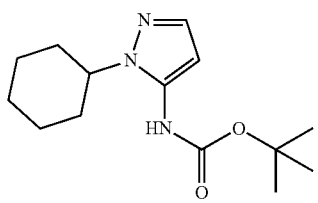 [SMILES: CC(C)(C)OC(=O)Nc1ccnn1C1CCCCC1]

DPPA (2267 mg, 8.24 mmol) followed by TEA (2296 µl, 16.47 mmol) were added slowly to a stirred solution of 1-cyclohexyl-1H-pyrazole-5-carboxylic acid (800 mg, 4.12 mmol) in t-BuOH (10 mL) at 15° C. The resulting solution was stirred at 80° C. for 16 h under a N₂(g) atmosphere. The solvent was removed under reduced pressure and the residue was purified by reversed phase flash chromatography on a C18 column, (gradient: 6-59% MeCN in water) and then by preparative HPLC, PrepMethod Q, (gradient: 48-60%) to afford the title compound (0.352 g, 32%) as a white solid; MS m/z (ESI) [M+H]⁺ 266.

Intermediate 26: tert-Butyl (1-cyclohexyl-1H-pyrazol-5-yl)(methyl)carbamate

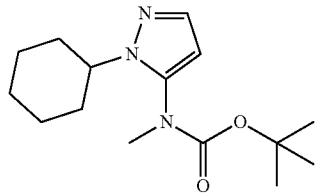 [SMILES: CN(C(=O)OC(C)(C)C)c1ccnn1C1CCCCC1]

NaH (60%, 249 mg, 6.22 mmol) was added to tert-butyl (1-cyclohexyl-1H-pyrazol-5-yl)carbamate Intermediate 25 (330 mg, 1.24 mmol) in DMF (4 mL) at 0° C. and the reaction mixture was stirred at rt for 1 h. MeI (0.101 mL, 1.62 mmol) was added and the reaction mixture was stirred at 25° C. for 1 h. The reaction was quenched by addition of cooled 2 M NH₄Cl (aq, 30 mL, 60 mmol) at 10° C. The reaction mixture was concentrated and diluted with EtOAc (50 mL), and then washed with sat NH₄Cl (3×50 mL). The organic layer was dried over Na₂SO₄, filtered and evaporated to afford the title compound (0.340 g, 98%) as a yellow solid; 1H NMR (300 MHz, DMSO-d6) δ 1.11-1.45 (11H, m), 1.61-1.88 (7H, m), 3.05 (3H, s), 3.46-3.63 (1H, m), 3.72-3.84 (1H, m), 6.09 (1H, d), 7.40 (1H, d).

Intermediate 27: 1-Cyclohexyl-N-methyl-1H-pyrazol-5-amine

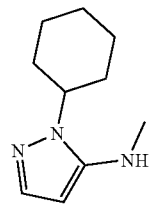

4 M HCl in 1,4-dioxane (3 mL, 12 mmol) was added to tert-butyl (1-cyclohexyl-1H-pyrazol-5-yl)(methyl)carbamate Intermediate 26 (340 mg, 1.22 mmol) in 1,4-dioxane (3 mL) at 25° C. The resulting solution was stirred at 25° C. for 5 h. The solvent was removed under reduced pressure to afford the title compound (0.250 g, 95%) as a yellow oil; MS m/z (ESI) [M+H]⁺ 180.

Intermediate 28: tert-Butyl 3-(4-fluoro-3-methoxyphenyl)isoxazole-5-carboxylate

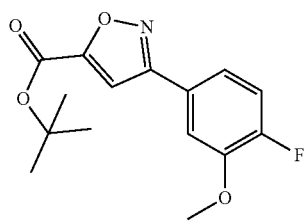 [SMILES: COc1cc(-c2cc(C(=O)OC(C)(C)C)on2)ccc1F]

tert-Butyl propiolate (373 mg, 2.96 mmol) was added to a mixture of 4-fluoro-3-methoxybenzaldehyde oxime (200 mg, 1.18 mmol), KCl (88 mg, 1.18 mmol) and OXONE (1090 mg, 1.77 mmol) in MeCN (2 mL) and H₂O (2 mL) cooled to 0° C. The temperature was allowed to reach rt and the resulting suspension was stirred at 10° C. for 15 h. The reaction mixture was filtered through CELITE. The process was repeated 17 times using a total of 21.4 mmol 4-fluoro-3-methoxybenzaldehyde oxime. The combined filtrates were concentrated under reduced pressure and the residue was purified by reversed phase flash chromatography on a C18 column, (gradient: 16-63% MeCN in H₂O) to afford the title compound (0.397 g, 6%) as a light brown solid; MS m/z (ESI) [M+H]⁺ 294.

Intermediate 29: 3-(4-Fluoro-3-methoxyphenyl)isoxazole-5-carboxylic acid

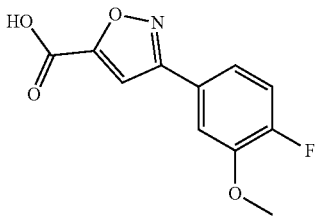 [SMILES: COc1cc(-c2cc(C(=O)O)on2)ccc1F]

TFA (5 mL, 64.90 mmol) was added to tert-butyl 3-(4-fluoro-3-methoxyphenyl)isoxazole-5-carboxylate Intermediate 28 (390 mg, 1.33 mmol) in DCM (10 mL) at 15° C. The resulting solution was stirred at 15° C. for 2.5 h. The solvent was removed under reduced pressure to afford the title compound (0.325 g, 99%) as a beige solid; MS m/z (ESI) [M+H]⁺ 238.

Intermediate 30: N-(1-Cyclohexyl-1H-pyrazol-5-yl)-3-(4-fluoro-3-methoxyphenyl)-N-methylisoxazole-5-carboxamide

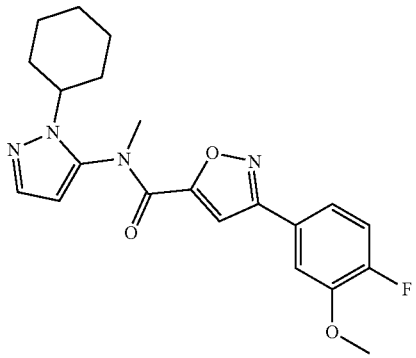 [SMILES: COc1cc(-c2cc(C(=O)N(C)c3ccnn3C3CCCCC3)on2)ccc1F]

DIC (215 μl, 1.38 mmol) was added slowly to a stirred solution of 3-(4-fluoro-3-methoxyphenyl)isoxazole-5-carboxylic acid Intermediate 29 (170 mg, 0.69 mmol), TFA (170 mg, 0.69 mmol) and 1-cyclohexyl-N-methyl-1H-pyrazol-5-amine Intermediate 27 (148 mg, 0.83 mmol) in DMF (2 mL) at 15° C. The resulting solution was stirred at 80° C. for 16 h. The reaction mixture was diluted with water (20 mL), and extracted with EtOAc (3×50 mL). The organic layers were combined and washed with sat brine (10×20 mL), dried over Na₂SO₄, filtered and evaporated. The residue was purified by preparative TLC (EtOAc:PE, 1:2) and then by reversed phase flash chromatography on a C18 column (gradient: 0-69% MeCN in water) to afford the title compound (0.109 g, 40%) as a colourless oil which solidified on standing; MS m/z (ESI) [M+H]⁺ 399.

Intermediate 31: (3-(4-Fluoro-3-methoxyphenyl)isoxazol-5-yl)(3-phenylpyrrolidin-1-yl)methanone

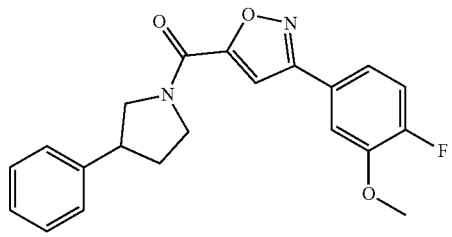 [SMILES: COc1cc(-c2cc(C(=O)N3CCC(c4ccccc4)C3)on2)ccc1F]

DIPEA (255 μl, 1.46 mmol) was added to 3-(4-fluoro-3-methoxyphenyl)isoxazole-5-carboxylic acid Intermediate 29 (120 mg, 0.49 mmol), 3-phenylpyrrolidine (86 mg, 0.58 mmol) and HATU (370 mg, 0.97 mmol) in DMF (2.5 mL) at 15° C. The resulting solution was stirred at 15° C. for 2 h. The reaction mixture was diluted with sat NaHCO₃ (aq, 20 mL) and extracted with EtOAc (3×50 mL). The combined organic layers were washed sequentially with sat brine (5×20 mL) and water (20 mL). The organic layer was dried over Na₂SO₄, filtered and evaporated and the residue was purified by preparative TLC (EtOAc:PE, 1:1), to afford the title compound (0.119 g, 67%) as a beige solid; MS m/z (ESI) [M+H]⁺ 367.

Intermediate 32: Ethyl 4-(4-fluoro-3-hydroxyphenyl)-2,4-dioxobutanoate

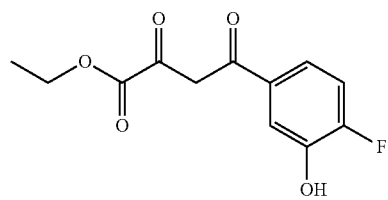 [SMILES: CCOC(=O)C(=O)CC(=O)c1ccc(F)c(O)c1]

LiHMDS in THF (1 M, 14.27 ml, 14.27 mmol) was added dropwise at −20° C. to 1-(4-fluoro-3-hydroxyphenyl)ethan-1-one (1.0 g, 6.49 mmol) in THF (15 mL) and the reaction mixture was stirred at −20° C. for 1 h. Diethyl oxalate (2.84 g, 19.46 mmol) was added and the reaction mixture was stirred for 2 h at rt. The reaction was quenched by addition of 2 M HCl (10 mL). The reaction mixture was diluted with EtOAc (150 ml) and washed with 2 M HCl (2×50 ml). The organic layer was dried over Na₂SO₄, filtered and evaporated to afford the title compound (1.50 g, 91%) as a solid; 1H NMR (300 MHz, CDCl₃) δ 15.17 (s, 1H), 7.70 (dd, 1H), 7.58 (ddd, 1H), 7.22 (dd, 1H), 7.04 (s, 1H), 5.56 (s, 1H), 4.43 (q, 2H), 1.44 (t, 3H).

Intermediate 33: Ethyl 5-(4-fluoro-3-hydroxyphenyl)isoxazole-3-carboxylate

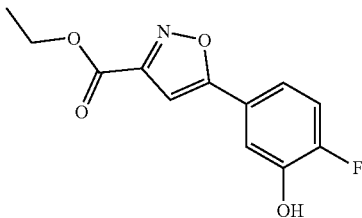 [SMILES: CCOC(=O)c1cc(-c2ccc(F)c(O)c2)on1]

A mixture of hydroxylamine HCl (274 mg, 3.94 mmol) and ethyl 4-(4-fluoro-3-hydroxyphenyl)-2,4-dioxobutanoate Intermediate 32 (500 mg, 1.97 mmol) in AcOH (20 mL) was stirred for 2 h at 100° C. The solvent was removed under reduced pressure and the residue was diluted with EtOAc (50 mL) and washed with sat NaHCO$_3$ (2×20 mL). The organic layer was dried over Na$_2$SO$_4$, filtered and concentrated. The residue was washed with Et$_2$O (50 mL) and dried to afford the title compound (0.150 g, 30%) as a light brown solid; MS m/z (ESI) [M+H]$^+$ 252.

Intermediate 34: 5-(4-Fluoro-3-hydroxyphenyl)isoxazole-3-carboxylic acid

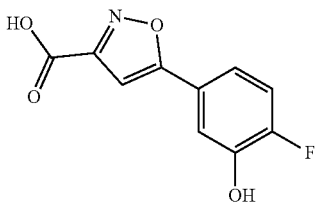 [SMILES: O=C(O)c1cc(-c2ccc(F)c(O)c2)on1]

A solution of NaOH (191 mg, 4.78 mmol) in water (2 mL) was added to ethyl 5-(4-fluoro-3-hydroxyphenyl)isoxazole-3-carboxylate Intermediate 33 (400 mg, 1.59 mmol) in EtOH (2 mL). The reaction mixture was stirred vigorously at 50° C. for 4 h. The pH of the reaction mixture was adjusted to 2 using 0.1 M HCl. The solvent was removed under reduced pressure and the crude product was purified by reversed phase flash chromatography on a C18 column, (gradient: 0-40% MeCN in water containing 0.1% FA) to afford the title compound (0.280 g, 79%) as an off-white solid; $^1$H NMR (300 MHz, DMSO-d$_6$) δ 7.23-7.35 (m, 2H), 7.39 (ddd, 1H), 7.48 (dd, 1H), 10.44 (s, 1H).

Intermediate 35: 3-Ethynyl-2,5,6-trifluorophenol

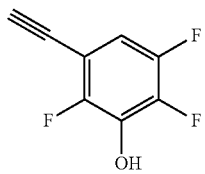

Dimethyl (1-diazo-2-oxopropyl)phosphonate (2.62 g, 13.63 mmol) was added to 2,4,5-trifluoro-3-hydroxybenzaldehyde (1.6 g, 9.09 mmol) and K$_2$CO$_3$ (3.77 g, 27.26 mmol) in MeOH (20 mL) at 20° C., and the resulting solution was stirred at 20° C. for 4 h. The reaction mixture was filtered through CELITE and the filtrate was concentrated under reduced pressure. The residue was purified by preparative TLC (MeOH:DCM, 1:15), to afford the title compound (0.450 g, 29%) as a yellow oil; MS m/z (ESI) [M−H]$^-$ 171.

Intermediate 36: Ethyl 5-(2,4,5-Trifluoro-3-hydroxyphenyl)isoxazole-3-carboxylate

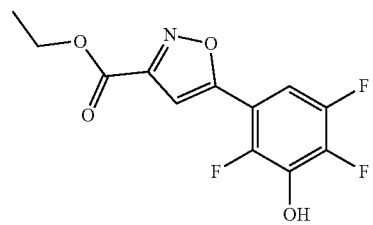 [SMILES: CCOC(=O)c1cc(-c2cc(F)c(F)c(O)c2F)on1]

TEA (1215 µl, 8.72 mmol) was added to 3-ethynyl-2,5,6-trifluorophenol Intermediate 35 (300 mg, 1.74 mmol) and ethyl (Z)-2-chloro-2-(hydroxyimino)acetate (1.32 g, 8.72 mmol) in DCM (5 mL) at 20° C., and the resulting solution was stirred at 45° C. for 70 h. The reaction mixture was concentrated, diluted with EtOAc (25 mL) and washed with water (25 mL). The organic layer was dried over Na$_2$SO$_4$, filtered and evaporated. The residue was purified by preparative TLC (MeOH:DCM, 1:15), to afford the title compound (0.300 g, 60%) as a yellow solid; $^1$H NMR (300 MHz, DMSO-d$_6$) δ 1.13-1.30 (m, 3H), 4.23-4.40 (m, 2H), 7.27 (d, 1H), 7.57 (m, 1H), 11.48 (s, 1H).

Intermediate 37: 5-(2,4,5-Trifluoro-3-hydroxyphenyl)isoxazole-3-carboxylic acid

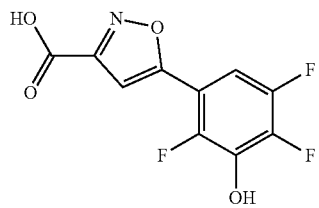 [SMILES: O=C(O)c1cc(-c2cc(F)c(F)c(O)c2F)on1]

LiOH (117 mg, 4.87 mmol) was added to ethyl 5-(2,4,5-trifluoro-3-hydroxyphenyl)isoxazole-3-carboxylate Intermediate 36 (280 mg, 0.97 mmol) in a mixture of EtOH (3 mL) and water (0.75 mL) at 20° C. The resulting solution was stirred at 20° C. for 3 h. The reaction mixture was adjusted to pH 7 using 0.1 M HCl. The solvent was removed under reduced pressure to afford the title compound (0.250 g, 99%) as a yellow solid; MS m/z (ESI) [M−H]$^-$ 258.

Intermediate 38: Ethyl 5-(2-oxo-6-(trifluoromethyl)-1,2-dihydropyridin-4-yl)-1,2,4-oxadiazole-3-carboxylate

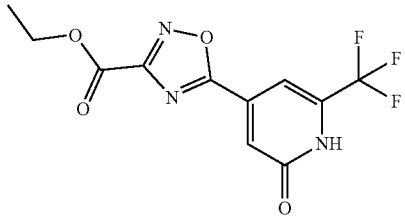 [SMILES: CCOC(=O)c1noc(-c2cc(C(F)(F)F)[nH]c(=O)c2)n1]

NaHCO₃ (1.908 g, 22.71 mmol) was added to 2-oxo-6-(trifluoromethyl)-1,2-dihydropyridine-4-carboxylic acid (1.568 g, 7.57 mmol), EDC (2.90 g, 15.14 mmol) and HOBt monohydrate (2.046 g, 15.14 mmol) in DMF (30 mL) at 25° C. The mixture was stirred at 25° C. for 10 min. A solution of ethyl (Z)-2-amino-2-(hydroxyimino)acetate (1 g, 7.6 mmol) in DMF (10 mL) was added and the resulting mixture was stirred at 25° C. for 30 min and then at 80° C. for 3 h. The reaction mixture was diluted with EtOAc (75 mL) and washed with water (4×300 mL). The organic layer was dried over Na₂SO₄, filtered and evaporated. The residue was purified by reversed phase flash chromatography on a C18 column, (gradient: 30-60% MeCN in water) to afford the title compound (0.940 g, 41%) as a white solid; MS m/z (ESI) [M+H]⁺ 304.

Intermediate 39: Ethyl 5-(4-fluoro-3-hydroxyphenyl)-1,2,4-oxadiazole-3-carboxylate

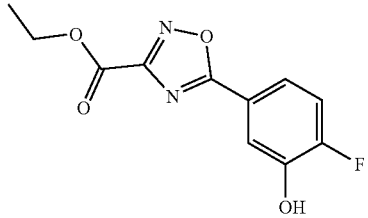 [SMILES: CCOC(=O)c1noc(-c2ccc(F)c(O)c2)n1]

EDC (2.90 g, 15.1 mmol) was added to ethyl (Z)-2-amino-2-(hydroxyimino)acetate (1.00 g, 7.57 mmol), 4-fluoro-3-hydroxybenzoic acid (1772 mg, 11.35 mmol) and NaHCO₃ (1.91 g, 22.7 mmol) in DMF (20 mL) and the resulting mixture was stirred at 100° C. for 2 h. The reaction mixture was diluted with EtOAc (750 mL) and extracted with EtOAc (3×250 mL). The combined organic layer was dried over Na₂SO₄, filtered and evaporated. The residue was purified by straight phase flash chromatography on silica, (gradient 40-50% EtOAc in PE) to afford the title compound (1.200 g, 63%) as a white solid; MS m/z (ESI) [M+H]⁺ 253.

Intermediate 40: 5-(4-Fluoro-3-hydroxyphenyl)-1,2,4-oxadiazole-3-carboxylic acid

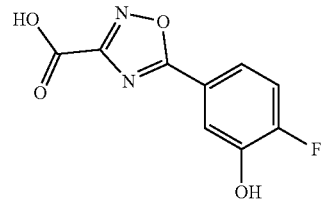 [SMILES: O=C(O)c1noc(-c2ccc(F)c(O)c2)n1]

A mixture of ethyl 5-(4-fluoro-3-hydroxyphenyl)-1,2,4-oxadiazole-3-carboxylate Intermediate 39 (470 mg, 1.86 mmol) and 2 M LiOH (aq, 9.32 mL, 18.6 mmol) in EtOH (10 mL) was stirred at 60° C. for 1 h. The organic solvent was removed under reduced pressure and the reaction mixture was adjusted to pH 5-6 with 2 M HCl. The mixture was diluted with H₂O (50 mL) and extracted with EtOAc (3×50 mL). The organic layer was dried over Na₂SO₄, filtered and evaporated to afford the title compound (0.400 g, 96%); MS m/z (ESI) [M+H]⁺ 225.

Intermediate 41: 2-(4-Fluoro-3-hydroxyphenyl)oxazole-5-carboxylic acid

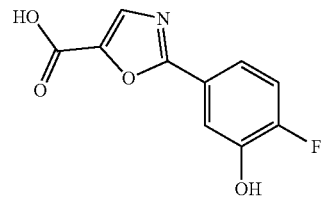 [SMILES: O=C(O)c1cnc(-c2ccc(F)c(O)c2)o1]

Methyl 2-bromooxazole-5-carboxylate (470 mg, 2.28 mmol), (4-fluoro-3-hydroxyphenyl)boronic acid (391 mg, 2.51 mmol), K₃PO₄ hydrate (1576 mg, 6.84 mmol) and XPhos Pd G3 (97 mg, 0.11 mmol) were added to a vial and the reaction mixture was flushed with N₂(g). THF (10 mL) and water (10 mL) were added and the reaction mixture was flushed with N₂(g) again. The reaction mixture was heated in a preheated heating block at 60° C. overnight. The reaction mixture was allowed to reach rt. Another batch was prepared as described above starting with methyl 2-bromooxazole-5-carboxylate (50 mg, 0.24 mmol). The combined reaction mixtures were diluted with EtOAc and sat NH₄Cl (aq). The aqueous layer was extracted with EtOAc (×3). The combined organic layers were dried over MgSO₄, filtered and concentrated under reduced pressure to give a residue. The aqueous layer was then acidified to pH ~1 using 2 M HCl, and extracted with EtOAc (×4), and the combined organic layers were dried over MgSO₄, filtered and concentrated under reduced pressure to give a second residue. The residues were combined and purified by straight phase flash chromatography on silica (gradient: 0-10% MeOH in EtOAc). The product containing fractions were combined, concentrated and dissolved in EtOAc. The organic layer was extracted with 0.1 M NaOH (aq). The aqueous layer was acidified using 2 M HCl and extracted with EtOAc (×3). The combined organic layers were dried over MgSO₄, filtered

Intermediate 42: 3-(4-Fluoro-3-hydroxyphenyl)-3-oxopropanenitrile

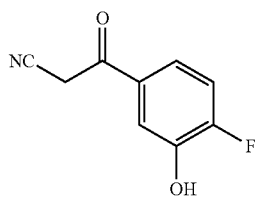 [SMILES: N#CCC(=O)c1ccc(F)c(O)c1]

MeCN (0.62 mL, 1.18 mmol) was added to a stirred suspension of NaH (60% in oil, 0.094 g, 2.35 mmol) in THF (1 mL), and the resulting mixture was stirred at rt for 10 min. Methyl 4-fluoro-3-hydroxybenzoate (0.100 g, 0.59 mmol) was added, and the resulting mixture was heated to 50° C. for 70 h. H$_2$O was added, the mixture was acidified with 3.8 M HCl and extracted with EtOAc. The organic layer was concentrated, and the residue was purified by straight phase flash chromatography on silica (gradient: 0-100% EtOAc in heptane) to give the title compound (0.075 g, 71%) as a white solid; MS (ESI) m/z [M–H]$^-$ 311.

Intermediate 43: Ethyl 4-cyano-5-(4-fluoro-3-hydroxyphenyl)isoxazole-3-carboxylate

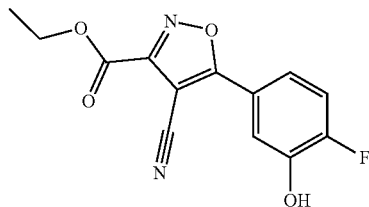 [SMILES: CCOC(=O)c1noc(-c2ccc(F)c(O)c2)c1C#N]

TEA (0.117 mL, 0.84 mmol) was added to a stirred suspension of 3-(4-fluoro-3-hydroxyphenyl)-3-oxopropanenitrile Intermediate 42 (0.075 g, 0.42 mmol) in EtOH (99.5%, 1.5 mL), and the resulting mixture was stirred at rt for 10 min. Ethyl (Z)-2-chloro-2-(hydroxyimino)acetate (0.063 g, 0.42 mmol) was added and the reaction mixture was stirred at rt for 18 h. The mixture was concentrated, and the residue was purified by straight phase flash chromatography on silica (gradient: 0-50% EtOAc in heptane) to give the title compound (0.056 g, 48%) as a white solid; MS (ESI) m/z [M–H]$^-$ 275.

Intermediate 44: Ethyl 4-cyano-5-(2,4,5-trifluoro-3-hydroxyphenyl)isoxazole-3-carboxylate

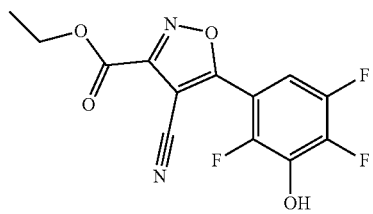 [SMILES: CCOC(=O)c1noc(-c2cc(F)c(F)c(O)c2F)c1C#N]

MeCN (1.53 mL, 29.1 mmol) was added to a stirred suspension of NaH (60% in oil, 2.33 g, 58.2 mmol) in THF (24 mL), and the resulting mixture was stirred at rt for 15 min. Methyl 2,4,5-trifluoro-3-hydroxybenzoate (3.00 g, 14.6 mmol) in THF (6 mL) was added dropwise, and the resulting mixture was heated to 50° C. for 20 h. H$_2$O (450 mL) was added, and the mixture was washed with heptane, acidified with 3.8 M HCl and extracted with EtOAc. The organic layer was concentrated, and the residue was suspended in EtOH (99.5%, 75 mL). TEA (4.66 mL, 33.4 mmol) was added, and the resulting mixture was stirred at rt for 10 min. Ethyl (Z)-2-chloro-2-(hydroxyimino)acetate (2.53 g, 16.7 mmol) was added and the mixture was stirred at rt for 18 h. The mixture was concentrated, and the residue was purified by straight phase flash chromatography on silica (gradient: 8-13% EtOAc in heptane). The impure product was combined with the crude product from another batch prepared as described above, starting with methyl 2,4,5-trifluoro-3-hydroxybenzoate (1.32 g, 6.14 mmol), and the combined crude product was resolidified from DCM to give the title compound as a white solid (0.900 g, 12%); MS (ESI) m/z [M–H]$^-$ 311; 1H NMR (500 MHz, CD$_3$OD) δ 7.37 (ddd, 1H), 4.53 (q, 2H), 1.47 (t, 3H).

Intermediate 45: N-Methyl-1-phenyl-1H-tetrazol-5-amine

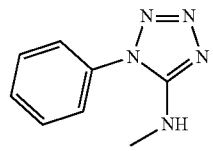

A solution of 5-chloro-1-phenyl-1H-tetrazole (2 g, 11.07 mmol) in methanamine (33% in EtOH, 2 mL) was stirred at 25° C. for 1 h. The solvent was removed under reduced pressure. The crude product was purified by flash chromatography on silica (gradient: 0-60% EtOAc in PE) to give the title compound (1.2 g, 61%) as a white solid; MS (ESI) m/z [M+H]$^+$=176.0

Intermediate 46: tert-Butyl (5-(2,4,5-trifluoro-3-methoxyphenyl)thiophene-2-carbonyl)prolinate

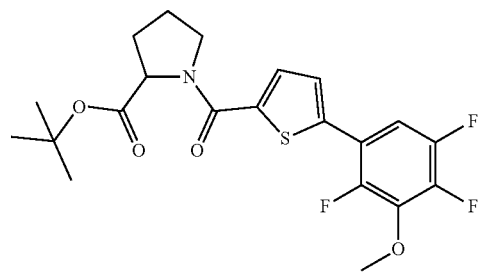 [SMILES: COc1c(F)c(F)cc(-c2ccc(C(=O)N3CCCC3C(=O)OC(C)(C)C)s2)c1F]

DIPEA (771 μL, 4.41 mmol) was added slowly to 5-(2,4,5-trifluoro-3-methoxyphenyl)thiophene-2-carboxylic acid Intermediate 23 (424 mg, 1.47 mmol), tert-butyl prolinate (252 mg, 1.47 mmol) and HATU (1398 mg, 3.68 mmol) in DMF (10 mL) cooled to 10° C. under N$_2$ atmosphere. The resulting solution was stirred at 20° C. for 14 h. The reaction

Intermediate 47: (5-(2,4,5-Trifluoro-3-methoxyphenyl)thiophene-2-carbonyl)proline

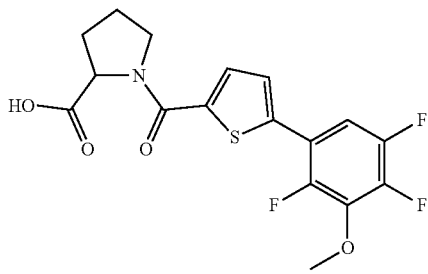 [SMILES: COc1c(F)c(F)cc(-c2ccc(C(=O)N3CCCC3C(=O)O)s2)c1F]

A solution of HCl (4 M in dioxane, 60.8 µL, 2 mmol) in 1,4-dioxane (0.5 mL) was added dropwise to a stirred solution of tert-butyl (5-(2,4,5-trifluoro-3-methoxyphenyl)thiophene-2-carbonyl)prolinate Intermediate 46 (120 mg, 0.27 mmol) in 1,4-dioxane (0.5 mL) cooled to 10° C. The resulting solution was stirred at 20° C. for 14 h. The solvent was removed under reduced pressure. The crude product was purified by crystallisation from EtOAc to give the title compound (0.105 g, 100%) as a white solid; MS (ESI) m/z [M+H]$^+$=386.0

Intermediate 48: N,N-Dimethyl-1-(5-(2,4,5-trifluoro-3-methoxyphenyl)thiophene-2-carbonyl)pyrrolidine-2-carboxamide

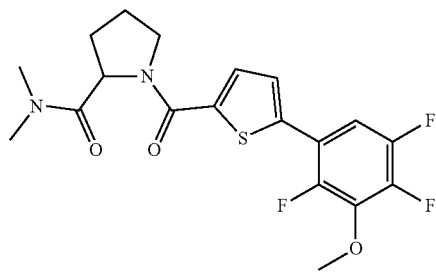 [SMILES: COc1c(F)c(F)cc(-c2ccc(C(=O)N3CCCC3C(=O)N(C)C)s2)c1F]

EDC (80 mg, 0.42 mmol) and HOBt (56.1 mg, 0.42 mmol) were added to (5-(2,4,5-trifluoro-3-methoxyphenyl)thiophene-2-carbonyl)proline Intermediate 47 (80 mg, 0.21 mmol), dimethylamine HCl (16.93 mg, 0.21 mmol) and DIPEA (109 µL, 0.62 mmol) in DMF (1 mL) at 20° C. under N$_2$ atmosphere. The resulting solution was stirred at 20° C. for 2 h. The reaction mixture was concentrated, diluted with EtOAc (20 mL) and washed sequentially with water (20 mL). The organic layer was dried over Na$_2$SO$_4$, filtered and evaporated. The residue was purified by preparative TLC (MeOH:DCM, 1:10) to give the title compound (0.060 g, 70%) as a white solid; MS (ESI) m/z [M+H]$^+$=413

Intermediate 49: tert-Butyl (Z)-4-((((1-amino-2-methylpropylidene)amino)oxy)carbonyl)-3,6-dihydropyridine-1(2H)-carboxylate

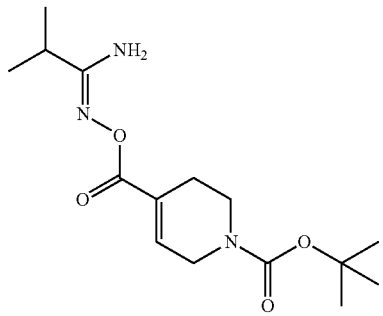 [SMILES: CC(C)/C(N)=N/OC(=O)C1=CCN(C(=O)OC(C)(C)C)CC1]

TBTU (524 mg, 1.63 mmol) was added to a solution of 1-(tert-butoxycarbonyl)-1,2,3,6-tetrahydropyridine-4-carboxylic acid (309 mg, 1.36 mmol) and DIPEA (0.521 mL, 2.99 mmol) in DCM (6 mL) at rt. The mixture was stirred for ~10 min after which a solution/mixture of (Z)—N'-hydroxyisobutyrimidamide (176 mg, 1.72 mmol) in DCM (2 mL) was added. The reaction mixture was stirred for 3 h at rt and was then washed with 8% NaHCO$_3$ (aq, 3×5 mL) using a phase separator. The organic layer was concentrated and the residue was purified by flash chromatography on silica (gradient: 0-75% EtOAc in heptane) to give the title compound (141 mg, 33%) as a white solid; MS (ESI) m/z [M+H]$^+$=312.4

Intermediate 50: tert-Butyl 4-(3-isopropyl-1,2,4-oxadiazol-5-yl)-3,6-dihydropyridine-1(2H)-carboxylate

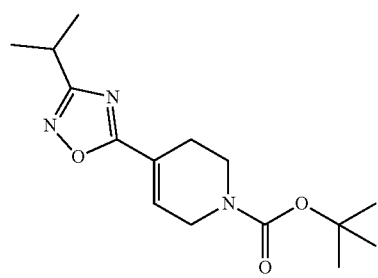 [SMILES: CC(C)c1noc(C2=CCN(C(=O)OC(C)(C)C)CC2)n1]

A solution of sodium acetate (0.784 mL, 2.15 mmol) in water (0.784 mL) was added to a mixture of tert-butyl (Z)-4-((((1-amino-2-methylpropylidene)amino)oxy)carbonyl)-3,6-dihydropyridine-1(2H)-carboxylate Intermediate 49 (610 mg, 1.96 mmol) in EtOH (6 mL) and the mixture was stirred at 86° C. for 5.5 h. The solvents were removed under reduced pressure and the residue was partitioned between DCM and water using a phase separator. The organic layer was concentrated under reduced pressure and the residue was purified by preparative HPLC, PrepMethod J (gradient: 40-80%) to give the title compound (339 mg, 59%); MS m/z (ESI) [M-tBu]$^+$=238.2

--- mixture was diluted with EtOAc (50 mL) and washed sequentially with sat brine (1×100 mL), sat NaHCO$_3$ (1×100 mL) and water (1×100 mL). The organic layer was dried over Na$_2$SO$_4$, filtered and evaporated. The residue was purified by preparative TLC (EtOAc:PE, 1:3) to give the title compound (0.255 g, 39%) as a pale yellow solid; MS (ESI) m/z [M+H]$^+$=442.0

Intermediate 51: 3-Isopropyl-5-(1,2,3,6-tetrahydro-pyridin-4-yl)-1,2,4-oxadiazole

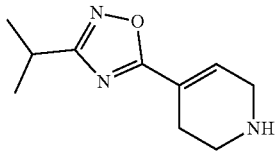

TFA (3 mL) was added to a solution of tert-butyl 4-(3-isopropyl-1,2,4-oxadiazol-5-yl)-3,6-dihydropyridine-1(2H)-carboxylate Intermediate 50 (325 mg, 1.11 mmol) in DCM (3 mL) at rt and the solution was stirred at rt for 45 min. The solvents were removed under reduced pressure and the residue was dissolved in DCM and washed with 1 M NaOH (aq) and water. The organic layer was concentrated to give crude title compound (204 mg, 95%) as a light brown oil; MS (ESI) m/z [M+H]$^+$=194.2

Intermediate 52: Methyl 3-(2,4,5-trifluoro-3-hydroxyphenyl)-1,2,4-oxadiazole-5-carboxylate

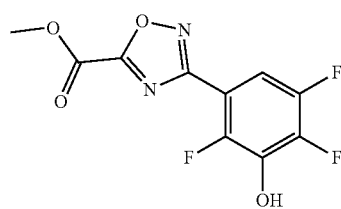 [SMILES: COC(=O)c1nc(-c2cc(F)c(F)c(O)c2F)no1]

A mixture of 2,4,5-trifluoro-3-hydroxybenzonitrile (249 mg, 1.44 mmol), hydroxylammonium chloride (120 mg, 1.73 mmol) and NaHCO$_3$ (193 mg, 2.30 mmol) in MeOH (2.5 mL) was stirred at 50° C. for 23 h. The reaction mixture was concentrated and the residue was suspended in pyridine and cooled to 0° C. Methyl 2-chloro-2-oxoacetate (0.199 mL, 2.16 mmol) was added and the mixture was stirred at rt for 20 min and then at 50° C. for 1.5 h. The reaction mixture was allowed to cool to rt and was poured onto a mixture of ice and 4 M HCl (aq, 7 mL). The resulting mixture was extracted with EtOAc and the organic layer was washed with water and brine, passed through a phase-separator and concentrated. The residue was purified by preparative HPLC, PrepMethod J, (gradient: 20-65%) to give the title compound (153 mg, 39%) as a white solid; MS m/z (ESI) [M−H]$^−$ 273.0.

Intermediate 53: Ethyl 5-(3,4-difluoro-5-hydroxyphenyl)-1,2,4-oxadiazole-3-carboxylate

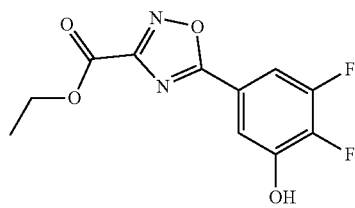 [SMILES: CCOC(=O)c1noc(-c2cc(O)c(F)c(F)c2)n1]

Oxalyl dichloride (4.09 mL, 47.7 mmol) and a catalytic amount of DMF (0.154 mL, 1.99 mmol) were added to a stirred suspension of 3,4-difluoro-5-hydroxybenzoic acid (3.46 g, 19.9 mmol) in DCM (50 mL) at rt, and the resulting mixture was stirred at rt for 20 h. The reaction mixture was concentrated and co-evaporated twice from toluene. The residue was dissolved in in THF (20 mL) and added dropwise to a stirred solution of ethyl (Z)-2-amino-2-(hydroxyimino)acetate (2.63 g, 19.9 mmol) in pyridine (40 mL, 494 mmol) at rt. The resulting mixture was heated to 70° C. for 5 days, cooled to rt and poured out on a stirred mixture (400 mL) of 3.8 M HCl (150 mL) and ice. The mixture was stirred at rt for 1 h. The solid was filtered off and washed with H$_2$O to yield the crude product as a brown solid. The crude product was dissolved in DCM (~50 mL) and loaded on a plug of silica (14 g). The product was eluted with DCM (40 mL) and heptane/EtOAc (1:1, 100 mL). The impure product was combined with the crude product from another batch prepared as described above, starting with 3,4-difluoro-5-hydroxybenzoic acid (1.00 g, 5.74 mmol), and the combined crude product was resolidified from DCM to give the title compound (1.75 g, 25%) as an off-white solid; MS (ESI) m/z [M−H]$^−$ 269.

Intermediate 54: 2,4,5-Trifluoro-3-methoxybenzothioamide

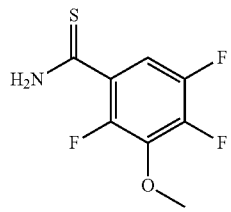

Lawesson's reagent (1.774 g, 4.39 mmol) was added to a solution of 2,4,5-trifluoro-3-methoxybenzamide (1.5 g, 7.31 mmol) in THF (30 mL) and the reaction mixture was heated at 50° C. for 50 min. The reaction mixture was concentrated and the residue was purified by straight phase flash chromatography on silica (0-20% EtOAc in heptane) to give the title compound (1.225 g, 76%) as a yellow solid; MS m/z (ESI) [M−H]$^−$ 220.1.

Intermediate 55: Ethyl 2-(2,4,5-trifluoro-3-methoxyphenyl)thiazole-5-carboxylate

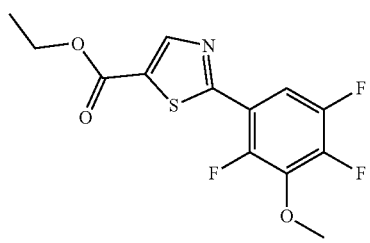 [SMILES: CCOC(=O)c1cnc(-c2cc(F)c(F)c(OC)c2F)s1]

A solution of 2,4,5-trifluoro-3-methoxybenzothioamide Intermediate 54 (1.095 g, 4.95 mmol) and ethyl 2-chloro-3-oxopropanoate (0.820 g, 5.45 mmol) in toluene (25 mL) was heated at 105-110° C. for 4 h. The reaction mixture was concentrated under reduced pressure and the residue was purified by straight phase flash chromatography on silica, (0-30% EtOAc in heptane) to give an orange solid which was further purified by trituration with heptane to give the title compound (282 mg, 18%) as a pale orange solid; MS m/z (ESI) [M+H]+ 318.1.

Intermediate 56: ((2R,6S)-2,6-Dimethylmorpholino) (2-(2,4,5-trifluoro-3-methoxyphenyl)thiazol-5-yl) methanone

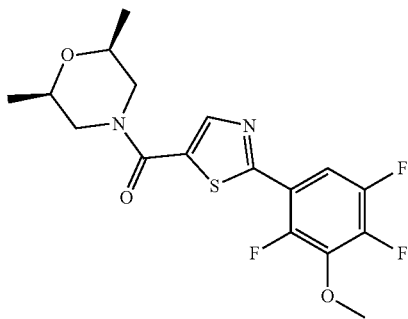 [SMILES: COc1c(F)c(F)cc(-c2ncc(C(=O)N3C[C@@H](C)O[C@@H](C)C3)s2)c1F]

Me3Al (2 M in toluene) (0.989 ml, 1.98 mmol) was added dropwise to a solution of (2R,6S)-2,6-dimethylmorpholine (0.140 mL, 1.11 mmol) in anhydrous toluene (1.1 mL) under an atmosphere of N2(g) at rt. The reaction mixture was stirred at rt for 1 h and was then added dropwise at rt to a stirred slurry of ethyl 2-(2,4,5-trifluoro-3-methoxyphenyl) thiazole-5-carboxylate Intermediate 55 (251 mg, 0.79 mmol) in toluene (1.6 mL) under an atmosphere of N2(g). The resulting solution was heated at 60° C. for 9 h and then cooled to 0° C. Tartaric acid (30%, aq, 10 mL) was added dropwise and then the mixture was extracted with EtOAc× 2). The combined organic layer was washed with water, dried over Na2SO4, filtered and concentrated under reduced pressure. DCM was added to the residue and the resulting mixture was filtered. The filtrate was concentrated to give the title compound (288 mg, 94%); MS m/z (ESI) [M+H]+ 387.2.

Example 1: (R)-(5-(4-Fluoro-3-hydroxyphenyl)-1,3,4-oxadiazol-2-yl)(3-phenylpyrrolidin-1-yl)methanone

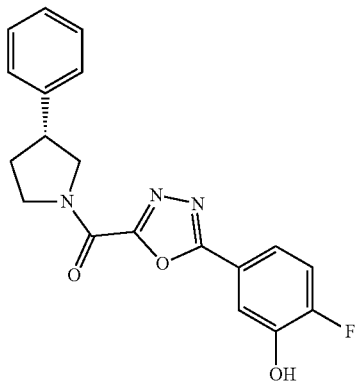 [SMILES: O=C(c1nnc(-c2ccc(F)c(O)c2)o1)N1CC[C@H](c2ccccc2)C1]

DIPEA (0.440 mL, 2.52 mmol) was added dropwise to methyl 5-(4-fluoro-3-hydroxyphenyl)-1,3,4-oxadiazole-2-carboxylate Intermediate 20 (100 mg, 0.42 mmol) and (R)-3-phenylpyrrolidine, HCl (463 mg, 2.52 mmol) in DMF (4 mL) at 25° C. and under a N2(g) atmosphere, and the reaction mixture was stirred at 80° C. for 16 h. The reaction was quenched with water (100 mL), extracted with EtOAc (3×100 mL), and the organic layer was dried over Na2SO4, filtered and evaporated. The crude product was purified by preparative HPLC, PrepMethod E, (gradient: 42-52%) to afford the title compound (61 mg, 41%) as a white solid; HRMS (ESI) m/z [M+H]+ calcd for $C_{19}H_{17}FN_3O_3$: 354.1248, found: 354.1254; 1H NMR (300 MHz, DMSO-d6) δ 1.97-2.18 (1H, m), 2.22-2.45 (overlapping with solvent, m), 3.41-3.72 (overlapping with solvent, m), 3.72-4.15 (2H, m), 4.17-4.56 (1H, m), 7.13-7.56 (7H, m), 7.59-7.72 (1H, m), 10.64 (1H, s).

Example 2: (3-Phenoxyazetidin-1-yl)(5-(2,4,5-trifluoro-3-hydroxyphenyl)-1,2,4-oxadiazol-3-yl)methanone

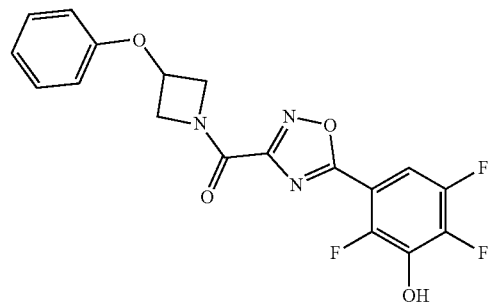 [SMILES: O=C(c1noc(-c2cc(F)c(F)c(O)c2F)n1)N1CC(Oc2ccccc2)C1]

COMU (1.08 g, 2.51 mmol) was added to 5-(2,4,5-trifluoro-3-hydroxyphenyl)-1,2,4-oxadiazole-3-carboxylic acid Intermediate 2 (436 mg, 1.68 mmol), DIPEA (2.93 mL, 16.8 mmol) and 3-phenoxyazetidine (250 mg, 1.68 mmol) in DMF (2.5 mL) under a N2(g) atmosphere. The resulting mixture was stirred at 25° C. for 3 h. Brine (75 mL) was added and the mixture was extracted with EtOAc (3×50 mL). The combined organic layers was dried over Na2SO4, filtered and evaporated. The residue was purified by reversed phase flash chromatography on a C18 column (gradient: 40-60% MeCN in water) to afford the title compound (0.089 g, 14%) as a yellow solid; HRMS (ESI) m/z [M+H]+ calcd for $C_{18}H_{13}F_3N_3O_4$: 392.0852, found: 392.0840; 1H NMR (400 MHz, DMSO-d6) δ 11.71 (s, 1H), 7.68 (ddd, 1H), 7.38-7.28 (m, 2H), 7.05-6.96 (m, 1H), 6.93-6.85 (m, 2H), 5.15 (ddd, 1H), 5.00 (ddd, 1H), 4.62 (ddd, 1H), 4.47 (ddd, 1H), 4.08 (ddd, 1H).

Example 3: ((2R,6S)-2,6-Dimethylmorpholino)(5-(2,4,5-trifluoro-3-hydroxyphenyl)thiophen-2-yl)methanone

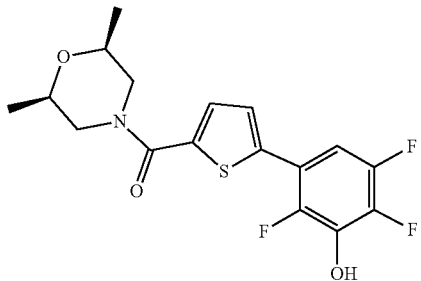 [SMILES: C[C@@H]1CN(C(=O)c2ccc(-c3cc(F)c(F)c(O)c3F)s2)C[C@H](C)O1]

BBr₃ in DCM (1 M, 1.06 mL, 1.06 mmol) was added dropwise to a solution of ((2R,6S)-2,6-dimethylmorpholino)(5-(2,4,5-trifluoro-3-methoxyphenyl)thiophen-2-yl)methanone Intermediate 24 (136 mg, 0.35 mmol) in DCM (5 mL) at 0° C. The reaction mixture was stirred for 1.5 h at rt. The reaction mixture was diluted with DCM and water was carefully added. The layers were separated and the aqueous layer was acidified with 1 M KHSO₄ and extracted with EtOAc (×2). The combined organic layers were passed through a phase separator and concentrated. The residue was purified by preparative HPLC, PrepMethod J, (gradient: 30-70%) to give the title compound (110 mg, 84%) as a white solid; HRMS (ESI) m/z [M+H]$^+$ calcd for C$_{17}$H$_{17}$F$_3$NO$_3$S: 372.0876, found: 372.0892; $^1$H NMR (500 MHz, DMSO-d$_6$) δ 1.11 (6H, d), 2.66 (overlapping with solvent, bs), 3.33 (1H, s), 3.52-3.62 (2H, m), 4.16 (2H, s), 7.44 (1H, ddd), 7.48 (1H, dd), 7.59 (1H, d), 11.17 (1H, s).

Example 4: (3-(2-Methoxyphenyl)pyrrolidin-1-yl)(5-(2,4,5-trifluoro-3-hydroxyphenyl)-1,2,4-oxadiazol-3-yl)methanone

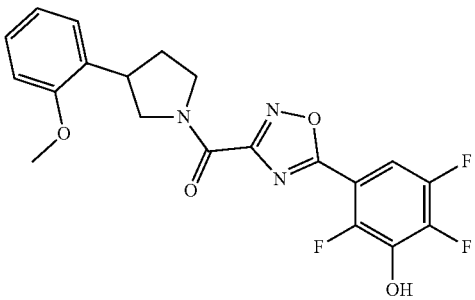 [SMILES: COc1ccccc1C1CCN(C(=O)c2noc(-c3cc(F)c(F)c(O)c3F)n2)C1]

(2-Methoxyphenyl)pyrrolidine HCl (0.102 g, 0.48 mmol) was suspended in EtOAc and washed with 10% Na₂CO₃. The organic layer was concentrated, toluene (1 mL) and Me₃Al in toluene (2 M, 0.599 mL, 1.20 mmol) was added to the residue under a N₂(g) atmosphere and the resulting mixture was stirred at rt for 1 h. The mixture was added to a stirred slurry of ethyl 5-(2,4,5-trifluoro-3-hydroxyphenyl)-1,2,4-oxadiazole-3-carboxylate Intermediate 1 (0.138 g, 0.48 mmol) in toluene (1.5 mL), and the resulting mixture was heated to 60° C. for 22 h. The mixture was cooled to rt, tartaric acid (30%, aq, 5 mL) was added and the mixture was extracted with EtOAc (5 mL). The organic layer was concentrated and the residue purified by reversed phase HPLC, PrepMethod C, (gradient 20-80%), to afford the title compound (120 mg, 60%) as a colorless syrup; HRMS (ESI) m/z [M+H]$^+$ calcd for C$_{20}$H$_{17}$F$_3$N$_3$O$_4$: 420.1166, found: 420.1164; $^1$H NMR (500 MHz, CDCl$_3$) 2.15-2.28 (1H, m), 2.30-2.40 (1H, m), 3.64-3.94 (6H, m), 4.00-4.1 (1H, m), 4.21-4.31 (1H, m), 6.89 (1H, ddd), 6.94 (1H, tdd), 7.19 (1H, dd), 7.22-7.31 (1H, m), 7.37 (1H, m).

Example 5: N-(1-Cyclohexyl-1H-pyrazol-5-yl)-3-(4-fluoro-3-hydroxyphenyl)-N-methylisoxazole-5-carboxamide

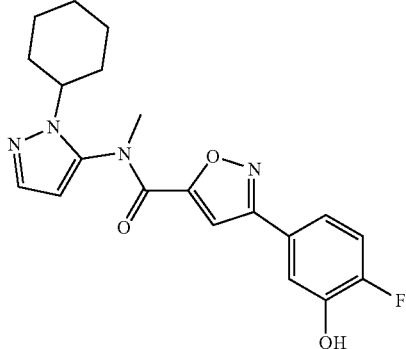 [SMILES: CN(C(=O)c1cc(-c2ccc(F)c(O)c2)no1)c1ccnn1C1CCCCC1]

BBr₃ in DCM (1 M, 10 mL, 10.00 mmol) was added slowly to a stirred solution of N-(1-cyclohexyl-1H-pyrazol-5-yl)-3-(4-fluoro-3-methoxyphenyl)-N-methylisoxazole-5-carboxamide Intermediate 30 (90 mg, 0.23 mmol) in anhydrous DCM (2 mL) cooled to 0° C. and under a N₂(g) atmosphere. The resulting solution was stirred at 15° C. for 2 h. Additional BBr₃ in DCM (1 M, 20 mL, 20.00 mmol) was added slowly to the solution above, cooled to 0° C., and under a N₂(g) atmosphere. The resulting solution was stirred at 15° C. for 2 h. The reaction mixture was poured into 2 M NaOH (aq, 50 mL) and extracted with EtOAc (3×75 mL). The organic layers were combined, dried over Na₂SO₄, filtered and evaporated. The residue was purified by preparative TLC (EtOAc:PE, 1:2) and then further purified by preparative HPLC, PrepMethod N, (gradient: 45-55%) to afford the title compound (0.014 g, 16%) as a white solid; HRMS (ESI) m/z [M+H]$^+$ calcd for C$_{20}$H$_{22}$FN$_4$O$_3$: 385.1670, found: 385.1674; $^1$H NMR (300 MHz, DMSO-d$_6$) δ 1.06-1.92 (10H, m), 3.31 (3H, s), 3.92-4.1 (1H, m), 6.30 (1H, d), 6.69 (1H, s), 7.12-7.36 (3H, m), 7.51 (1H, d), 10.38 (1H, s).

Example 6: (3-(4-Fluoro-3-hydroxyphenyl)isoxazol-5-yl)(3-phenylpyrrolidin-1-yl)methanone

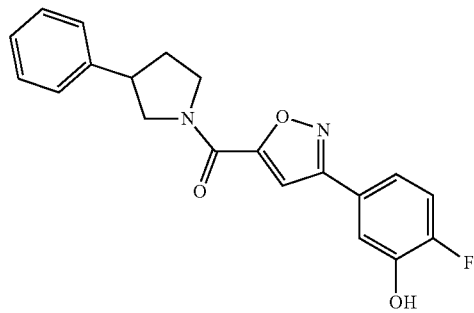 [SMILES: O=C(c1cc(-c2ccc(F)c(O)c2)no1)N1CCC(c2ccccc2)C1]

BBr$_3$ in DCM (1 M, 5 mL, 5 mmol) was added slowly to a stirred solution of (3-(4-fluoro-3-methoxyphenyl)isoxazol-5-yl)(3-phenylpyrrolidin-1-yl)methanone Intermediate 31 (110 mg, 0.30 mmol) in anhydrous DCM (4 mL) cooled to 0° C. over a period of 5 min and under a N$_2$(g) atmosphere. The resulting solution was stirred at 15° C. for 3 h under a N$_2$(g) atmosphere. The reaction mixture was poured into sat NaHCO$_3$ (aq, 20 mL), cooled to 0° C., and extracted with EtOAc (4×50 mL). The organic layers were combined, dried over Na$_2$SO$_4$, filtered and evaporated. The residue was purified by preparative HPLC, PrepMethod N, (gradient: 46-56%) to afford the title compound (0.050 g, 47%) as a white solid; HRMS (ESI) m/z [M+H]$^+$ calcd for C$_{20}$H$_{18}$FN$_2$O$_3$: 353.1296, found: 353.1304; $^1$H NMR (300 MHz, DMSO-d$_6$) δ 1.94-2.2 (m, 1H), 2.24-2.42 (1H, m), 3.41-4.29 (5H, m), 7.2-7.47 (7H, m), 7.51-7.61 (2H, m), 10.27 (1H, s).

Example 7: N-(1-Cyclohexyl-1H-pyrazol-5-yl)-5-(4-fluoro-3-hydroxyphenyl)-N-methylisoxazole-3-carboxamide

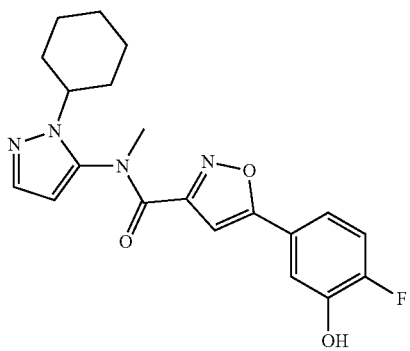 [SMILES: CN(C(=O)c1cc(-c2ccc(F)c(O)c2)on1)c1ccnn1C1CCCCC1]

(COCl)$_2$ (50.8 mg, 0.40 mmol) was added slowly to a mixture of 5-(4-fluoro-3-hydroxyphenyl)isoxazole-3-carboxylic acid Intermediate 34 (100 mg, 0.45 mmol) and DMF (1 µl, 0.01 mmol) in DCM (5 mL), cooled to 5° C. and under a N$_2$(g) atmosphere. The resulting solution was stirred at 28° C. for 0.5 h. 1-Cyclohexyl-N-methyl-1H-pyrazol-5-amine Intermediate 27 (80 mg, 0.45 mmol) and TEA (836 µl, 6 mmol) were added at 20° C. The resulting solution was stirred at 28° C. for 45 h. Water (20 mL) was added and the mixture was extracted with EtOAc (3×20 mL). The combined organic layers were dried over MgSO$_4$, filtered and evaporated. The residue was purified by reversed phase HPLC, PrepMethod O, (gradient: 28-61%) to afford the title compound (1.1 mg, 1%) as a white solid; HRMS (ESI) m/z [M+H]$^+$ calcd for C$_{20}$H$_{22}$FN$_4$O$_3$: 385.1670, found: 385.1680; $^1$H NMR (400 MHz, DMSO-d6) δ 1.14-1.48 (6H, m), 1.61-1.86 (7H, m), 3.30 (overlapping with solvent, s), 6.17 (1H, d), 7.00 (1H, s), 7.23-7.34 (3H, m), 7.37 (1H, s).

Example 8: (R)-(3-(4-Chlorophenyl)pyrrolidin-1-yl)(5-(2,4,5-trifluoro-3-hydroxyphenyl)isoxazol-3-yl)methanone

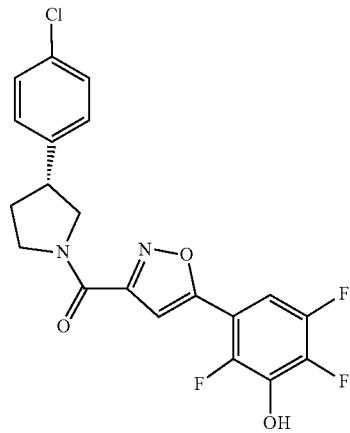 [SMILES: O=C(c1cc(-c2cc(F)c(F)c(O)c2F)on1)N1CC[C@H](c2ccc(Cl)cc2)C1]

EDC (118 mg, 0.62 mmol), DMAP (7.54 mg, 0.06 mmol) and HOBt (83 mg, 0.62 mmol) were added to 5-(2,4,5-trifluoro-3-hydroxyphenyl)isoxazole-3-carboxylic acid Intermediate 37 (80 mg, 0.31 mmol), (R)-3-(4-chlorophenyl)pyrrolidine (56 mg, 0.31 mmol) and DIPEA (162 µl, 0.93 mmol) in DMF (2 mL) at 20° C. The resulting solution was stirred at 60° C. for 2 h under a N$_2$(g) atmosphere. The reaction mixture was concentrated, diluted with EtOAc (25 mL) and washed with water (25 mL). The organic layer was dried over Na$_2$SO$_4$, filtered and evaporated. The residue was purified by preparative TLC (MeOH:DCM, 1:10) and further purified by preparative HPLC, PrepMethod P, (gradient 60-85%) to afford the title compound (0.025 g, 19%) as a white solid; HRMS (ESI) m/z [M+H]$^+$ calcd for C$_{20}$H$_{15}$ClF$_3$N$_2$O$_3$: 423.0718, found: 423.0718; $^1$H NMR (400 MHz, DMSO-d$_6$, 80° C.) δ 2.01 (m, 1H), 2.23-2.36 (m, 1H), 3.45-4.25 (m, 5H), 6.96-7.08 (m, 2H), 7.27-7.39 (m, 4H).

Example 9: 4-(3-(3-Phenylpyrrolidine-1-carbonyl)-1,2,4-oxadiazol-5-yl)-6-(trifluoromethyl)pyridin-2(1H)-one

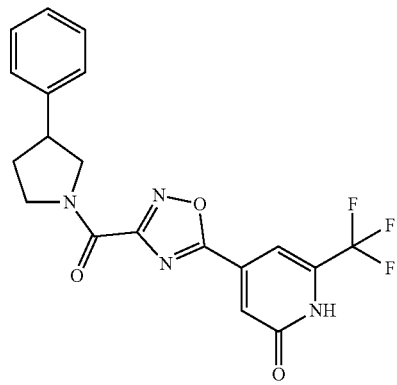 [SMILES: O=C(c1noc(-c2cc(C(F)(F)F)[nH]c(=O)c2)n1)N1CCC(c2ccccc2)C1]

Me$_3$Al in toluene (2 M, 0.5 mL, 1.00 mmol) was added to a solution of 3-phenylpyrrolidine (73 mg, 0.49 mmol) in toluene (0.5 mL) at 25° C. stirred for 40 min. The resulting solution was added to a suspension of ethyl 5-(2-oxo-6-(trifluoromethyl)-1,2-dihydropyridin-4-yl)-1,2,4-oxadiazole-3-carboxylate Intermediate 38 (100 mg, 0.33 mmol) in toluene (0.5 mL) and under a $N_2(g)$ atmosphere, and the mixture was stirred at 60° C. for 3 h. The reaction mixture was diluted with water (75 mL) and filtered through a pad of CELITE. The aqueous layer was extracted with EtOAc (3×20 mL). The organic layer was dried over $Na_2SO_4$, filtered and evaporated. The residue was purified by preparative HPLC, PrepMethod Q, (gradient: 50-62%) to afford the title compound (34 mg, 25%) as a white solid; HRMS (ESI) m/z [M+H]$^+$ calcd for $C_{19}H_{16}F_3N_4O_3$: 405.1168, found: 405.1166; $^1$H NMR (300 MHz, DMSO-$d_6$) δ 2.00-2.18 (1H, m), 2.22-2.38 (1H, m), 3.42-4.18 (m, 5H), 7.20-7.40 (5H, m), 7.57 (1H, d), 7.83 (1H, d), 12.65 (1H, s).

Example 10: 4-(3-(4-(3-Methoxyphenyl)piperazine-1-carbonyl)-1,2,4-oxadiazol-5-yl)-6-(trifluoromethyl)pyridin-2(1H)-one

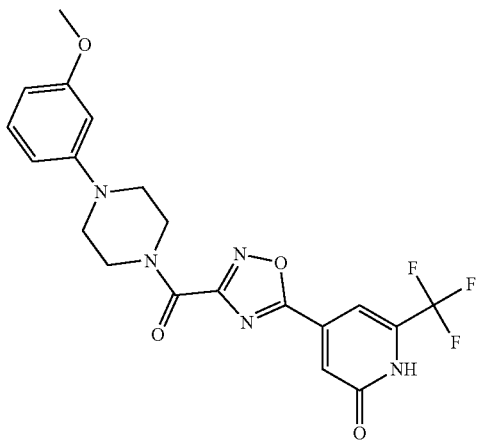 [SMILES: COc1cccc(N2CCN(C(=O)c3noc(-c4cc(C(F)(F)F)[nH]c(=O)c4)n3)CC2)c1]

DABAL-Me$_3$ (127 mg, 0.49 mmol) was added portionwise to 1-(3-methoxyphenyl)piperazine HCl (95 mg, 0.42 mmol) in THF (1 mL). The resulting mixture was stirred at 80° C. for 2 h under a $N_2(g)$ atmosphere. A solution of ethyl 5-(2-oxo-6-(trifluoromethyl)-1,2-dihydropyridin-4-yl)-1,2,4-oxadiazole-3-carboxylate Intermediate 38 (100 mg, 0.33 mmol) in THF (1 mL) was added portionwise to the mixture at 50° C. under a $N_2(g)$ atmosphere. The resulting solution was stirred at 80° C. for 2 h. The solvent was removed under reduced pressure. The residue was diluted with DMSO and filtered through a syringe filter. The filtrate was collected and purified by preparative HPLC, PrepMethod Q, (gradient 33-63%) to afford the title compound (72 mg, 48%) as a yellow solid; HRMS (ESI) m/z [M+H]+ calcd for $C_{20}H_{19}F_3N_5O_4$: 450.1384, found: 450.1380; 1H NMR (300 MHz, DMSO-$d_6$) δ 2.94-3.11 (4H, m), 3.62-3.71 (2H, m), 3.79 (3H, s), 3.81-3.89 (2H, m), 6.83-7.06 (4H, m), 7.58 (1H, s), 7.85 (1H, s), 12.60 (1H, s).

Example 11: (R)-(5-(4-Fluoro-3-hydroxyphenyl)-1,2,4-oxadiazol-3-yl)(3-phenylpyrrolidin-1-yl)methanone

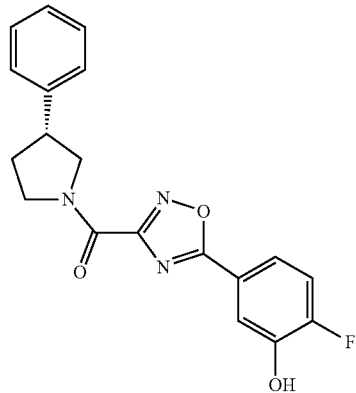 [SMILES: O=C(c1noc(-c2ccc(F)c(O)c2)n1)N1CC[C@H](c2ccccc2)C1]

(R)-3-Phenylpyrrolidine HCl (295 mg, 1.61 mmol), 5-(4-fluoro-3-hydroxyphenyl)-1,2,4-oxadiazole-3-carboxylic acid Intermediate 40 (300 mg, 1.34 mmol), HOBt hydrate (246 mg, 1.61 mmol) and EDC (385 mg, 2.01 mmol) were suspended in DMF (8 mL) under a $N_2(g)$ atmosphere. The resulting mixture was stirred at rt for 2 h and then purified by reversed phase flash chromatography on a C18 column (gradient: 40-50% MeCN in water (0.1% $NH_4HCO_3$)) to afford the title compound (0.188 g, 40%) as a white solid; HRMS (ESI) m/z [M+H]$^+$ calcd for $C_{19}H_{17}FN_3O_3$: 354.1248, found: 354.1256; $^1$H NMR (400 MHz, CD$_3$OD) δ 2.10-2.24 (1H, m), 2.36-2.48 (1H, m), 3.49-3.78 (2H, m), 3.79-4.39 (3H, m), 7.23-7.32 (2H, m), 7.32-7.38 (4H, m), 7.64-7.70 (1H, m), 7.71-7.78 (1H, m).

Example 12: N-(1-Cyclohexyl-1H-pyrazol-5-yl)-2-(4-fluoro-3-hydroxyphenyl)oxazole-5-carboxamide

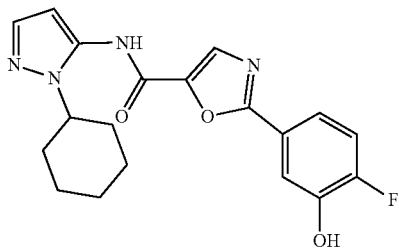 [SMILES: O=C(Nc1ccnn1C1CCCCC1)c1cnc(-c2ccc(F)c(O)c2)o1]

2-(4-Fluoro-3-hydroxyphenyl)oxazole-5-carboxylic acid Intermediate 41 (70 mg, 0.31 mmol), 1-cyclohexyl-1H-pyrazol-5-amine (52 mg, 0.31 mmol) and HATU (131 mg, 0.35 mmol) was dissolved in DMF (2.95 mL). 2,6-Dimethylpyridine (183 μl, 1.57 mmol) was added and the reaction mixture was stirred at rt overnight. The reaction mixture was diluted with EtOAc (20 mL), washed with sat NaHCO$_3$ (10 mL), and brine (3×10 mL). The organic layer was dried over MgSO$_4$, filtered and the solvent was removed under reduced pressure. The residue was purified by reversed phase HPLC, PrepMethod S, (gradient: 20-25%) to afford the title compound (0.012 g, 10%); HRMS (ESI) m/z [M+H]$^+$ calcd for $C_{19}H_{20}FN_4O_3$: 371.1514, found: 371.1516; 1H NMR (600 MHz, DMSO-$d_6$) δ 1.13-1.22 (1H, m), 1.27-1.38 (2H, m), 1.59-1.66 (1H, m), 1.73-1.88 (6H, m), 4-4.09 (1H, m), 6.18 (1H, d), 7.38 (1H, dd), 7.47 (1H, d), 7.62 (1H, s), 7.74 (1H, dd), 8.07 (1H, s), 10.40 (2H, s).

Example 13: 5-(4-Fluoro-3-hydroxyphenyl)-3-(3-phenylpyrrolidine-1-carbonyl)isoxazole-4-carbonitrile

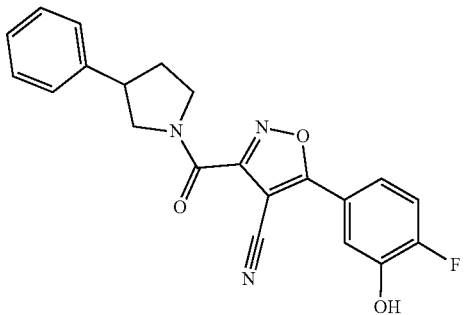 [SMILES: N#Cc1c(C(=O)N2CCC(c3ccccc3)C2)noc1-c1ccc(F)c(O)c1]

Me₃Al in toluene (2 M, 0.185 mL, 0.37 mmol) was added to a stirred solution of 3-phenylpyrrolidine (0.054 g, 0.37 mmol) in toluene (0.3 mL) under a N₂(g) atmosphere and the resulting mixture was stirred at rt for 1 h. The mixture was added to ethyl 4-cyano-5-(4-fluoro-3-hydroxyphenyl)isoxazole-3-carboxylate Intermediate 43 (0.034 g, 0.12 mmol), and the resulting mixture was heated to 60° C. for 22 h, and then cooled to rt. Tartaric acid (30%, aq, 2 mL) was added, and the mixture was extracted with EtOAc (5 mL). The organic layer was concentrated, and the residue was purified by straight phase flash chromatography on silica (gradient: 0-100% EtOAc in heptane) to give the title compound as a white solid (22 mg, 47%); HRMS (ESI) m/z [M+H]⁺; calcd for $C_{21}H_{17}FN_3O_3$: 378.1248, found: 378.1248; Mixture of rotamers, ratio major:minor 1.2:1;1H NMR (500 MHz, DMSO-d₆) δ 2.08 (p), 2.26-2.39 (m), 3.42-3.56 (m), 3.56-3.7 (m), 3.75-3.9 (m), 4-4.13 (m), 4.27 (dd), 7.19-7.29 (m), 7.29-7.4 (m), 7.44-7.6 (m), 7.66 (ddd), 10.78 (s), total no of protons in spectrum: 16.

Examples 14 to 29 below were prepared from ethyl 4-cyano-5-(2,4,5-trifluoro-3-hydroxyphenyl)isoxazole-3-carboxylate Intermediate 44 in analogy to Example 13 using appropriate commercially available amines. HCl- and AcOH-salts of the amines were dissolved in MeOH, passed through a 5 g ISOLUTE NH₂ ion exchange column and concentrated prior to use. The crude products were purified by the specified method.

Example 14: 3-(4-(3-(4-Fluorophenoxy)propyl)piperazine-1-carbonyl)-5-(2,4,5-trifluoro-3-hydroxyphenyl)isoxazole-4-carbonitrile

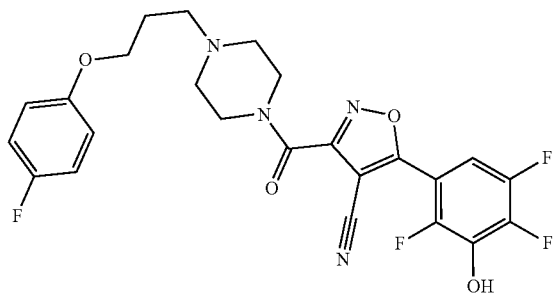 [SMILES: N#Cc1c(C(=O)N2CCN(CCCOc3ccc(F)cc3)CC2)noc1-c1cc(F)c(F)c(O)c1F]

The crude product was purified by preparative HPLC, PrepMethod C, (gradient: 20-80%) to give the title compound as an off-white solid (24 mg, 37%); HRMS (ESI) m/z [M+H]⁺; calcd for $C_{24}H_{21}F_4N_4O_4$: 505.1494, found: 505.1486; ¹H NMR (500 MHz, CD₃OD) δ 2.04 (p, 2H), 2.7-2.82 (m, 6H), 3.81-3.92 (m, 4H), 4.04 (t, 2H), 6.86-6.93 (m, 2H), 6.95-7.03 (m, 2H), 7.31 (ddd, 1H).

Example 15: 3-(4-(Pyridin-2-yl)piperazine-1-carbonyl)-5-(2,4,5-trifluoro-3-hydroxyphenyl)isoxazole-4-carbonitrile

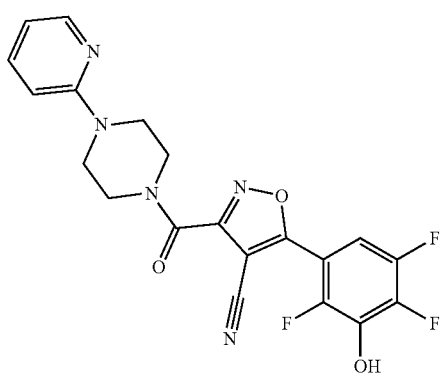 [SMILES: N#Cc1c(C(=O)N2CCN(c3ccccn3)CC2)noc1-c1cc(F)c(F)c(O)c1F]

The crude product was purified by preparative HPLC, PrepMethod C, (gradient: 20-80%) to give the title compound as an off-white solid (9 mg, 16%); HRMS (ESI) m/z [M+H]⁺; calcd for $C_{20}H_{15}F_3N_5O_3$: 430.1122, found: 430.1126; ¹H NMR (500 MHz, CD₃OD) δ 3.68 (dt, 4H), 3.93 (q, 4H), 6.73 (dd, 1H), 6.89 (d, 1H), 7.35 (ddd, 1H), 7.61 (ddd, 1H), 8.09-8.17 (m, 1H).

Example 16: 3-(4-(3-Methoxyphenyl)piperazine-1-carbonyl)-5-(2,4,5-trifluoro-3-hydroxyphenyl)isoxazole-4-carbonitrile

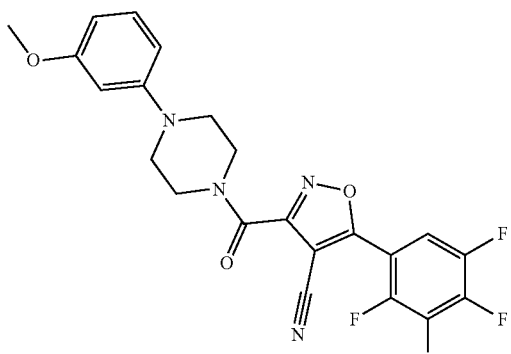

The crude product was purified by preparative HPLC, PrepMethod C, (gradient: 20-80%) to give the title compound as an off-white solid (25 mg, 43%); HRMS (ESI) m/z [M+H]⁺; calcd for $C_{22}H_{18}F_3N_4O_4$: 459.1274, found: 459.1258; 1H NMR (500 MHz, CD₃OD) δ 3.27 (dt, 4H), 3.76 (s, 3H), 3.89-3.99 (m, 4H), 6.46 (dd, 1H), 6.53 (t, 1H), 6.59 (dd, 1H), 7.15 (t, 1H), 7.35 (ddd, 1H).

Example 17: 5-(2,4,5-Trifluoro-3-hydroxyphenyl)-3-(4-(3-(trifluoromethyl)-[1,2,4]triazolo[4,3-b]pyridazin-6-yl)piperazine-1-carbonyl)isoxazole-4-carbonitrile

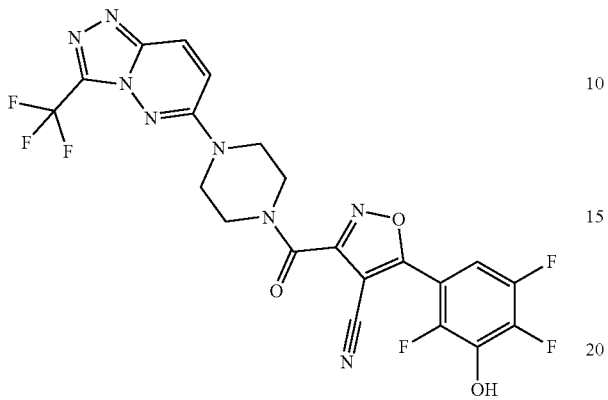

The crude product was purified by preparative HPLC, PrepMethod C, (gradient: 20-80%) to give the title compound as an off-white solid (20 mg, 29%); HRMS (ESI) m/z [M+H]$^+$; calcd for C$_{21}$H$_{13}$FN$_8$O$_3$: 539.1008, found: 539.1016; $^1$H NMR (500 MHz, CD$_3$OD) δ 3.85 (dt, 4H), 4.01 (dt, 4H), 7.36 (ddd, 1H), 7.56 (d, 1H), 8.11 (d, 1H).

Example 18: 3-(5-Fluoroisoindoline-2-carbonyl)-5-(2,4,5-trifluoro-3-hydroxyphenyl)isoxazole-4-carbonitrile

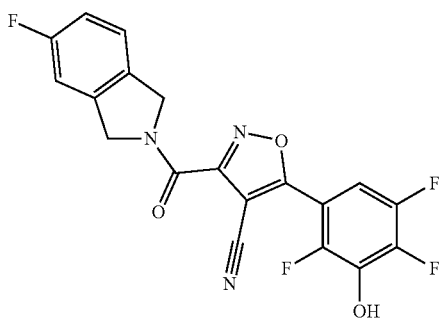 [SMILES: N#Cc1c(C(=O)N2Cc3ccc(F)cc3C2)noc1-c1cc(F)c(F)c(O)c1F]

The crude product was purified by preparative HPLC, PrepMethod C, (gradient: 20-80%) to give the title compound as an off-white solid (12 mg, 27%); HRMS (ESI) m/z [M+H]$^+$; calcd for C$_{19}$H$_{10}$F$_4$N$_3$O$_3$: 404.0652, found: 404.0638; Mixture of rotamers, ratio major:minor 1:1: $^1$H NMR (500 MHz, CD$_3$OD) δ 5.00 (d), 5.26 (d), 7.04-7.14 (m), 7.17 (d), 7.31-7.45 (m), total no of protons in spectrum: 8.

Example 19: N-(tert-Butyl)-4-cyano-N-(pyridin-2-ylmethyl)-5-(2,4,5-trifluoro-3-hydroxyphenyl)isoxazole-3-carboxamide

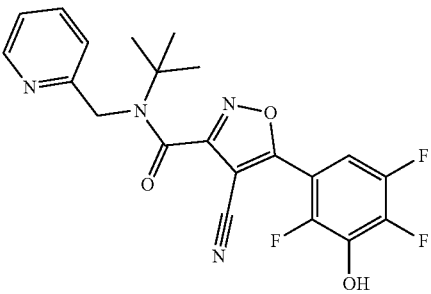 [SMILES: CC(C)(C)N(Cc1ccccn1)C(=O)c1noc(-c2cc(F)c(F)c(O)c2F)c1C#N]

The crude product was purified by preparative HPLC, PrepMethod A, (gradient: 5-95%) to give the title compound (2 mg, 4%); HRMS (ESI) m/z [M+H]$^+$; calcd for C$_{21}$H$_{18}$F$_3$N$_4$O$_3$: 431.1326, found: 431.1334; $^1$H NMR (600 MHz, DMSO-d$_6$) δ 1.39 (s, 9H), 4.85 (s, 2H), 7.29 (m, 2H), 7.38 (d, 1H), 7.78 (td, 1H), 8.54 (d, 1H), 11.88 (s, 1H).

Example 20: 3-(3-Cyclopropyl-1-methyl-4,5,6,7-tetrahydro-1H-pyrazolo[4,3-c]pyridine-5-carbonyl)-5-(2,4,5-trifluoro-3-hydroxyphenyl)isoxazole-4-carbonitrile

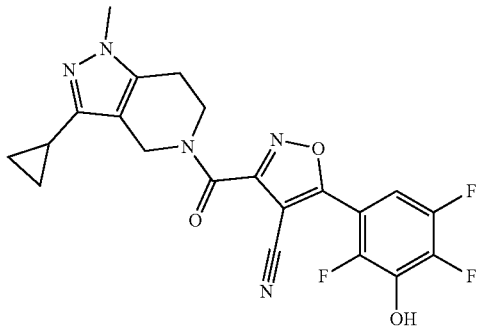 [SMILES: Cn1nc(C2CC2)c2c1CCN(C(=O)c1noc(-c3cc(F)c(F)c(O)c3F)c1C#N)C2]

The crude product was purified by preparative HPLC, PrepMethod U, to give the title compound (12 mg, 23%); HRMS (ESI) m/z [M+H]$^+$; calcd for C$_{21}$H$_{17}$F$_3$N$_5$O$_3$: 444.1278, found: 444.1276; Mixture of rotamers: ratio major:minor 2:1: $^1$H NMR (600 MHz, DMSO-d$_6$) δ 0.64-0.68 (m), 0.7-0.73 (m), 0.73-0.77 (m), 0.81-0.85 (m), 1.66 (tt), 1.79 (tt), 2.79 (q), 3.91 (t), 3.98 (t), 4.68 (s), 4.72 (s), 7.48-7.56 (m), 11.86 (s), total no of protons in spectrum: 13.

Example 21: (S)-3-(3-(4-Chlorophenyl)pyrrolidine-1-carbonyl)-5-(2,4,5-trifluoro-3-hydroxyphenyl)isoxazole-4-carbonitrile

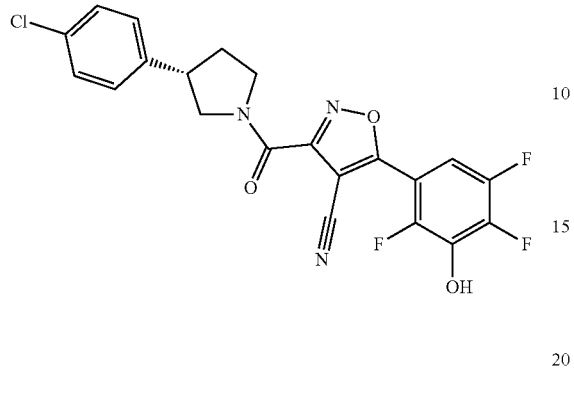

The crude product was purified by preparative HPLC, PrepMethod C, (gradient: 20-80%) to give the title compound as an off-white solid (18 mg, 36%); HRMS (ESI) m/z [M+H]$^+$; calcd for $C_{21}H_{14}ClF_3N_3O_3$: 448.0670, found: 448.0682; Mixture of rotamers: ratio major:minor: 1:1: $^1$H NMR (500 MHz, DMSO-d$_6$) δ 2.06 (p), 2.26-2.39 (m), 3.42-3.55 (m), 3.56-3.68 (m), 3.75-3.88 (m), 3.99-4.12 (m), 4.26 (dd), 7.33-7.44 (m), 7.45-7.56 (m), 11.81 (s). total no of protons in spectrum: 13.

Example 22: 3-((2R,6S)-2,6-Dimethylmorpholine-4-carbonyl)-5-(2,4,5-trifluoro-3-hydroxyphenyl)isoxazole-4-carbonitrile

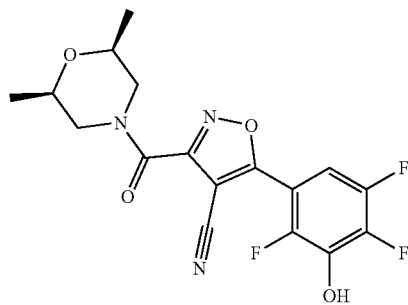 [SMILES: C[C@@H]1CN(C(=O)c2noc(-c3cc(F)c(F)c(O)c3F)c2C#N)C[C@H](C)O1]

The crude product was purified by preparative HPLC, PrepMethod C, (gradient: 20-80%) to give the title compound as an off-white solid (5 mg, 9%); HRMS (ESI) m/z [M+H]$^+$; calcd for $C_{17}H_{15}F_3N_3O_4$: 382.1008, found: 382.1008; $^1$H NMR (500 MHz, CD$_3$OD) δ 1.16 (d, 3H), 1.25 (d, 3H), 2.61-2.71 (m, 1H), 2.98 (dd, 1H), 3.6-3.75 (m, 2H), 4.13 (dt, 1H), 4.50 (dt, 1H), 7.34 (ddd, 1H).

Example 23: 3-(4-(Benzo[d]oxazol-2-yl)piperazine-1-carbonyl)-5-(2,4,5-trifluoro-3-hydroxyphenyl)isoxazole-4-carbonitrile

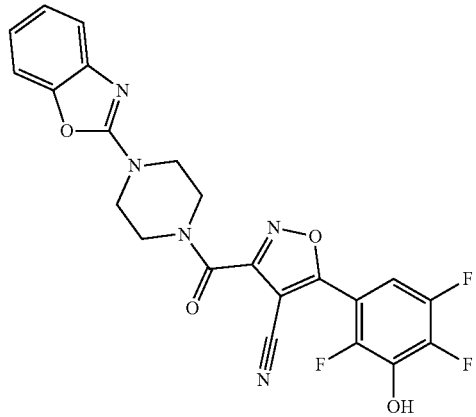 [SMILES: N#Cc1c(C(=O)N2CCN(c3nc4ccccc4o3)CC2)noc1-c1cc(F)c(F)c(O)c1F]

The crude product was purified by preparative HPLC, PrepMethod C, (gradient: 20-80%) to give the title compound as an off-white solid (23 mg, 38%); HRMS (ESI) m/z [M+H]$^+$; calcd for $C_{22}H_{15}F_3N_5O_4$: 470.1070, found: 470.1048; 1H NMR (500 MHz, CD$_3$OD) δ 3.84 (dt, 4H), 4.00 (q, 4H), 7.08 (td, 1H), 7.19 (td, 1H), 7.29-7.4 (m, 3H).

Example 24: 3-(4-(4-(4-Fluorophenyl)-2-oxo-2,3-dihydro-1H-imidazol-1-yl)piperidine-1-carbonyl)-5-(2,4,5-trifluoro-3-hydroxyphenyl)isoxazole-4-carbonitrile

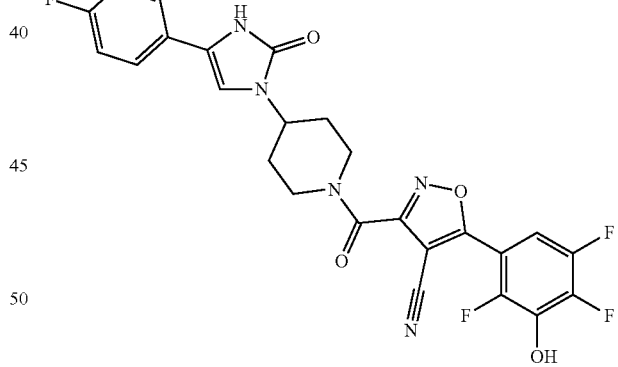

The crude product was purified by preparative HPLC, PrepMethod C, (gradient: 20-80%) to give the title compound as an off-white solid (5 mg, 7%); HRMS (ESI) m/z [M+H]$^+$; calcd for $C_{25}H_{18}F_4N_5O_4$: 528.1290, found: 528.1276; $^1$H NMR (500 MHz, CD$_3$OD) δ 1.9-2.16 (m, 4H), 3.10 (td, 1H), 3.38-3.49 (m, 1H), 4.3-4.46 (m, 2H), 4.80-4.87 (m, 1H, obscured by solvent OH), 6.97 (s, 1H), 7.04-7.14 (m, 2H), 7.29-7.38 (m, 1H), 7.46-7.53 (m, 2H).

Example 25: 3-(4-((5-Methoxypyridin-2-yl)oxy)piperidine-1-carbonyl)-5-(2,4,5-trifluoro-3-hydroxyphenyl)isoxazole-4-carbonitrile

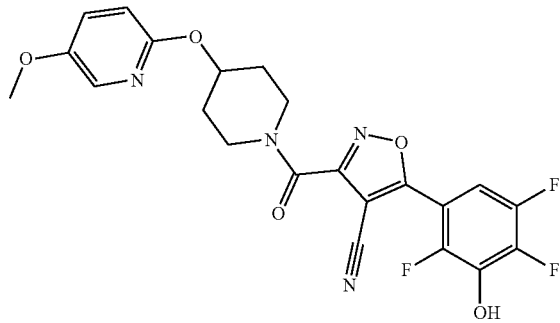 [SMILES: COc1ccc(OC2CCN(C(=O)c3noc(-c4cc(F)c(F)c(O)c4F)c3C#N)CC2)nc1]

The crude product was purified by preparative HPLC, PrepMethod C, (gradient: 20-80%) to give the title compound as an off-white solid (32 mg, 53%); HRMS (ESI) m/z [M+H]$^+$; calcd for $C_{22}H_{18}F_3N_4O_5$: 475.1224, found: 475.1216; $^1$H NMR (500 MHz, CD$_3$OD) δ 1.82-1.94 (m, 2H), 2.06-2.16 (m, 2H), 3.73 (ddd, 1H), 3.77-3.87 (m, 4H), 3.96 (ddd, 1H), 4.02 (ddd, 1H), 5.19-5.27 (m, 1H), 6.76 (d, 1H), 7.29-7.39 (m, 2H), 7.77 (d, 1H).

Example 26: 3-(4-Hydroxy-4-(trifluoromethyl)piperidine-1-carbonyl)-5-(2,4,5-trifluoro-3-hydroxyphenyl)isoxazole-4-carbonitrile

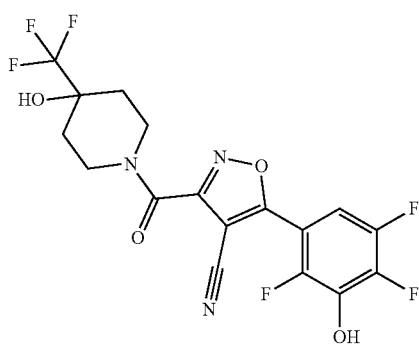 [SMILES: N#Cc1c(C(=O)N2CCC(O)(C(F)(F)F)CC2)noc1-c1cc(F)c(F)c(O)c1F]

The crude product was purified by preparative HPLC, PrepMethod C, (gradient: 20-80%) to give the title compound as an off-white solid (9 mg, 16%); HRMS (ESI) m/z [M+H]$^+$; calcd for $C_{17}H_{12}F_6N_3O_4$: 436.0726, found: 436.0732; $^1$H NMR (500 MHz, CD$_3$OD) δ 1.79-1.93 (m, 4H), 3.24 (td, 1H), 3.56 (td, 1H), 4.15-4.25 (m, 1H), 4.59-4.7 (m, 1H), 7.32 (ddd, 1H).

Example 27: 3-(3-Cyclopropyl-3-fluoroazetidine-1-carbonyl)-5-(2,4,5-trifluoro-3-hydroxyphenyl)isoxazole-4-carbonitrile

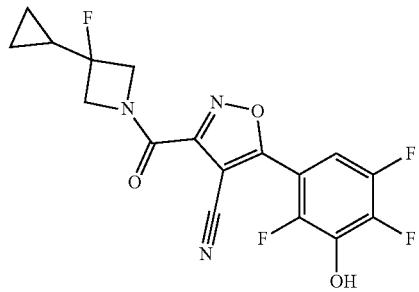 [SMILES: N#Cc1c(C(=O)N2CC(F)(C3CC3)C2)noc1-c1cc(F)c(F)c(O)c1F]

The crude product was purified by preparative HPLC, PrepMethod C, (gradient: 20-80%) to give the title compound as an off-white solid (10 mg, 23%); HRMS (ESI) m/z [M+H]$^+$; calcd for $C_{17}H_{12}F_4N_3O_3$: 382.0810, found: 382.0816; $^1$H NMR (500 MHz, CD$_3$OD) δ 0.49-0.58 (m, 2H), 0.63-0.73 (m, 2H), 1.44 (dddd, 1H), 4.14-4.28 (m, 2H), 4.5-4.66 (m, 2H), 7.33 (ddd, 1H).

Example 28: 5-(2,4,5-Trifluoro-3-hydroxyphenyl)-3-(3-(trifluoromethyl)azetidine-1-carbonyl)isoxazole-4-carbonitrile

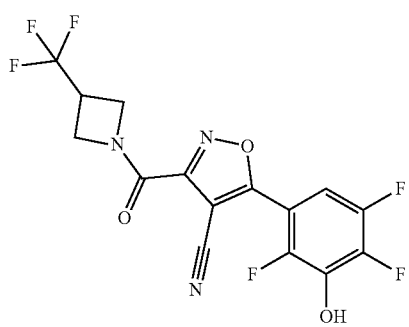 [SMILES: N#Cc1c(C(=O)N2CC(C(F)(F)F)C2)noc1-c1cc(F)c(F)c(O)c1F]

The crude product was purified by preparative HPLC, PrepMethod U, to give the title compound as an off-white solid (10 mg, 24%); HRMS (ESI) m/z [M+H]$^+$; calcd for $C_{15}H_8F_6N_3O_3$: 392.0464, found: 392.0450; $^1$H NMR (500 MHz, CD$_3$OD) δ $^1$H NMR δ 3.65 (m, 1H), 4.21-4.26 (m, 1H), 4.41-4.48 (m, 1H), 4.59-4.66 (m, 1H), 4.77-4.83 (m, 1H), 7.15 (ddd, 1H).

Example 29: 3-(7-Cyano-1,2,3,4-tetrahydroisoquinoline-2-carbonyl)-5-(2,4,5-trifluoro-3-hydroxyphenyl)isoxazole-4-carbonitrile

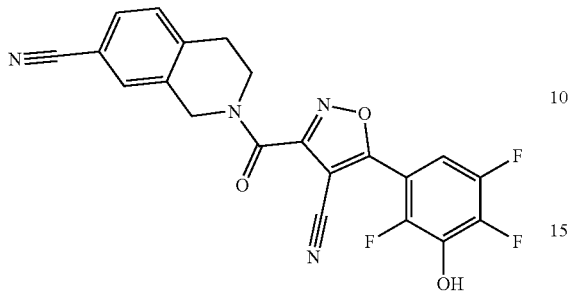

The crude product was purified by preparative HPLC, PrepMethod C, (gradient: 20-80%) to give the title compound as an off-white solid (17 mg, 34%); HRMS (ESI) m/z [M+H]$^+$; calcd for $C_{21}H_{12}F_3N_4O_3$: 425.0856, found: 425.0828; Mixture of rotamers, ratio major:minor 1.5:1: $^1$H NMR (500 MHz, CD$_3$OD) δ 3.10 (t), 4.04 (td), 4.97 (s), 5.04 (s), 7.35 (dddd), 7.40 (dd), 7.53 (s), 7.56 (dd), 7.66 (s), total no of protons in spectrum: 10.

Example 30: 2-(5-(2-Bromo-3,4,6-trifluoro-5-hydroxyphenyl)-1,2,4-oxadiazole-3-carbonyl)-1,2,3,4-tetrahydroisoquinoline-5-carbonitrile

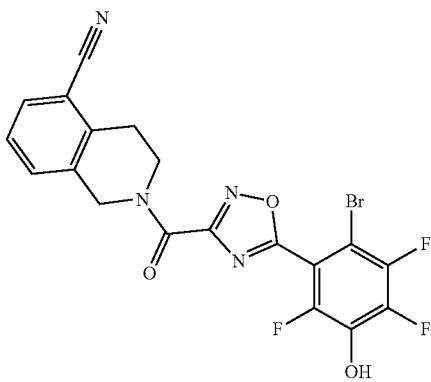 [SMILES: N#Cc1cccc2c1CCN(C(=O)c1noc(-c3c(F)c(O)c(F)c(F)c3Br)n1)C2]

A mixture of 2-(5-(2,4,5-trifluoro-3-hydroxyphenyl)-1,2,4-oxadiazole-3-carbonyl)-1,2,3,4-tetrahydroisoquinoline-5-carbonitrile Example 66 (0.006 g, 0.01 mmol) and NBS (5 mg, 0.03 mmol) in AcOH (0.5 mL) was stirred at 80° C. for 1 h. The mixture was concentrated, and the residue was purified by preparative HPLC, PrepMethod C, (gradient: 20-80%) to give the title compound as a white solid (3 mg, 42%); HRMS (ESI) m/z [M+H]$^+$ calcd for $C_{19}H_{11}BrF_3N_4O_3$: 478.9960, found: 478.9970; Mixture of rotamers, ratio major:minor 2:1: $^1$H NMR (500 MHz, DMSO-d$_6$) δ 3.09 (q), 3.87 (t), 4.01 (t), 4.85 (s), 4.93 (s), 7.40 (t), 7.46 (t), 7.50 (d), 7.67 (d), 7.75 (dd), 12.08 (s), total no of protons in spectrum: 10.

Example 31: 2-(5-(2,4,5-Trifluoro-3-hydroxyphenyl)-1,2,4-oxadiazole-3-carbonyl)-1,2,3,4-tetrahydroisoquinoline-6-carbonitrile

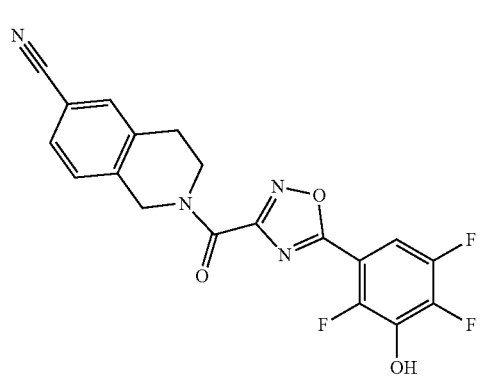 [SMILES: N#Cc1ccc2c(c1)CCN(C(=O)c1noc(-c3cc(F)c(F)c(O)c3F)n1)C2]

5-(2,4,5-Trifluoro-3-hydroxyphenyl)-1,2,4-oxadiazole-3-carboxylic acid Intermediate 2 (38 mg, 0.15 mmol), HATU (111 mg, 0.29 mmol) and DMF (0.5 mL) were mixed in a vial. 1,2,3,4-Tetrahydroisoquinoline-6-carbonitrile HCl (28 mg, 0.15 mmol) dissolved in DMF (0.5 mL) was added followed by DIPEA (153 μL, 0.88 mmol). The resulting yellow solution was stirred at rt over night. The reaction mixture was diluted with DMSO and purified by preparative HPLC, PrepMethod A, (gradient: 5-95%) to give the title compound (15 mg, 26%); HRMS (ESI) m/z [M+H]$^+$ calcd for $C_{19}H_{12}F_3N_4O_3$: 401.0856, found: 401.0834; Mixture of rotamers ratio major:minor: 1:0.6: $^1$H NMR (600 MHz, DMSO-d$_6$) δ 2.97 (2H, dt), 3.79 (1.2H, t), 3.92 (0.8H, t), 4.84 (0.8H, s), 4.94 (1.2H, s), 7.52 (0.6H, d), 7.31 (0.4H, d) 7.62-7.75 (3H, m), 11.71 (1H, s). Total no of protons in spectrum: 11.

Example 32: (2,2,6,6-Tetramethylmorpholino)(5-(2,4,5-trifluoro-3-hydroxyphenyl)-1,2,4-oxadiazol-3-yl)methanone

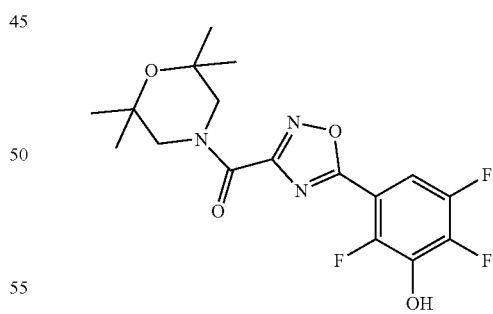

5-(2,4,5-Trifluoro-3-hydroxyphenyl)-1,2,4-oxadiazole-3-carboxylic acid Intermediate 2 (40 mg, 0.15 mmol), HATU (70 mg, 0.18 mmol) and DMF (1 mL) were mixed in a vial. DIPEA (0.081 ml, 0.46 mmol) was added followed by 2,2,6,6-tetramethylmorpholine (33 mg, 0.23 mmol). The resulting yellow solution was stirred at rt for 2 h. The reaction mixture was diluted with DMSO and purified by preparative HPLC, PrepMethod B, (gradient: 5-95%) to give the title compound (17 mg, 29%); HRMS (ESI) m/z [M+H]$^+$ calcd for $C_{17}H_{19}F_3N_3O_4$: 386.1322, found: 386.1324; 1H NMR (600 MHz, DMSO-$d_6$) δ 1.09 (6H, s), 1.17 (6H, s), 3.32 (2H, s), 3.49 (2H, s), 6.99-7.12 (1H, m).

Example 33: (R)-(3-Phenylpyrrolidin-1-yl)(5-(2,4,5-trifluoro-3-hydroxyphenyl)thiophen-2-yl)methanone

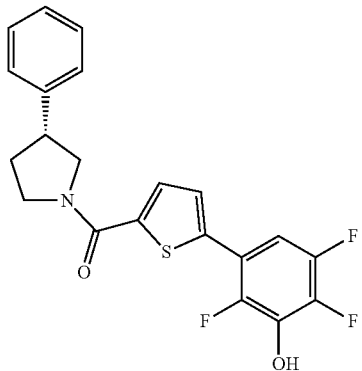 [SMILES: O=C(c1ccc(-c2cc(F)c(F)c(O)c2F)s1)N1CC[C@H](c2ccccc2)C1]

BBr$_3$ in DCM (1 M, 122 µL, 0.12 mmol) was added dropwise to a solution of (R)-(3-phenylpyrrolidin-1-yl)(5-(2,4,5-trifluoro-3-methoxyphenyl)thiophen-2-yl)methanone Intermediate 3 (17 mg, 0.04 mmol) in DCM (0.8 mL) at 0° C. The reaction was stirred for 2.5 h at rt. The yellow reaction mixture was diluted with DCM and water was carefully added. The organic phase was separated. 1 M KHSO$_4$ was added to the water phase, and it was extracted with EtOAc (×3). The combined organic layers were dried using a phase separator and concentrated to give a white solid. The residue was purified by preparative HPLC, Prep-Method C, (gradient: 25-65%) to give the title compound (12 mg, 73%); HRMS (ESI) m/z [M+H]$^+$ calcd for C$_{21}$H$_{17}$F$_3$NO$_2$S: 404.0926, found: 404.0924; Mixture of rotamers: $^1$H NMR (500 MHz, DMSO-$d_6$) δ 1.95-2.21 (1H, m), 2.23-2.44 (1H, m), 3.42-3.64 (2H, m, overlapping with water peak), 3.77 (1H, t), 3.84-4.08 (1H, m), 4.23 (1H, t), 7.21-7.3 (1H, m), 7.3-7.49 (5H, m), 7.54-7.73 (2H, m), 11.17 (1H, bs), total no of protons in spectrum: 16.

General Preparation A

The appropriate amine (0.08 mmol, 2 eq) was added to a solution of 5-(2,4,5-trifluoro-3-hydroxyphenyl)-1,2,4-oxadiazole-3-carboxylic acid Intermediate 2 in DMF (0.08-0.2 M, 0.04 mmol, 1 eq) and HATU in DMF (0.15-0.4 M, 0.08 mmol, 2 eq). DIPEA (0.23 mmol, 6 eq) was added and the reaction was shaken at rt for 20 h. The solvent was removed under reduced pressure and the crude product was dissolved in DMSO (0.3 mL), filtered and purified by preparative HPLC, using one of the following methods; PrepMethod F, G, H or I (gradient 2-94%).

TABLE 1

Examples 34-76 were prepared as described in General Preparation A using the appropriate amine described in the table below. The amines are commercially available if not otherwise stated.

| Example No | Structure | Name | HRMS (ESI) m/z [M + H]$^+$ | Purification Method |
|---|---|---|---|---|
| 34 | 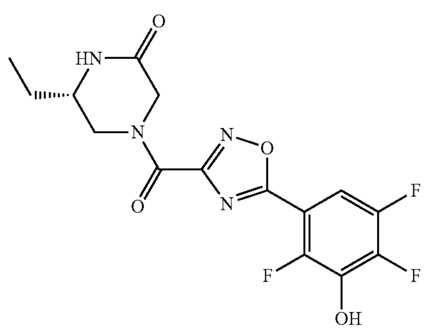 [SMILES: CC[C@H]1CN(C(=O)c2noc(-c3cc(F)c(F)c(O)c3F)n2)CC(=O)N1] | (S)-6-Ethyl-4-(5-(2,4,5-trifluoro-3-hydroxyphenyl)-1,2,4-oxadiazole-3-carbonyl)piperazin-2-one | calcd for C$_{15}$H$_{14}$F$_3$N$_4$O$_4$: 371.0962, found: 371.0952 | F |
| 35 | 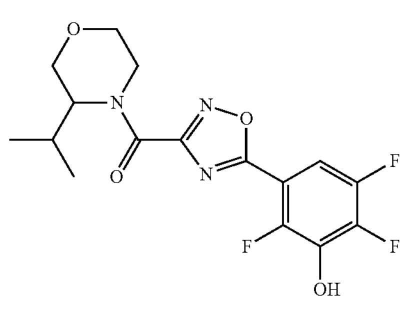 [SMILES: CC(C)C1COCCN1C(=O)c1noc(-c2cc(F)c(F)c(O)c2F)n1] | (3-Isopropylmorpholino)(5-(2,4,5-trifluoro-3-hydroxyphenyl)-1,2,4-oxadiazol-3-yl)methanone | calcd for C$_{16}$H$_{17}$F$_3$N$_3$O$_4$: 372.1166, found: 372.1154 | F |

TABLE 1-continued

Examples 34-76 were prepared as described in General Preparation A using the appropriate amine described in the table below. The amines are commercially available if not otherwise stated.

| Example No | Structure | Name | HRMS (ESI) m/z [M + H]+ | Purification Method |
|---|---|---|---|---|
| 36 | 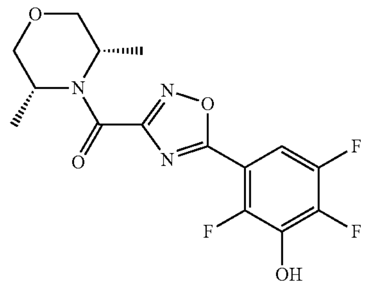 [SMILES: C[C@@H]1COC[C@H](C)N1C(=O)c1noc(-c2cc(F)c(F)c(O)c2F)n1] | ((3R,5S)-3,5-Dimethylmorpholino)(5-(2,4,5-trifluoro-3-hydroxyphenyl)-1,2,4-oxadiazol-3-yl)methanone | calcd for $C_{15}H_{15}F_3N_3O_4$: 358.1008, found: 358.1004 | G |
| 37 | 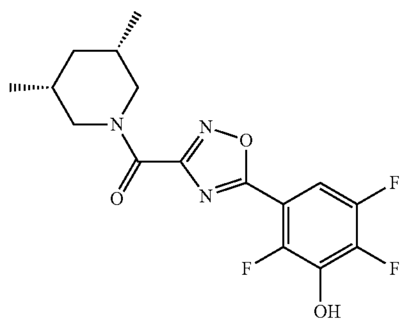 [SMILES: C[C@@H]1C[C@H](C)CN(C(=O)c2noc(-c3cc(F)c(F)c(O)c3F)n2)C1] | ((3R,5S)-3,5-Dimethylpiperidin-1-yl)(5-(2,4,5-trifluoro-3-hydroxyphenyl)-1,2,4-oxadiazol-3-yl)methanone | calcd for $C_{16}H_{17}F_3N_3O_3$: 356.1216, found: 356.1202 | G |
| 38 | 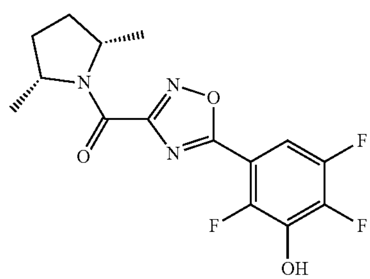 [SMILES: C[C@@H]1CC[C@H](C)N1C(=O)c1noc(-c2cc(F)c(F)c(O)c2F)n1] | ((2R,5S)-2,5-Dimethylpyrrolidin-1-yl)(5-(2,4,5-trifluoro-3-hydroxyphenyl)-1,2,4-oxadiazol-3-yl)methanone | calcd for $C_{15}H_{15}F_3N_3O_3$: 342.1060, found: 342.1030 | F |
| 39 | 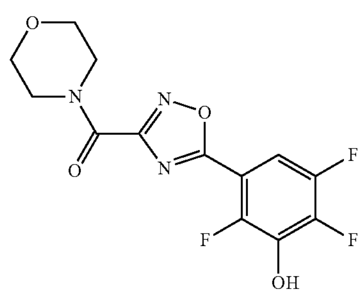 [SMILES: O=C(c1noc(-c2cc(F)c(F)c(O)c2F)n1)N1CCOCC1] | Morpholino(5-(2,4,5-trifluoro-3-hydroxyphenyl)-1,2,4-oxadiazol-3-yl)methanone | calcd for $C_{13}H_{11}F_3N_3O_4$: 330.0696, found: 330.0674 | G |
| 40 | 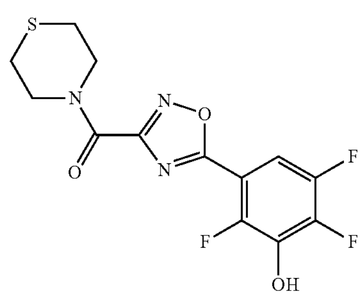 [SMILES: O=C(c1noc(-c2cc(F)c(F)c(O)c2F)n1)N1CCSCC1] | Thiomorpholino(5-(2,4,5-trifluoro-3-hydroxyphenyl)-1,2,4-oxadiazol-3-yl)methanone | calcd for $C_{13}H_{11}F_3N_3O_3S$: 346.0468, found: 346.0456 | G |

TABLE 1-continued

Examples 34-76 were prepared as described in General Preparation A using the appropriate amine described in the table below. The amines are commercially available if not otherwise stated.

| Example No | Structure | Name | HRMS (ESI) m/z [M + H]$^+$ | Purification Method |
|---|---|---|---|---|
| 41 | 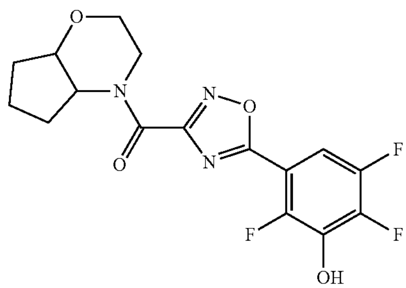 [SMILES: O=C(c1noc(-c2cc(F)c(F)c(O)c2F)n1)N1CCOC2CCCC21] | (Hexahydrocyclopenta[b][1,4]oxazin-4(4aH)-yl)(5-(2,4,5-trifluoro-3-hydroxyphenyl)-1,2,4-oxadiazol-3-yl)methanone | calcd for $C_{16}H_{15}F_3N_3O_4$: 370.1008, found: 370.0992 | F |
| 42 | 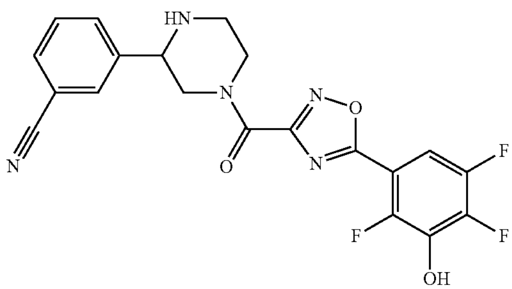 [SMILES: N#Cc1cccc(C2CN(C(=O)c3noc(-c4cc(F)c(F)c(O)c4F)n3)CCN2)c1] | 3-(4-(5-(2,4,5-Trifluoro-3-hydroxyphenyl)-1,2,4-oxadiazole-3-carbonyl)piperazin-2-yl)benzonitrile | calcd for $C_{20}H_{15}F_3N_5O_3$: 430.1122, found: 430.1122 | H |
| 43 | 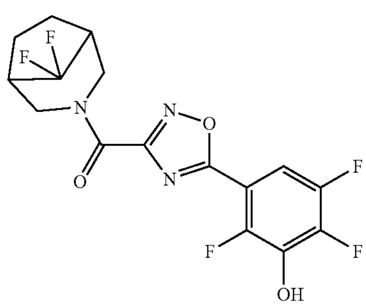 [SMILES: O=C(c1noc(-c2cc(F)c(F)c(O)c2F)n1)N1CC2CCC(C1)C2(F)F] | (8,8-difluoro-3-azabicyclo[3.2.1]octan-3-yl)(5-(2,4,5-trifluoro-3-hydroxyphenyl)-1,2,4-oxadiazol-3-yl)methanone | calcd for $C_{16}H_{13}F_5N_3O_3$: 390.0872, found: 390.0848 | F |
| 44 | 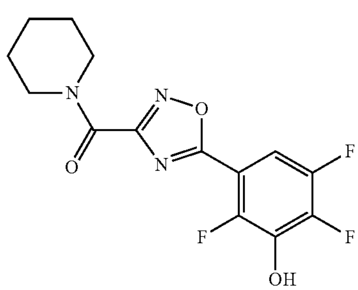 [SMILES: O=C(c1noc(-c2cc(F)c(F)c(O)c2F)n1)N1CCCCC1] | Piperidin-1-yl(5-(2,4,5-trifluoro-3-hydroxyphenyl)-1,2,4-oxadiazol-3-yl)methanone | calcd for $C_{14}H_{13}F_3N_3O_3$: 328.0904, found: 328.0896 | F |
| 45 | 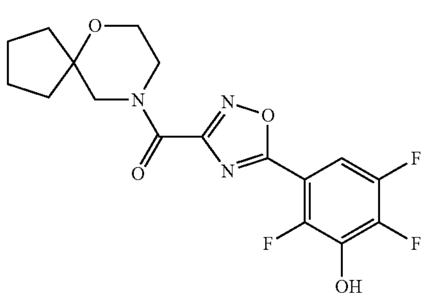 [SMILES: O=C(c1noc(-c2cc(F)c(F)c(O)c2F)n1)N1CCOC2(CCCC2)C1] | (6-Oxa-9-azaspiro[4.5]decan-9-yl)(5-(2,4,5-trifluoro-3-hydroxyphenyl)-1,2,4-oxadiazol-3-yl)methanone | calcd for $C_{17}H_{17}F_3N_3O_4$: 384.1166, found: 384.1180 | F |

TABLE 1-continued

Examples 34-76 were prepared as described in General Preparation A using the appropriate amine described in the table below. The amines are commercially available if not otherwise stated.

| Example No | Structure | Name | HRMS (ESI) m/z [M + H]+ | Purification Method |
|---|---|---|---|---|
| 46 | 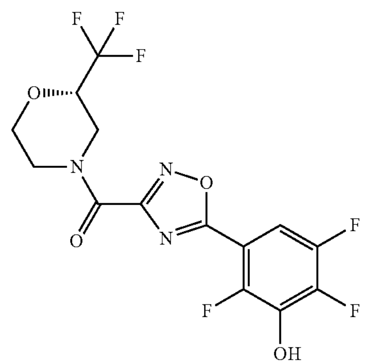 [SMILES: O=C(c1noc(-c2cc(F)c(F)c(O)c2F)n1)N1CCO[C@H](C(F)(F)F)C1] | (S)-(5-(2,4,5-Trifluoro-3-hydroxyphenyl)-1,2,4-oxadiazol-3-yl)(2-(trifluoromethyl)morpholino)methanone | calcd for $C_{14}H_{10}F_6N_3O_4$: 398.0570, found: 398.0558 | F |
| 47 | 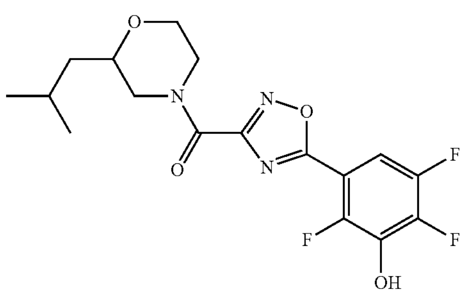 [SMILES: CC(C)CC1CN(C(=O)c2noc(-c3cc(F)c(F)c(O)c3F)n2)CCO1] | (2-Isobutylmorpholino)(5-(2,4,5-trifluoro-3-hydroxyphenyl)-1,2,4-oxadiazol-3-yl)methanone | calcd for $C_{17}H_{19}F_3N_3O_4$: found: 386.1284 | F |
| 48 | 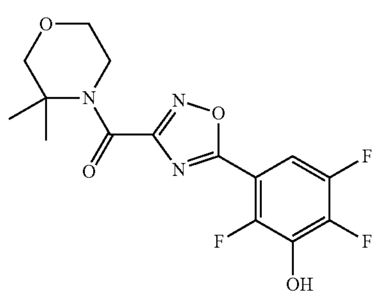 [SMILES: CC1(C)COCCN1C(=O)c1noc(-c2cc(F)c(F)c(O)c2F)n1] | (3,3-Dimethylmorpholino)(5-(2,4,5-trifluoro-3-hydroxyphenyl)-1,2,4-oxadiazol-3-yl)methanone | calcd for $C_{15}H_{15}F_3N_3O_4$: 358.1008, found: 358.0990 | F |
| 49 | 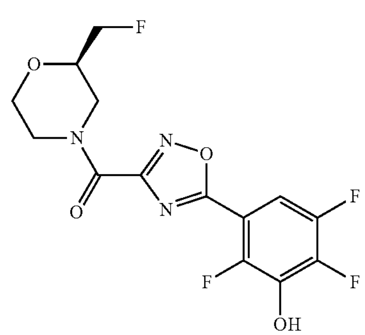 [SMILES: O=C(c1noc(-c2cc(F)c(F)c(O)c2F)n1)N1CCO[C@@H](CF)C1] | (R)-(2-(Fluoromethyl)morpholino)(5-(2,4,5-trifluoro-3-hydroxyphenyl)-1,2,4-oxadiazol-3-yl)methanone | calcd for $C_{14}H_{12}F_4N_3O_4$: 362.0758, found: 362.0742 | F |

TABLE 1-continued

Examples 34-76 were prepared as described in General Preparation A using the appropriate amine described in the table below. The amines are commercially available if not otherwise stated.

| Example No | Structure | Name | HRMS (ESI) m/z [M + H]$^+$ | Purification Method |
|---|---|---|---|---|
| 50 | 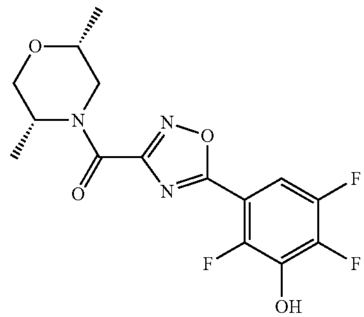 [SMILES: C[C@@H]1CN(C(=O)c2noc(-c3cc(F)c(F)c(O)c3F)n2)[C@H](C)CO1] | ((2R,5R)-2,5-Dimethylmorpholino)(5-(2,4,5-trifluoro-3-hydroxyphenyl)-1,2,4-oxadiazol-3-yl)methanone | calcd for $C_{15}H_{15}F_3N_3O_4$: 358.1008, found: 358.0982 | F |
| 51 | 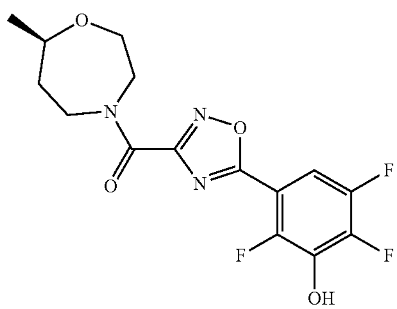 [SMILES: C[C@@H]1CCN(C(=O)c2noc(-c3cc(F)c(F)c(O)c3F)n2)CCO1] | (R)-(7-Methyl-1,4-oxazepan-4-yl)(5-(2,4,5-trifluoro-3-hydroxyphenyl)-1,2,4-oxadiazol-3-yl)methanone | calcd for $C_{15}H_{15}F_3N_3O_4$: 358.1008, found: 358.0994 | F |
| 52 | 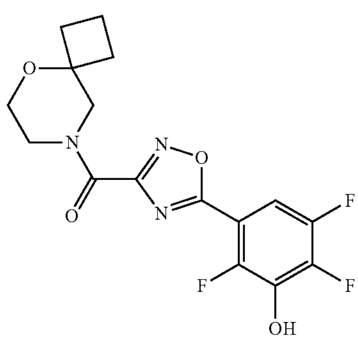 [SMILES: O=C(c1noc(-c2cc(F)c(F)c(O)c2F)n1)N1CCOC2(CCC2)C1] | (5-Oxa-8-azaspiro[3.5]nonan-8-yl)(5-(2,4,5-trifluoro-3-hydroxyphenyl)-1,2,4-oxadiazol-3-yl)methanone | calcd for $C_{16}H_{15}F_3N_3O_4$: 370.1008, found: 370.1006 | F |
| 53 | 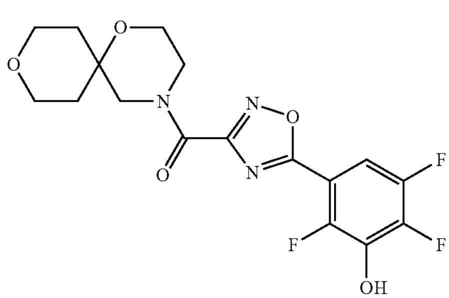 [SMILES: O=C(c1noc(-c2cc(F)c(F)c(O)c2F)n1)N1CCOC2(CCOCC2)C1] | (1,9-Dioxa-4-azaspiro[5.5]undecan-4-yl)(5-(2,4,5-trifluoro-3-hydroxyphenyl)-1,2,4-oxadiazol-3-yl)methanone | calcd for $C_{17}H_{17}F_3N_3O_5$: 400.1114, found: 400.1104 | F |

TABLE 1-continued

Examples 34-76 were prepared as described in General Preparation A using the appropriate amine described in the table below. The amines are commercially available if not otherwise stated.

| Example No | Structure | Name | HRMS (ESI) m/z [M + H]+ | Purification Method |
|---|---|---|---|---|
| 54 | 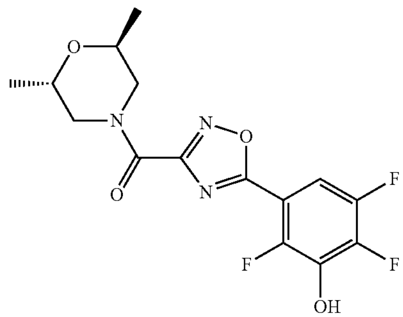 [SMILES: C[C@H]1CN(C(=O)c2noc(-c3cc(F)c(F)c(O)c3F)n2)C[C@H](C)O1] | ((2S,6S)-2,6-Dimethylmorpholino)(5-(2,4,5-trifluoro-3-hydroxyphenyl)-1,2,4-oxadiazol-3-yl)methanone | calcd for $C_{15}H_{15}F_3N_3O_4$: 358.1008, found: 358.1012 | G |
| 55 | 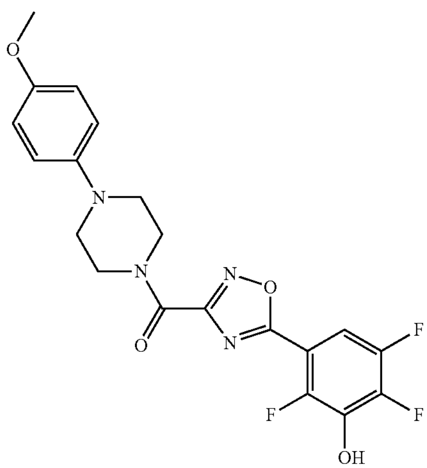 [SMILES: COc1ccc(N2CCN(C(=O)c3noc(-c4cc(F)c(F)c(O)c4F)n3)CC2)cc1] | (4-(4-Methoxyphenyl)piperazin-1-yl)(5-(2,4,5-trifluoro-3-hydroxyphenyl)-1,2,4-oxadiazol-3-yl)methanone | calcd for $C_{20}H_{18}F_3N_4O_4$: 435.1274, found: 435.1276 | I |
| 56 | 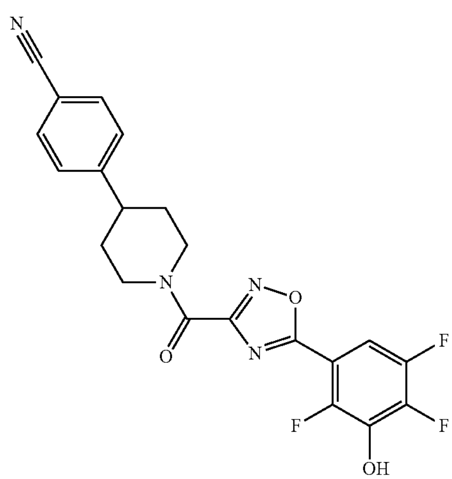 [SMILES: N#Cc1ccc(C2CCN(C(=O)c3noc(-c4cc(F)c(F)c(O)c4F)n3)CC2)cc1] | 4-(1-(5-(2,4,5-Trifluoro-3-hydroxyphenyl)-1,2,4-oxadiazole-3-carbonyl)piperidin-4-yl)benzonitrile | calcd for $C_{21}H_{16}F_3N_4O_3$: 429.1168, found: 429.1172 | G |

TABLE 1-continued

Examples 34-76 were prepared as described in General Preparation A using the appropriate amine described in the table below. The amines are commercially available if not otherwise stated.

| Example No | Structure | Name | HRMS (ESI) m/z [M + H]$^+$ | Purification Method |
|---|---|---|---|---|
| 57 | 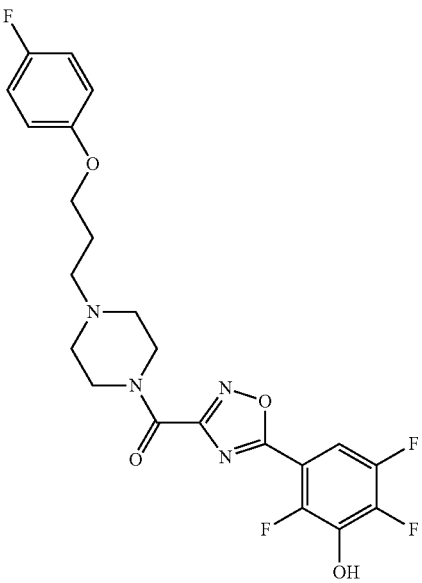 [SMILES: O=C(c1noc(-c2cc(F)c(F)c(O)c2F)n1)N1CCN(CCCOc2ccc(F)cc2)CC1] | (4-(3-(4-Fluorophenoxy)propyl)piperazin-1-yl)(5-(2,4,5-trifluoro-3-hydroxyphenyl)-1,2,4-oxadiazol-3-yl)methanone | calcd for $C_{22}H_{21}F_4N_4O_4$: 481.1494, found: 481.1500 | G |
| 58 | 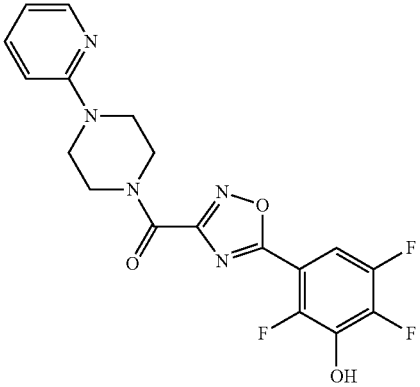 [SMILES: O=C(c1noc(-c2cc(F)c(F)c(O)c2F)n1)N1CCN(c2ccccn2)CC1] | (4-(Pyridin-2-yl)piperazin-1-yl)(5-(2,4,5-trifluoro-3-hydroxyphenyl)-1,2,4-oxadiazol-3-yl)methanone | calcd for $C_{18}H_{15}F_3N_5O_3$: 406.1122, found: 406.1126 | G |
| 59 | 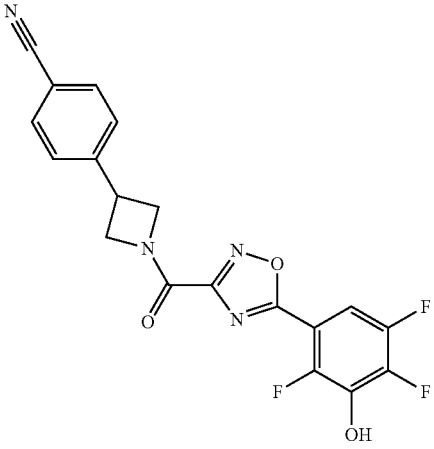 [SMILES: N#Cc1ccc(C2CN(C(=O)c3noc(-c4cc(F)c(F)c(O)c4F)n3)C2)cc1] | 4-(1-(5-(2,4,5-Trifluoro-3-hydroxyphenyl)-1,2,4-oxadiazole-3-carbonyl)azetidin-3-yl)benzonitrile | calcd for $C_{19}H_{12}F_3N_4O_3$: 401.0856, found: 401.0858 | I |

TABLE 1-continued

Examples 34-76 were prepared as described in General Preparation A using the appropriate amine described in the table below. The amines are commercially available if not otherwise stated.

| Example No | Structure | Name | HRMS (ESI) m/z [M + H]+ | Purification Method |
|---|---|---|---|---|
| 60 | 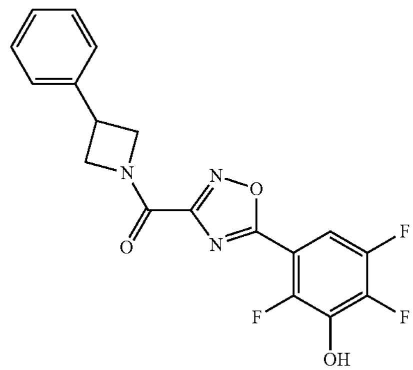 [SMILES: O=C(c1noc(-c2cc(F)c(F)c(O)c2F)n1)N1CC(c2ccccc2)C1] | (3-Phenylazetidin-1-yl)(5-(2,4,5-trifluoro-3-hydroxyphenyl)-1,2,4-oxadiazol-3-yl)methanone | calcd for $C_{18}H_{13}F_3N_3O_3$: 376.0904, found: 376.0906 | G |
| 61 | 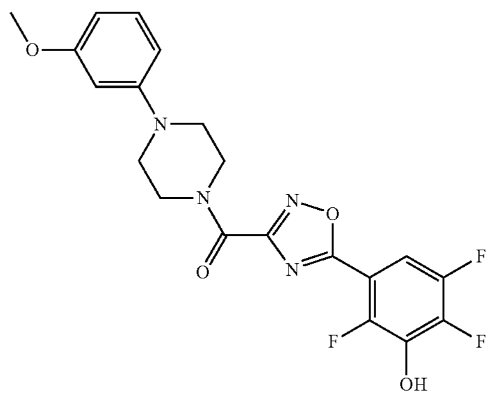 [SMILES: COc1cccc(N2CCN(C(=O)c3noc(-c4cc(F)c(F)c(O)c4F)n3)CC2)c1] | (4-(3-Methoxyphenyl)piperazin-1-yl)(5-(2,4,5-trifluoro-3-hydroxyphenyl)-1,2,4-oxadiazol-3-yl)methanone | calcd for $C_{20}H_{18}F_3N_4O_4$: found: 435.1276 | I |
| 62 | 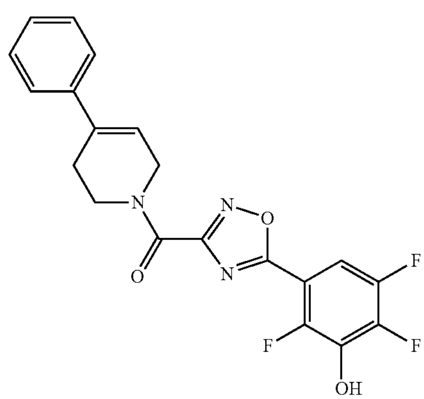 [SMILES: O=C(c1noc(-c2cc(F)c(F)c(O)c2F)n1)N1CC=C(c2ccccc2)CC1] | (4-Phenyl-3,6-dihydropyridin-1(2H)-yl)(5-(2,4,5-trifluoro-3-hydroxyphenyl)-1,2,4-oxadiazol-3-yl)methanone | calcd for $C_{20}H_{15}F_3N_3O_3$: 402.1060, found: 402.1060 | G |
| 63 | 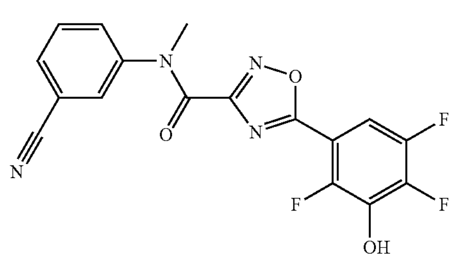 [SMILES: CN(C(=O)c1noc(-c2cc(F)c(F)c(O)c2F)n1)c1cccc(C#N)c1] | N-(3-Cyanophenyl)-N-methyl-5-(2,4,5-trifluoro-3-hydroxyphenyl)-1,2,4-oxadiazole-3-carboxamide | MS m/z (ESI) [M − H]− 373.1 | G |

TABLE 1-continued

Examples 34-76 were prepared as described in General Preparation A using the appropriate amine described in the table below. The amines are commercially available if not otherwise stated.

| Example No | Structure | Name | HRMS (ESI) m/z [M + H]+ | Purification Method |
|---|---|---|---|---|
| 64 | 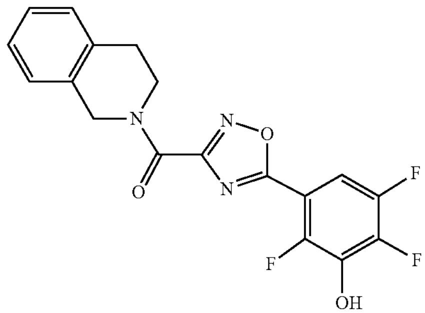 [SMILES: O=C(c1noc(-c2cc(F)c(F)c(O)c2F)n1)N1CCc2ccccc2C1] | (3,4-Dihydroisoquinolin-2(1H)-yl)(5-(2,4,5-trifluoro-3-hydroxyphenyl)-1,2,4-oxadiazol-3-yl)methanone | calcd for $C_{18}H_{13}F_3N_3O_3$: 376.0904, found: 376.0904 | G |
| 65 | 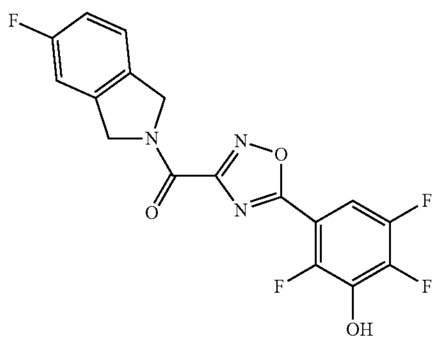 | (5-Fluoroisoindolin-2-yl)(5-(2,4,5-trifluoro-3-hydroxyphenyl)-1,2,4-oxadiazol-3-yl)methanone | calcd for $C_{17}H_{10}F_4N_3O_3$: 380.0652, found: 380.0654 | I |
| 66 | 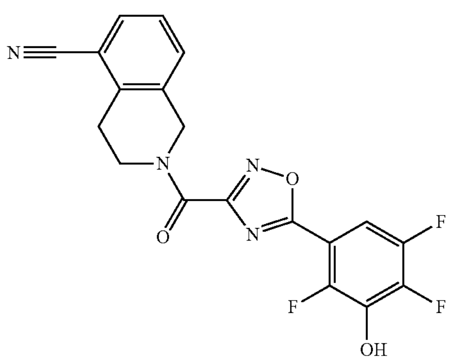 [SMILES: N#Cc1cccc2c1CCN(C(=O)c1noc(-c3cc(F)c(F)c(O)c3F)n1)C2] | 2-(5-(2,4,5-Trifluoro-3-hydroxyphenyl)-1,2,4-oxadiazole-3-carbonyl)-1,2,3,4-tetrahydroisoquinoline-5-carbonitrile | calcd for $C_{19}H_{12}F_3N_4O_3$: 401.0856, found: 401.0862 | I |

TABLE 1-continued

Examples 34-76 were prepared as described in General Preparation A using the appropriate amine described in the table below. The amines are commercially available if not otherwise stated.

| Example No | Structure | Name | HRMS (ESI) m/z [M + H]+ | Purification Method |
|---|---|---|---|---|
| 67 | 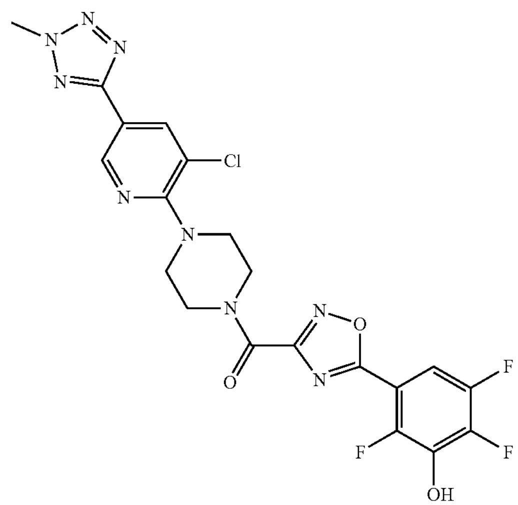 [SMILES: Cn1nnc(-c2cnc(N3CCN(C(=O)c4noc(-c5cc(F)c(F)c(O)c5F)n4)CC3)c(Cl)c2)n1] | (4-(3-Chloro-5-(2-methyl-2H-tetrazol-5-yl)pyridin-2-yl)piperazin-1-yl)(5-(2,4,5-trifluoro-3-hydroxyphenyl)-1,2,4-oxadiazol-3-yl)methanone | calcd for $C_{20}H_{16}ClF_3N_9O_3$: 522.1012, found: 522.1020 | I |
| 68 | 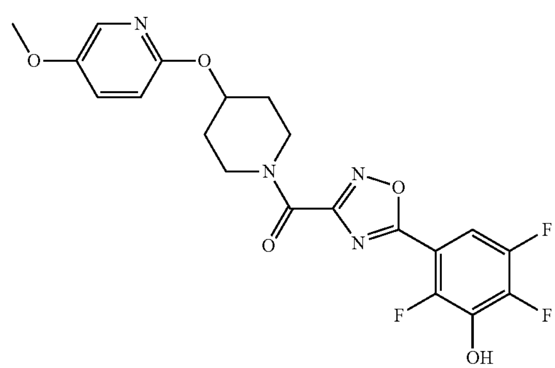 [SMILES: COc1ccc(OC2CCN(C(=O)c3noc(-c4cc(F)c(F)c(O)c4F)n3)CC2)nc1] | (4-((5-Methoxypyridin-2-yl)oxy)piperidin-1-yl)(5-(2,4,5-trifluoro-3-hydroxyphenyl)-1,2,4-oxadiazol-3-yl)methanone | calcd for $C_{20}H_{18}F_3N_4O_5$: 451.1224, found: 451.1230 | G |
| 69 | 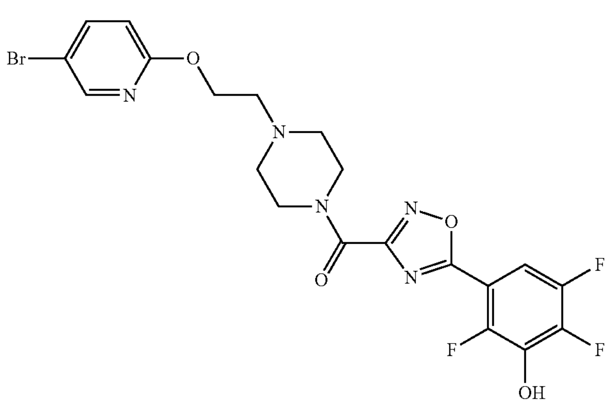 [SMILES: O=C(c1noc(-c2cc(F)c(F)c(O)c2F)n1)N1CCN(CCOc2ccc(Br)cn2)CC1] | (4-(2-((5-Bromopyridin-2-yl)oxy)ethyl)piperazin-1-yl)(5-(2,4,5-trifluoro-3-hydroxyphenyl)-1,2,4-oxadiazol-3-yl)methanone | calcd for $C_{20}H_{18}BrF_3N_5O_4$: 528.0488, found: 528.0490 | H |

TABLE 1-continued

Examples 34-76 were prepared as described in General Preparation A using the appropriate amine described in the table below. The amines are commercially available if not otherwise stated.

| Example No | Structure | Name | HRMS (ESI) m/z [M + H]+ | Purification Method |
|---|---|---|---|---|
| 70 | 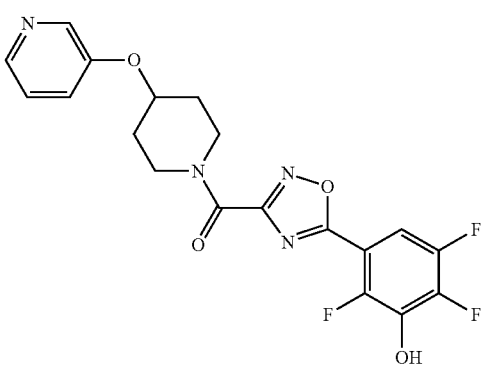 [SMILES: O=C(c1noc(-c2cc(F)c(F)c(O)c2F)n1)N1CCC(Oc2cccnc2)CC1] | (4-(Pyridin-3-yloxy)piperidin-1-yl)(5-(2,4,5-trifluoro-3-hydroxyphenyl)-1,2,4-oxadiazol-3-yl)methanone | calcd for $C_{19}H_{16}F_3N_4O_4$: 421.1118, found: 421.1122 | H |
| 71 | 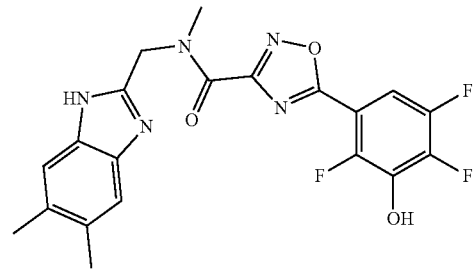 [SMILES: Cc1cc2nc(CN(C)C(=O)c3noc(-c4cc(F)c(F)c(O)c4F)n3)[nH]c2cc1C] | N-((5,6-Dimethyl-1H-benzo[d]imidazol-2-yl)methyl)-N-methyl-5-(2,4,5-trifluoro-3-hydroxyphenyl)-1,2,4-oxadiazole-3-carboxamide | calcd for $C_{20}H_{17}F_3N_5O_3$: 432.1278, found: 432.1280 | I |
| 72 | 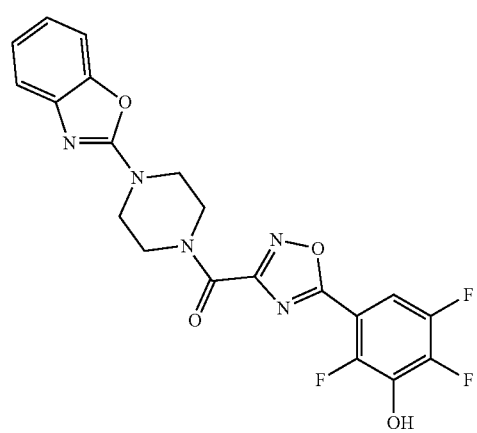 [SMILES: O=C(c1noc(-c2cc(F)c(F)c(O)c2F)n1)N1CCN(c2nc3ccccc3o2)CC1] | (4-(Benzo[d]oxazol-2-yl)piperazin-1-yl)(5-(2,4,5-trifluoro-3-hydroxyphenyl)-1,2,4-oxadiazol-3-yl)methanone | calcd for $C_{20}H_{15}F_3N_5O_4$: 446.1070, found: 446.1076 | H |
| 73 | 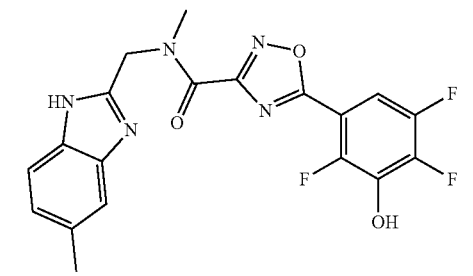 [SMILES: Cc1ccc2[nH]c(CN(C)C(=O)c3noc(-c4cc(F)c(F)c(O)c4F)n3)nc2c1] | N-Methyl-N-((5-methyl-1H-benzo[d]imidazol-2-yl)methyl)-5-(2,4,5-trifluoro-3-hydroxyphenyl)-1,2,4-oxadiazole-3-carboxamide | calcd for $C_{19}H_{15}F_3N_5O_3$: 418.1122, found: 418.1124 | I |

TABLE 1-continued

Examples 34-76 were prepared as described in General Preparation A using the appropriate amine described in the table below. The amines are commercially available if not otherwise stated.

| Example No | Structure | Name | HRMS (ESI) m/z [M + H]+ | Purification Method |
|---|---|---|---|---|
| 74 | 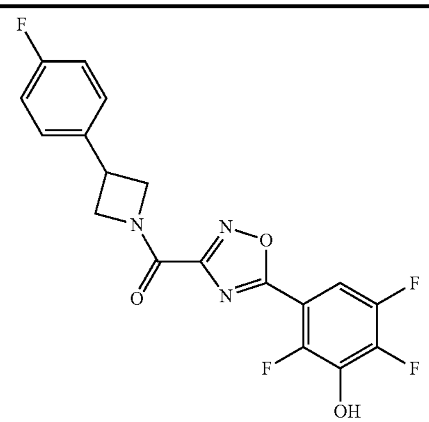 | (3-(4-Fluorophenyl)azetidin-1-yl)(5-(2,4,5-trifluoro-3-hydroxyphenyl)-1,2,4-oxadiazol-3-yl)methanone | calcd for $C_{18}H_{12}F_4N_3O_3$: 394.0810, found: 394.0810 | I |
| 75 | 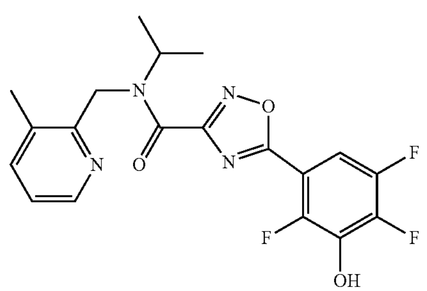 [SMILES: Cc1cccnc1CN(C(=O)c1noc(-c2cc(F)c(F)c(O)c2F)n1)C(C)C] | N-Isopropyl-N-((3-methylpyridin-2-yl)methyl)-5-(2,4,5-trifluoro-3-hydroxyphenyl)-1,2,4-oxadiazole-3-carboxamide | calcd for C19H18F3N4O3: 407.1326, found: 407.1330 | G |
| 76 | 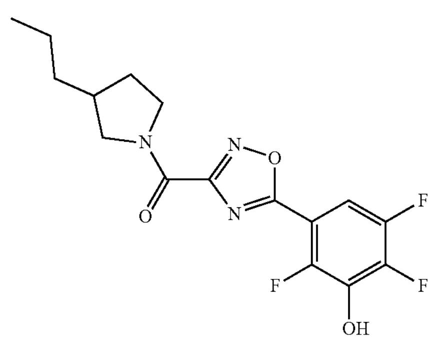 [SMILES: CCCC1CCN(C(=O)c2noc(-c3cc(F)c(F)c(O)c3F)n2)C1] | (3-Propylpyrrolidin-1-yl)(5-(2,4,5-trifluoro-3-hydroxyphenyl)-1,2,4-oxadiazol-3-yl)methanone | calcd for $C_{16}H_{17}F_3N_3O_3$: 356.1216, found: 356.1214 | I |

General Preparation B 5-(2,4,5-Trifluoro-3-hydroxyphenyl)-1,2,4-oxadiazole-3-carboxylic acid Intermediate 2 in DMF (0.4 M, 0.06 mmol, 1 eq) followed by DIPEA (0.35 mmol, 6 eq) and HATU in DMF (0.47 M, 0.12 mmol, 2 eq) were added to a vial containing the appropriate amine (0.12 mmol, 2 eq). The reaction mixture was shaken at rt over night. The reaction mixture was concentrated under reduced pressure. The residue was dissolved in DMSO (0.3 ml) and purified by preparative HPLC, using one of the following methods; PrepMethod F, G, H or I (gradient 2-94%).

TABLE 2

Examples 77-84 were synthesized and purified as described in General Preparation B using the appropriate amines either as the free base or as the corresponding HCl salt. The amine is commercially available if not otherwise stated.

| Example No | Structure | Name | HRMS (ESI) m/z [M + H]+ | Purification Method |
|---|---|---|---|---|
| 77 | 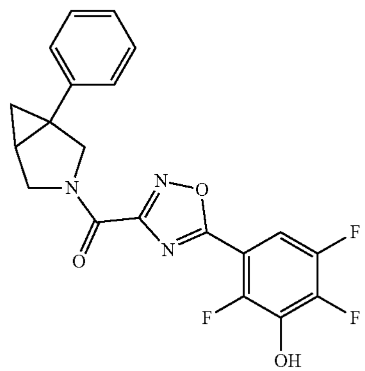 [SMILES: O=C(c1noc(-c2cc(F)c(F)c(O)c2F)n1)N1CC2CC2(c2ccccc2)C1] | (1-Phenyl-3-azabicyclo[3.1.0]hexan-3-yl)(5-(2,4,5-trifluoro-3-hydroxyphenyl)-1,2,4-oxadiazol-3-yl)methanone | calcd for $C_{20}H_{15}F_3N_3O_3$: 402.1060, found: 402.1062 | G |
| 78 | 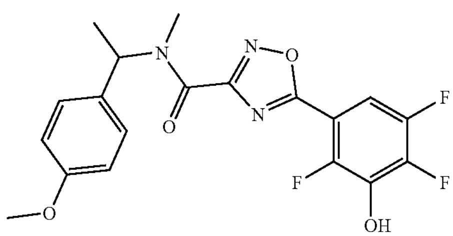 [SMILES: COc1ccc(C(C)N(C)C(=O)c2noc(-c3cc(F)c(F)c(O)c3F)n2)cc1] | N-(1-(4-Methoxyphenyl)ethyl)-N-methyl-5-(2,4,5-trifluoro-3-hydroxyphenyl)-1,2,4-oxadiazole-3-carboxamide | calcd for $C_{19}H_{17}F_3N_3O_4$: 408.1166, found: 408.1162 | H |
| 79 | 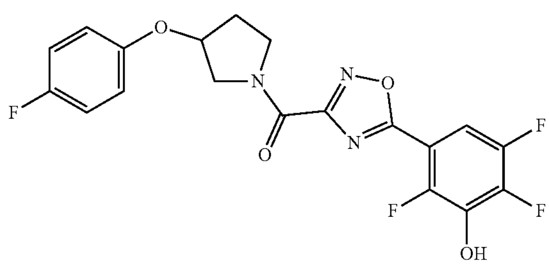 [SMILES: O=C(c1noc(-c2cc(F)c(F)c(O)c2F)n1)N1CCC(Oc2ccc(F)cc2)C1] | (3-(4-Fluorophenoxy)pyrrolidin-1-yl)(5-(2,4,5-trifluoro-3-hydroxyphenyl)-1,2,4-oxadiazol-3-yl)methanone | calcd for $C_{19}H_{14}F_4N_3O_4$: 424.0914, found: 424.0920 | G |
| 80 | 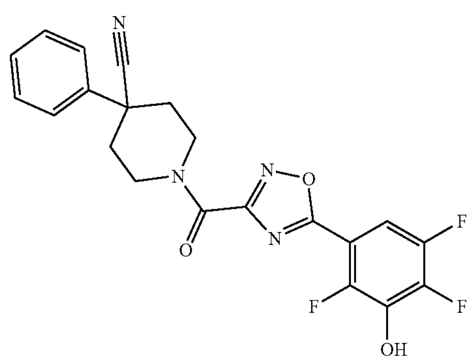 [SMILES: N#CC1(c2ccccc2)CCN(C(=O)c2noc(-c3cc(F)c(F)c(O)c3F)n2)CC1] | 4-Phenyl-1-(5-(2,4,5-trifluoro-3-hydroxyphenyl)-1,2,4-oxadiazole-3-carbonyl)piperidine-4-carbonitrile | calcd for $C_{21}H_{16}F_3N_4O_3$: 429.1168, found: 429.1166 | G |

TABLE 2-continued

Examples 77-84 were synthesized and purified as described in General Preparation B using the appropriate amines either as the free base or as the corresponding HCl salt. The amine is commercially available if not otherwise stated.

| Example No | Structure | Name | HRMS (ESI) m/z [M + H]+ | Purification Method |
|---|---|---|---|---|
| 81 | 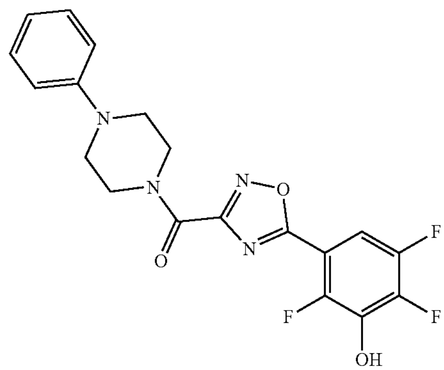 [SMILES: O=C(c1noc(-c2cc(F)c(F)c(O)c2F)n1)N1CCN(c2ccccc2)CC1] | (4-Phenylpiperazin-1-yl)(5-(2,4,5-trifluoro-3-hydroxyphenyl)-1,2,4-oxadiazol-3-yl)methanone | calcd for $C_{19}H_{16}F_3N_4O_3$: 405.1168, found: 405.1170 | G |
| 82 | 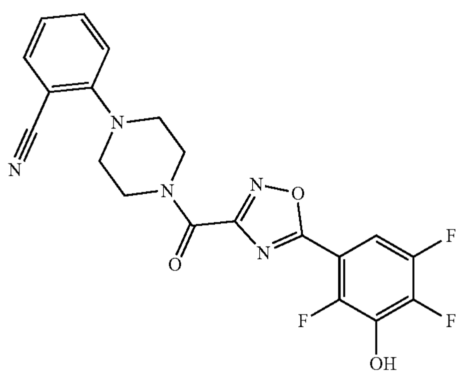 [SMILES: N#Cc1ccccc1N1CCN(C(=O)c2noc(-c3cc(F)c(F)c(O)c3F)n2)CC1] | 2-(4-(5-(2,4,5-Trifluoro-3-hydroxyphenyl)-1,2,4-oxadiazole-3-carbonyl)piperazin-1-yl)benzonitrile | calcd for $C_{20}H_{15}F_3N_5O_3$: 430.1122, found: 430.1124 | G |
| 83 | 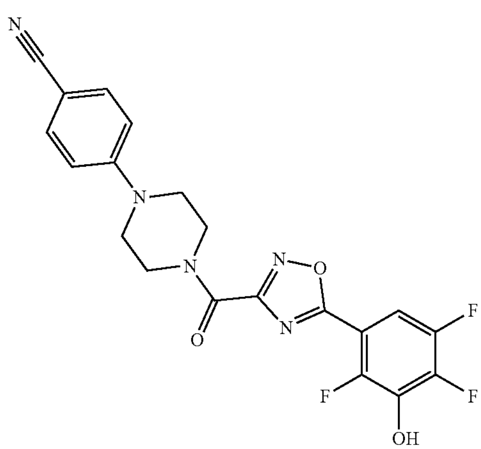 [SMILES: N#Cc1ccc(N2CCN(C(=O)c3noc(-c4cc(F)c(F)c(O)c4F)n3)CC2)cc1] | 4-(4-(5-(2,4,5-Trifluoro-3-hydroxyphenyl)-1,2,4-oxadiazole-3-carbonyl)piperazin-1-yl)benzonitrile | calcd for $C_{20}H_{15}F_3N_5O_3$: 430.1122, found: 430.1124 | H |

TABLE 2-continued

Examples 77-84 were synthesized and purified as described in General Preparation B using the appropriate amines either as the free base or as the corresponding HCl salt. The amine is commercially available if not otherwise stated.

| Example No | Structure | Name | HRMS (ESI) m/z [M + H]+ | Purification Method |
|---|---|---|---|---|
| 84 | 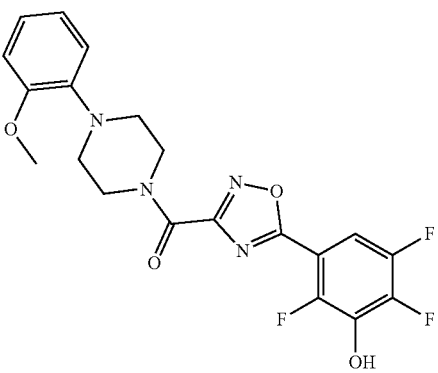 [SMILES: COc1ccccc1N1CCN(C(=O)c2noc(-c3cc(F)c(F)c(O)c3F)n2)CC1] | (4-(2-Methoxyphenyl)piperazin-1-yl)(5-(2,4,5-trifluoro-3-hydroxyphenyl)-1,2,4-oxadiazol-3-yl)methanone | calcd for $C_{20}H_{18}F_3N_4O_4$: 435.1274, found: 435.1276 | G |

Example 85: 3-(1-(5-(2,4,5-Trifluoro-3-hydroxyphenyl)-1,2,4-oxadiazole-3-carbonyl)azetidin-3-yl)benzonitrile

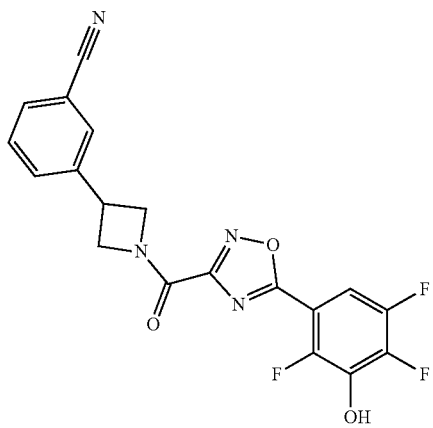 [SMILES: N#Cc1cccc(C2CN(C(=O)c3noc(-c4cc(F)c(F)c(O)c4F)n3)C2)c1]

5-(2,4,5-Trifluoro-3-hydroxyphenyl)-1,2,4-oxadiazole-3-carboxylic acid Intermediate 2 (93 mg, 0.36 mmol), HATU (272 mg, 0.72 mmol) and DMF (3 mL) were mixed in a vial. 3-(Azetidin-3-yl)benzonitrile HCl (80 mg, 0.41 mmol) was added followed by DIPEA (375 µL, 2.15 mmol). The resulting solution was stirred at rt over night. The reaction mixture was filtered and purified by preparative HPLC, PrepMethod D (gradient 20-60%). The pure fractions were combined and the MeCN was evaporated. The remaining water phase was extracted with EtOAc (×2). The combined organic layer was concentrated to give a yellow oil that was purified by preparative HPLC, PrepMethod D (gradient 30-80%). The relevant fractions were combined and evaporated. The residue was dissolved in MeCN and purified by preparative HPLC, PrepMethod J (gradient 15-55%). The pure fractions were combined and evaporated by freeze drying over night. The residue was dissolved in EtOAc and washed with 1 M KHSO₄. The water phase was extracted with EtOAc (×2). The organic layers were combined and evaporated. The residue was dissolved in MeCN/water and freeze dried over night to give the title compound (8.4 mg, 6%) as a white solid; HRMS (ESI) m/z [M+H]+ calcd for $C_{19}H_{12}F_3N_4O_3$: 401.0856, found: 401.0846; ¹H NMR (500 MHz, DMSO-d₆) 7.97-8.02 (1H, m), 7.73-7.82 (2H, m), 7.58 (1H, t), 7.38 (1H, s), 4.94 (1H, t), 4.49-4.62 (2H, m), 4.03-4.21 (2H, m).

Example 86: 2-(5-(2,4,5-Trifluoro-3-hydroxyphenyl)-1,2,4-oxadiazole-3-carbonyl)-1,2,3,4-tetrahydroisoquinoline-7-carbonitrile 5-(2,4,5-Trifluoro-3-hydroxyphenyl)-1,2,4-oxadiazole-3-carboxylic acid Intermediate 2 (80 mg, 0.31 mmol), HATU (234 mg, 0.62 mmol) and DMF (1 mL) were mixed in a vial. 1,2,3,4-Tetrahydroisoquinoline-7-carbonitrile (54 mg, 0.34 mmol) was added followed by DIPEA (322 µL, 1.85 mmol). The resulting yellow solution was stirred at rt for 4 h. The reaction mixture was filtered and purified by preparative HPLC, PrepMethod D (gradient 15-55%). The pure fractions were combined and the MeCN was evaporated. The remaining water phase was extracted with EtOAc (×2). The combined organic layers were concentrated to give a beige oil. The oil was dissolved in MeCN and water was added. The compound was freeze dried over night to give a solid. Water was added to give a slurry that was sonicated for 5 min. The slurry was freeze dried over night to give the title compound (76 mg, 62%) as a beige solid; HRMS (ESI) m/z [M+H]+ calcd for $C_{19}H_{12}F_3N_4O_3$: 401.0856, found: 401.0838; Mixture of rotamers: ratio major:minor: 1:0.6; ¹H NMR (500 MHz, DMSO-d₆) δ 3.01 (2H, dt), 3.79 (1.2H, t), 3.93 (0.8H, t), 4.79 (0.8H, s), 4.90 (1.2H, s), 7.4-7.49 (1H, m), 7.5-7.64 (1H, m), 7.64-7.71 (1H, m), 7.84 (1H, s), 11.81 (1H, bs). Total no of protons in spectrum: 11.

Example 87: ((2R,6S)-2,6-Dimethylmorpholino)(5-(2,4,5-trifluoro-3-hydroxyphenyl)-1,2,4-oxadiazol-3-yl)methanone

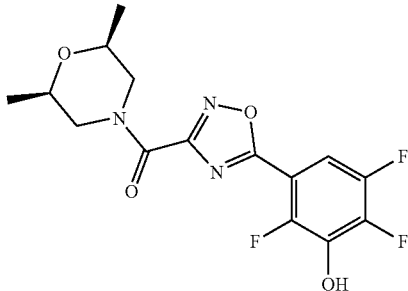 [SMILES: C[C@@H]1CN(C(=O)c2noc(-c3cc(F)c(F)c(O)c3F)n2)C[C@H](C)O1]

(2R,6S)-2,6-Dimethylmorpholine (0.520 g, 4.51 mmol) was suspended in dry toluene (12 mL) and Me$_3$Al in toluene (2 M, 4.34 mL, 8.68 mmol) was added under a N$_2$(g) atmosphere, and the resulting mixture was stirred at rt for 1 h. The above mixture was added to a stirred slurry of ethyl 5-(2,4,5-trifluoro-3-hydroxyphenyl)-1,2,4-oxadiazole-3-carboxylate Intermediate 1 (1 g, 3.47 mmol) in toluene (12 mL). The resulting solution was heated to 60° C. for 20 h. The mixture was cooled to rt, tartaric acid (30%, aq, 100 mL) was added and the mixture was extracted with EtOAc. The organic layer was concentrated, and the residue was purified by preparative HPLC, PrepMethod D (gradient 20-80%) to give the title compound (1.01 g, 81%) as a white solid; HRMS (ESI) m/z [M+H]$^+$ calcd for C$_{15}$H$_{15}$F$_3$N$_3$O$_4$: 358.1008, found: 358.0978; $^1$H NMR (500 MHz, CD$_3$OD) δ 1.14 (3H, d), 1.25 (3H, d), 2.65 (1H, dd), 2.96 (1H, dd), 3.57-3.79 (2H, m), 3.98 (1H, dt), 4.52 (1H, dt), 7.43-7.67 (1H, m).

Example 88: ((2R,6R)-2,6-Dimethylmorpholino)(5-(2,4,5-trifluoro-3-hydroxyphenyl)-1,2,4-oxadiazol-3-yl)methanone

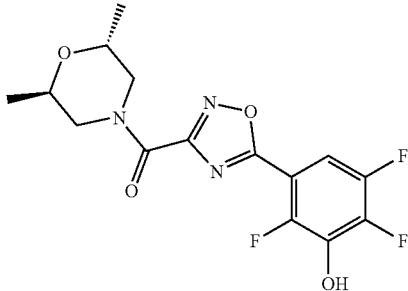 [SMILES: C[C@@H]1CN(C(=O)c2noc(-c3cc(F)c(F)c(O)c3F)n2)C[C@@H](C)O1]

The title compound was prepared analogous to Example 87 from (2R,6R)-2,6-dimethylmorpholine and ethyl 5-(2,4,5-trifluoro-3-hydroxyphenyl)-1,2,4-oxadiazole-3-carboxylate Intermediate 1. The crude product was purified by preparative HPLC, PrepMethod D (gradient 20-80%) to give the title compound (59 mg, 48%); HRMS (ESI) m/z [M+H]$^+$ calcd for C$_{15}$H$_{15}$F$_3$N$_3$O$_4$: 358.1008, found: 358.1008; $^1$H NMR (500 MHz, CD$_3$OD) δ 1.20 (3H, d), 1.26 (3H, d), 3.43 (1H, dd), 3.52 (1H, dd), 3.76 (1H, dd), 3.88 (1H, dd), 4.02-4.1 (1H, m), 4.1-4.18 (1H, m), 7.46-7.64 (1H, m).

Example 89: ((2R,6S)-2,6-Dimethylmorpholino)(5-(2,4,5-trifluoro-3-hydroxyphenyl)isoxazol-3-yl)methanone

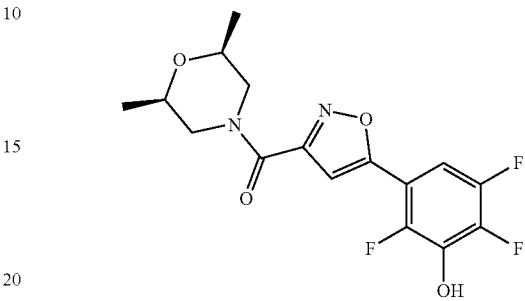

The title compound was prepared analogous to Example 33 from ((2R,6S)-2,6-dimethylmorpholino)(5-(2,4,5-trifluoro-3-methoxyphenyl)isoxazol-3-yl)methanone Intermediate 18, but using 6 eq of BBr$_3$ in DCM (1 M). The crude product was purified by preparative HPLC, PrepMethod D (gradient 15-55%) to give the title compound (74 mg, 57%); HRMS (ESI) m/z [M+H]$^+$ calcd for C$_{16}$H$_{16}$F$_3$N$_2$O$_4$: 357.1056, found: 357.1066; $^1$H NMR (500 MHz, DMSO-d$_6$) δ 1.05 (3H, d), 1.16 (3H, d), 2.55 (1H, dd, overlapping with water peak), 2.88 (1H, dd), 3.52-3.62 (2H, m), 3.90 (1H, dt), 4.38 (1H, td), 7.14 (1H, d), 7.48-7.57 (1H, m), 11.47 (1H, s).

The following compounds, Example 90-111, were also made by methods analogous to those described hereinbefore.

Example 90: (5-(4-Fluoro-3-hydroxyphenyl)-1,3,4-oxadiazol-2-yl)(5-oxa-8-azaspiro[3.5]nonan-8-yl)methanone

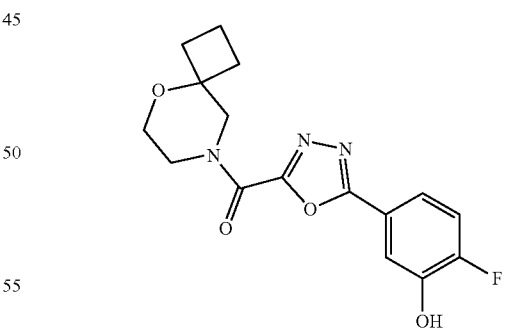

A solution of methyl 5-(4-fluoro-3-hydroxyphenyl)-1,3,4-oxadiazole-2-carboxylate Intermediate 20 (100 mg, 0.42 mmol) and 5-oxa-8-azaspiro[3.5]nonane (160 mg, 1.26 mmol) in DMF (5 mL) was stirred at 80° C. for 4 h. The crude product was purified by preparative HPLC, Prep-Method E, (gradient: 38-50%) to give the title compound (42 mg, 30%) as a white solid; HRMS (ESI) m/z [M+H]$^+$ calcd for C$_{16}$H$_{17}$FN$_3$O$_4$: 334.1198, found: 334.1176; $^1$H NMR (300 MHz, DMSO-d$_6$) δ ppm 1.54-1.85 (2H, m) 1.87-2.12

(4H, m) 3.58-3.67 (3H, m) 3.71 (1H, s) 3.91-4.02 (2H, m) 7.35-7.47 (1H, m) 7.47-7.56 (1H, m) 7.61-7.70 (1H, m) 10.49-10.75 (1H, m).

Example 91: 5-(4-Fluoro-3-hydroxyphenyl)-N-methyl-N-(1-phenyl-1H-tetrazol-5-yl)-1,3,4-oxadiazole-2-carboxamide

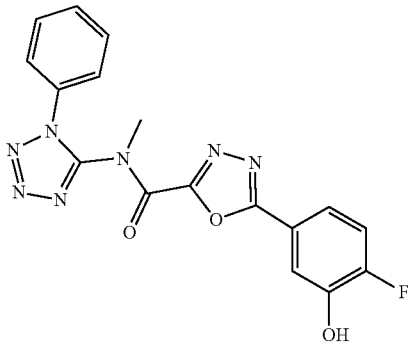 [SMILES: CN(C(=O)c1nnc(-c2ccc(F)c(O)c2)o1)c1nnnn1-c1ccccc1]

Me₃Al (1 M in heptane, 2.52 mL, 2.52 mmol) was added dropwise to a mixture of methyl 5-(4-fluoro-3-hydroxyphenyl)-1,3,4-oxadiazole-2-carboxylate Intermediate 20 (200 mg, 0.84 mmol) and N-methyl-1-phenyl-1H-tetrazol-5-amine Intermediate 45 (441 mg, 2.52 mmol) in DCM (2 mL) and THF (10 mL) at 25° C. under an atmosphere of N₂(g). The resulting mixture was stirred at 25° C. for 3 days. The reaction mixture was poured into 0.1 M HCl (100 mL) and extracted with EtOAc (3×50 mL). The organic layer was dried over Na₂SO₄, filtered and evaporated. The solid was purified by preparative HPLC, PrepMethod V, (gradient: 50-65%) to give the title compound (112 mg, 35%) as a white solid; HRMS (ESI) m/z [M+H]⁺ calcd for C₁₇H₁₃FN₇O₃: 382.1058, found: 382.1036; 1H NMR (300 MHz, DMSO-d₆) δ ppm 3.35 (3H, s) 7.32-7.45 (2H, m) 7.47-7.64 (6H, m) 10.65 (1H, s).

Example 92: 5-(4-Fluoro-3-hydroxyphenyl)-N-methyl-N-(1-phenyl-1H-tetrazol-5-yl)-1,2,4-oxadiazole-3-carboxamide

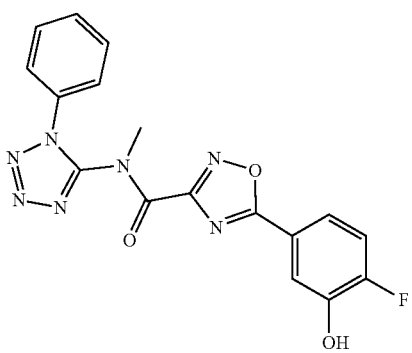 [SMILES: CN(C(=O)c1noc(-c2ccc(F)c(O)c2)n1)c1nnnn1-c1ccccc1]

Me₃Al (2 M in hexane, 3425 µl, 6.85 mmol) was added to a mixture of ethyl 5-(4-fluoro-3-hydroxyphenyl)-1,2,4-oxadiazole-3-carboxylate Intermediate 39 (288 mg, 1.14 mmol) and N-methyl-1-phenyl-1H-tetrazol-5-amine Intermediate 45 (200 mg, 1.14 mmol) in THF (20 mL). The resulting mixture was stirred at 60° C. for 16 h. The reaction mixture was poured into 2 M HCl (10 mL) and extracted with EtOAc (3×25 mL). The organic layer was dried over Na₂SO₄, filtered and evaporated. The crude orange oil was purified by flash chromatography on silica (gradient: 40-50% EtOAc in PE) to give the title compound (0.225 g, 51%) as a white solid; HRMS (ESI) m/z [M+H]⁺ calcd for C₁₇H₁₃FN₇O₃: 382.1058, found: 382.1058; 1H NMR (400 MHz, CD₃OD) δ 3.45 (3H, s), 7.22-7.30 (1H, m), 7.44-7.57 (2H, m), 7.62 (5H, s).

Example 93: (S)-(3-Phenoxypyrrolidin-1-yl)(5-(2,4,5-trifluoro-3-hydroxyphenyl)-1,2,4-oxadiazol-3-yl)methanone

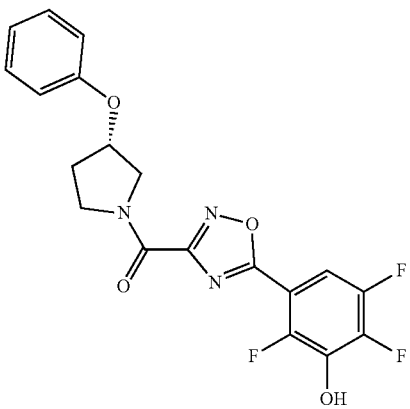 [SMILES: O=C(c1noc(-c2cc(F)c(F)c(O)c2F)n1)N1CC[C@H](Oc2ccccc2)C1]

(S)-3-Phenoxypyrrolidine (250 mg, 1.53 mmol) was added to a mixture of DIPEA (990 mg, 7.66 mmol), HATU (1165 mg, 3.06 mmol) and 5-(2,4,5-trifluoro-3-hydroxyphenyl)-1,2,4-oxadiazole-3-carboxylic acid Intermediate 2 (598 mg, 2.30 mmol) in DMF (5 mL). The reaction mixture was stirred vigorously at 25° C. for 3 h. The reaction mixture was quenched with water (50 mL) and extracted with EtOAc (3×50 mL). The organic layer was dried over MgSO₄, filtered and evaporated. The solid was purified by preparative HPLC, PrepMethod Z (gradient: 50-65%) to give the title compound (0.040 g, 6%) as an off-white solid; HRMS (ESI) m/z [M+H]⁺ calcd for C₁₉H₁₅F₃N₃O₄: 406.1008, found: 406.1008; ¹H NMR (300 MHz, DMSO-d₆) δ ppm 2.09-2.37 (2H, m) 3.52-4.17 (4H, m) 5.05-5.22 (1H, m) 6.88-7.04 (3H, m) 7.23-7.37 (2H, m) 7.52-7.72 (1H, m).

Example 94: (3-(Benzyloxy)piperidin-1-yl)(5-(2,4,5-trifluoro-3-hydroxyphenyl)-1,2,4-oxadiazol-3-yl)methanone

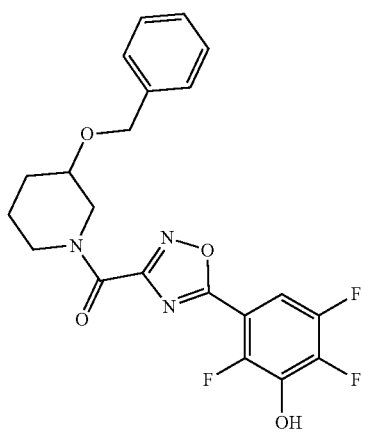 [SMILES: O=C(c1noc(-c2cc(F)c(F)c(O)c2F)n1)N1CCCC(OCc2ccccc2)C1]

3-(Benzyloxy)piperidine (1 g, 5.23 mmol) was added to a mixture of DIPEA (3.38 g, 26.14 mmol), HATU (3.98 g, 10.46 mmol) and 5-(2,4,5-trifluoro-3-hydroxyphenyl)-1,2,4-oxadiazole-3-carboxylic acid Intermediate 2 (2.040 g, 7.84 mmol) in DMF (20 mL). The reaction mixture was stirred vigorously at 25° C. for 3 h. The reaction mixture was quenched with water (50 mL) and extracted with EtOAc (3×50 mL). The organic layer was dried over $MgSO_4$, filtered and evaporated. The solid was purified by preparative HPLC, PrepMethod X (gradient: 28-38%) to give the title compound (33.5 mg, 1%) as an off-white solid; HRMS (ESI) m/z [M+H]$^+$ calcd for $C_{21}H_{19}F_3N_3O_4$: 434.1322, found: 434.1314; $^1$H NMR (400 MHz, DMSO-$d_6$) δ ppm 1.37-1.56 (1H, m) 1.66-1.98 (2H, m) 3.37-3.65 (4H, m) 3.73-3.84 (2H, m) 4.41 (1H, s) 4.49-4.67 (1H, m) 6.76-7.92 (5H, m).

Example 95: (R)-(3-(4-Chlorophenyl)pyrrolidin-1-yl)(5-(2,4,5-trifluoro-3-hydroxyphenyl)-1,2,4-oxadiazol-3-yl)methanone

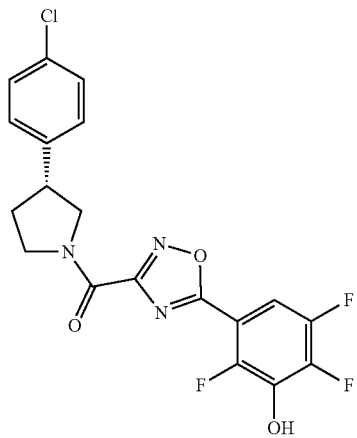 [SMILES: O=C(c1noc(-c2cc(F)c(F)c(O)c2F)n1)N1CC[C@H](c2ccc(Cl)cc2)C1]

COMU (884 mg, 2.06 mmol) was added to a mixture of (R)-3-(4-chlorophenyl)pyrrolidine (250 mg, 1.38 mmol), 5-(2,4,5-trifluoro-3-hydroxyphenyl)-1,2,4-oxadiazole-3-carboxylic acid Intermediate 2 (358 mg, 1.38 mmol) and DIPEA (2.40 mL, 13.76 mmol) in DMF (2.5 mL) under an atmosphere of $N_2$(g). The resulting mixture was stirred at 25° C. for 2 h. The reaction mixture was quenched with sat brine (50 mL) and extracted with EtOAc (3×50 mL). The organic layer was dried over $Na_2SO_4$, filtered and evaporated. The yellow oil was purified by flash chromatography on a C18 column (gradient: 40-60% MeCN in water) to give the title compound (0.076 g, 13%) as a yellow solid; HRMS (ESI) m/z [M+H]$^+$ calcd for $C_{19}H_{14}ClF_3N_3O_3$: 424.0670, found: 424.0668; $^1$H NMR (400 MHz, DMSO-$d_6$) δ ppm 1.96-2.15 (1H, m) 2.25-2.39 (1H, m) 3.40-3.99 (4H, m) 4.02-4.22 (1H, m) 7.30-7.46 (4H, m) 7.59-7.78 (1H, m) 11.68 (1H, s).

Example 96: (3-Phenylpyrrolidin-1-yl)(5-(2,4,5-trifluoro-3-hydroxyphenyl)-1,2,4-oxadiazol-3-yl)methanone

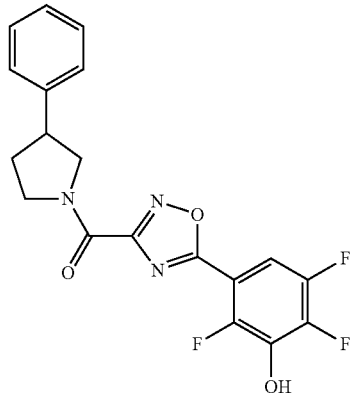 [SMILES: O=C(c1noc(-c2cc(F)c(F)c(O)c2F)n1)N1CCC(c2ccccc2)C1]

$Me_3Al$ (2 M in toluene, 3460 µL, 6.92 mmol) was added to a mixture of 5-(2,4,5-trifluoro-3-hydroxyphenyl)-1,2,4-oxadiazole-3-carboxylic acid Intermediate 2 (300 mg, 1.15 mmol) and 3-phenylpyrrolidine (340 mg, 2.31 mmol) in THF (3 mL) at 25° C. under an atmosphere of $N_2$(g). The resulting solution was stirred at 60° C. for 3 h. The reaction mixture was acidified with 2 M HCl and then concentrated. The residue was diluted with EtOAc and washed sequentially with water and sat $NaHCO_3$. The organic layer was dried over $Na_2SO_4$, filtered and evaporated. The crude product was purified by preparative HPLC, PrepMethod E (gradient: 55-70%) to give the title compound (0.030 g, 6%) as a white solid; HRMS (ESI) m/z [M+H]$^+$ calcd for $C_{19}H_{15}F_3N_3O_3$: 390.1060, found: 390.1070; $^1$H NMR (400 MHz, DMSO-$d_6$) δ ppm 2.04-2.13 (1H, m) 2.29-2.36 (1H, m) 3.46-3.51 (1H, m) 3.55-3.65 (1H, m) 3.73-3.86 (1H, m) 3.90-3.99 (1H, m) 4.06-4.20 (1H, m) 7.21-7.29 (1H, m) 7.30-7.41 (4H, m) 7.58-7.71 (1H, m) 11.61-11.77 (1H, m).

Example 97: (3-(Benzyloxy)pyrrolidin-1-yl)(5-(2,4,5-trifluoro-3-hydroxyphenyl)-1,2,4-oxadiazol-3-yl)methanone

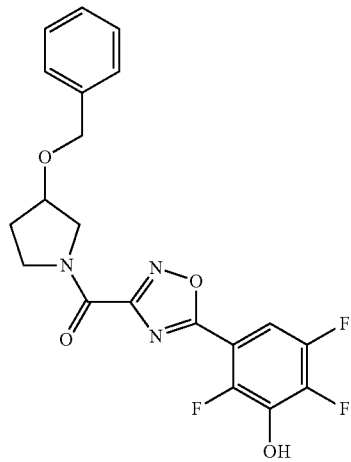 [SMILES: O=C(c1noc(-c2cc(F)c(F)c(O)c2F)n1)N1CCC(OCc2ccccc2)C1]

Me₃Al (2 M in toluene, 4613 µL, 9.23 mmol) was added to 5-(2,4,5-trifluoro-3-hydroxyphenyl)-1,2,4-oxadiazole-3-carboxylic acid Intermediate 2 (400 mg, 1.54 mmol) and 3-(benzyloxy)pyrrolidine (273 mg, 1.54 mmol) in DMF (5 mL) at 25° C. under an atmosphere of N₂(g). The resulting solution was stirred at 25° C. for 2 h. The reaction mixture was acidified with 2 M HCl and then concentrated. The residue was diluted with EtOAc, and washed sequentially with water. The organic layer was dried over Na₂SO₄, filtered and evaporated to give a crude product that was purified by preparative HPLC, PrepMethod V (gradient: 50-62%) to give the title compound (0.048 g, 7%) as a white solid; HRMS (ESI) m/z [M+H]⁺ calcd for $C_{20}H_{17}F_3N_3O_4$: 420.1166, found: 420.1168; 1H NMR (400 MHz, DMSO-d₆) δ ppm 1.99-2.22 (2H, m) 3.53-3.88 (4H, m) 4.23-4.36 (1H, m) 4.45-4.65 (2H, m) 7.26-7.45 (5H, m) 7.49-7.73 (1H, m) 11.43 (1H, s).

Example 98: (R)-(3-Phenoxypyrrolidin-1-yl)(5-(2,4,5-trifluoro-3-hydroxyphenyl)-1,2,4-oxadiazol-3-yl)methanone

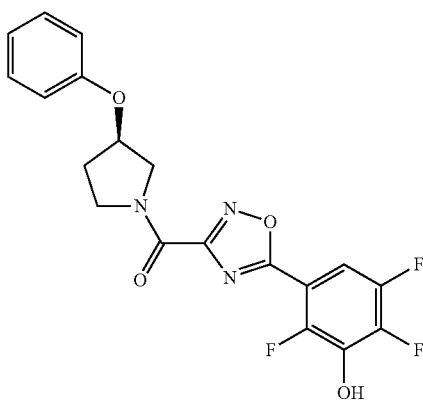 [SMILES: O=C(c1noc(-c2cc(F)c(F)c(O)c2F)n1)N1CC[C@@H](Oc2ccccc2)C1]

(R)-3-Phenoxypyrrolidine (300 mg, 1.84 mmol) was added to a mixture of 5-(2,4,5-trifluoro-3-hydroxyphenyl)-1,2,4-oxadiazole-3-carboxylic acid Intermediate 2 (1.195 g, 4.60 mmol), HATU (1.398 g, 3.68 mmol) and DIPEA (963 µl, 5.51 mmol) in DMF (10 mL) at 0° C. under an atmosphere of N₂(g). The resulting mixture was stirred at 25° C. for 3 h. The reaction mixture was concentrated, diluted with DCM (50 mL) and washed sequentially with water (3×50 mL) and sat brine (3×50 mL). The organic layer was dried over Na₂SO₄, filtered and evaporated. The residue was purified by preparative TLC (DCM:MeOH, 20:1) and then by preparative HPLC, PrepMethod N (gradient: 50-65%) to give the crude compound. The crude was diluted with DCM (100 mL) and washed sequentially with sat NaHCO₃ (3×100 mL) and water (3×100 mL). The organic layer was dried over Na₂SO₄, filtered and evaporated. As the residue still contained impurities it was again diluted with DCM and washed as above with sat NaHCO₃ and water, dried over Na₂SO₄, filtered and evaporated to give the title compound (0.031 g, 34%) as a white solid; HRMS (ESI) m/z [M+H]⁺ calcd for $C_{19}H_{15}F_3N_3O_4$: 406.1008, found: 406.1040; 1H NMR (400 MHz, DMSO-d₆) δ ppm 2.12-2.32 (2H, m) 3.59-3.71 (1H, m) 3.72-4.10 (3H, m) 5.15 (1H, br s) 6.90-7.06 (3H, m) 7.24-7.39 (2H, m) 7.57-7.77 (1H, m) 11.52 (1H, br s).

Example 99: N-(1-Cyclohexyl-1H-pyrazol-5-yl)-5-(4-fluoro-3-hydroxyphenyl)isoxazole-3-carboxamide

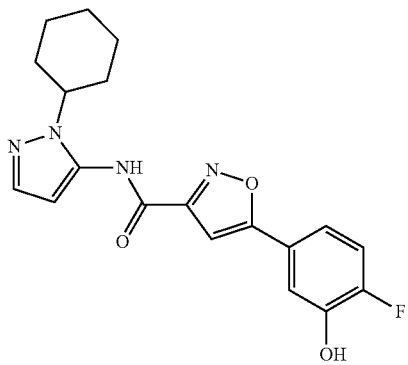 [SMILES: O=C(Nc1ccnn1C1CCCCC1)c1cc(-c2ccc(F)c(O)c2)on1]

1-Cyclohexyl-1H-pyrazol-5-amine (120 mg, 0.73 mmol) was added to a mixture of HATU (387 mg, 1.02 mmol), DIPEA (634 µL, 3.63 mmol) and 5-(4-fluoro-3-hydroxyphenyl)isoxazole-3-carboxylic acid Intermediate 34 (211 mg, 0.94 mmol) in DMF (5 mL). The resulting mixture was stirred at 25° C. for 3 h. Water was added and the aqueous layer was extracted with EtOAc (×3). The combined organic layer was washed with sat NaHCO₃ (aq, ×2), dried over anhydrous Na₂SO₄ and evaporated to dryness. The residue was purified by preparative TLC (PE:EtOAc, 1:1) followed by flash chromatography on a C18 column (gradient: 0-100% MeCN in water) to give the title compound (0.072 g, 26%) as a white solid; HRMS (ESI) m/z [M+H]⁺ calcd for $C_{19}H_{20}FN_4O_3$: 371.1514, found: 371.1514; ¹H NMR (400 MHz, DMSO-d₆) δ ppm 1.09-1.42 (3H, m) 1.64 (1H, br d) 1.69-1.93 (6H, m) 4.01-4.18 (1H, m) 6.21 (1H, d) 7.32-7.40 (1H, m) 7.41-7.48 (3H, m) 7.51 (1H, dd) 10.43 (1H, br s) 10.74 (1H, br s).

Example 100: N-((1-Cyclohexyl-1H-pyrazol-5-yl)methyl)-2-(4-fluoro-3-hydroxyphenyl)oxazole-5-carboxamide

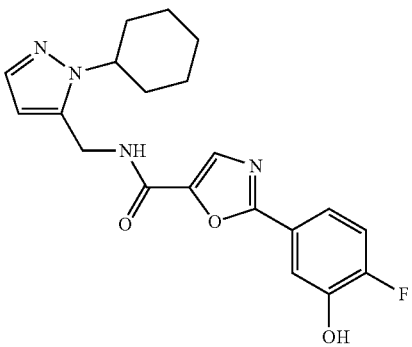 [SMILES: O=C(NCc1ccnn1C1CCCCC1)c1cnc(-c2ccc(F)c(O)c2)o1]

2,6-Dimethylpyridine (130 µL, 1.12 mmol) was added to a mixture of 2-(4-fluoro-3-hydroxyphenyl)oxazole-5-carboxylic acid Intermediate 41 (50 mg, 0.22 mmol), (1-cyclohexyl-1H-pyrazol-5-yl)methanamine (40.2 mg, 0.22 mmol) and HATU (94 mg, 0.25 mmol) in DMF (2.11 mL). The reaction was left at rt overnight. The reaction was diluted with EtOAc (20 mL), washed with sat NaHCO₃ (10 mL) and brine (3×10 mL). The organic layer was dried over MgSO₄, filtered and concentrated under reduced pressure. The crude product was purified by preparative HPLC, PrepMethod SFC-A (gradient: 5-90%) to give the title compound (10.90 mg, 12%); HRMS (ESI) m/z [M+H]+ calcd for $C_{20}H_{22}FN_4O_3$: 385.1670, found: 385.1660; 1H NMR (600 MHz, DMSO-$d_6$) δ 9.18 (t, 1H), 7.89 (s, 1H), 7.69 (dd, 1H), 7.56 (ddd, 1H), 7.32-7.37 (m, 2H), 6.17 (d, 1H), 4.56 (d, 2H), 4.2-4.26 (m, 1H), 4.09 (s, 1H), 1.74-1.83 (m, 6H), 1.64 (d, 1H), 1.35 (qt, 2H), 1.17 (qt, 1H).

Example 101: (R)-(5-(4-Fluoro-3-hydroxyphenyl) isoxazol-3-yl)(3-phenylpyrrolidin-1-yl)methanone

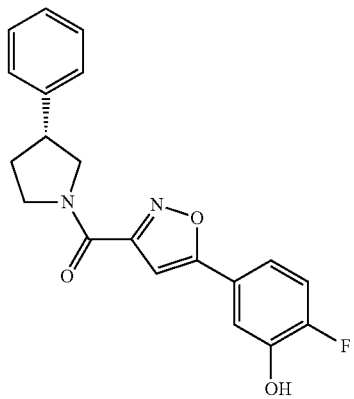 [SMILES: O=C(c1cc(-c2ccc(F)c(O)c2)on1)N1CC[C@H](c2ccccc2)C1]

(R)-3-Phenylpyrrolidine (100 mg, 0.68 mmol) was added to a mixture of COMU (291 mg, 0.68 mmol), DIPEA (263 mg, 2.04 mmol) and 5-(4-fluoro-3-hydroxyphenyl)isoxazole-3-carboxylic acid Intermediate 34 (182 mg, 0.82 mmol) in DMF (5 mL). The reaction mixture was stirred vigorously at 25° C. for 3 h. The solvent was removed under reduced pressure and the crude product was purified by flash chromatography on a C18 column (gradient: 0-60% MeCN in water) followed by preparative HPLC, PrepMethod Y (gradient: 32-62%) to give the title compound (0.037 g, 15%) as a white solid; HRMS (ESI) m/z [M+H]+ calcd for $C_{20}H_{18}FN_2O_3$: 353.1296, found: 353.1304; 1H NMR (300 MHz, DMSO-$d_6$) δ ppm 1.96-2.18 (1H, m) 2.22-2.43 (1H, m) 3.42-3.68 (2H, m) 3.71-3.88 (1H, m) 3.93-4.10 (1H, m) 4.23 (1H, dd) 6.90-7.82 (9H, m).

Example 102: (3H-Spiro[isobenzofuran-1,3'-pyrrolidin]-1'-yl)(5-(2,4,5-trifluoro-3-hydroxyphenyl)-1,2,4-oxadiazol-3-yl)methanone

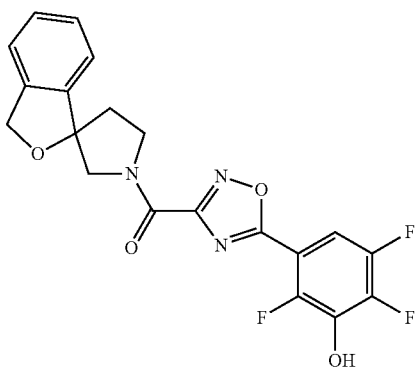 [SMILES: O=C(c1noc(-c2cc(F)c(F)c(O)c2F)n1)N1CCC2(C1)OCc1ccccc12]

DIC (89 μL, 0.57 mmol) was added to a mixture of 3H-spiro[isobenzofuran-1,3'-pyrrolidine] (50 mg, 0.29 mmol), 5-(2,4,5-trifluoro-3-hydroxyphenyl)-1,2,4-oxadiazole-3-carboxylic acid Intermediate 2 (74.2 mg, 0.29 mmol) in DMF (1 mL) at 0° C. under an atmosphere of $N_2$(g). The resulting mixture was stirred at 25° C. for 16 h. The reaction mixture was quenched with sat NaHCO$_3$ (25 mL) and extracted with EtOAc (3×25 mL). The combined organic layer was dried over Na$_2$SO$_4$, filtered and evaporated. The crude product was purified by flash chromatography on a C18 column (gradient: 60-70% MeCN in water) to give the title compound (9 mg, 7%) as a white solid; HRMS (ESI) m/z [M+H]+ calcd for $C_{20}H_{15}F_3N_3O_4$: 418.1008, found: 418.1014; 1H NMR (400 MHz, DMSO-$d_6$) δ ppm 2.13-2.26 (1H, m) 2.37-2.48 (1H, m) 3.66-4.01 (3H, m) 4.06 (1H, t) 4.97-5.18 (2H, m) 7.27-7.42 (3H, m) 7.44-7.62 (2H, m).

Example 103: (S)-(3-(4-Chlorophenyl)pyrrolidin-1-yl)(5-(2,4,5-trifluoro-3-hydroxyphenyl)-1,2,4-oxadiazol-3-yl)methanone

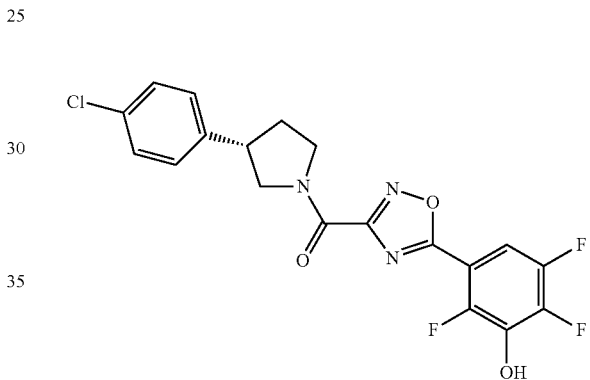

(S)-3-(4-Chlorophenyl)pyrrolidine (200 mg, 1.10 mmol) was added to a mixture of DIPEA (427 mg, 3.30 mmol), HATU (837 mg, 2.20 mmol) and 5-(2,4,5-trifluoro-3-hydroxyphenyl)-1,2,4-oxadiazole-3-carboxylic acid Intermediate 2 (430 mg, 1.65 mmol) in DMF (10 mL). The reaction mixture was stirred vigorously at rt for 3 h, then quenched with sat brine (50 mL) and extracted with EtOAc (3×50 mL). The combined organic layer was dried over Na$_2$SO$_4$, filtered and evaporated. The yellow oil was purified by preparative HPLC, PrepMethod Y (gradient: 28-38%) to give the title compound (0.039 g, 8%) as a white solid; HRMS (ESI) m/z [M+H]+ calcd for $C_{19}H_{14}ClF_3N_3O_3$: 424.0670, found: 424.0676; 1H NMR (400 MHz, DMSO-$d_6$) δ ppm 1.96-2.17 (1H, m) 2.25-2.42 (1H, m) 3.41-3.99 (4H, m) 4.12 (1H, ddd) 7.29-7.51 (4H, m) 7.53-7.82 (1H, m) 11.73 (1H, br s).

Example 104: (R)-(3-Phenylpyrrolidin-1-yl)(5-(2,4,5-trifluoro-3-hydroxyphenyl)isoxazol-3-yl)methanone

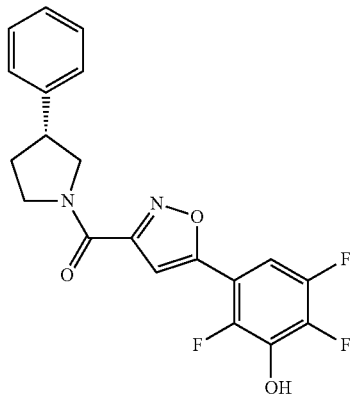 [SMILES: O=C(c1cc(-c2cc(F)c(F)c(O)c2F)on1)N1CC[C@H](c2ccccc2)C1]

EDC (118 mg, 0.62 mmol) and HOBt (83 mg, 0.62 mmol) were added to a mixture of 5-(2,4,5-trifluoro-3-hydroxyphenyl)isoxazole-3-carboxylic acid Intermediate 37 (80 mg, 0.31 mmol), (R)-3-phenylpyrrolidine (45.4 mg, 0.31 mmol), DIPEA (162 μL, 0.93 mmol) and DMAP (7.54 mg, 0.06 mmol) in DMF (2 mL) at 20° C. The resulting solution was stirred at 60° C. for 3 h under an atmosphere of $N_2(g)$. The reaction mixture was concentrated, diluted with EtOAc (25 mL) and washed with water (25 mL). The organic layer was dried over $Na_2SO_4$, filtered and evaporated. The residue was purified by preparative TLC (MeOH:DCM, 1:10) followed by preparative HPLC, PrepMethod N (gradient: 45-55%) to give the title compound (0.018 g, 15%) as a white solid; HRMS (ESI) m/z $[M+H]^+$ calcd for $C_{20}H_{16}F_3N_2O_3$: 389.1108, found: 389.1094; $^1$H NMR (300 MHz, DMSO-$d_6$) δ ppm 1.96-2.19 (1H, m) 2.30-2.43 (1H, m) 3.40-4.29 (5H, m) 7.16 (1H, d) 7.22-7.31 (1H, m) 7.31-7.39 (4H, m) 7.40-7.64 (1H, m) 11.56 (1H, br s).

Example 105: N,N-Dimethyl-1-(5-(2,4,5-trifluoro-3-hydroxyphenyl)thiophene-2-carbonyl)pyrrolidine-2-carboxamide

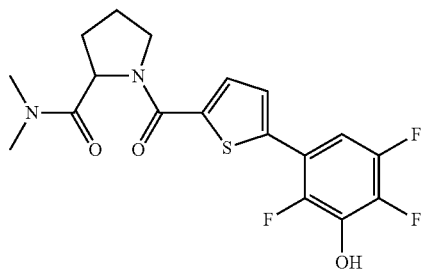 [SMILES: CN(C)C(=O)C1CCCN1C(=O)c1ccc(-c2cc(F)c(F)c(O)c2F)s1]

BBr$_3$ (1 M in DCM, 0.2 mL, 0.20 mmol) was added dropwise to N,N-dimethyl-1-(5-(2,4,5-trifluoro-3-methoxyphenyl)thiophene-2-carbonyl)pyrrolidine-2-carboxamide Intermediate 48 (50 mg, 0.12 mmol) in DCM (1 mL) at 0° C. under an atmosphere of $N_2(g)$. The resulting solution was stirred at 20° C. for 8 h. The reaction was quenched with MeOH (2 mL). The residue was purified by preparative TLC (MeOH:DCM, 1:10) followed by preparative HPLC, Prep-Method N, (gradient: 31-44%) to give the title compound (0.014 g, 29%) as a white solid; HRMS (ESI) m/z $[M+H]^+$ calcd for $C_{18}H_{18}F_3N_2O_3S$: 399.0984, found: 399.0976; Mixture of rotamers: $^1$H NMR (300 MHz, DMSO-$d_6$) δ ppm 1.69-1.84 (1H, m) 1.89-2.11 (2H, m) 2.14-2.31 (1H, m) 2.76-2.88 (3H, m) 2.96-3.17 (3H, m) 3.53-3.72 (0.4H, m) 3.78-4.02 (1.6H, m) 4.96 (0.8H, dd) 5.27 (0.2H, dd) 7.18-7.79 (3H, m) 11.27 (1H, s). Total no of protons in spectrum: 17.

Example 106: 2-(5-(2,4,5-Trifluoro-3-hydroxyphenyl)-1,2,4-oxadiazole-3-carbonyl)isoindoline-5-carbonitrile

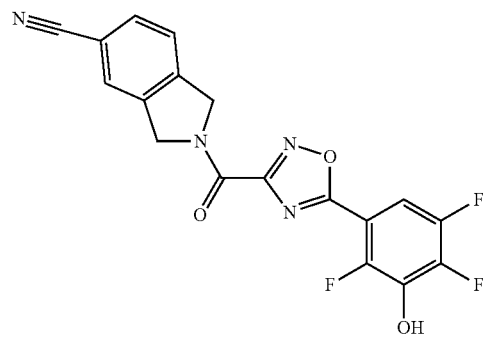 [SMILES: N#Cc1ccc2c(c1)CN(C(=O)c1noc(-c3cc(F)c(F)c(O)c3F)n1)C2]

5-(2,4,5-Trifluoro-3-hydroxyphenyl)-1,2,4-oxadiazole-3-carboxylic acid Intermediate 2 (34 mg, 0.13 mmol), HATU (99 mg, 0.26 mmol) and DMF (0.5 mL) were mixed in a vial. Isoindoline-5-carbonitrile HCl (23.61 mg, 0.13 mmol) dissolved in DMF (0.500 mL) was added followed by DIPEA (137 μL, 0.78 mmol). The resulting yellow solution was stirred at rt overnight. The reaction mixture was diluted with DMSO and purified by preparative HPLC, PrepMethod C (gradient: 15-60%) to give the title compound (0.012 g, 24%) as a white solid; HRMS (ESI) m/z $[M+H]^+$ calcd for $C_{18}H_{10}F_3N_4O_3$: 387.0700, found: 387.0686; $^1$H NMR (500 MHz, DMSO-$d_6$) δ 4.99 (2H, d), 5.22 (2H, d), 7.56-7.7 (2H, m), 7.77-7.84 (1H, m), 7.91 (1H, d).

Example 107: (4-(3-Isopropyl-1,2,4-oxadiazol-5-yl)-3,6-dihydropyridin-1(2H)-yl)(5-(2,4,5-trifluoro-3-hydroxyphenyl)-1,2,4-oxadiazol-3-yl)methanone

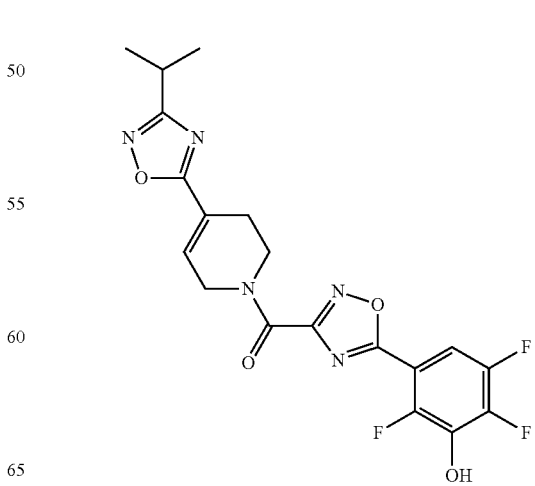

Me₃Al (2 M in toluene, 0.985 mL, 1.97 mmol) was added to 3-isopropyl-5-(1,2,3,6-tetrahydropyridin-4-yl)-1,2,4-oxadiazole Intermediate 51 (198 mg, 1.02 mmol) in toluene (2 mL) under an atmosphere of N₂(g). The resulting mixture was stirred at rt for 45 min. The mixture was added to a stirred slurry of ethyl 5-(2,4,5-trifluoro-3-hydroxyphenyl)-1,2,4-oxadiazole-3-carboxylate Intermediate 1 (227 mg, 0.79 mmol) in toluene (2 mL). The resulting mixture was heated to 60° C. for 5 h, then cooled to rt. Tartaric acid (30%, aq, 12 mL) was added and the mixture was extracted with EtOAc (×2). The combined organic layer was concentrated under reduced pressure and the residue was purified by preparative HPLC, PrepMethod C (gradient: 35-75%) to give the title compound (209 mg, 61%) as an off-white solid; HRMS (ESI) m/z [M+H]⁺ calcd for $C_{19}H_{17}F_3N_5O_4$: 436.1228, found: 436.1210; Mixture of rotamers: ¹H NMR (500 MHz, MeOD) 1.33 (6H, dd), 2.74-2.82 (2H, m), 3.03-3.12 (1H, m), 3.92 (1.3H, t), 4.05 (0.7H, t), 4.51-4.57 (2H, m), 6.95-7 (0.4H, m), 7.07-7.11 (0.6H, m), 7.51-7.6 (1H, m). Total no of protons in spectrum: 15.

Example 108: ((2S,6R)-2,6-Dimethylmorpholino)(5-(2,4,5-trifluoro-3-hydroxy-6-iodophenyl)-1,2,4-oxadiazol-3-yl)methanone

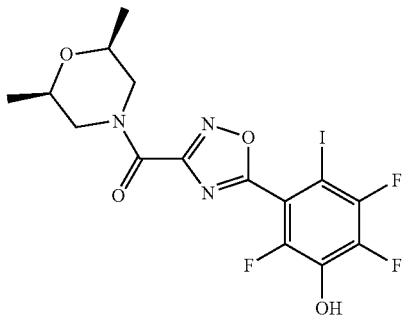 [SMILES: C[C@@H]1CN(C(=O)c2noc(-c3c(F)c(O)c(F)c(F)c3I)n2)C[C@H](C)O1]

A mixture of ((2S,6R)-2,6-dimethylmorpholino)(5-(2,4,5-trifluoro-3-hydroxyphenyl)-1,2,4-oxadiazol-3-yl)methanone Example 87 (29 mg, 0.08 mmol) and NIS (73.0 mg, 0.32 mmol) in AcOH (2 mL) was stirred at rt for 20 h. The mixture was concentrated and the residue was diluted with MeCN and DMSO and purified by preparative HPLC, PrepMethod C (gradient: 20-80%) to give the title compound (27 mg, 68%) as a brown-yellow solid; HRMS (ESI) m/z [M+H]⁺ calcd for $C_{15}H_{14}F_{31}N_3O_4$: 483.9976, found: 483.9962; ¹H NMR (500 MHz, CDCl₃) δ 1.22 (3H, d), 1.29 (3H, d), 2.6-2.72 (2H, m), 3.00 (1H, dd), 3.6-3.81 (2H, m), 4.20 (1H, dt), 4.63 (1H, dt).

Example 109: 2-(5-(2,4,5-Trifluoro-3-hydroxy-6-iodophenyl)-1,2,4-oxadiazole-3-carbonyl)-1,2,3,4-tetrahydroisoquinoline-5-carbonitrile

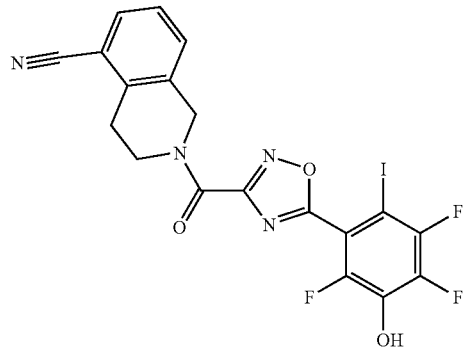 [SMILES: N#Cc1cccc2c1CCN(C(=O)c1noc(-c3c(F)c(O)c(F)c(F)c3I)n1)C2]

A mixture of 2-(5-(2,4,5-trifluoro-3-hydroxyphenyl)-1,2,4-oxadiazole-3-carbonyl)-1,2,3,4-tetrahydroisoquinoline-5-carbonitrile Example 66 (0.149 g, 0.24 mmol) and NIS (0.218 g, 0.97 mmol) in AcOH (10 mL) was stirred at rt for 20 h. The mixture was concentrated and the residue purified by preparative HPLC, PrepMethod D (gradient: 20-80%) to give the title compound (0.063 mg, 50%) as a white solid; HRMS (ESI) m/z [M+H]⁺ calcd for $C_{19}H_{11}F_{31}N_4O_3$: 526.9822, found: 526.9808; ¹H NMR (500 MHz, CDCl₃) 3.26 (2H, t), 4.14 (2H, t), 5.01 (2H, s), 7.38 (1H, t), 7.46 (1H, d), 7.59 (1H, d), 9.23 (1H, s).

Example 110: ((2R,6S)-2,6-Dimethylmorpholino)(3-(2,4,5-trifluoro-3-hydroxyphenyl)-1,2,4-oxadiazol-5-yl)methanone

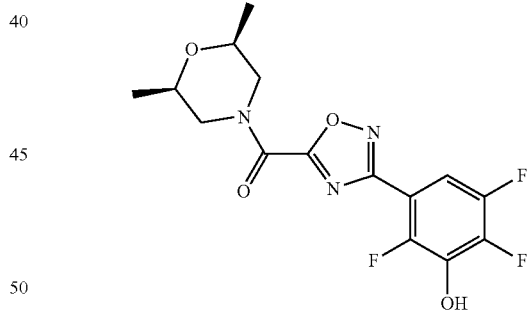

Me₃Al (2 M in toluene, 0.347 mL, 0.69 mmol) was added dropwise under an atmosphere of N₂(g) and at rt to a solution of (2R,6S)-2,6-dimethylmorpholine (0.048 mL, 0.38 mmol) in anhydrous toluene (0.5 mL). The reaction mixture was stirred at rt for 1 h. and was then added dropwise at rt to a stirred mixture of methyl 3-(2,4,5-trifluoro-3-hydroxyphenyl)-1,2,4-oxadiazole-5-carboxylate Intermediate 52 (80 mg, 0.29 mmol) in toluene (0.75 mL) under an atmosphere of N₂(g). The resulting solution was heated at 60° C. for 6 h and was then cooled to 0° C. Tartaric acid (30%, aq, 4 mL) was added dropwise and the resulting mixture was extracted with EtOAc (×2). The combined organic layer was washed with H₂O (×2), passed through a phase separator, and concentrated under reduced pressure. The residue was purified by preparative HPLC, PrepMethod D, (gradient: 25-65%) to give the title compound (52 mg, 49%) as a white solid; HRMS (ESI) m/z [M+H]⁺ calcd for $C_{15}H_{15}F_3N_3O_4$: 358.1008, found: 358.1022; ¹H NMR (500 MHz, DMSO-d₆) δ 1.08 (3H, d), 1.17 (3H, d), 2.64 (1H, dd), 2.95 (1H, dd), 3.56-3.66 (2H, m), 4.1-4.17 (1H, m), 4.32-4.38 (1H, m), 7.48 (1H, ddd), 11.50 (1H, s).

Example 111: ((3R,5S)-3,5-Dimethylpiperidin-1-yl)(3-(2,4,5-trifluoro-3-hydroxyphenyl)-1,2,4-oxadiazol-5-yl)methanone

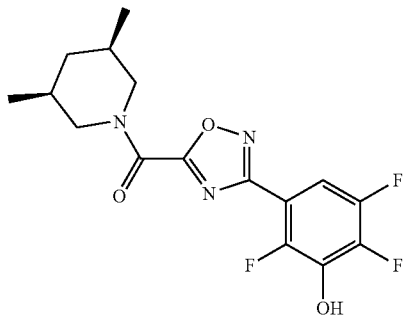 [SMILES: C[C@@H]1C[C@H](C)CN(C(=O)c2nc(-c3cc(F)c(F)c(O)c3F)no2)C1]

The title compound was prepared from methyl 3-(2,4,5-trifluoro-3-hydroxyphenyl)-1,2,4-oxadiazole-5-carboxylate Intermediate 52 (80 mg, 0.29 mmol) and (3S,5R)-3,5-dimethylpiperidine (44 mg, 0.39 mmol) in analogy to the preparation of Example 110. The crude product was purified by preparative HPLC, PrepMethod D, (gradient: 35-75%) to give the title compound (67 mg, 65%) as a white solid; HRMS (ESI) m/z [M+H]⁺ calcd for $C_{16}H_{17}F_3N_3O_3$: 356.1216, found: 356.1224; ¹H NMR (500 MHz, DMSO-d₆) δ 0.83 (3H, d), 0.84-0.91 (1H, m), 0.93 (3H, d), 1.57-1.72 (2H, m), 1.77-1.84 (1H, m), 2.42 (1H, t), 2.74 (1H, dd), 3.89-3.96 (1H, m), 4.37-4.45 (1H, m), 7.45 (1H, ddd), 11.47 (1H, s).

Example 112: ((4aR,7aS)-Hexahydrocyclopenta[b][1,4]oxazin-4(4aH)-yl)(5-(2,4,5-trifluoro-3-hydroxyphenyl)-1,2,4-oxadiazol-3-yl)methanone

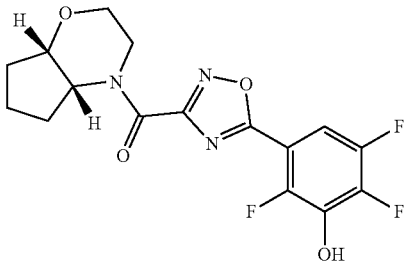 [SMILES: O=C(c1noc(-c2cc(F)c(F)c(O)c2F)n1)N1CCO[C@H]2CCC[C@H]21]

(4aR,7aS)-Octahydrocyclopenta[b][1,4]oxazine HCl (0.052 g, 0.32 mmol) was dissolved in MeOH and passed through an Isolute NH₂ column (1 g). The compound was eluted with MeOH. The MeOH was evaporated and the residue was dissolved in dry toluene (0.5 mL). Me₃Al (2 M in toluene, 0.304 mL, 0.61 mmol) was added dropwise at rt under a N₂(g) atmosphere. The solution was stirred at rt for 45 min, then added dropwise at rt to a stirred solution of ethyl 5-(2,4,5-trifluoro-3-hydroxyphenyl)-1,2,4-oxadiazole-3-carboxylate Intermediate 1 (0.07 g, 0.24 mmol) in toluene (0.6 mL) under nitrogen. The solution was heated to 60° C. for 20 h. Tartaric acid (30%, aq, 5 mL) was added dropwise. The mixture was extracted with EtOAc. The phases were separated and the water phase was extracted again with EtOAc. The organic phases were combined and concentrated under reduced pressure. The residue was dissolved in DMSO and purified by preparative HPLC, PrepMethod D (gradient: 30-100%) to give the title compound (0.032 g, 36%) as a white solid; HRMS (ESI) m/z [M+H]⁺ calcd for $C_{16}H_{15}F_3N_3O_4$: 370.1014, found: 370.0996; Mixture of rotamers: ¹H NMR (500 MHz, DMSO-d₆) δ 1.42-2.13 (6H, m), 3.1-3.19 (0.6H, m), 3.37-3.51 (1.4H, m), 3.58 (0.4H, d), 3.71-3.79 (1H, m), 3.83-3.97 (1.6H, m), 4.16 (0.6H, dd), 4.48-4.57 (0.4H, m), 7.51-7.8 (1H, m), 11.71 (1H, s). Total number of protons in spectrum: 14.

Example 113: ((4aS,7aR)-Hexahydrocyclopenta[b][1,4]oxazin-4(4aH)-yl)(5-(2,4,5-trifluoro-3-hydroxyphenyl)-1,2,4-oxadiazol-3-yl)methanone

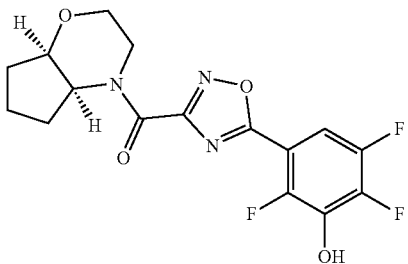 [SMILES: O=C(c1noc(-c2cc(F)c(F)c(O)c2F)n1)N1CCO[C@@H]2CCC[C@@H]21]

(4aS,7aR)-Octahydrocyclopenta[b][1,4]oxazine HCl (0.052 g, 0.32 mmol) was dissolved in MeOH and passed through an Isolute NH₂ ion exchange column (1 g). The compound was eluted with MeOH. The MeOH was evaporated and the residue was dissolved in dry toluene (0.5 mL). Me₃Al (2 M in toluene, 0.304 mL, 0.61 mmol) was added dropwise under a N₂ (g) atmosphere at rt. The solution was stirred at rt for 45 min, then added dropwise at rt to a stirred solution of ethyl 5-(2,4,5-trifluoro-3-hydroxyphenyl)-1,2,4-oxadiazole-3-carboxylate Intermediate 1 (0.07 g, 0.24 mmol) in toluene (0.6 mL) under an atmosphere of N₂(g). The solution was heated to 60° C. for 20 h. Tartaric acid (30%, aq, 5 mL) was added dropwise. The mixture was extracted with EtOAc. The phases were separated and the water phase was extracted again with EtOAc. The organic phases were combined and concentrated under reduced pressure. The residue was dissolved in DMSO and purified by preparative HPLC, PrepMethod D (gradient: 30-100%), to give the title compound (0.032 g, 36%) as a white solid; HRMS (ESI) m/z [M+H]⁺ calcd for $C_{16}H_{15}F_3N_3O_4$: 370.1014, found: 370.1002; Mixture of rotamers: ¹H NMR (500 MHz, DMSO-d₆) δ 1.44-2.04 (6H, m), 3.08-3.21 (0.6H, m), 3.36-3.51 (1.4H, m), 3.55-3.61 (0.4H, m), 3.71-3.8 (1H, m), 3.83-3.99 (1.6H, m), 4.16 (0.6H, dd), 4.43-4.65 (0.4H, m), 7.52-7.82 (1H, m), 11.68 (1H, s). Total number of protons in spectrum: 14.

Example 114: ((4aR,7aR)-Hexahydrocyclopenta[b][1,4]oxazin-4(4aH)-yl)(5-(2,4,5-trifluoro-3-hydroxyphenyl)-1,2,4-oxadiazol-3-yl)methanone

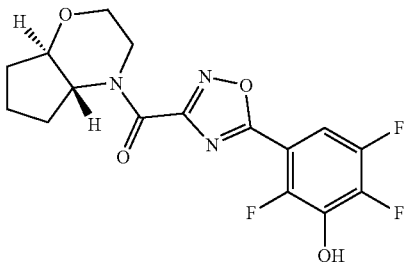 [SMILES: O=C(c1noc(-c2cc(F)c(F)c(O)c2F)n1)N1CCO[C@@H]2CCC[C@H]21]

(4aR,7aR)-Octahydrocyclopenta[b][1,4]oxazine (0.040 g, 0.32 mmol) was dissolved in dry toluene (0.5 mL). Me₃Al (2 M in toluene, 0.304 mL, 0.61 mmol) was added dropwise at rt under an atmosphere of $N_2(g)$. The resulting solution was stirred at rt for 45 min, then added dropwise to a stirred solution of ethyl 5-(2,4,5-trifluoro-3-hydroxyphenyl)-1,2,4-oxadiazole-3-carboxylate Intermediate 1 (0.07 g, 0.24 mmol) in toluene (0.6 mL) under an atmosphere of $N_2(g)$. The solution was heated to 60° C. for 20 h. Tartaric acid (30%, aq, 5 mL) was added dropwise and the mixture was extracted with EtOAc. The aqueous layer was extracted with EtOAc. The combined organic layer was concentrated under reduced pressure. The residue was dissolved in DMSO and purified by preparative HPLC, PrepMethod C (gradient: 30-100%), to give the title compound (0.023 g, 26%) as a white solid; HRMS (ESI) m/z [M+H]⁺ calcd for $C_{16}H_{15}F_3N_3O_4$: 370.1014, found: 370.1024; Mixture of rotamers, ¹H NMR (500 MHz, DMSO-d₆) δ 1.03-2.01 (6H, m), 3.03-3.28 (2H, m), 3.37-3.52 (1H, m), 3.54-3.78 (1.7H, m), 3.8-4.11 (1H, m), 4.32-4.46 (0.3H, m), 7.57-7.8 (1H, m), 11.70 (1H, s). Total number of protons in spectrum: 14.

Example 115: ((4aS,7aS)-Hexahydrocyclopenta[b][1,4]oxazin-4(4aH)-yl)(5-(2,4,5-trifluoro-3-hydroxyphenyl)-1,2,4-oxadiazol-3-yl)methanone

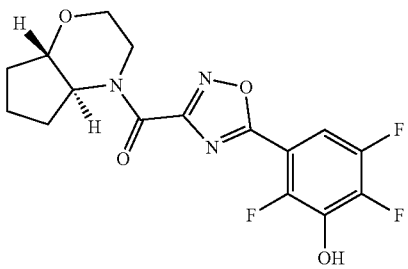 [SMILES: O=C(c1noc(-c2cc(F)c(F)c(O)c2F)n1)N1CCO[C@H]2CCC[C@@H]21]

5-(2,4,5-Trifluoro-3-hydroxyphenyl)-1,2,4-oxadiazole-3-carboxylic acid Intermediate 2 (0.08 g, 0.31 mmol), HATU (0.234 g, 0.62 mmol) and DMF (1.2 ml) were mixed in a vial. (4aS,7aS)-Octahydrocyclopenta[b][1,4]oxazine HCl Bioorganic & Medicinal Chemistry Letters (2015), 25(5), 1086-1091 (0.050 g, 0.31 mmol) was added followed by DIPEA (0.322 ml, 1.85 mmol)). The resulting yellow solution was stirred at rt for 4 h. The reaction mixture was diluted with DMSO and purified by preparative HPLC, PrepMethod D (gradient: 30-100%), to give the title compound (0.039 g, 34%) as a light yellow solid. HRMS (ESI) m/z [M+H]⁺ calcd for $C_{16}H_{15}F_3N_3O_4$: 370.1014, found: 370.0981; Mixture of rotamers, ¹H NMR (500 MHz, DMSO-d₆) δ 0.98-2.01 (6H, m), 2.98-3.27 (2H, m), 3.36-3.53 (1H, m), 3.51-3.79 (1.7H, m), 3.79-4.19 (1H, m), 4.40 (0.3H, s), 7.51-7.84 (1H, m), 11.70 (1H, s). Total number of protons in spectrum: 14.

Example 116: (5-(3,4-Difluoro-5-hydroxyphenyl)-1,2,4-oxadiazol-3-yl)((2R,6S)-2,6-dimethylmorpholino)methanone

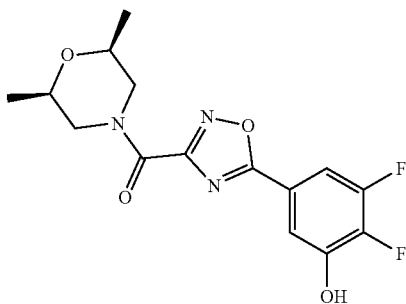 [SMILES: C[C@@H]1CN(C(=O)c2noc(-c3cc(O)c(F)c(F)c3)n2)C[C@H](C)O1]

Me₃Al (2 M in toluene, 0.407 mL, 0.81 mmol) was added to a stirred solution of (2S,6R)-2,6-dimethylmorpholine (0.076 mL, 0.63 mmol) in toluene (1 mL) under an atmosphere of $N_2(g)$ and the resulting mixture was stirred at rt for 1 h. The mixture was added to a stirred slurry of ethyl 5-(3,4-difluoro-5-hydroxyphenyl)-1,2,4-oxadiazole-3-carboxylate Intermediate 53 (0.100 g, 0.37 mmol) in toluene (1 mL), and the resulting mixture was heated to 60° C. for 22 h, and then cooled to rt. Tartaric acid (30%, aq, 5 mL) was added, and the mixture was extracted with EtOAc (5 mL). The organic layer was concentrated, and the residue was purified by preparative HPLC, PrepMethod C, (gradient: 50-80%) to yield the product (65 mg, 52%) as an off-white solid; HRMS (ESI) m/z [M+H]⁺; calcd for $C_{15}H_{16}F_2N_3O_4$: 340.1104, found: 340.1124; ¹H NMR (500 MHz, DMSO-d₆) δ 1.04 (3H, d), 1.16 (3H, d), 2.59 (1H, dd), 2.86 (1H, dd), 3.55 (2H, dddt), 3.77 (1H, d), 4.36 (1H, d), 7.55 (1H, d), 7.62 (1H, ddd), 11.29 (1H, s).

Example 117: (5-(2,4,5-Trifluoro-3-hydroxyphenyl)-1,2,4-oxadiazol-3-yl)(2,2,6-trimethylmorpholino)methanone

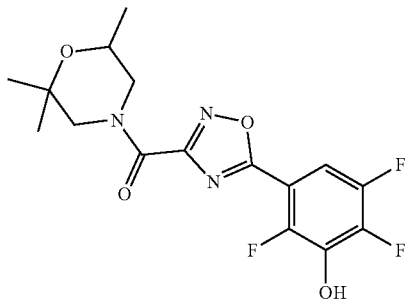 [SMILES: CC1CN(C(=O)c2noc(-c3cc(F)c(F)c(O)c3F)n2)CC(C)(C)O1]

2,2,6-Trimethylmorpholine (0.041 g, 0.32 mmol) was dissolved in dry toluene (0.5 mL). Me₃Al (2 M in toluene, 0.304 mL, 0.61 mmol) was added dropwise at rt under an atmosphere of $N_2(g)$. The resulting solution was stirred at rt for 45 min, then added dropwise at rt to a stirred solution of ethyl 5-(2,4,5-trifluoro-3-hydroxyphenyl)-1,2,4-oxadiazole-3-carboxylate Intermediate 1 (0.07 g, 0.24 mmol) in toluene (0.6 mL) under an atmosphere of $N_2(g)$. The solution was heated to 60° C. for 20 h. Tartaric acid (30%, aq, 5 mL) was added dropwise. The mixture was extracted with EtOAc. The aqueous layer was extracted with EtOAc. The combined organic layer was concentrated under reduced pressure. The residue was dissolved in DMSO and purified by preparative HPLC, PrepMethod D (gradient: 35-85%), to give the title compound (0.034 g, 38%) as a white solid; HRMS (ESI) m/z [M+H]$^+$ calcd for $C_{16}H_{17}F_3N_3O_4$: 372.1166, found: 372.1158; Mixture of rotamers: $^1$H NMR (500 MHz, DMSO-d$_6$) δ 0.99 (1H, d), 1.05-1.13 (3H, m), 1.13-1.24 (5H, m), 2.56 (0.7H, dd), 2.76 (0.4H, d), 2.83 (0.4H, dd), 3.02 (0.5H, d), 3.56 (0.5H, dd), 3.73-3.9 (1.5H, m), 4.23 (0.4H, dd), 4.36 (0.5H, dt), 7.51-7.84 (1H, m). Total number of protons in spectrum: 15.

Example 118: (4-Oxa-7-azaspiro[2.5]octan-7-yl)(5-(2,4,5-trifluoro-3-hydroxyphenyl)-1,2,4-oxadiazol-3-yl)methanone

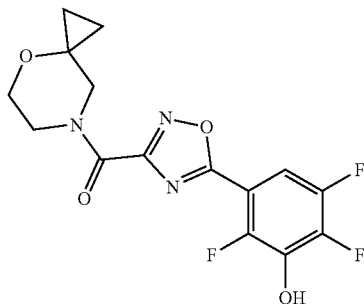 [SMILES: O=C(c1noc(-c2cc(F)c(F)c(O)c2F)n1)N1CCOC2(CC2)C1]

5-(2,4,5-Trifluoro-3-hydroxyphenyl)-1,2,4-oxadiazole-3-carboxylic acid Intermediate 2 (64 mg, 0.25 mmol), HATU (122 mg, 0.32 mmol) and DMF (1 mL) were mixed in a vial. DIPEA (0.129 mL, 0.74 mmol)) was added followed by 4-oxa-7-azaspiro[2.5]octane HCl (55.2 mg, 0.37 mmol). The resulting solution was stirred at rt overnight. The reaction was diluted with DMSO and purified by preparative HPLC, PrepMethod C (gradient: 20-80%), to give the title compound (20 mg, 23%) as a white solid; HRMS (ESI) m/z [M+H]$^+$ calcd for $C_{15}H_{13}F_3N_3O_4$: 356.0852, found: 356.0854; $^1$H NMR (500 MHz, DMSO-d$_6$) δ 0.56-0.61 (1H, m), 0.64-0.68 (1H, m), 0.68-0.74 (1H, m), 0.74-0.79 (1H, m), 3.50 (1H, s), 3.65 (2H, s), 3.70 (1H, s), 3.71-3.76 (1H, m), 3.76-3.8 (1H, m), 7.5-7.82 (1H, m), 11.67 (1H, s).

Example 119: ((3R,5S)-3,5-Dimethyl piperazin-1-yl)(5-(2,4,5-trifluoro-3-hydroxyphenyl)-1,2,4-oxadiazol-3-yl)methanone

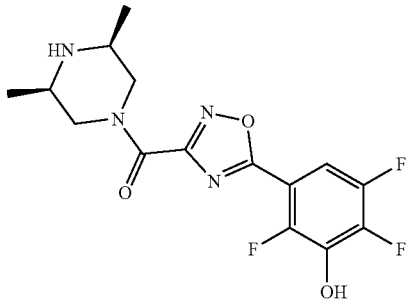 [SMILES: C[C@@H]1CN(C(=O)c2noc(-c3cc(F)c(F)c(O)c3F)n2)C[C@H](C)N1]

tert-Butyl (2R,6S)-2,6-dimethylpiperazine-1-carboxylate (0.145 g, 0.68 mmol) was dissolved in dry toluene (1 mL). Me$_3$Al (2 M in toluene, 0.651 mL, 1.30 mmol) was added dropwise at rt under an atmosphere of $N_2(g)$. The resulting solution was stirred at rt for 45 min, then added dropwise to a stirred solution of ethyl 5-(2,4,5-trifluoro-3-hydroxyphenyl)-1,2,4-oxadiazole-3-carboxylate Intermediate 1 (0.15 g, 0.52 mmol) in toluene (1.3 mL) under nitrogen. The solution was heated to 60° C. for 20 h. Tartaric acid (30%, aq, 5 mL) was added dropwise. The aqueous phase was washed with EtOAc. The aqueous phase was purified by preparative HPLC, PrepMethod D (gradient: 5-45%), to give the title compound (0.126 g, 68%) as a white solid; HRMS (ESI) m/z [M+H]$^+$ calcd for $C_{15}H_{16}F_3N_4O_3$: 357.1168, found: 357.1158; 1H NMR (500 MHz, DMSO-d$_6$) δ 1.03 (3H, d), 1.15 (3H, d), 2.56-2.69 (1H, m), 2.84-3.09 (3H, m), 3.86 (1H, d), 4.47 (1H, d), 7.16-7.46 (1H, m).

Example 120: ((2R,6S)-2,6-Dimethylmorpholino)(2-(2,4,5-trifluoro-3-hydroxyphenyl)thiazol-5-yl)methanone

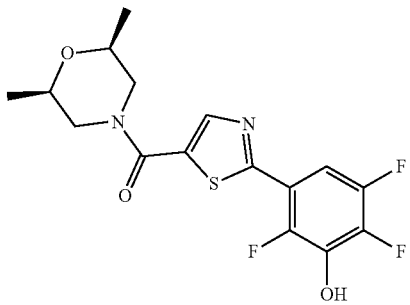 [SMILES: C[C@@H]1CN(C(=O)c2cnc(-c3cc(F)c(F)c(O)c3F)s2)C[C@H](C)O1]

BBr$_3$ (1 M in DCM, 1.025 mL, 1.02 mmol) was added dropwise to a solution of ((2S,6R)-2,6-dimethylmorpholino)(2-(2,4,5-trifluoro-3-methoxyphenyl)thiazol-5-yl)methanone Intermediate 56 (132 mg, 0.34 mmol) in DCM (5 mL) at 0° C. The reaction mixture was stirred for 2 h at rt. Additional BBr$_3$ (1 M in DCM, 1.025 mL, 1.02 mmol) was added dropwise and stirring was continued for 1.5 h. The reaction mixture was diluted with DCM, cooled by an ice-bath and water was carefully added. The organic layer was separated and the aqueous layer was extracted with EtOAc (×2). The combined organic layer was passed Example 121: rac-((2R,6S)-2-Ethyl-6-methylmorpholino)(5-(2,4,5-trifluoro-3-hydroxyphenyl)-1,2,4-oxadiazol-3-yl)methanone

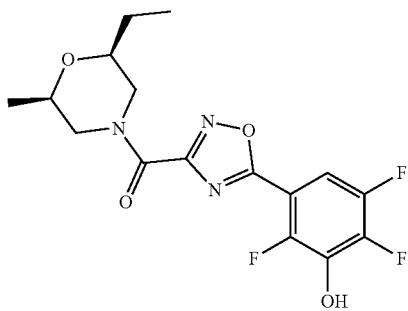 [SMILES: CC[C@H]1CN(C(=O)c2noc(-c3cc(F)c(F)c(O)c3F)n2)C[C@@H](C)O1]

(Racemic)

2 M AlMe$_3$ in toluene (2.17 mL, 4.34 mmol) was added dropwise under N$_2$ at rt to a solution of rac-(2R,6S)-2-ethyl-6-methylmorpholine (314 mg, 2.43 mmol) in anhydrous toluene (2.5 mL). The resulting solution was stirred for 1 h and was then added dropwise at rt to a stirred mixture of ethyl 5-(2,4,5-trifluoro-3-hydroxyphenyl)-1,2,4-oxadiazole-3-carboxylate Intermediate 1 (500 mg, 1.74 mmol) in anhydrous toluene (3.5 mL) under N$_2$. The resulting solution was stirred at 60° C. for 7.5 h. The reaction was allowed to cool to rt overnight and was then further cooled to 0° C. 30% tartaric acid (aq, 25 mL) was added dropwise and the resulting mixture was extracted with EtOAc (×2). The organic layers were combined, washed with H$_2$O, passed through a phase separator and concentrated under reduced pressure. The residue was purified by preparative HPLC, PrepMethod D, (gradient 0-75%, then 100%) to give the title compound (62 mg, 10%) as a white solid; HRMS (ESI) m/z [M+H]$^+$ calcd for C16 H17 F3 N3 O4: 372.1171, found: 372.1156;

$^1$H NMR (500 MHz, DMSO, 25° C., mixture of rotamers) δ 0.85 (1.4H, t), 0.93 (1.6H, t), 1.05 (1.6H, d), 1.17 (1.4H, d), 1.34-1.43 (1H, m), 1.46-1.56 (1H, m), 2.07 (0H, s), 2.62 (1H, ddd), 2.89 (1H, ddd), 3.34-3.4 (1H, m), 3.46-3.61 (1H, m), 3.73-3.82 (1H, m), 4.34-4.42 (1H, m), 7.61-7.69 (1H, m), 11.68 (1H, s).

Example 122 rac-((2R,6S)-2-isopropyl-6-methylmorpholino)(5-(2,4,5-trifluoro-3-hydroxyphenyl)-1,2,4-oxadiazol-3-yl)methanone

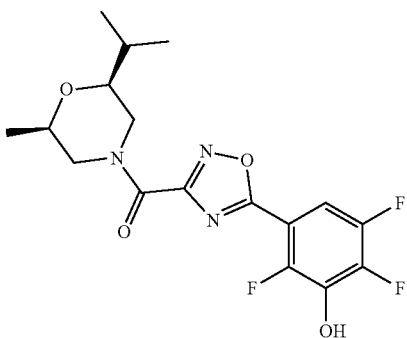 [SMILES: CC(C)[C@H]1CN(C(=O)c2noc(-c3cc(F)c(F)c(O)c3F)n2)C[C@@H](C)O1]

(Racemic)

2 M AlMe$_3$ in toluene (2.17 mL, 4.34 mmol) was added dropwise under N$_2$ at rt to a solution of rac-(2R,6S)-2-isopropyl-6-methylmorpholine (348 mg, 2.43 mmol) in anhydrous toluene (2.5 mL). The resulting solution was stirred at rt for 1 h and was then added dropwise at rt to a stirred mixture of ethyl 5-(2,4,5-trifluoro-3-hydroxyphenyl)-1,2,4-oxadiazole-3-carboxylate Intermediate 1 (500 mg, 1.74 mmol) in anhydrous toluene (3.5 mL) under N$_2$. The resulting solution was stirred at 60° C. for 7.5 h. The reaction was allowed to cool to rt overnight and then further cooled to 0° C. 30% tartaric acid (aq, 25 mL) was added dropwise and the mixture was extracted with EtOAc (×2). The organic layers were combined and washed with H$_2$O, dried over Na$_2$SO$_4$, filtered and concentrated under reduced pressure. The residue was purified by preparative HPLC, PrepMethod D, (gradient 40-80%) to give the title compound (367 mg, 55%) as a white solid; HRMS (ESI) m/z [M+H]$^+$ calcd for C17 H19 F3 N3 O4: 386.1328, found: 386.1328; 1H NMR (500 MHz, DMSO, 25° C., mixture of rotamers) δ 0.83 (1.3H, d), 0.88 (1.3H, d), 0.93 (1.7H, d), 0.96 (1.7H, d), 1.05 (1.7H, d), 1.18 (1.3H, d), 1.59-1.68 (0.4H, m), 1.69-1.77 (0.6H, m), 2.61 (0.4H, dd), 2.69 (0.6H, dd), 2.87 (0.6H, dd), 2.96 (0.4H, dd), 3.14-3.23 (1H, m), 3.45-3.62 (1H, m), 3.76 (0.6H, dt), 3.84 (0.4H, dt), 4.34-4.45 (1H, m), 7.6-7.69 (1H, m), 11.5-11.88 (1H, m).

Example 123 (6-Methyl-5-oxa-8-azaspiro[3.5]nonan-8-yl)(5-(2,4,5-trifluoro-3-hydroxyphenyl)-1,2,4-oxadiazol-3-yl)methanone

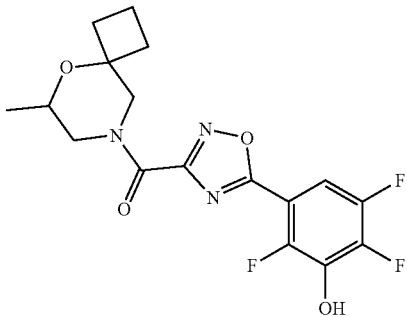 [SMILES: CC1CN(C(=O)c2noc(-c3cc(F)c(F)c(O)c3F)n2)CC2(CCC2)O1]

(Racemic)

2 M AlMe₃ (1.09 ml, 2.17 mmol) was added dropwise under N₂ at rt to a solution of rac-(R)-6-methyl-5-oxa-8-azaspiro[3.5]nonane (172 mg, 1.21 mmol) in anhydrous toluene. The resulting solution was stirred at rt for 1 h and was then added dropwise at rt to a stirred mixture of ethyl 5-(2,4,5-trifluoro-3-hydroxyphenyl)-1,2,4-oxadiazole-3-carboxylate Intermediate 1 (0.25 g, 0.87 mmol) in anhydrous toluene (1.75 ml) under N₂. The resulting solution was heated at 60° C. for 4 h. The heat was turned off and the reaction was allowed to cool to rt overnight and then further cooled to 0° C. 30% tartaric acid (aq, 13 mL) was added dropwise and the mixture was extracted with EtOAc (×2). The organic layers were combined, washed with water, dried over Na₂SO₄, filtered and concentrated under reduced pressure. The residue was purified by preparative HPLC, Prep-Method J, (gradient: 35-75%). The fractions containing product were acidified to pH5 using HOAc and the MeCN was removed under reduced pressure. The resulting aqueous oil/water mixture was extracted with DCM (×3). The combined organic layer was concentrated and the residue was purified by preparative HPLC, prepmethod D, (gradient: 35-75%) to give the title compound (208 mg, 63%) as a white solid; HRMS (ESI) m/z [M+H]⁺ calcd for C17 H17 F3 N3 O4: 384.1171, found: 384.1185; ¹H NMR (500 MHz, DMSO, 25° C., 3:2 mixture of rotamers) δ 1.02 (1.3H, d), 1.13 (1.7H, d), 1.47-2.08 (5.4H, m), 2.13-2.22 (0.5H, m), 2.62 (0.6H, dd), 2.82 (0.4H, dd), 2.89 (0.4H, dd), 3.05 (0.6H, dd), 3.48-3.63 (1.1H, m), 3.74 (0.4H, dt), 3.84 (0.6H, dd), 4.31 (0.6H, dt), 4.53 (0.4H, dd), 7.6-7.69 (1H, m), 11.72 (1H, s).

Example 124 (5-(2-Bromo-3,4,6-trifluoro-5-hydroxyphenyl)-1,2,4-oxadiazol-3-yl)((2R,6S)-2,6-dimethylmorpholino)methanone

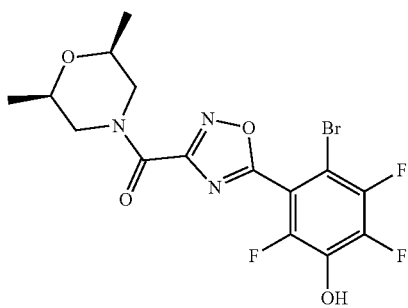 [SMILES: C[C@@H]1CN(C(=O)c2noc(-c3c(F)c(O)c(F)c(F)c3Br)n2)C[C@H](C)O1]

A mixture of ((2R,6S)-2,6-dimethylmorpholino)(5-(2,4,5-trifluoro-3-hydroxyphenyl)-1,2,4-oxadiazol-3-yl)methanone Example 87 (4.84 g, 13.6 mmol) and NBS (2.89 g, 16.26 mmol) in AcOH (50 mL) was stirred at 80° C. for 20 min. The reaction mixture was allowed to cool to rt and was then concentrated under reduced pressure. The residue was dissolved in EtOAc (75 mL) and washed with water (5×50 mL). Small aliquots of 30% NaCl(aq), (typically 1-3 mL) was added to speed up phase separation. The organic layer was washed with 30% NaCl(aq), dried over Na₂SO₄, filtered and concentrated under reduced pressure to give the title compound (5.91 g, 100%) as a pale yellow solid foam.

A small part of the title compound (200 mg) was further purified by preparative HPLC, PrepMethod D, gradient (30-70%) to give the title compound (133 mg) as a white solid; HRMS (ESI) m/z [M+H]⁺ calcd for C15 H14 Br F3 N3 O4: 436.0120, found: 436.0116; ¹H NMR (500 MHz, DMSO, 25° C.) δ 1.06 (3H, d), 1.17 (3H, d), 2.63 (1H, dd), 2.94 (1H, dd), 3.54-3.65 (2H, m), 3.70 (1H, dt), 4.37 (1H, dt), 12.05 (1H, s).

In Vitro 17bHSD13 Enzyme Assay 10 concentration of compounds (0.2 μl) in DMSO was added to GREINER PP 384 well plate (781280) using ECHO dispensing (BECKMAN COULTER) followed by 20 μl of recombinant 17bHSD13 (N2-K300). The enzyme reaction was initiated by addition, using CERTUS-FLEX dispenser (GYGER), of 20 μl of substrate solution containing NAD (SIGMA, N1511) and Estradiol (SIGMA, E8875). After each addition plates were centrifuged for 1 min at 150×g (EPPENDORF, 5810R, A-4-81). Final assay conditions were 80 nM of 17bHSD13, 0.5 mM of NAD, 20 μM Estradiol and various concentrations of compound in buffer (5 mM EDTA (TEKNOVA E0306), 0.01% DDM (AF-FYMETRIX D310) in 50 mM Tris-Cl, pH 7.4). After 2.5 h the reaction were stopped by addition of 20 μl of 0.6% Formic acid (MERCK 5.33002) and samples were analyzed using LC-MS/MS.

SCIEX LC-MS/MS system: Sample was injected with CTC analytical injector, SHIMATZU LC pumps LC20 and analyzed on the SCIEX API 5000 LCMSMS system with the following settings. Samples were chromatographed on a WATERS, SYMMETRY, C8, 3.5 μm, 2.1×50 mm) column at constant flow rate of 0.5 mL/min. The mobile phases consist of A (water with 0.2% formic acid) and B (acetonitrile with 0.2% formic acid). The LC gradient profile is as follows: 50% B during 0 to 0.5 min, a linear increase to 100% B during 0.5 to 1 min, hold at 100% B during 1 to 1.6 min then back to 50% B from 1.6 to 2 min. The run time was 2 min with retention times of approximately 0.8 and 1.07 min for Estradiol and Estrone, respectively. Detection was performed on a API 5000 LC/MS/MS system with a triple quadrupole mass spectrometer, a TURBO V ion source, in multiple reaction monitoring (MRM) mode at positive polarity with APCI probe. The MRM pairs were m/z 273.1 to m/z 107.0 and m/z 271.3 to 107.0. for Estradiol and Estrone, respectively. The dwell times were 100 ms for each transition and a depolarization and collision energy of 100 and 40, respectively. Data from MS signals was using area under curve (AUC). Ratio=Estrone/(Estrone+Estradiol)

In Vitro 17bHSD13 Cell Assay

Inhibition of 17bHSD13 was measured in a cell-based assay with over expressed HSD17β13 in HEK293S cells, measuring estradiol to estrone conversion by LCMS/MS.

Cells were plated in 384 well plates (GREINER CELL culture plate 384w black/clear Poly-D-Lysine) at 10 K c/w in 30 μl of culture media (DMEM with GLUTAMAX plus 10% FBS). After the cells were allowed to attach for 6 h, 0.15 μl of 10 concentration of compounds and 0.03 μl of 10 mM Estradiol (SIGMA, E8875) in DMSO, was added using ECHO dispensing (BECKMAN COULTIER). After 18 h of cell culturing for 20 μl of media was transferred using BRAVO dispensing robot (AGILENT) to a GREINER PP 384 well plate (781280) and 40 μl of 50% acetonitrile was added. Samples were analyzed using LC-MS/MS.

SCIEX LC-MS/MS system: Sample was injected with CTC analytical injector, SHIMATZU LC pumps LC20 and analysed on the SCIEX API 5000 LCMSMS system with the following settings. Samples were chromatographed on a WATERS, symmetry, C8, 3.5 μm, 2.1×50 mm) column at constant flow rate of 0.5 mL/min. The mobile phases consist of A (water with 0.2% formic acid) and B (acetonitrile with 0.2% formic acid). The LC gradient profile is as follows: 50% B during 0 to 0.5 min, a linear increase to 100% B during 0.5 to 1 min, hold at 100% B during 1 to 1.6 min then back to 50% B from 1.6 to 2 min. The run time was 2 min with retention times of approximately 0.8 and 1.07 min for Estradiol and Estrone, respectively. Detection was performed on a API 5000 LC/MS/MS system with a triple quadrupole mass spectrometer, a TURBO V ion source, in multiple reaction monitoring (MRM) mode at positive polarity with APCI probe. The MRM pairs were m/z 273.1 to m/z 107.0 and m/z 271.3 to 107.0. for Estradiol and Estrone, respectively. The dwell times were 100 ms for each transition and a depolarization and collision energy of 100 and 40, respectively. Data from MS signals was using area under curve (AUC). Ratio=Estrone/(Estrone+Estradiol)

In Vitro 17bHSD4 Enzyme Assay 10 concentration of compounds (0.2 μl) in DMSO was added to GREINER FLUOTRAC 200 384 well plate (781076) using ECHO dispensing (BECKMAN COULTER). 80 nl of 10 mM Estradiol (SIGMA, E8875) was added using Echo dispensing. The enzyme reaction was initiated by addition, using MULTIDROP COMBI dispensing (THERMO FISHER), of 40 μl of a mix containing recombinant 17bHSD4 (M1-N311) and NAD. Final assay conditions were 40 nM of 17bHSD4, 0.125 mM of NAD, 15 μM Estradiol and various concentrations of compound in buffer (5 mM EDTA (TEKNOVA E0306), 0.01% DDM (AFFYMETRIX D310) in 50 mM Tris-Cl, pH 7.4). After each addition plates were centrifuged for 1 min at 150×g (EPPENDORF, 5810R, A-4-81). NADH formation was measured by fluorescence intensity (FI) (Ex360/Em460) at time zero (t0) and at 1.5 h ($t_1$) in a PHERASTAR FSX (BMG LABTECH). FI for each sample was calculated as FI at $t_1$ minus FI at $t_0$.

In Vitro 17bHSD9 Cell Assay

Inhibition of 17bHSD9 was measured in a cell-based assay with over expressed HSD17β9 in HEK293S cells, measuring retinol to retinal conversion by LCMS/MS.

Cells were plated in 384 well plates (GREINER CELL culture plate 384w black/clear Poly-D-Lysine) at 10 K c/w in 30 μl of culture media (DMEM with GLUTAMAX plus 10% FBS). After the cells were allowed to attach for 6 h, 0.15 μl of 10 concentration of compounds and 0.015 μl of 10 mM all-trans-retinol (CAYMAN CHEMICAL, 20241) in DMSO, was added using ECHO dispensing (BECKMAN COULTIER). After 18 h of cell culturing for 20 μl of media was transferred using BRAVO dispensing robot (AGILENT) to a GREINER PP 384 well plate (781280) and 40 μl of 50% acetonitrile was added. Samples were analyzed using LC-MS/MS.

SCIEX LC-MS/MS system: Sample was injected with CTC analytical injector, SHIMATZU LC pumps LC20 and analysed on the SCIEX API 5000 LCMSMS system with the following settings. Samples were chromatographed on a WATERS, symmetry, C8, 3.5 μm, 2.1×50 mm) column at constant flow rate of 0.5 mL/min. The mobile phases consists of A (water with 0.2% formic acid) and B (acetonitrile with 0.2% formic acid). The LC gradient profile is as follows: 50% B during 0 to 0.1 min, a linear increase to 100% B during 0.1 to 0.8 min, hold at 100% B during 0.8 to 1.5 min then back to 50% B from 1.5 to 1.6 min and hold during run time. The run time was 2 min with retention times of approximately 1.54 and 1.62 min for Retinol and Retinal, respectively. Detection was performed on a API 5000 LC/MS/MS system with a triple quadrupole mass spectrometer, a TURBO V ion source, in multiple reaction monitoring (MRM) mode at positive polarity with ESI probe. The MRM pairs were m/z 269.3 to m/z 93.0 and m/z 285.2 to 161.0. for Retinol and Retinal, respectively. The dwell times were 100 ms for each transition and a depolarization and collision energy of 50 and 25, respectively. Data from MS signals was using area under curve (AUC). Ratio=Retinal/(Retinal+ Retinol).

Data Analysis

GENEDATA SCREENER was used for curve fitting and calculation of $IC_{50}$ values.

Compound effect was calculated with the formula below:

$$\text{Compound\% effect} = -100 \times ((X - \min)/(\max - \min))$$

where X represents the effect in the presence of test compound, min is DMSO and max is the maximum inhibition of enzyme using a known inhibitor as control.

TABLE 3

| Example | 17bHSD13 Enzyme assay $IC_{50}$ (μM) | 17HSD17b4 Enzyme assay $IC_{50}$ (μM) | 17bHSD1713 Cell assay $IC_{50}$ (μM) | 17bHSD9 Cell assay $IC_{50}$ (μM) |
|---|---|---|---|---|
| 1 | 0.308 | 32.4 | 0.75 | |
| 2 | 0.075 | 6.7 | 1.61 | >50 |
| 3 | 0.036 | 31.5 | 0.03 | >50 |
| 4 | 0.036 | 6.1 | 0.08 | 13.0 |
| 5 | 0.093 | | 2.61 | >50 |
| 6 | 0.041 | 89.1 | 0.98 | >50 |
| 7 | 0.083 | >50 | 5.05 | |
| 8 | 0.047 | 6.7 | 0.61 | 25.0 |
| 9 | 0.422 | >50 | 5.55 | 24.9 |
| 10 | 0.474 | >50 | 4.14 | >50 |
| 11 | 0.069 | >50 | 0.80 | >50 |
| 12 | 4.335 | | >50 | |
| 13 | 0.040 | 15.6 | 0.46 | |
| 14 | 0.126 | 41.4 | 0.26 | >50 |
| 15 | 0.489 | 37.7 | 0.97 | |
| 16 | 0.137 | 15.4 | 4.56 | >50 |
| 17 | 0.525 | | 3.10 | |
| 18 | 0.080 | 17.8 | 0.79 | 6.2 |
| 19 | 0.108 | 19.6 | 2.01 | |
| 20 | 0.063 | 9.3 | 2.40 | 29.4 |
| 21 | 0.032 | 5.7 | 0.66 | 22.6 |
| 22 | 0.532 | >50 | 1.12 | >50 |
| 23 | 0.141 | 33.9 | 0.93 | >50 |
| 24 | 0.198 | | 3.50 | |
| 25 | 0.288 | 24.8 | 0.82 | 22.7 |
| 26 | 0.278 | | 2.97 | |
| 27 | 0.382 | | 4.09 | |
| 28 | 0.368 | | 4.13 | |
| 29 | 0.157 | 17.6 | 0.44 | 16.3 |
| 30 | 0.061 | 17.2 | 2.52 | 15.8 |
| 31 | 0.165 | 11.5 | 1.06 | 30.0 |
| 32 | 0.159 | >50 | 0.30 | 15.8 |
| 33 | 0.034 | 8.5 | 1.21 | >50 |
| 34 | 0.581 | >50 | >50 | >50 |
| 35 | 0.640 | 42.2 | 2.22 | 4.2 |
| 36 | 1.034 | >50 | 1.32 | >50 |
| 37 | 0.057 | 30.5 | 0.03 | 10.0 |
| 38 | 0.207 | 24.0 | 0.27 | 8.7 |
| 39 | 1.745 | >50 | 1.48 | >50 |
| 40 | 0.700 | >50 | 1.46 | >50 |
| 41 | 0.082 | >50 | 0.09 | 49.6 |
| 42 | 0.908 | >50 | 10.01 | >50 |
| 43 | 0.339 | 39.0 | 0.24 | 18.4 |
| 44 | 0.432 | 38.4 | 0.19 | 11.2 |
| 45 | 0.466 | >50 | 0.51 | 4.1 |
| 46 | 0.517 | >50 | 0.37 | 7.7 |
| 47 | 0.183 | 47.4 | 0.23 | 2.1 |
| 48 | 0.388 | >50 | 1.10 | >50 |
| 49 | 1.669 | >50 | 0.54 | >50 |
| 50 | 0.499 | >50 | 0.22 | 39.5 |
| 51 | 1.687 | >50 | 2.69 | >50 |
| 52 | 0.281 | 34.6 | 0.48 | 1.2 |
| 53 | 2.782 | >50 | 5.61 | >50 |
| 54 | 0.392 | >50 | 0.15 | >50 |
| 55 | 0.112 | | 0.96 | |

TABLE 3-continued

| Example | 17bHSD13 Enzyme assay IC$_{50}$ (μM) | 17HSD17b4 Enzyme assay IC$_{50}$ (μM) | 17bHSD1713 Cell assay IC$_{50}$ (μM) | 17bHSD9 Cell assay IC$_{50}$ (μM) |
|---|---|---|---|---|
| 56 | 0.142 | 23.5 | 1.36 | |
| 57 | 0.088 | 32.3 | 0.14 | >50 |
| 58 | 0.103 | 20.6 | 1.08 | |
| 59 | 0.608 | | 3.47 | >50 |
| 60 | 0.137 | 11.0 | 2.98 | |
| 61 | 0.050 | | 0.73 | >50 |
| 62 | 0.046 | 3.0 | 0.96 | 15.8 |
| 63 | 0.151 | | 1.19 | |
| 64 | 0.048 | 5.6 | 0.27 | 11.2 |
| 65 | 0.134 | | 0.20 | |
| 66 | 0.187 | 19.3 | 0.25 | >50 |
| 67 | 0.079 | 4.0 | 0.53 | >50 |
| 68 | 0.044 | 26.3 | 0.80 | 30.4 |
| 69 | 0.131 | 48.7 | 0.11 | 21.9 |
| 70 | 0.242 | | 2.22 | |
| 71 | 0.068 | | 28.36 | |
| 72 | 0.062 | 19.0 | 1.12 | >50 |
| 73 | 0.088 | | 21.57 | >50 |
| 74 | 0.089 | 21.1 | 3.00 | >50 |
| 75 | 0.268 | | 5.60 | |
| 76 | 0.128 | 44.8 | 0.14 | 19.6 |
| 77 | 0.075 | 7.0 | 0.17 | 6.8 |
| 78 | 0.127 | 8.5 | 0.80 | |
| 79 | 0.106 | | 1.39 | |
| 80 | 0.111 | 21.9 | 0.46 | 8.2 |
| 81 | 0.095 | | 0.41 | >50 |
| 82 | 0.062 | 25.9 | 0.45 | >50 |
| 83 | 0.102 | 14.4 | 2.88 | |
| 84 | 0.198 | 19.8 | 0.30 | >50 |
| 85 | 0.317 | 21.7 | 3.38 | |
| 86 | 0.102 | 8.5 | 0.54 | 21.1 |
| 87 | 0.285 | >200 | 0.06 | 36.3 |
| 88 | 0.468 | 36.4 | 0.19 | 41.7 |
| 89 | 0.168 | >50 | 0.07 | >50 |
| 90 | 0.626 | >50 | 1.69 | |
| 91 | 0.166 | | >50 | |
| 92 | 0.041 | >50 | 1.54 | >50 |
| 93 | 0.063 | 22.2 | 0.70 | 40.3 |
| 94 | 0.048 | 23.6 | 1.42 | >50 |
| 95 | 0.053 | 6.9 | 0.21 | 17.0 |
| 96 | 0.047 | 18.0 | 0.17 | 17.3 |
| 97 | 0.122 | 26.2 | 0.89 | |
| 98 | 0.063 | 9.5 | 0.52 | 40.2 |
| 99 | 0.114 | 41.8 | 15.82 | 38.9 |
| 100 | 5.338 | | 18.13 | |
| 101 | 0.050 | >50 | 0.42 | >50 |
| 102 | 0.052 | >50 | 0.70 | >50 |
| 103 | 0.026 | 6.5 | 0.53 | 24.9 |
| 104 | 0.057 | 9.6 | 0.54 | |
| 105 | 3.759 | | 1.26 | |
| 106 | 0.516 | 8.2 | 1.22 | >50 |
| 107 | 0.143 | 10.5 | 0.37 | 5.0 |
| 108 | 0.080 | >50 | 0.49 | >50 |
| 109 | 0.046 | 11.7 | 1.70 | >50 |
| 110 | 1.009 | >50 | 0.24 | >50 |
| 111 | 0.093 | >50 | 0.10 | >50 |
| 112 | 0.197 | >50 | 0.39 | 32.4 |
| 113 | 0.211 | 45.3 | 0.10 | >50 |
| 114 | 0.046 | >50 | 0.12 | 15.8 |
| 115 | 0.154 | >50 | 0.10 | 32.5 |
| 116 | 0.117 | >50 | 0.06 | >50 |
| 117 | 0.234 | 39.9 | 0.09 | >50 |
| 118 | 1.080 | >50 | 0.22 | >50 |
| 119 | 1.735 | >50 | 2.75 | >50 |
| 120 | 0.044 | >50 | 0.14 | >50 |
| 121 | 0.130 | >50 | 0.02 | 16.4 |
| 122 | 0.085 | >50 | 0.04 | 8.3 |
| 123 | 0.077 | 32.0 | 0.08 | 30.0 |
| 124 | 0.042 | | | 24.1 |

The data in Table 3 may be from a single experiment or an average of two or more experiments.

Assay A: Metabolic Stability in Human Hepatocytes

Hepatocyte metabolic stability was determined in accordance with the method described by Jacobson et al., An optimized automated assay for determination of metabolic stability using hepatocytes: assay validation, variance component analysis, and in vivo relevance. *Assay Drug Dev Technol* 2007, 5 (3), 403-415. DOI: 10.1089/adt.2007.059, which is incorporated herein by reference. Cryopreserved hepatocytes at a concentration of $10^6$ viable cells/mL were used. After thawing, hepatocytes were incubated for 10 min to warm to 37° C. and test compounds, dissolved in acetonitrile, were added to give a final concentration of 1 μM. At 0.5, 5, 15, 30, 45, 60, 80, 100 and 120 min, the incubation system was mixed and 20 μL aliquots were transferred at each time point to wells in a separate plate filled with 80 μL MeCN to stop the reaction. The quenching plate was then vortexed followed by centrifugation, and supernatants were analyzed by LC-MS/MS. Peak areas were determined from extracted ion chromatograms, and the in vitro intrinsic clearance (in vitro CLint, in μL/min/$10^6$ cells) of parent compound was calculated from the slope in the regression analysis of the natural logarithm of parent concentration vs time curve.

Assay B: Cytochrome P450 Inhibition 2C9

A fluorescence-based method in 96-well format was used to determine the inhibition of 2C9 (Crespi, C. L. et al., Microtiter plate assays for inhibition of human, drug-metabolizing cytochromes P450. *Anal Biochem* 1997, 248 (1), 188-190. DOI: 10.1006/abio.1997.2145, which is incorporated herein by reference). The recombinant human enzymes used were prepared in house, except for CYP2D6 (CYPEX LTD, Dundee, UK). Different coumarin substrates, biotransformed into fluorescent metabolites, were used as probes for each individual CYP. A fluorescence plate reader (SPECTRAMAX GEMINIXS, MOLECULAR DEVICES, Sunnyvale, California, USA) was used to measure the levels of metabolites formed. A dilution series of the test substrates was prepared at eight different concentrations. For each CYP, a mixture of the enzyme, corresponding coumarin substrate, potassium phosphate buffer pH 7.4 and water (concentrations and volumes were CYP-dependent) were added to each well in a black 96-well plate. The test substrates at different concentrations were added. After 10 min pre-incubation, the co-factor NADPH was added to initiate the reaction. After 20-50 min (CYP and substrate-dependent) the reaction was terminated by addition of trisbase/MeCN (20:80). The plates were transferred to the fluorescence plate reader where the wavelengths were set individually for the different coumarin substrates and their respective fluorescent metabolite. The responses were exported to Excel where the IC$_{50}$ curves were plotted (percent inhibition versus concentration) and IC$_{50}$ values calculated for each test substrate and enzyme using XL-fit.

Assay C: CB1 Agonism Assay

Evaluation of the agonist activity of compounds at the human CB1 receptor expressed in transfected CHO cells, determined by measuring their effects on cAMP modulation using the HTRF detection method.

Experimental protocol: The cells are suspended in HBSS buffer (INVITROGEN) complemented with 20 mM HEPES (pH 7.4), then distributed in microplates at a density of 5.103 cells/well in the presence of either of the following: HBSS (basal control), the reference agonist at 30 nM (stimulated control) or various concentrations (EC$_{50}$ determination), or the test compounds. Thereafter, the adenylyl cyclase activator NKH 477 is added at a final concentration of 3 μM. Following 20 min incubation at 37° C., the cells are lysed and the fluorescence acceptor (D2-labeled cAMP) and fluorescence donor (anti-cAMP antibody labeled with europium cryptate) are added. After 60 min at room temperature, the fluorescence transfer is measured at gex=337 nm and gem=620 and 665 nm using a microplate reader (RUBYSTAR, BMG). The cAMP concentration is determined by dividing the signal measured at 665 nm by that measured at 620 nm (ratio). The results are expressed as a percent of the control response to 30 nM CP 55940. The standard reference agonist is CP 55940, which is tested in each experiment at several concentrations to generate a concentration-response curve from which its $EC_{50}$ value is calculated.

Bibliographic reference Felder, C. C. et al., (1995), Comparison of the pharmacology and signal transduction of the human cannabinoid CB1 and CB2 receptors, *Mol. Pharmacol.*, 48: 443, which is incorporated herein by reference.

TABLE 4

| Example | Assay A: Human Heps Met Clint GMean CLint (µl/min/1E6) | Assay B: CYP2C9 HLM Diclofenac LC/MSMS GMean $IC_{50}$ (µM) | Assay C: CB1 Hu CHO cAMP TRF Ag CR GMean $EC_{50}$ (µM) |
|---|---|---|---|
| 2 | 14.7 | 1.8 | |
| 3 | | 1.6 | >100 |
| 4 | 47.4 | 0.6 | 1.9 |
| 5 | | 3.0 | |
| 7 | | 8.4 | |
| 9 | 262.2 | 5.7 | |
| 11 | >300 | 12.8 | 3.1 |
| 12 | | 21.2 | |
| 14 | 14.3 | 1.1 | |
| 15 | 59.8 | 2.1 | |
| 16 | 56.8 | 0.8 | |
| 17 | 6.5 | 0.2 | |
| 18 | 17.2 | 0.4 | |
| 19 | 4.3 | 1.0 | |
| 20 | 16.8 | 0.4 | |
| 21 | 13.3 | 0.2 | |
| 22 | 6.3 | 1.2 | |
| 26 | 9.2 | 4.4 | |
| 27 | 14.0 | 3.1 | |
| 29 | 16.9 | 0.2 | |
| 30 | 15.6 | 3.9 | |
| 31 | 12.6 | 5.0 | |
| 32 | 4.1 | 8.3 | |
| 33 | 124.3 | 0.2 | |
| 37 | 6.7 | 7.8 | 2.5 |
| 38 | 2.1 | 14.8 | |
| 41 | 5.9 | 15.4 | |
| 43 | 3.3 | 13.9 | |
| 47 | 17.4 | 1.0 | |
| 50 | 4.3 | 17.2 | |
| 56 | 5.9 | 5.1 | |
| 57 | 9.5 | 3.7 | |
| 58 | 24.6 | 7.3 | |
| 59 | 10.2 | 13.1 | |
| 60 | 13.8 | 3.9 | |
| 66 | 12.1 | 3.1 | 3.2 |
| 67 | 6.6 | 3.0 | |
| 69 | 13.1 | 2.4 | |
| 70 | 12.4 | 18.4 | |
| 74 | 14.4 | 1.8 | |
| 76 | 18.2 | 2.6 | |
| 77 | 13.4 | 0.3 | |
| 78 | 28.2 | 3.0 | |
| 79 | 10.1 | 2.0 | |
| 80 | 9.8 | 3.3 | |
| 82 | 15.4 | 4.3 | |
| 83 | 11.8 | 6.2 | |
| 85 | 14.1 | 3.4 | 9.3 |
| 86 | 12.3 | 4.0 | 5.7 |
| 87 | 2.7 | 15.4 | 46.0 |
| 88 | 3.6 | 16.8 | |
| 89 | 14.6 | 3.7 | 78.2 |
| 90 | >300 | >30 | |
| 93 | 15.6 | 1.3 | |
| 94 | 17.3 | 1.2 | |
| 95 | 12.9 | 1.1 | |
| 96 | | 1.3 | |
| 97 | 46.6 | 1.8 | |
| 98 | 26.7 | 0.8 | |
| 99 | >300 | >30 | |
| 103 | | 0.8 | |
| 106 | 16.1 | 5.9 | |
| 108 | 8.8 | 7.0 | |
| 109 | 13.0 | 14.8 | |
| 111 | | 4.9 | 3.4 |
| 112 | 7.4 | 5.4 | |

TABLE 4-continued

| Example | Assay A: Human Heps Met Clint GMean CLint (µl/min/1E6) | Assay B: CYP2C9 HLM Diclofenac LC/MSMS GMean IC$_{50}$ (µM) | Assay C: CB1 Hu CHO cAMP TRF Ag CR GMean EC$_{50}$ (µM) |
|---|---|---|---|
| 113 | 7.3 | 4.2 | 0.4 |
| 114 | 6.4 | 7.2 | 60.5 |
| 115 | 6.2 | 9.8 | >100 |
| 117 | 4.2 | 4.9 | 0.5 |
| 118 | 4.6 | 7.8 | |
| 119 | 1.0 | 12.3 | |
| 120 | 13.3 | 12.8 | 8.5 |
| 121 | 6.8 | 7.7 | >10 |
| 122 | 8.8 | 4.4 | 22.3 |
| 123 | 8.3 | 9.3 | >3.0 |
| 124 | 11.1 | 27.0 | |

The data in Table 4 may be from a single experiment or an average of two or more experiments.

Metabolism Study

An in vitro study to identify metabolites of Example 87 yielded Metabolite 1 and Metabolite 2, as defined below. Metabolites 1 and 2 were subsequently synthesised and characterised.

Metabolite 1: 3-(3-((2R,6S)-2,6-dimethylmorpholine-4-carbonyl)-1,2,4-oxadiazol-5-yl)-2,5,6-trifluorophenyl hydrogen sulfate

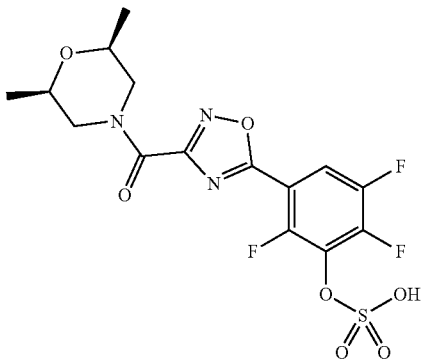 [SMILES: C[C@@H]1CN(C(=O)c2noc(-c3cc(F)c(F)c(OS(=O)(=O)O)c3F)n2)C[C@H](C)O1]

A solution of ((2R,6S)-2,6-dimethylmorpholino)(5-(2,4,5-trifluoro-3-hydroxyphenyl)-1,2,4-oxadiazol-3-yl)methanone, Example 87, (60 mg, 0.17 mmol) and TEA (38 µL, 0.27 mmol) in anhydrous DCM (2.76 mL) was treated with pyridine-sulfur trioxide (1/1) (160 mg, 1.01 mmol) and the reaction mixture was stirred at rt for 5 min. The solid formed was removed by filtration, water was added to the filtrate, and the aqueous phase was washed with DCM. The pH of the aqueous phase was adjusted to 7-8 using NaHCO$_3$. Freeze drying gave the sodium salt of the desired product (23 mg, 30%); HRMS (ESI) m/z [M+H]$^+$ calcd for C$_{15}$H$_{14}$F$_3$N$_3$O$_7$S: 436.0426, found: 436.0429.

Metabolite 2: (2S,3S,4S,5R,6S)-6-(3-(3-((2R,6S)-2,6-dimethylmorpholine-4-carbonyl)-1,2,4-oxadiazol-5-yl)-2,5,6-trifluorophenoxy)-3,4,5-trihydroxytetrahydro-2H-pyran-2-carboxylic acid

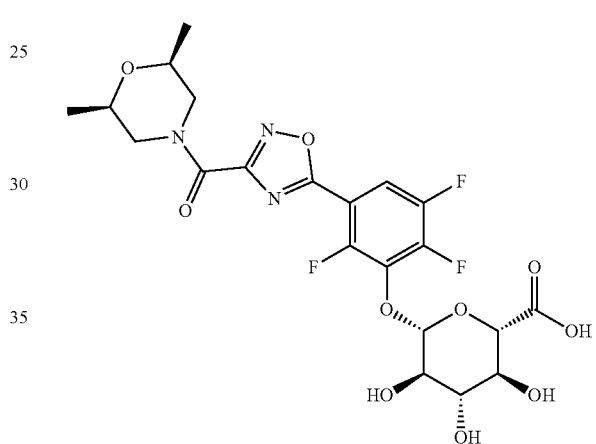

Ag$_2$O (2.5 eq) was added to a solution of ((2R,6S)-2,6-dimethylmorpholino)(5-(2,4,5-trifluoro-3-hydroxyphenyl)-1,2,4-oxadiazol-3-yl)methanone, Example 87, (1 eq), and (2R,3R,4S,5S,6S)-2-bromo-6-(methoxycarbonyl)tetrahydro-2H-pyran-3,4,5-triyl triacetate (0.9 eq) in MeCN (0.1 M) in a reaction vessel covered with aluminum foil, and the reaction mixture was stirred at room temperature overnight The reaction mixture was filtered through CELITE and the filtrate was diluted with EtOAc and then concentrated at reduced pressure. The crude compound was purified by preparative HPLC on a XBRIDGE C18 column (10 µm, 250×19 mm ID) using a gradient of MeCN in H$_2$O/MeCN/NH$_3$ (95/5/0.2) as mobile phase. The acetate groups and the ester were hydrolyzed in MeCN (0.07 M) by treatment with TEA (12 eq) and LiBr (40 eq) at rt for 4 h. Water was added to the reaction mixture and the mixture was acidified using HCl. The mixture was concentrated at reduced pressure and the crude compound was purified by preparative HPLC, PrepMethod D (gradient: 0-100%) to give the title compound; HRMS (ESI) m/z [M−H]$^−$ calcd for C$_{21}$H$_{21}$F$_3$N$_3$O$_{10}$: 532.1179, found: 532.1195.

The above description of illustrative embodiments is intended only to acquaint others skilled in the art with the Applicant's specification, its principles, and its practical application so that others skilled in the art may readily adapt and apply the specification in its numerous forms, as they may be best suited to the requirements of a particular use. This description and its specific examples, while indicating embodiments of this specification, are intended for purposes of illustration only. This specification, therefore, is not limited to the illustrative embodiments described in this specification, and may be variously modified. In addition, it is to be appreciated that various features of the specification that are, for clarity reasons, described in the context of separate embodiments, also may be combined to form a single embodiment. Conversely, various features of the specification that are, for brevity reasons, described in the context of a single embodiment, also may be combined to form sub-combinations thereof.

The invention claimed is:

1. A compound Formula (III):

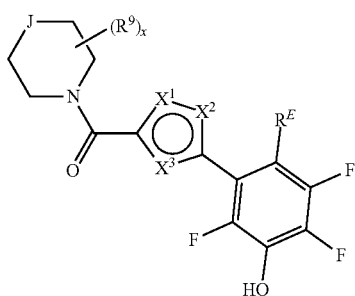

wherein
one of $X^1$, $X^2$ and $X^3$ is selected from NH, O and S and the other two of $X^1$, $X^2$ and $X^3$ are independently selected from N and $CR^Y$, wherein each $R^Y$ is independently H, —CN, —C(=O)N($R^7$)$_2$ or $R^{XA}$ wherein $R^{XA}$ is independently $C_{1-3}$ alkyl optionally substituted with one to three F;
J is selected from O, S, and a covalent bond,
x is selected from 0 to 3;
each $R^9$ is independently selected from $R^3$, $R^4$ and $R^5$;
$R^E$ is H or halo,
each $R^3$ is independently $C_{1-4}$ alkyl or $C_{3-6}$ cycloalkyl, each of which are optionally substituted with one or more groups independently selected from $R^{4X}$, $R^{5x}$, —O($R^{4X}$), —O($R^{5X}$) and F;
each $R^{3X}$ is independently $C_{1-4}$ alkyl or $C_{3-6}$ cycloalkyl, each of which are optionally substituted with one or more F;
each $R^4$ is independently monocyclic or bicyclic 5 to 9 membered heteroaryl, each of which are optionally substituted with one or more groups independently selected from $R^{4X}$, —O($R^{4X}$), $R^{5X}$, —O($R^{5X}$), —OH, —CN, $C_{1-4}$ alkoxy, —C(=O) OH, —C(=O)O($C_{1-4}$ alkyl), —C(=O)N($R^{7B}$)$_2$, $R^3$ and halo;
each $R^5$ is independently phenyl, each of which are optionally substituted with one or more groups independently selected from $R^{4X}$, —O($R^{4X}$), $R^{5X}$, —O($R^{5X}$), —OH, —CN, $C_{1-4}$ alkoxy, —C(=O) OH, —C(=O)O($C_{1-4}$ alkyl), —C(=O)N($R^{7B}$)$_2$, $R^3$ and halo;
each $R^{4X}$ is independently monocyclic or bicyclic 5 to 9 membered heteroaryl, each of which are optionally substituted with one or more groups independently selected from —OH, —CN, $C_{1-4}$ alkoxy, —C(=O) OH, —C(=O)N($R^{7B}$)$_2$, $R^{3x}$ and halo;

each $R^{5X}$ is independently phenyl, each of which are optionally substituted with one or more groups independently selected from —OH, —CN, $C_{1-4}$ alkoxy, —C(=O) OH, —C(=O)N($R^{7B}$)$_2$, $R^{3x}$ and halo;
each $R^7$ and $R^{7B}$ are independently H, $C_{1-4}$ alkyl or $C_{3-6}$ cycloalkyl; and
wherein each heteroaryl is independently an aromatic ring containing one or more heteroatoms independently selected from N, O and S,
or a pharmaceutically acceptable salt thereof.

2. The compound of Formula (III) or a pharmaceutically acceptable salt thereof, as claimed in claim 1, wherein
(i) $X^1$ is N, $X^2$ is O and $X^3$ is N;
(ii) $X^1$ is N, $X^2$ is N and $X^3$ is O;
(iii) $X^1$ is $CR^Y$, $X^2$ is $CR^Y$ and $X^3$ is S;
(iv) $X^1$ is O, $X^2$ is N and $X^3$ is $CR^Y$;
(v) $X^1$ is N, $X^2$ is O and $X^3$ is $CR^Y$;
(vi) $X^1$ is $CR^Y$, $X^2$ is N and $X^3$ is O;
(vii) $X^1$ is O, $X^2$ is N and $X^3$ is N;
(viii) $X^1$ is N, $X^2$ is N and $X^3$ is S;
(ix) $X^1$ is $CR^Y$, $X^2$ is S and $X^3$ is $CR^Y$; or
(x) $X^1$ is $CR^Y$, $X^2$ is N and $X^3$ is S.

3. The compound of Formula (III) or a pharmaceutically acceptable salt thereof, as claimed in claim 1, wherein
(i) $X^1$ is N, $X^2$ is O and $X^3$ is N;
(ii) $X^1$ is CH, $X^2$ is N and $X^3$ is S; or
(iii) $X^1$ is N, $X^2$ is O and $X^3$ is CH.

4. The compound of Formula (III) or a pharmaceutically acceptable salt thereof, as claimed in claim 1, wherein $X^1$ is N, $X^2$ is O and $X^3$ is N.

5. The compound of Formula (III) or a pharmaceutically acceptable salt thereof, as claimed in claim 1, wherein each $R^3$ is independently $C_{1-4}$ alkyl optionally substituted with one to three F.

6. The compound of Formula (III) or a pharmaceutically acceptable salt thereof, as claimed claim 1, wherein each $R^4$ is independently monocyclic or bicyclic 5 to 9 membered heteroaryl, each of which are optionally substituted with one or more groups independently selected from OH, —CN, $C_{1-4}$ alkoxy, —C(=O) OH, —C(=O)O($C_{1-4}$ alkyl)—C(=O)N($R^{7B}$)$_2$, $R^{3X}$ and halo.

7. The compound of Formula (III) or a pharmaceutically acceptable salt thereof, as claimed in claim 1, wherein each $R^5$ is independently phenyl, each of which are optionally substituted with one or more groups independently selected from OH, —CN, $C_{1-4}$ alkoxy, —C(=O) OH, —C(=O)O($C_{1-4}$ alkyl), —C(=O)N($R^{7B}$)$_2$, $R^{3X}$ and halo.

8. The compound of Formula (III), or a pharmaceutically acceptable salt thereof, as claimed in claim 1, wherein J is O.

9. The compound of Formula (III), or a pharmaceutically acceptable salt thereof, as claimed in claim 1, wherein $R^E$ is H.

10. The compound of Formula (III), or a pharmaceutically acceptable salt thereof, as claimed in claim 1, that is
(i) ((2R,6S)-2,6-dimethylmorpholino) (5-(2,4,5-trifluoro-3-hydroxyphenyl)-1,2,4-oxadiazol-3-yl) methanone

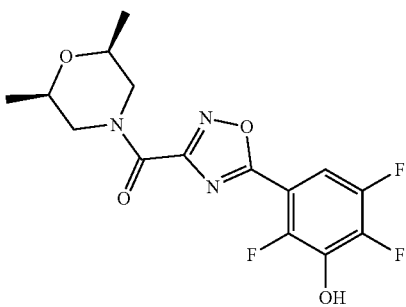 [SMILES: C[C@@H]1CN(C(=O)c2noc(-c3cc(F)c(F)c(O)c3F)n2)C[C@H](C)O1]

or a pharmaceutically acceptable salt thereof, (ii) ((2R,6S)-2,6-dimethylmorpholino) (2-(2,4,5-trifluoro-3-hydroxyphenyl) thiazol-5-yl) methanone

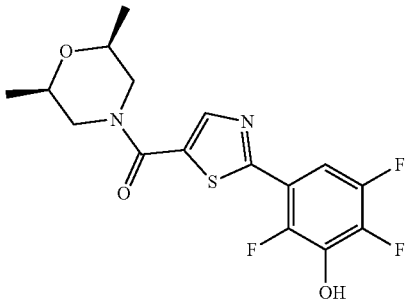 [SMILES: C[C@@H]1CN(C(=O)c2cnc(-c3cc(F)c(F)c(O)c3F)s2)C[C@H](C)O1]

or a pharmaceutically acceptable salt thereof, or (iii) ((2R,6S)-2,6-dimethylmorpholino) (5-(2,4,5-trifluoro-3-hydroxyphenyl) isoxazol-3-yl) methanone

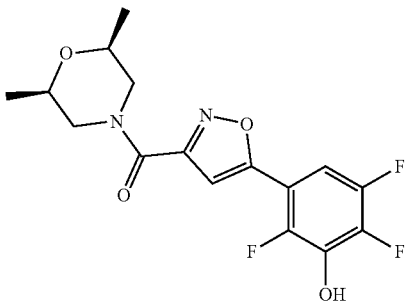 [SMILES: C[C@@H]1CN(C(=O)c2cc(-c3cc(F)c(F)c(O)c3F)on2)C[C@H](C)O1]

or a pharmaceutically acceptable salt thereof.

11. A pharmaceutical composition comprising the compound of Formula (III) or a pharmaceutically acceptable salt thereof, as claimed in claim 1, and a pharmaceutically acceptable excipient.

12. A method of treating liver disease in a patient comprising administering to the patient a compound of Formula (III) or a pharmaceutically acceptable salt thereof, as claimed in claim 1.

13. A method of treating liver disease as claimed in claim 12, wherein the liver disease is liver fibrosis.

14. A method of treating liver disease as claimed in claim 12, wherein the liver disease is cirrhosis.

15. A method of treating liver disease as claimed in claim 12, wherein the compound of Formula (III) or a pharmaceutically acceptable salt thereof is administered in combination a glucagon-like peptide-1 receptor (GLP1) agonist.

16. A method of treating liver disease as claimed in claim 12, wherein the compound of Formula (III) or a pharmaceutically acceptable salt thereof is administered in combination with a sodium-glucose transport protein 2 (SGLT2) inhibitor.

17. A method of treating liver disease as claimed in claim 12, wherein the compound of Formula (III) or a pharmaceutically acceptable salt thereof is administered in combination with a ThrB agonist.

18. A compound that is ((2R,6S)-2,6-dimethylmorpholino) (5-(2,4,5-trifluoro-3-hydroxyphenyl)-1,2,4-oxadiazol-3-yl) methanone

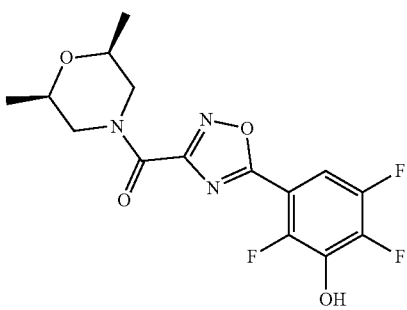 [SMILES: C[C@@H]1CN(C(=O)c2noc(-c3cc(F)c(F)c(O)c3F)n2)C[C@H](C)O1]

or a pharmaceutically acceptable salt thereof.

19. The compound as claimed in claim 18, that is ((2R,6S)-2,6-dimethylmorpholino) (5-(2,4,5-trifluoro-3-hydroxyphenyl)-1,2,4-oxadiazol-3-yl) methanone.

20. A pharmaceutical composition comprising ((2R,6S)-2,6-dimethylmorpholino) (5-(2,4,5-trifluoro-3-hydroxyphenyl)-1,2,4-oxadiazol-3-yl) methanone or a pharmaceutically acceptable salt thereof, as claimed in claim 18, and a pharmaceutically acceptable excipient.

21. A method of treating liver disease in a patient comprising administering to the patient ((2R,6S)-2,6-dimethylmorpholino) (5-(2,4,5-trifluoro-3-hydroxyphenyl)-1,2,4-oxadiazol-3-yl) methanone or a pharmaceutically acceptable salt thereof, as claimed in claim 18.

22. A method of treating liver disease as claimed in claim 21, wherein the liver disease is liver fibrosis.

23. A method of treating liver disease as claimed in claim 21, wherein the liver disease is cirrhosis.

24. A method of treating liver disease as claimed in claim 21, wherein the ((2R,6S)-2,6-dimethylmorpholino) (5-(2,4,5-trifluoro-3-hydroxyphenyl)-1,2,4-oxadiazol-3-yl) methanone or a pharmaceutically acceptable salt thereof is administered in combination a glucagon-like peptide-1 receptor (GLP1) agonist.

25. A method of treating liver disease as claimed in claim 21, wherein the ((2R,6S)-2,6-dimethylmorpholino) (5-(2,4,5-trifluoro-3-hydroxyphenyl)-1,2,4-oxadiazol-3-yl) methanone or a pharmaceutically acceptable salt thereof is administered in combination with a sodium-glucose transport protein 2 (SGLT2) inhibitor.

26. A method of treating liver disease as claimed in claim 21, wherein the ((2R,6S)-2,6-dimethylmorpholino) (5-(2,4,5-trifluoro-3-hydroxyphenyl)-1,2,4-oxadiazol-3-yl) methanone or a pharmaceutically acceptable salt thereof is administered in combination with a ThrB agonist.

* * * * *